United States Patent [19]

Wissner

[11] 4,212,969
[45] Jul. 15, 1980

[54] 1-HYDROXYMETHYL-1-OXO-PROSTANE DERIVATIVES OF THE $A_2$ SERIES

[75] Inventor: Allan Wissner, Ardsley, N.Y.

[73] Assignee: American Cyanamid Company, Stamford, Conn.

[21] Appl. No.: 858,579

[22] Filed: Dec. 8, 1977

[51] Int. Cl.$^2$ .......................................... C07C 177/00
[52] U.S. Cl. .................................. 542/429; 568/379; 560/231; 568/330; 568/367
[58] Field of Search ...................... 260/586 R, 590 C; 542/429; 560/231

Primary Examiner—Robert Gerstl
Attorney, Agent, or Firm—Richard J. Hammond

[57] ABSTRACT

Derivatives, analogs, and congeners of prostane having a 1-(hydroxymethyl)-1-oxo-prostane structure in the $A_2$ series.

189 Claims, No Drawings

1-HYDROXYMETHYL-1-OXO-PROSTANE DERIVATIVES OF THE $A_2$ SERIES

BACKGROUND OF THE INVENTION

Applicant is not aware of any prior art references which, in his judgement as one skilled in the prostaglandin art, would anticipate or render obvious the novel compounds of the instant invention; however, for the purpose of fully developing the background of the invention and establishing the state of the requesite art, the following references are set forth: U.S. Pat. Nos. 4,028,396, 3,849,487, and 3,813,433; Belgium Patent Specification No. 781978; Japanese Patent Specification No. 1004-151; Netherlands Patent Specification No. 7203126; and West German Patent Specification No. 2505-303.

BRIEF SUMMARY OF THE INVENTION

The first embodiment of the invention is represented by an optically active compound of the formula:

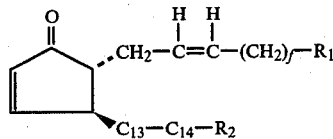

wherein f is an integer from 2 to 4, inclusive; $C_{13}$–$C_{14}$ is selected from the group consisting of ethylene and trans-vinylene; $R_1$ is a radical selected from the group consisting of

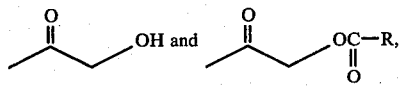

wherein R is selected from the group consisting of $C_1$–$C_4$ alkyl; $R_2$ is a moiety selected from the group consisting of

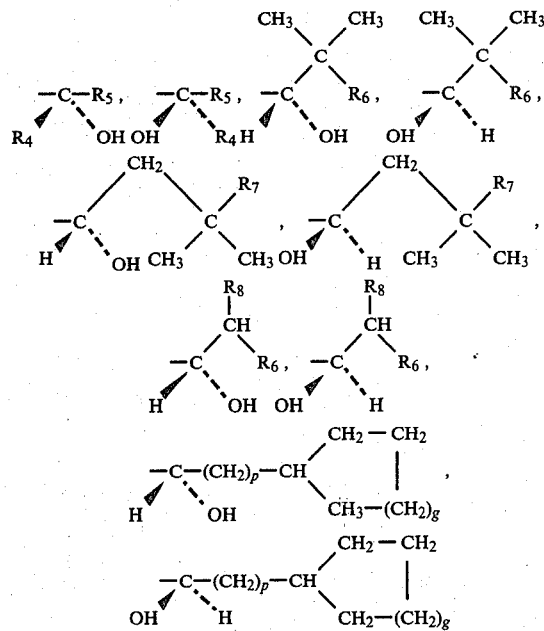

-continued

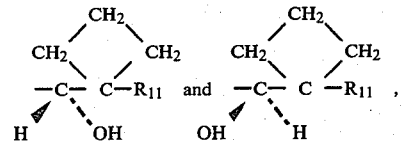

wherein $R_4$ is selected from the group consisting of hydrogen and methyl, $R_5$ is selected from the group consisting of $C_4$–$C_7$ alkyl, $R_6$ is selected from the group consisting of $C_3$–$C_5$ alkyl, $R_7$ is selected from the group consisting of $C_2$–$C_4$, $R_8$ is selected from the group consisting of $C_1$14 $C_2$ alkyl, $R_{11}$ is selected from the group consisting of $C_3$–$C_7$ alkyl, p is an integer from 0 to 3, and q is 1 or 2; the racemic mixture thereof; and the mirror image thereof.

A first preferred embodiment of the first embodiment consists of these compounds wherein f, and $R_2$ are as previously defined; $C_{13}$–$C_{14}$ is trans-vinylene; and $R_1$ is the moiety

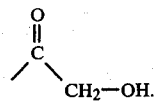

A second preferred embodiment of the first embodiment consists of those compounds wherein f, and $R_2$ are as previously defined; $C_{13}$–$C_{14}$ is trans-vinylene; and $R_1$ is the moiety

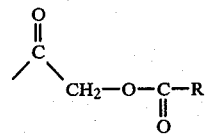

wherein R is as previously defined.

A first further preferred embodiment of the first preferred embodiment consists of those compounds wherein $R_1$, $C_{13}$–$C_{14}$ and f are as previously defined; and $R_2$ is a moiety selected from the group consisting of

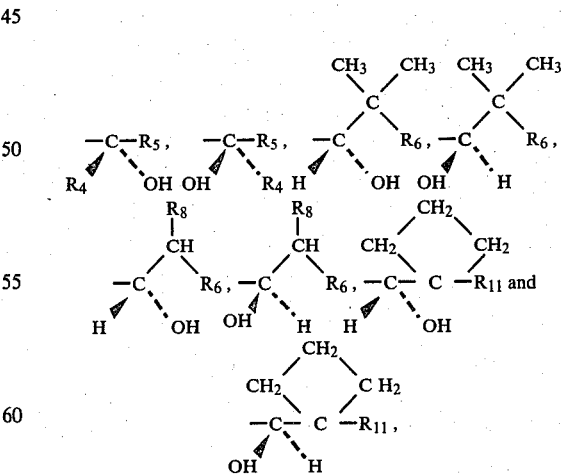

wherein $R_4$, $R_5$, $R_6$, $R_8$ and $R_{11}$ are as previously defined.

A second further preferred embodiment of the first preferred embodiment consists of those compounds wherein $R_1$, $C_{13}$–$C_{14}$ and f are as previously defined;

and $R_2$ is a moiety selected from the group consisting of

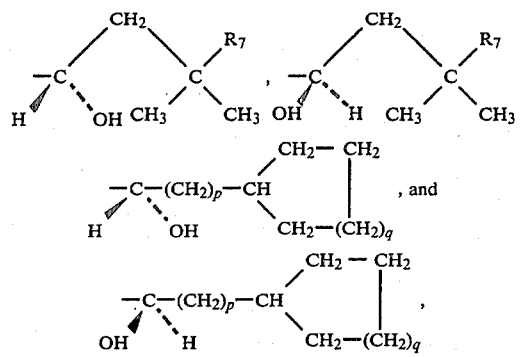

wherein $R_7$, p and q are as previously defined.

A still further preferred embodiment of the second further preferred embodiment consists of those compounds wherein $R_1$, $C_{13}$–$C_{14}$ and f are as previously defined; and $R_2$ is a moiety selected from the group consisting of

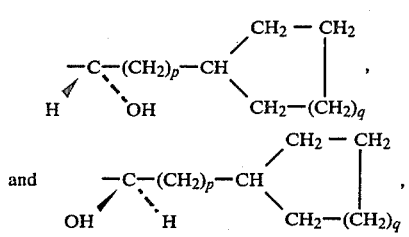

wherein p and q are as previously defined.

A first further preferred embodiment of the second preferred embodiment consists of those compounds wherein $R_1$, $C_{13}$–$C_{14}$ and f are as previously defined; and $R_2$ is a moiety selected from the group consisting of

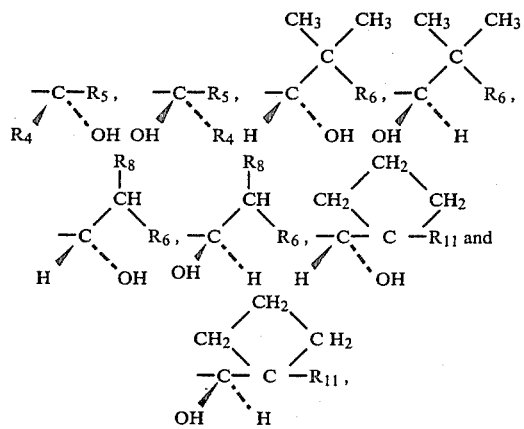

wherein $R_4$, $R_5$, $R_6$, $R_8$, and $R_{11}$ are as previously defined.

A second further preferred embodiment of the second preferred embodiment consists of those compounds wherein $R_1$, $C_{13}$–$C_{14}$ and f are as previously defined; and $R_2$ is a moiety selected from the group consisting of

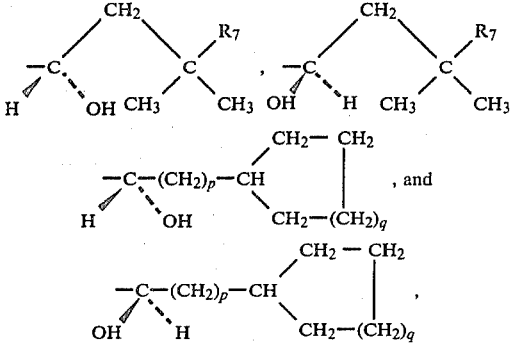

wherein $R_7$, p and q are as previously defined.

A still further preferred embodiment of the second further preferred embodiment consists of those compounds wherein $R_1$, $C_{13}$–$C_{14}$ and f are as previously defined; and R is a moiety selected from the group consisting of

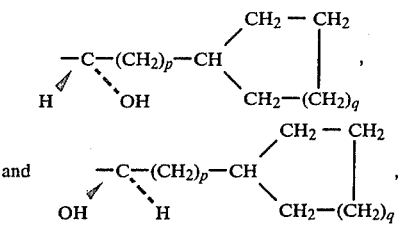

wherein p and q are as previously defined.

The second embodiment of the invention is represented by an optically active compound of the formula:

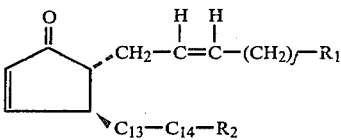

wherein f is an integer from 2 to 4, inclusive; $C_{13}$–$C_{14}$ is selected from the group consisting of ethylene and trans-vinylene; $R_1$ is a radical selected from the group consisting of

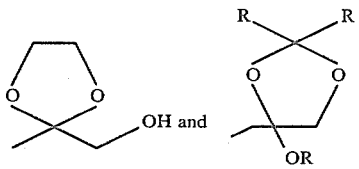

wherein R is selected from the group consisting of $C_1$–$C_4$ alkyl; $R_2$ is a moiety selected from the group consisting of

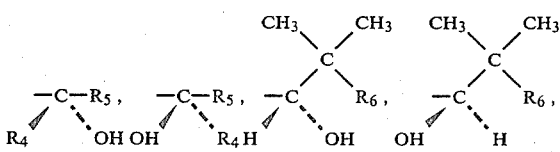

-continued

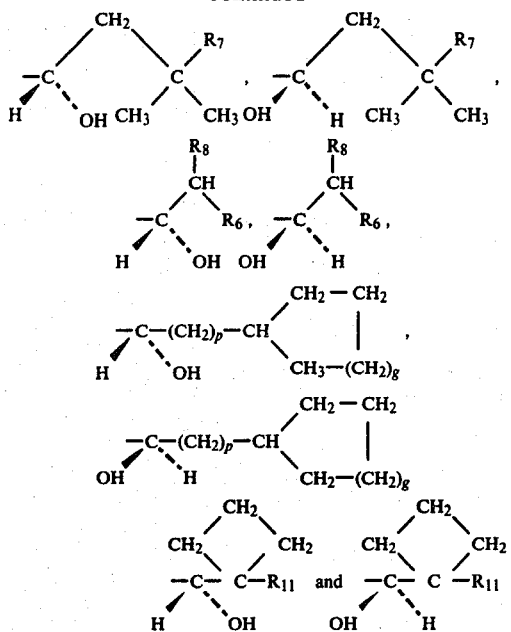

wherein $R_4$ is selected from the group consisting of hydrogen and methyl, $R_5$ is selected from the group consisting of $C_4$-$C_7$ alkyl, $R_6$ is selected from the group consisting of $C_2$-$C_4$, $R_8$ is selected from the group consisting of $C_1$-$C_2$ alkyl, $R_{11}$ is selected from the group consisting of $C_3$-$C_7$ alkyl, p is an integer from 0 to 3, and q is 1 or 2; the racemic mixture thereof and the mirror image thereof.

A first preferred embodiment of the second embodiment consists of those compounds wherein f, and $R_2$ are as previously defined; $C_{13}$-$C_{14}$ is trans-vinylene; and $R_1$ is the moiety

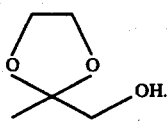

A second preferred embodiment of the second embodiment consists of those compounds wherein f, and $R_2$ are as previously defined; $C_{13}$-$C_{14}$ is trans-vinylene; and $R_1$ is the moiety

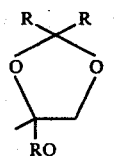

wherein R is as previously defined.

A first further preferred embodiment of the first preferred embodiment consists of those compounds wherein $R_1$, $C_{13}$-$C_{14}$ and f are as previously defined; and $R_2$ is a moiety selected from the group consisting of

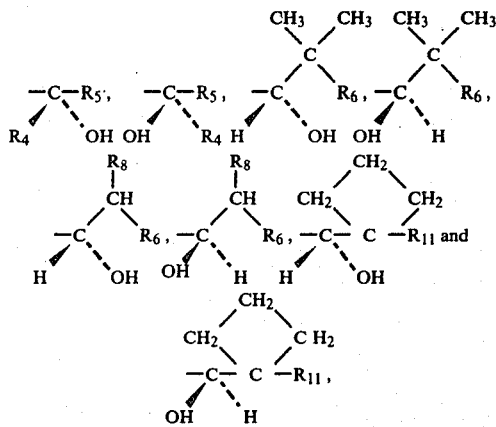

wherein $R_4$, $R_5$, $R_6$, $R_8$ and $R_{11}$ are as previously defined.

A second further preferred embodiment of the first preferred embodiment consists of those compounds wherein $R_1$, $C_{13}$-$C_{14}$ and f are as previously defined; and $R_2$ is a moiety selected from the group consisting of

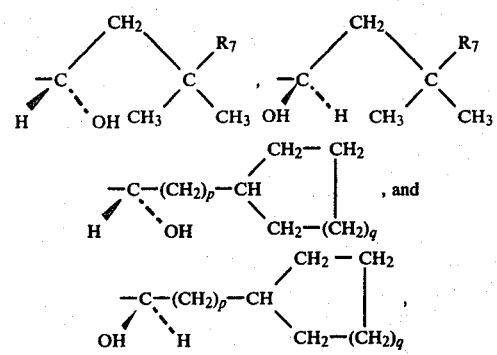

wherein $R_7$ p and q are as previously defined.

A still further preferred embodiment of the second further preferred embodiment consists of those compounds wherein $R_1$, $C_{13}$-$C_{14}$ and f are as previously defined; and $R_2$ is a moiety selected from the group consisting of

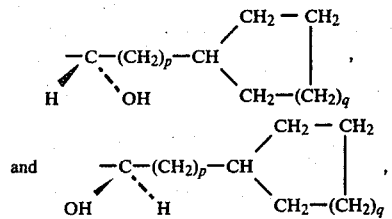

wherein p and q are as previously defined.

The third embodiment of the inventor is represented by an optically active compound of the formula:

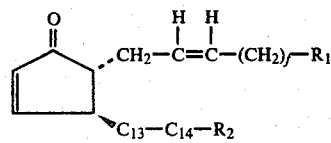

wherein f is an integer from 2 to 4, inclusive; $C_{13}$–$C_{14}$ is selected from the group consisting of ethylene and trans-vinylene; R is a radical selected from the group consisting of

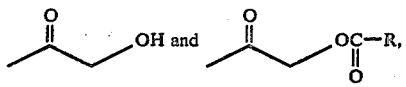

wherein R is se- from the group consisting of $C_1$–$C_4$ alkyl; $R_2$ is a moiety selected from the group consisting of

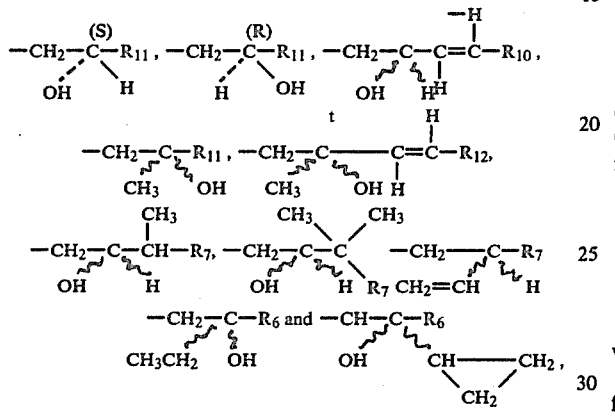

wherein $R_6$ is selected from the group consisting of $C_3$–$C_6$ alkyl, $R_7$ is selected from the group consisting of $C_2$–$C_4$ alkyl, $R_{10}$ is selected from the group consisting of $C_1$–$C_4$ alkyl, $R_{11}$ is selected from the group consisting of $C_3$–$C_7$ alkyl and $R_{12}$ is selected from the group consisting of $C_1$–$C_4$ alkyl; the racemic mixture thereof; and the mirror image thereof.

A first preferred embodiment of the third embodiment consists of those compounds wherein f, and $R_2$ are as previously defined; $C_{13}$–$C_{14}$ is trans-vinylene; and $R_1$ is the moiety

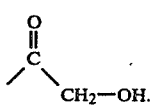

A second preferred embodiment of the third embodiment consists of these compounds wherein f, and $R_2$ are as previously defined; $C_{13}$–$C_{14}$ is trans-vinylene; and $R_1$ is the moiety

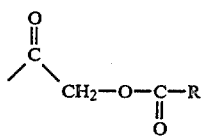

wherein R is as previously defined.

A first further preferred embodiment of the first preferred embodiment consists of those compounds wherein $R_1$, $C_{13}$–$C_{14}$ and f are as previously defined, and $R_2$ is the moiety selected from the group consisting of

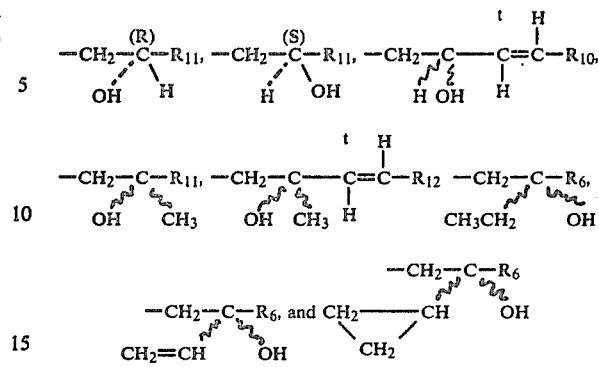

wherein $R_6$, $R_{10}$, $R_{11}$ and $R_{12}$ are as previously defined.

A second further embodiment of the first preferred embodiment consists of those compounds wherein $R_1$, $C_{13}$–$C_{14}$ and f are as previously defined; and $R_2$ is a moiety selected from the group consisting of

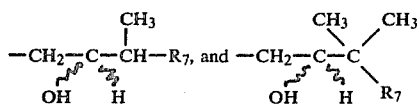

wherein $R_7$ is as previously defined.

A still further preferred embodiment of the second further preferred embodiment consists of those compounds wherein $R_1$, $C_{13}$–$C_{14}$ and f are as previously defined; and $R_2$ is a moiety selected from the group consisting of

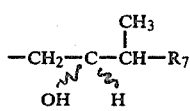

wherein $R_7$ is as previously defined.

A first still further preferred embodiment of the first ruther preferred embodiment consists of those compounds wherein $R_1$, $C_{13}$–$C_{14}$ and f are as previously defined; and $R_2$ is a moiety selected from the group consisting of

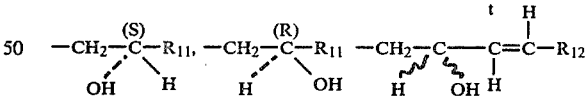

wherein $R_6$, $R_{11}$ and $R_{12}$ are as previously defined.

A second still further preferred embodiment of the first further preferred embodiment consists of those compounds wherein $R_1$, $C_{13}$–$C_{14}$ and f are as previously defined; and $R_2$ is a moiety selected from the group consisting of

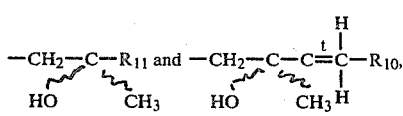

wherein $R_{10}$ and $R_{11}$ are as previously defined.

A first further preferred embodiment of the second preferred embodiment consists of the compounds wherein $R_1$, $C_{13}-C_{14}$ and f are as previously defined, and $R_2$ is a moiety selected from the group consisting of

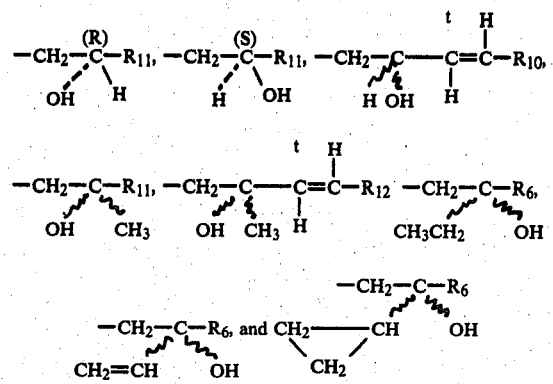

wherein $R_6$, $R_{10}$, $R_{11}$, and $R_{12}$ are as previously defined.

A second further preferred embodiment of the second preferred embodiment consists of those compounds wherein $R_1$, $C_{13}-C_{14}$ and f are as previously defined; and $R_2$ is a moiety selected from the group consisting of

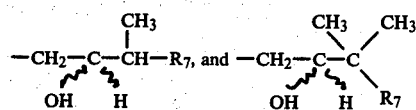

wherein $R_7$ is as previously defined.

A still further preferred embodiment of the second further preferred embodiment consists of those compounds wherein $R_1$, $C_{13}-C_{14}$ and f are as previously defined; and $R_2$ is a moiety selected from the group consisting of

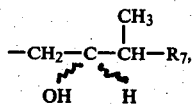

wherein $R_7$ is as previously defined.

A first still further preferred embodiment of the first further preferred embodiment consists of those compounds wherein $R_1$, $C_{13}-C_{14}$ and f are as previously defined; and $R_2$ is a moiety selected from the group consisting of

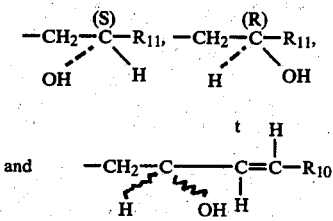

wherein $R_6$, $R_{11}$ and $R_{12}$ are as previously defined.

A second still further preferred embodiment of the first further preferred embodiment consists of those compounds wherein $R_1$, $C_{13}-C_{14}$ and f are as previously defined; and $R_2$ is a moiety selected from the group consisting of

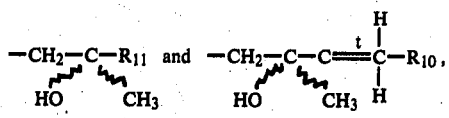

wherein $R_{10}$ and $R_{11}$ are as previously defined.

The fourth embodiment of the invention is represented by an optically active compound of the formula:

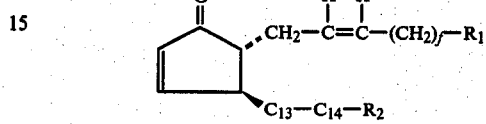

wherein f is an integer from 2 to 4, inclusive; $C_{13}-C_{14}$ is selected from the group consisting of ethylene and trans-vinylene; $R_1$ is a radical selected from the group consisting of

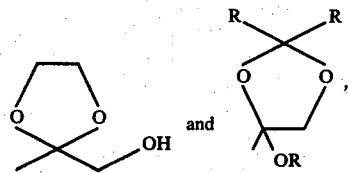

wherein R is selected from the group consisting of $C_1-C_4$ alkyl; $R_2$ is a moiety selected from the group consisting of

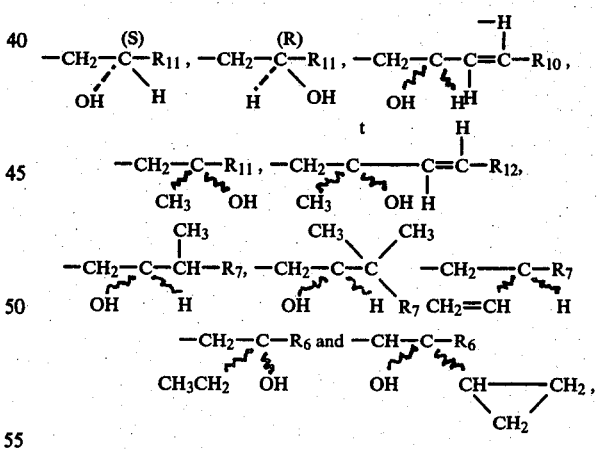

wherein $R_6$ is selected from the group consisting of $C_3-C_6$ alkyl, $R_7$ is selected from the group consisting of $C_2-C_4$ alkyl, $R_{10}$ is selected from the group consisting of $C_1-C_4$ alkyl, $R_{11}$ is selected from the group consisting of $C_3-C_7$ alkyl and $R_{12}$ is selected from the group consisting of $C_1-C_4$ alkyl; the racemic mixture thereof; and the mirror image thereof.

A first preferred embodiment of the forth embodiment consists of those compounds wherein f, and $R_2$ are as previously defined; $C_{13}-C_{14}$ is trans-vinylene; and $R_1$ is the moiety

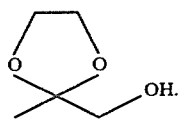

A second prefered embodiment of the fourth embodiment consists of those compounds wherein f, and $R_2$ are as previously defined. $C_{13}$–$C_{14}$ is trans-vinylene; and $R_1$ is the moiety

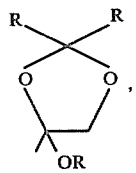

wherein R is as previously defined.

A first further prefered embodiment of the first prefered embodiment consists of those compounds wherein $R_1$ $C_{13}$–$C_{14}$ and f are as previously defined, and $R_2$ is a moiety selected from the group consisting of

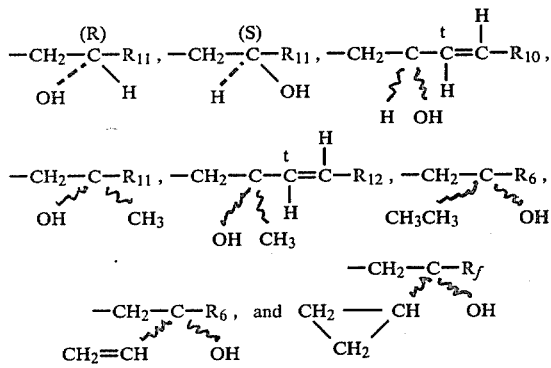

wherein $R_6$, $R_{10}$, $R_{11}$ and $R_{12}$ are as previously defined.

A second further preferred embodiment of the first prefered embodiment consists of those compounds wherein $R_1$, $C_{13}$–$C_{14}$ and f are as previously defined; and $R_2$ is a moiety selected from the group consisting of

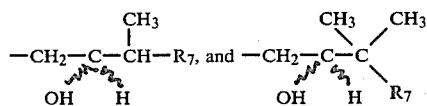

wherein $R_7$ is as previously defined.

A still further preferred embodiment of the second further preferred embodiment consists of those compounds wherein $R_1$, $C_{13}$–$C_{14}$ and f are as previously defined; and $R_2$ is a moiety selected from the group consisting of

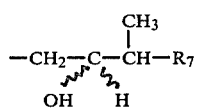

wherein $R_7$ is as previously defined.

A first still further preferred embodiment of the first further preferred embodiment consists of those compounds wherein $R_1$, $C_{13}$–$C_{14}$ and f are as previously defined; and $R_2$ is a moiety selected from the group consisting of

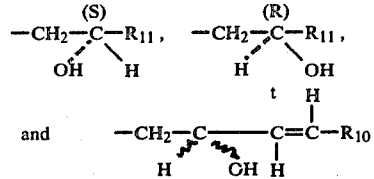

wherein $R_6$, $R_{11}$ and $R_{12}$ are as previously defined.

A second still further preferred embodiment of the first further prefered embodiment consists of those compounds wherein $R_1$, $C_{13}$–$C_{14}$ and f are as previously defined; and $R_2$ is a moiety selected from the group consisting of

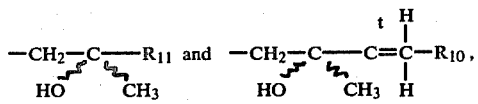

wherein $R_{10}$ and $R_{11}$ are as previously defined.

The fifth embodiment of the invention is represented by an optically active compound of the formula:

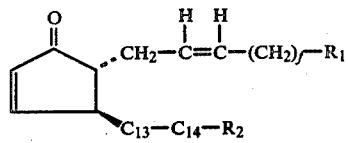

wherein f is an integer from 2 to 4, inclusive; $C_{13}$–$C_{14}$ is selected from the group consisting of ethylene and trans-vinylene; R is a radical selected from the group consisting of

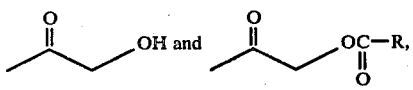

wherein R is selected from the group consisting of $C_1$–$C_4$ alkyl; $R_2$ is a moiety selected from the group consisting of

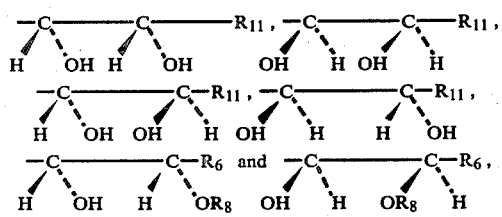

wherein $R_6$ is selected from the group consisting of $C_3$–$C_5$ alkyl, $R_8$ is selected from the group consisting of $C_1$–$C_2$ alkyl and $R_{11}$ is selected from the group consisting of $C_3$–$C_7$ alkyl; the racemic mixture thereof; and the mirror image thereof.

A first preferred embodiment of the fifth embodiment consists of those compounds wherein f, and $R_2$ are as previously defined; $C_{13}$–$C_{14}$ is trans-vinylene; and $R_1$ is the moiety

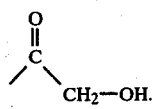

A second preferred embodiment of the fifth embodiment consists of those compounds wherein f, and $R_2$ are as previously defined; $C_{13}-C_{14}$ is trans-vinylene; and $R_1$ is the moiety

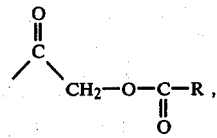

wherein R is as first previously defined.

A further preferred embodiment of the first preferred embodiment consists of those compounds wherein $R_1$, $C_{13}-C_{14}$ and f are as previously defined and $R_2$ is a moiety selected from the group consisting of

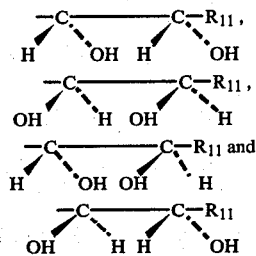

wherein $R_{11}$ is as previously defined.

A second further preferred embodiment of the first preferred embodiment consists of those compounds wherein $R_1$, $C_{13}-C_{14}$ and f are as previously defined; and $R_2$ is a moiety selected from the group consisting of

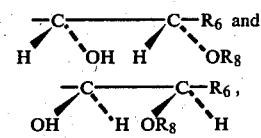

wherein $R_6$ and $R_8$ are as previously defined.

A first further preferred embodiment of the second preferred embodiment consists of those compounds wherein $R_1$, $C_{13}-C_{14}$ and f are as previously defined; and $R_2$ is a moiety selected from the group consisting of

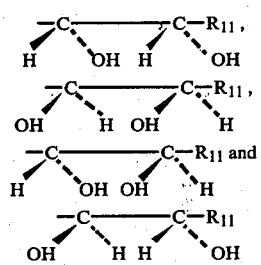

wherein $R_{11}$ is as previously defined.

A second further preferred embodiment of the second preferred embodiment consists of those compounds wherein $R_1$, $C_{13}-C_{14}$ and f are as previously defined; and $R_2$ is a moiety selected from the group consisting of

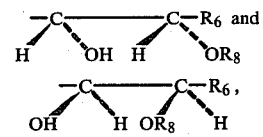

wherein $R_6$ and $R_8$ are as previously defined.

The sixth embodiment of the invention is represented by an optically active compound of the formula:

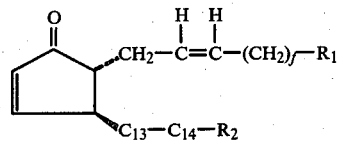

wherein f is an integer from 2 to 4, inclusive; $C_{13}-C_{14}$ is selected from the group consisting of ethylene and trans-vinylene; $R_1$ is a radical selected from the group consisting of

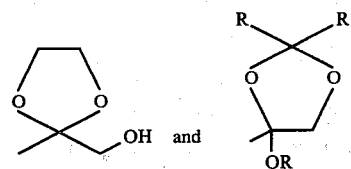

wherein R is selected from the group consisting of $C_1-C_4$ alkyl; $R_2$ is a moiety selected from the group consisting of

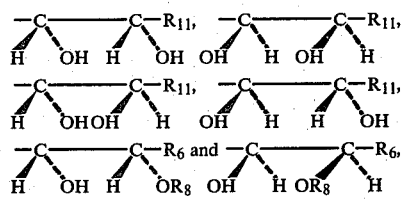

wherein $R_6$ is selected from the group consisting of $C_3-C_5$ alkyl, $R_8$ is selected from the group consisting of $C_1-C_2$ alkyl and $R_{11}$ is selected from the group consisting of $C_3-C_7$ alkyl; the racemic mixture thereof; and the mirror image thereof.

A first preferred embodiment of the sixth embodiment consists of those compounds wherein f, and $R_2$ are as previously defined; $C_{13}-C_{14}$ is trans-vinylene; and $R_1$ is the moiety

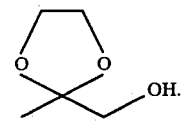

A second preferred embodiment of the sixth embodiment consists of those compounds wherein f, and $R_2$ are as previously defined; $C_{13}-C_{14}$ is trans-vinylene, and $R_1$ is the moiety

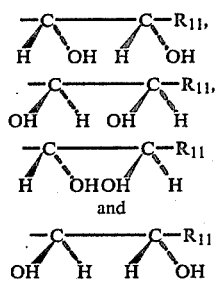

wherein R is as previously defined.

A first further preferred embodiment of the first preferred embodiment consists of those compounds wherein $R_1$ $C_{13}-C_{14}$ and f are as previously defined; and $R_2$ is a moiety selected from the group consisting of

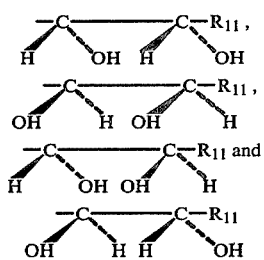

wherein $R_{11}$ is as previously defined.

A second further preferred embodiment of the first preferred embodiment consists of those compounds wherein $R_1$, $C_{13}-C_{14}$ and f are as previously defined; and $R_2$ is a moiety selected from the group consisting of

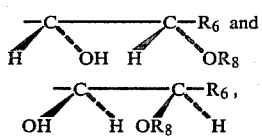

wherein $R_6$ and $R_8$ are as previously defined.

The seventh embodiment of the invention is represented by an optically active compound of the formula:

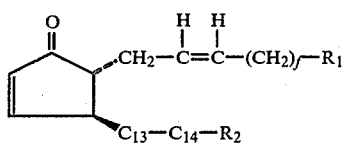

wherein f is an integer from 2 to 4, inclusive; $C_{13}-C_{14}$ is selected from the group consisting of ethylene and trans-vinylene; R is a radical selected from the group consisting of

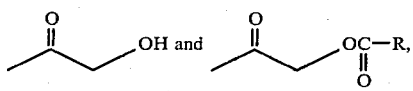

wherein R is selected from the group consisting of $C_1-C_4$ alkyl; $R_2$ is a moiety selected from the group consisting of

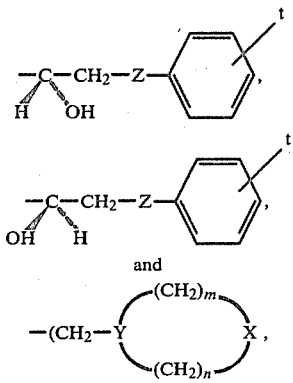

wherein x is a divalent radical selected from the group consisting of $$\diagdown_{C}\diagup^{H}_{R_5} \quad \text{and} \quad \diagdown_{C}\diagup^{R_5}_{H}$$

wherein $R_5$ is selected from the group consisting of $C_1-C_7$ alkyl, hydrogen and a phenoxy group optionally substituted from the group consisting of halogen, trifluoromethyl and $C_1-C_4$ alkyloxy, Y is a trivalent radical selected from the group consisting of $$\diagdown_{C}\diagup \qquad \diagdown_{C}\diagup$$
$$HO \quad CH_2- \quad \text{and} \quad HO \quad CH_2,$$

Z is a divalent radical selected from the group consisting of —O and —$CH_2$—, m is zero or an integer from 1 to 4, inclusive, n is zero or an integer from 1 to 4 inclusive, with the proviso that the sum of m and n has the value of 1 to 4, s is zero or the integer 1, t is selected from the group consisting of hydrogen, chloro, fluoro, dichloro, trifluoromethyl, methoxy and t-butyl; the racemic mixture thereof; and the mirror image thereof.

A first preferred embodiment of the seventh embodiment consists of those compounds wherein f, and $R_2$ are as previously defined; $C_{13}-C_{14}$ is trans-vinylene; and $R_1$ is the moiety $$\underset{\diagup}{\overset{O}{\underset{\|}{C}}}\diagdown_{CH_2-OH.}$$

A second preferred embodiment of the seventh embodiment consist of those compounds wherein f, and $R_2$ are as previously defined; $C_{13}-C_{14}$ is trans-vinylene; and $R_1$ is the moiety

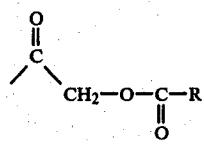

wherein R is as previously defined.

The eighth embodiment of the invention is represented by an optically active compound of the formula:

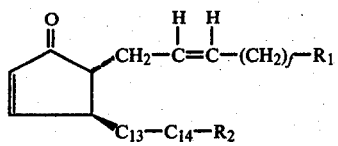

wherein f is an integer from 2 to 4, inclusive; $C_{13}$–$C_{14}$ is selected from the group consisting of ethylene and trans-vinylene; $R_1$ is a radical selected from the group consisting of

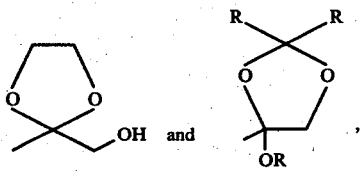

wherein R is selected from the group consisting of $C_1$–$C_4$ alkyl; $R_2$ is a moiety selected from the group consisting of

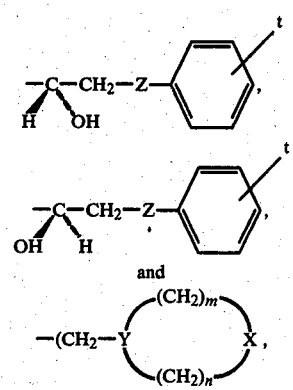

wherein X is a divalent radical selected from the group consisting of

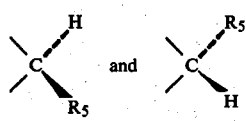

wherein $R_5$ is selected from the group consisting of $C_1$–$C_7$ alkyl, hydrogen and a phenoxy group optionally substituted from the group consisting of halogen, trifluoromethyl and $C_1$–$C_4$ alkyloxy, Y is a trivalent radical selected from the group consisting of

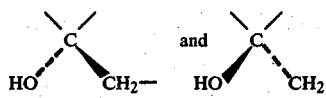

Z is a divalent radical selected from the group consisting of —O— and —$CH_2$—, m is zero or an integer from 1 to 4, inclusive, n is zero or an integer from 1 to 4, inclusive, with the proviso that the sum of m and n has the value of 1 to 4, s is zero or the integer 1, t is selected from the group consisting of hydrogen, chloro, fluoro, dichloro, trifluoromethyl, methoxy and t-butyl; the racemic mixture thereof; and the mirror image thereof.

A first preferred embodiment of the eight embodiment consists of those compounds wherein f, and $R_2$ are as previously defined; $C_{13}$–$C_{14}$ is trans-vinylene; and $R_1$ is the moiety

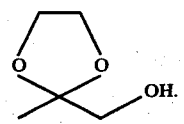

A second preferred embodiment of the eight embodiment consists of those compounds wherein f, and $R_2$ are as previously defined; $C_{13}$–$C_{14}$ is trans-vinylene; and $R_1$ is the moiety

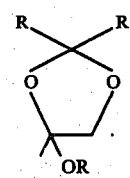

DESCRIPTION OF THE INVENTION

The compounds of this invention are administered in various ways for various purposes, e.g., intravenously, intramuscularly, subcutaneously, orally, intravaginally, rectally, bucally, sublingually, topically and in the form of sterile implants for prolonged action.

For intravenous injection or infusion, sterile aqueous isotonic suspensions are preferred. For subcutaneous or intramuscular injection, sterile suspensions of the compounds in aqueous or non-aqueous media are used. Tablets, capsules, and liquid preparations such as syrups, elixirs, and simple solutions, with the usual pharmaceutical carriers are used for oral or sublingual administration. For rectal or vaginal administration, suppositories prepared as known in the art are used. For tissue implants, a sterile tablet or silicone rubber capsule or other object containing or impregnated with the substance is used. On certain occasions it may be advantageous to administer the compounds of this invention as clathrate compounds with substances such as α-cyclodextrin.

The prostaglandins are a family of closely related compounds which have been obtained from various animal tissues and which stimulate smooth muscle, lower arterial blood pressure, antagonize epinephrine-induced mobilization of free fatty acids, and have other pharmacological and autopharmacological effects in mammals. See Bergstom, et al., J. Biol. Chem., 238, 3555 (1963) and Horton, Experientia, 21, 113 (1965) and references cited therein. All of the so called natural prostaglandins are derivatives of prostanoic acid:

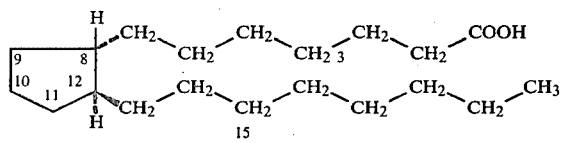

The hydrogen atoms attached to C-8 and C-12 are in transconfiguration. The natural prostaglandins represent only one of the possible optical isomers. The compounds of this invention include all possible optical isomers and racemates.

The configuration of substituents on the prostaglandin molecule are designed to be in the α-configuration if they lie beneath the plane of the molecule as drawn above and are designated with a --- bond. Those substituents which lie above the plane of the molecule as drawn above are designated β and are represented by a ▬ bond.

The compounds of this invention which have the structure as shown in formula (A) wherein T, Z, R$_3$, Y, m, n, s and X are as herein above defined are said to be in the same configuration as the natural prostaglandins with respect to the configurations at C$_8$, C$_{11}$ and C$_{12}$ and are designated by the prefix nat. The enantiomer, represented by formula (B) is said to be in the mirror image or ent configuration. A substituent at C$_{11}$ drawn with a dotted line (C$_{11}$--R$_3$) is said to have an α configuration; a solid line (C$_{11}$-R$_3$) indicates a β configuration. The configuration at Y and X will be expressed in terms of R and S as is understood in the art. For example, the compound represented by formula (C) is named nat-15S,16S-11α,15-dihydroxy-1-(hydroxymethyl)-1,9-dioxo-15,16-trimethylene-13-trans-prostene; its enantiomer (formula D) is named ent-15R,16R-11α,15-dihydroxy-1-(hydroxymethyl)-1,9-dioxo-15,16-trimethylene-13-trans-prostene. The racemate [1:1 mixture of (C) and (D)] is named nat-15S,16S-(and ent-15R,16R)11α,15-dihydroxy-1-(hydroxymethyl)-1,9-dioxo-15,16-trimethylene-13-trans-prostene. In a similar manner, the compounds represented by formulae (E) to (J) have the configurations shown below.

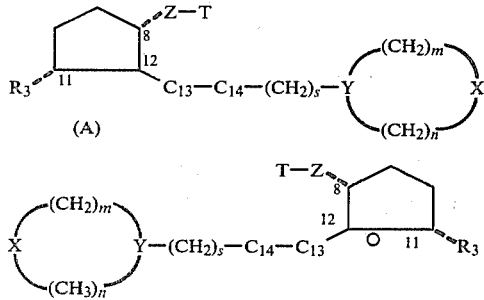

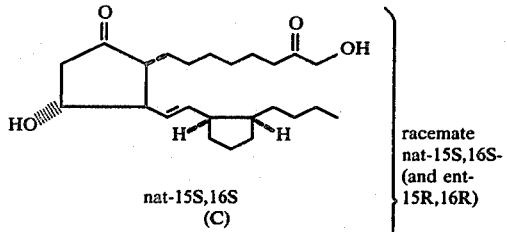

nat-15S,16S
(C)

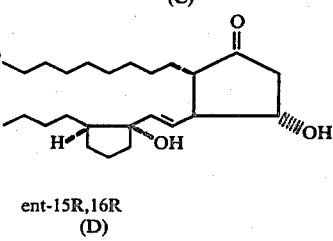

ent-15R,16R
(D)

} racemate nat-15S,16S- (and ent-15R,16R)

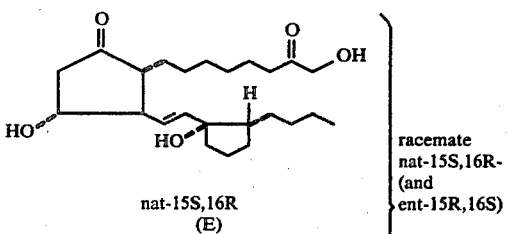

nat-15S,16R
(E)

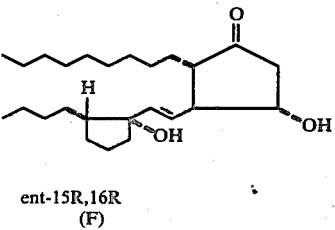

ent-15R,16R
(F)

} racemate nat-15S,16R- (and ent-15R,16S)

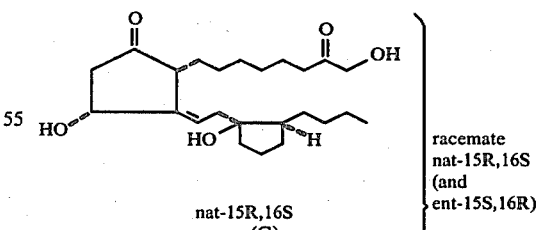

nat-15R,16S
(G)

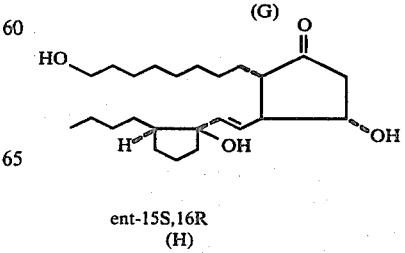

ent-15S,16R
(H)

} racemate nat-15R,16S (and ent-15S,16R)

21
-continued

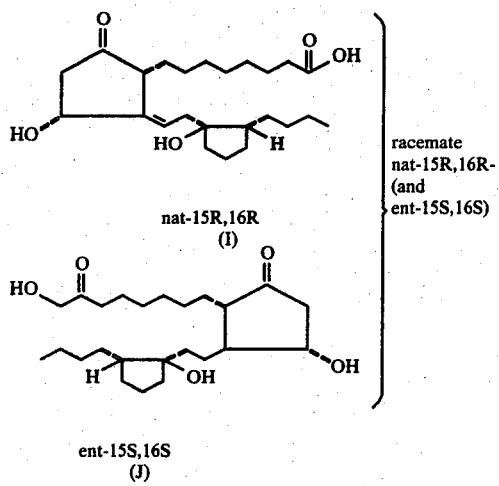

In each of the above formulae (C to J) the hydroxy group at $C_{11}$ is named "-11α-hydroxy".

The novel compounds of this invention can be prepared by a novel 1,4-conjugate-addition procedure involving treatment of the ether blocked cyclopentenone such as (129) or (111) with a lithio-cuprate reagent such as (117), (118), or (119) prepared as illustrated in Flowsheets A thru N.

The 1,4-conjugate-addition procedure is described hereinbelow in Flowsheet N. The preparation of the various requisite 1-iodo-trans-1-alkenyl or 1-tributyl-stannyl-trans-1-alkenyl derivative is illustrated in Flowsheets A-H and the novel and important methods of preparation of the 4-hydroxycyclopentenones embracing the 1-(hydroxymethyl)-1-oxo α chain is described in connection with Flowsheets I-M.

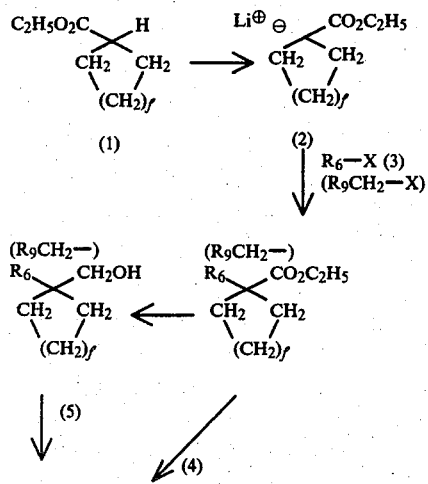

22
-continued
FLOWSHEET A wherein f' is one or two inclusive.

In accordance with the scheme as outlined hereinabove in Flowsheet A, carbethoxycyclobutane or carbethoxycyclopentane is converted to its enolate anion (2) by treatment with a strong base such as lithium cyclohexylisopropylamide, prepared from the corresponding amine and n-butyl lithium (hexane solution) in a solvent, such as anhydrous tetrahydrofuran, at very low temperatures, such as −78° C. The resulting enolate anion (2) is then alkylated with $R_6$3-X (3) to provide (4), the ester group of which is reduced to alcohol (5) by reaction with 2 equivalents of diisobutyl aluminum hydride, lithium aluminum hydride or the like. Oxidation of alcohol (5) with dipyridine chromium oxide complex ["Reagents for Organic Synthesis", L. F. Fieser and M. Fieser, John Wiley and Sons, Inc., New York, 4, 215 (1974)], prepared in situ in methylene chloride solution, provides the corresponding aldehyde (6), which can also be obtained directly from ester (4) by partial reduction with one equivalent of diisobutyl aluminum hydride at −78° C., but the former two-step procedure is preferable. Reaction of aldehyde (6) with lithium acetylide ethylene diamine complex provides the 3-hydroxy-1-alkyne (7), which is converted to its trimethylsilyl ether in the usual manner. The silylated derivative is then treated with disiamylborane (prepared in situ in tetrahydrofuran solution at ice bath temperatures from 2-methyl-2-butene, sodium borohydride and boron trifluoride ethereate) and then anhydrous trimethylamine oxide. The resulting solution and an iodine solution in tetrahydrofuran are then added simultaneously to an aqueous solution of sodium hydroxide to give the 1-iodo-3-trimethylsilyloxy-4,4-methylene-1-alkene (8). Also, the above sequences of reactions can be accomplished, as shown in Flowsheet A, using $R_9CH_2X$ where $R_9$ is a phenyl group.

FLOWSHEET B
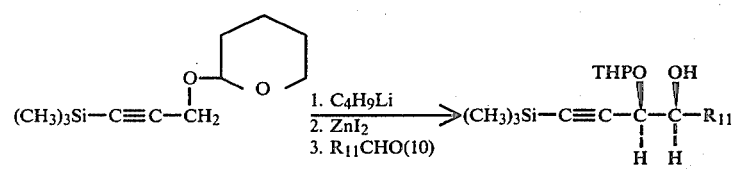
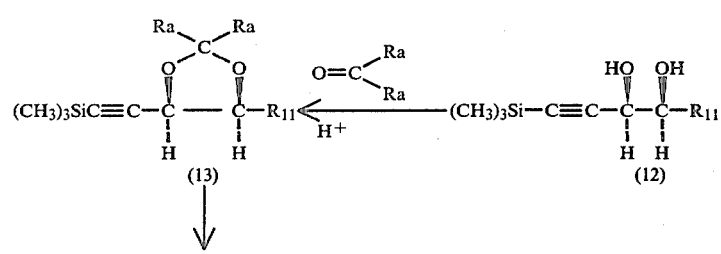
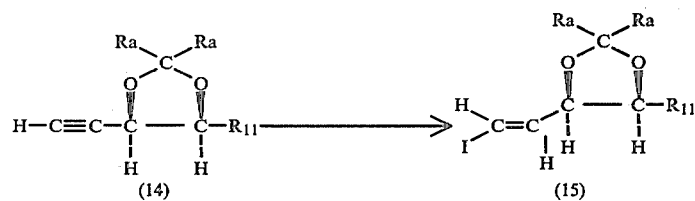
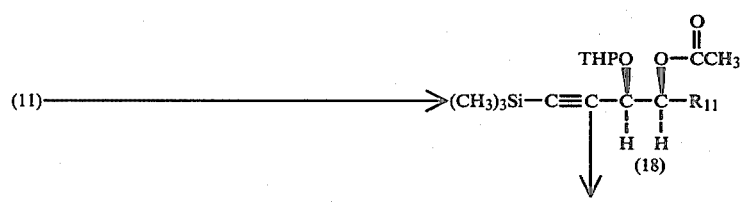
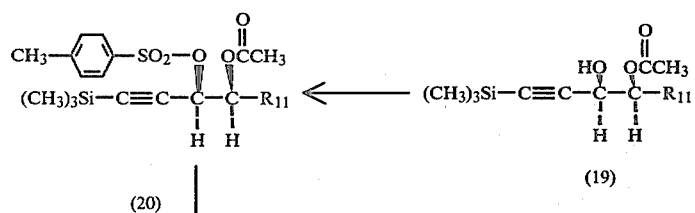
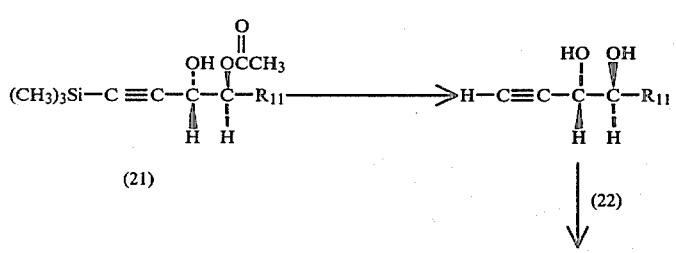

FLOWSHEET B

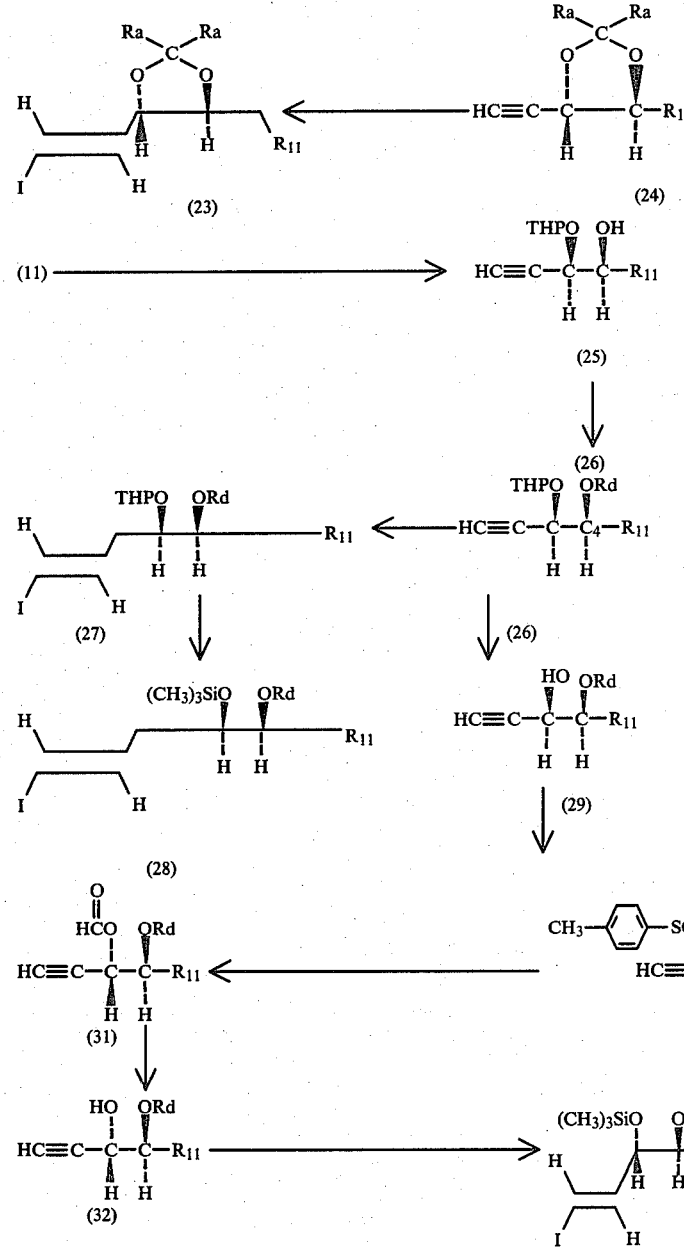

In accordance with the scheme as outlined hereinabove in Flowsheet B, 1-trimethylsilyl-3-tetrahydropyranyloxy-1-propyne (9) is treated with n-butyllithium at −78° C. and then with a freshly prepared solution of zinc iodide in anhydrous tetrahydrofuran, also at −78° C. Reaction of aldehyde (10) with the resulting reagent then provides the 4-hydroxy-3-tetrahydropyranyloxy-1-alkyne (11). This reaction procedes with great stereoselectivity and the product (11) is in the erythro configuration. [For additional information concerning this reaction see the examples which follow and F. Mercier, R. Epstein and S. Holland, Bull. Soc. Chim. France, 690 (1972).

The tetrahydropyranyl group in (11) is removed on weak acid treatment and the resulting erythro diol (12) can be reblocked by treating with an appropriate aldehyde or ketone

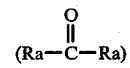

in the presence of strong acid catalyst in the usual way to give the ketal or acetal (13). Acetone is a useful ketone for this purpose and the product (13) is then a 3,4-isopropylidenedioxy-1-alkyne. It is also possible to utilize silyl blocking groups (introduced after removal of the 1-trimethylsilyl group) to ultimately give the vinyl iodides (16) or (17). Weak base treatment of (13), for example heating for about one hour in refluxing methanol with potassium carbonate, results in desilylation to give (14). The 1-alkene (14) is converted to the corresponding 1-iodo-trans-1-alkene (15) by treatment with disiamylborane (prepared in situ in tetrahydrofuran solution at ice bath temperatures form 2-methyl-2- butene, sodium borohydride and boron trifluoride etherate) and then anhydrous trimethylamine oxide. The resulting solution and an iodine solution in tetrahydrofuran are then added simultaneously to an aqueous solution of sodium hydroxide to give (15).

For the preparation of the threo derivatives, the 4-hydroxy-3-tetrahydropyranyloxy-1-alkyne (11) is acetylated to provide the corresponding 4-acetoxy-derivative (18). The tetrahydropyranyl group is preferentially hydrolized with weak acid to (19), which is then tosylated in the usual manner to afford the erythro-3-tosyloxy-4-acetoxy-1-alkyne (20). Solvolysis of (20) under essentially neutral conditions by heating in aqueous tetrahydrofuran in the presence of an insoluble acid-acceptor, such as calcium carbonate, results in inversion of $C_3$, furnishing the threo-3-hydroxy-4-acetoxy-1-alkyne (21), which is then deblocked with aqueous base to give the threo-3,4-diol (22). Diol (22) is converted to an acetal or ketal (23) [or silyl derivatives as in (16) or (17)] and thence to the 1-iodo-trans-1-alkene (16) as described hereinabove wherein Ra is lower alkyl ($C_1$ to $C_3$).

For the preparation of the 16-alkoxyprostanoic acids of this invention, the erythro-4-hydroxy-3-tetrahydropyranyloxy-1-alkyne (11) is desilylated by methanol-potassium carbonate treatment and the resulting (25) is alkylated to give the 4-alkoxy-3-tetrahydropyranyloxy-1-alkyne (26). A useful procedure for this last step involves treatment of (25) with a molar equivalent of sodium hydride to give the 4-alkoxide which is then alkylated with the appropriate alkylating agent, for example methyl iodide. The 4-alkoxy-1-alkyne (26) is then converted to the corresponding 1-iodo-trans-1-alkene (27) as described hereinabove for the preparation of (15). If desired the tetrahydropyranyl blocking group in (27) can be hydrolyzed (weak acid) and the resulting free 3-ol corresponding to (27) converted to the 3-trimethylsilyloxy derivative (28), all in the usual manner wherein Ra is lower alkyl ($C_1$ to $C_3$).

For the threo series, the tetrahydropyranyl group in erythro-4-alkoxy-1-alkyne (26) is cleaved and the resulting 3-hydroxy-4-alkoxy-1-alkyne (29) is tosylated to give the erythro-3-tosyloxy-4-alkoxy-1-alkyne (30). $Sn_2$ displacement reaction with (30) with reagents such as tetrahydroammonium formate results in inversion to the threo derivative (31) saponification of which provides threo-3-hydroxy-4-alkoxy-1-alkyne (32). Trimethylsilylation followed by the vinyl iodide conversion procedure described hereinabove furnishes the threo-1-iodo-1-alkene (33) wherein Rd is hydrogen or lower alkyl ($C_1$ to $C_3$).

The 15-alkyl and/or 16-alkyl derivatives of this invention can be prepared by substituting $$(CH_3)_3Si-C\equiv C-\overset{\overset{\displaystyle OTHP}{|}}{CH}-R'_5$$

for (9) and/or

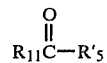

for (10) ($R'_5$=lower alkyl of 1 to 3 carbons) in Flowsheet B.

In accordance with the procedure as outlined in Flowsheet C, an aldehyde (34) is treated with propargylic magnesium halide to form the homopropargylic alcohol (35), which is converted to its trimethylsilyl ether in the usual manner. The silylated derivative is then treated with disiamylborane (prepared in situ in tetrahydrofuran solution at ice bath temperature from 2-methyl-2-butene, sodium borohydride and boron trifluoride etherate) and then anhydrous trimethylamine oxide. The resulting solution and an iodine solution in tetrahydrofuran are added simultaneously to a sodium hydroxide to give the 1-iodo-4-trimethylsilyloxy-trans-1-alkene (36), precursors for 16-hydroxy-prostaglandin.

The trimethylsilyl protecting group is removed with mild acid and the resulting vinyl iodide alcohol is oxidized with pyridinium chlorochromate to provide the 1-iodo-4-oxo-trans-1-alkene (37), which upon treatment with a Grignard reagent ($R_{13}MgX$) provides the 1-iodo-4-hydroxy-trans-1-alkene, which is silylated in the usual manner to provide the silyl ether (38) wherein $R'_{11}$ is lower alkyl ($C_3$ to $C_7$) or lower alkenyl group ($C_3$ to $C_5$) and $R_{13}$ is vinyl, cyclopropyl or ethyl.

FLOWSHEET C

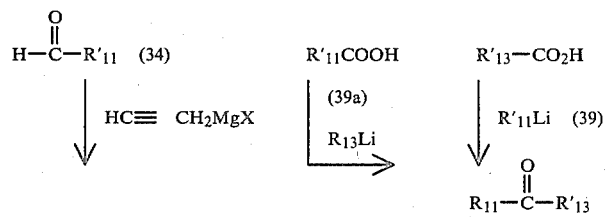

FLOWSHEET C

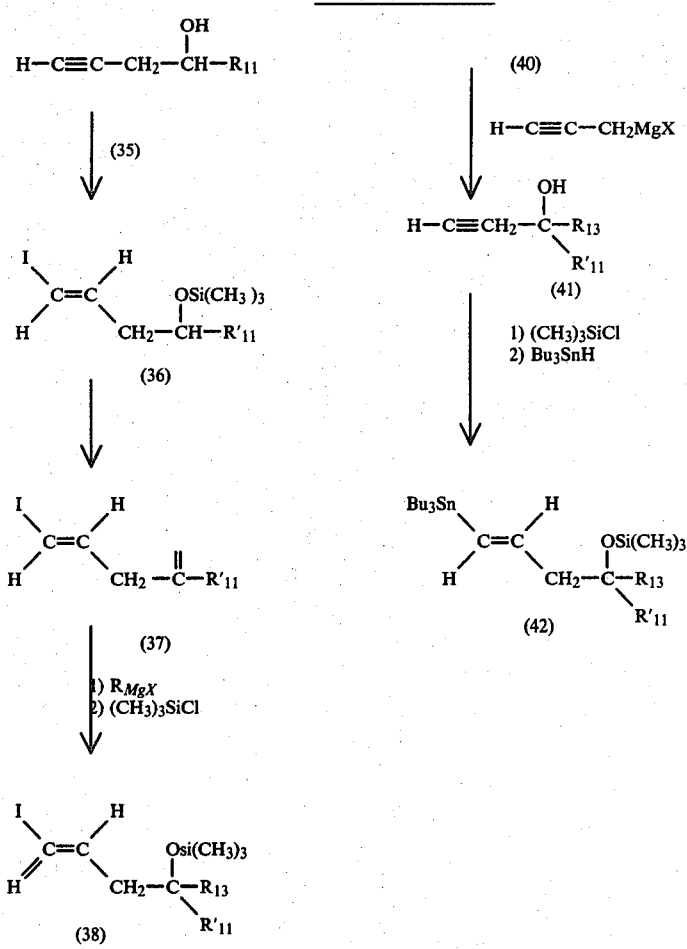

A more preferred method for the preparation of vinyllithium precursor is also described in Flowsheet C. Treatment of the requisite carboxylic acid (39a or 39) with the appropriate organolithium reagent ($R_{13}Li$ or $R'_{11}Li$ respectively), wherein $R'_{11}$ and $R_{13}$ are hereinabove defined, give the corresponding ketone (40) which upon treatment with propargylic magnesium halide provides the homopropargylic alcohol (41) which is converted to the trans vinylstannyl derivative by sequential treatment with chlorotrimethylsilane and tri-n-butyltin hydride. Treatment of the vinylstannyl reagent (42) with n-butyllithium at a temperature of $-10°$ C. to $-78°$ C. generates the corresponding vinyllithium reagent.

FLOWSHEET D

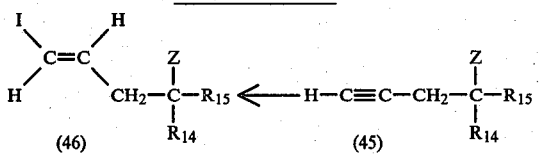

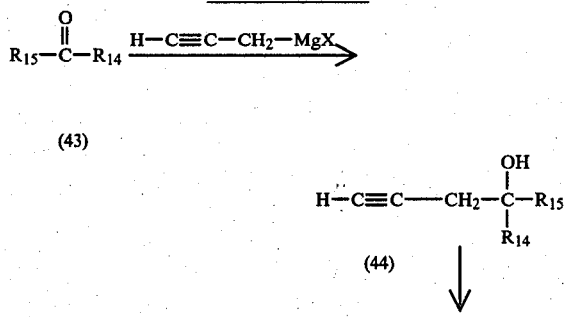

-continued
FLOWSHEET D

In accordance with Flowsheet D hereinabove, the precursors for other 16-hydroxy prostaglandins are prepared by treating an appropriate aldehyde or ketone (43) with a propargylic magnesium halide to yield the requisite homopropargylic alcohol (44). The alcohol is protected as a tritylether (45) (for secondary alcohols) or as a trimethylsilyl ether (45) (for tertiary alcohols). These ethers are then converted to the appropriate trans-vinyliodide (46) by treatment with disiamylborane generated in situ from 2-methyl-2-butene, sodium borohydride, and boron trifluoride, followed by treatment with trimethylamine oxide and then iodine and sodium hydroxide, wherein $R_{15}$ is hydrogen, methyl or ethyl; Z is $O\text{-}C(C_6H_5)_3$ when $R_{15}$ is hydrogen and Z is $O\text{-}Si(CH_3)_3$ when $R_{15}$ is methyl or ethyl; $R_{14}$ is selected from the group comprising lower alkyl ($C_3$ to $C_5$), lower 1-alkenyl ($C_3$ to $C_5$),

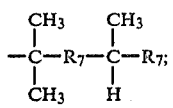

wherein R₇ is as described above with the proviso that when R₁₄ is

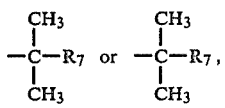

then R₁₅ must be hydrogen.

FLOWSHEET E

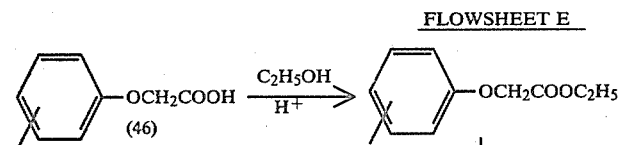

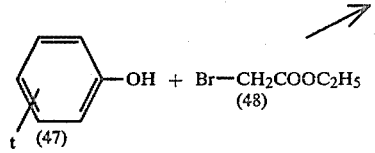

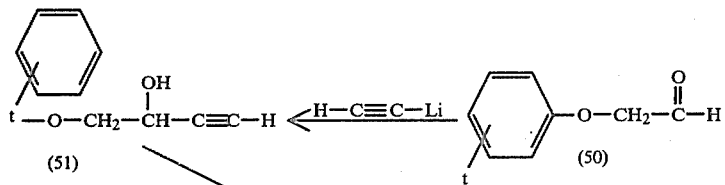

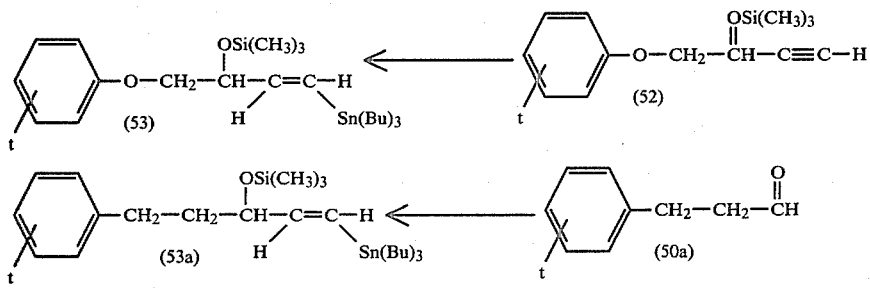

acetylene and aluminum trichloride to provide the vinylchloride (55) which upon treatment with sodium iodide furnishes the vinyliodide (56). Treatment of (56) with methylmagnesium halide followed by chlorotrimethylsilane gives the requisite protected vinyliodide (57)

FLOWSHEET F

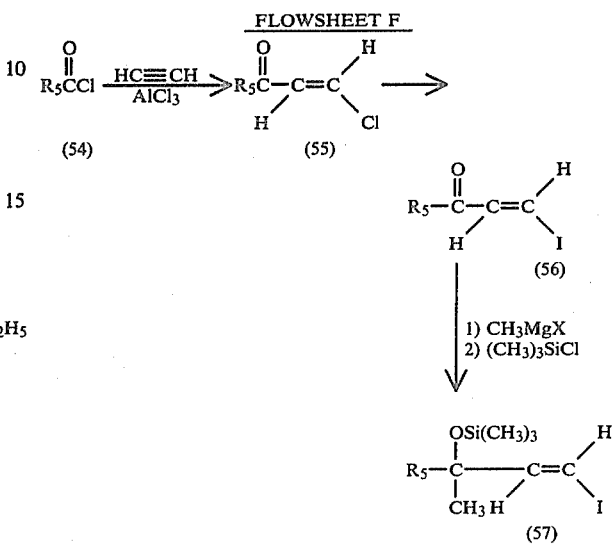

The preparation of the precursors for the synthesis of 16-aryloxy congeners is described in accordance with Flowsheet E hereinabove. The aryl esters (49) are prepared by esterifying the commercially available acids or by treatment of ethyl bromoacetate with the appropriate phenol. The ester (49) is carefully reduced to the aldehyde (50) which upon treatment with lithium acetylide provides the propargylic alcohol (51). Treatment of the alcohol (51) with chlorotrimethylsilane followed by tri-n-butyltin hydride furnishes the requisite vinylstannyl derivative (53). Similar treatment starting with substituted hydrocinnamaldehyde (50a) provides the respective vinylstannyl derivative (53a).

The preparation of the precursors for the synthesis of secondary 15-hydroxy congeners are described in the literature. The preparation of the precursor for 15-methyl-15-hydroxy is described in Flowsheet F hereinbelow. In accordance with Flowsheet F, an acid chloride, wherein R₅ is hereinabove defined, is treated with The precursors for the novel compounds of this invention which have a β chain represented by Formuler K

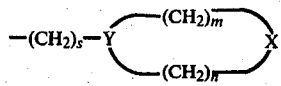

wherein s, y, m, n, and X are herein above defined is shown in Flowsheet G and Flowsheet H.

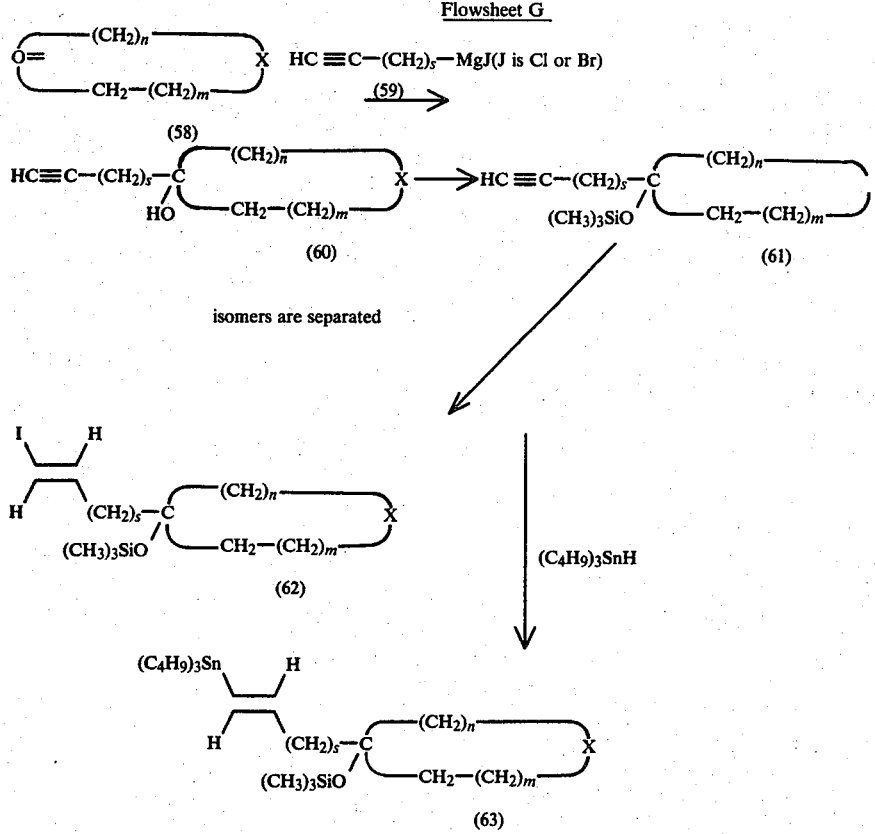

In accordance with the scheme as outlined hereinabove in Flowsheet G a ketone (58) is reacted with a Grignard reagent (59) such as acetylene magnesium chloride (59, s=0) or propargyl magnesium bromide (59, s=1) to give the acetylenic alcohols (60). In those cases where X is not —CH$_2$— two isomeric acetylenic alcohols are formed. These isomers can be separated by procedures well known to the art including fractional crystallization, fractional distillation and various chromatographic procedures. The individual isomers can then be carried through the remaining reactions outlined in Flowsheet G.

The acetylenic alcohol (60) is converted to its trimethylsilyl ether in the usual manner. The silylated derivative (61) is then treated with diisomaylborane (prepared in situ in tetrahydrofuran solution at ice bath temperatures from 2-methyl-2-butene, sodium borohydride and boron trifluoride ethereate) and then anhydrous trimethylamine oxide. The resulting solution and an iodine solution in tetrahydrofuran are then added simultaneously to an aqueous solution of sodium hydroxide to give the 1-iodo-3-trimethylsilyloxy-trans-1-alkene (62).

(63) in turn is readily prepared by the addition of tri-n-butyl tin hydride to the acetylene (61) in the presence of bisazoisobutyronitrile followed by vacuum distillation at a high enough temperature (about 170° C.) to isomerize any of the cis-vinyl tin compound to the trans-vinyl tin compound.

Certain of the ketones (67) of this invention are prepared as indicated in Flowsheet H below:

Flowsheet H

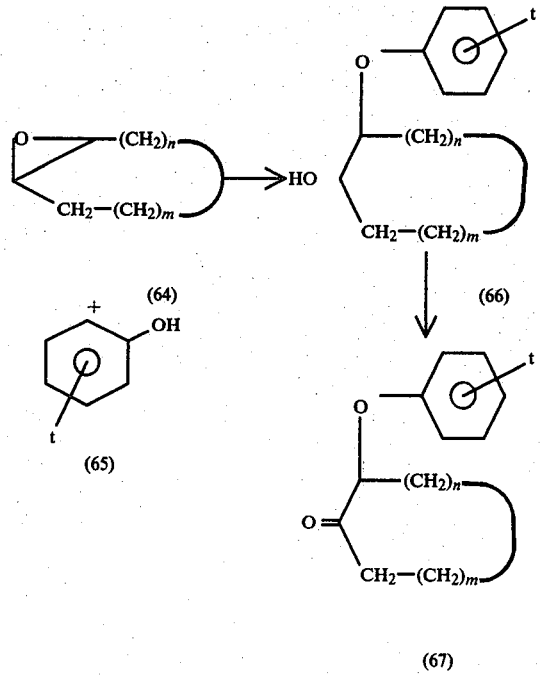

wherein n and m are as hereinabove defined and the moiety

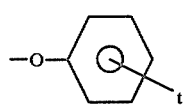

represents a phenoxy group which is optionally substituted with one or more halogen, trifluoromethyl, and lower alkoxy ($C_1$ to $C_4$) groups.

As indicated in Flowsheet H the reaction of an epoxide (64) with a substituted or unsubstituted phenol (65) in the presence of a catalytic amount of aqueous sodium hydroxide and a phase transfer catalyst such as methyl tricapryly ammonium chloride and the like at 70°–80° C. gives the phenoxy substituted alcohol (66) which in turn is oxidized with an oxidizing reagent such as pyridinium chlorochromate in methylene chloride to give the phenoxy substituted ketone (67). This ketone (67) is then carried through the reactions shown in Flowsheet G above.

The other ketones (58) used in this invention are known in the literature or can be made by procedures well known to the art [G. Lardelli, U. Lamberti, W. T. Walles and A. P. de Jonge, Rec. Trav. Chem. Pays-Bas, 86 481 (1967); Ng. Ph. Buu-Hoi, T. B. Loc and Ng. Dat Xuong., Bull. Soc. Chem. France, 174 (1958); and G. H. Posner, *Organic Reactions*, 19, 1 (1972)].

The preparation of the cyclopentenones of this invention containing the hydroxyketone feature (68) wherein Z is hereinabove defined and $R_3'$ is hydrogen or a hydroxy group can be accomplished in several ways one of which involves the conversion of the corresponding cyclopentenone containing a carboxylate function (69) to the respective hydroxyketone analog (68).

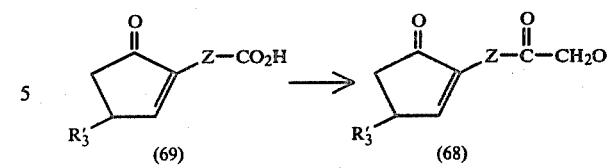

Most of the cyclopentenone carboxylic acids (69) required for the purposes of this invention have been described in the literature or can be prepared by procedures quite analogous to those already described. Appropriate references are provided in the examples which follow. The synthesis of certain non-reference requisite cyclopentenone carboxylic acids (69) is also described herein.

The preparation of the requisite 4-hydroxy-thiacyclopentenones (75) is described in Flowsheet I. In accordance with Flowsheet I which is hereinbelow described, treatment of 2-furyllithium (70) with a ω-chloroaldehyde (71) provides the chloroalcohol (72). Treatment of the chloroalcohol (72) with ethylmercaptoacetate furnishes the hydroxyester (73) which upon hydrolysis with sodium formate/formic acid provides the 3-hydroxy-cyclopentenone (74). Treatment of the cyclopentenone (74) with sulfuric acid provides the required 4-hydroxy-cyclopentenone (75).

FLOWSHEET I

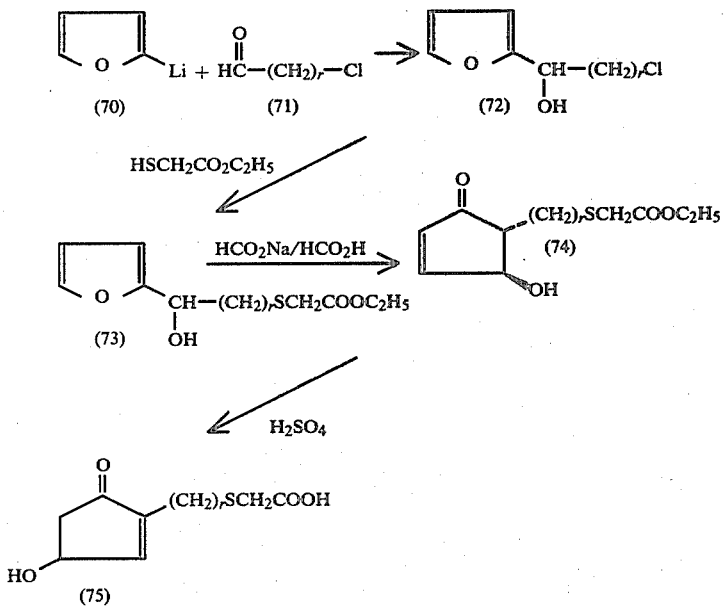

The conversion of the cyclopentenone carboxylic acid (69) to the respective hydroxyketone analogs (68) and the protection of these compounds for a conjugate addition reaction is described hereinbelow in Flowsheets J and K.

For the preparation of the cyclopentenones of the type (79) wherein Z is hereinabove defined, the carboxylic acid (76) is converted to the acid chloride (77) by first forming the sodium salt with sodium hydride in tetrahydrofuran (THF) and then reacting the resulting suspension with oxalyl chloride in the presence of a catalytic amount of dimmethylformamide (DMF). The resulting acid chloride (77), dissolved in ether, is then added dropwise to an ether solution containing two to three equivalents of diazomethane to produce the diazoketone (78). The diazoketone can by hydrolized to the hydroxy ketone (79) by refluxing an etheral solution in the presence of a dilute aqueous solution of sulfuric acid.

Alternatively, the acid chloride (77) can be heated with two equivalents of 1,1,2-tris-trimethylsilyloxyethylene at 90–100° for 2 to 4 hours to produce compound (81). Compound (81) can be readily hydrolized and decarboxylated to give the hydroxyketone (79) by treatment with dilute hydrochloric acid in tetrahydrofuran (THF).

Protection of the hydroxy ketone function of 79, suitable for a conjugate addition reaction, can be accomplished in two ways. Ketalization of 79 with ethylene glycol is accomplished by refluxing a benzene or toluene solution of 79 and ethylene glycol into a Dean-Stark trap. The resulting ketal (82) is then treated with trimethylsilylchloride (TMSCl) and imidazole in dimethylformamide (DMF) to give 83 which is suitablely protected for a conjugate addition reaction.

Alternatively 79 can be protected by the reaction with a mixture of 2-methoxy-1-propene (84) and 2,2-dimethoxypropane (85) in benzene in the presence of an acid catalyst such as p-toluenesulfonic acid to give the ketal 86 which is suitablely protected for a conjugate addition reaction.

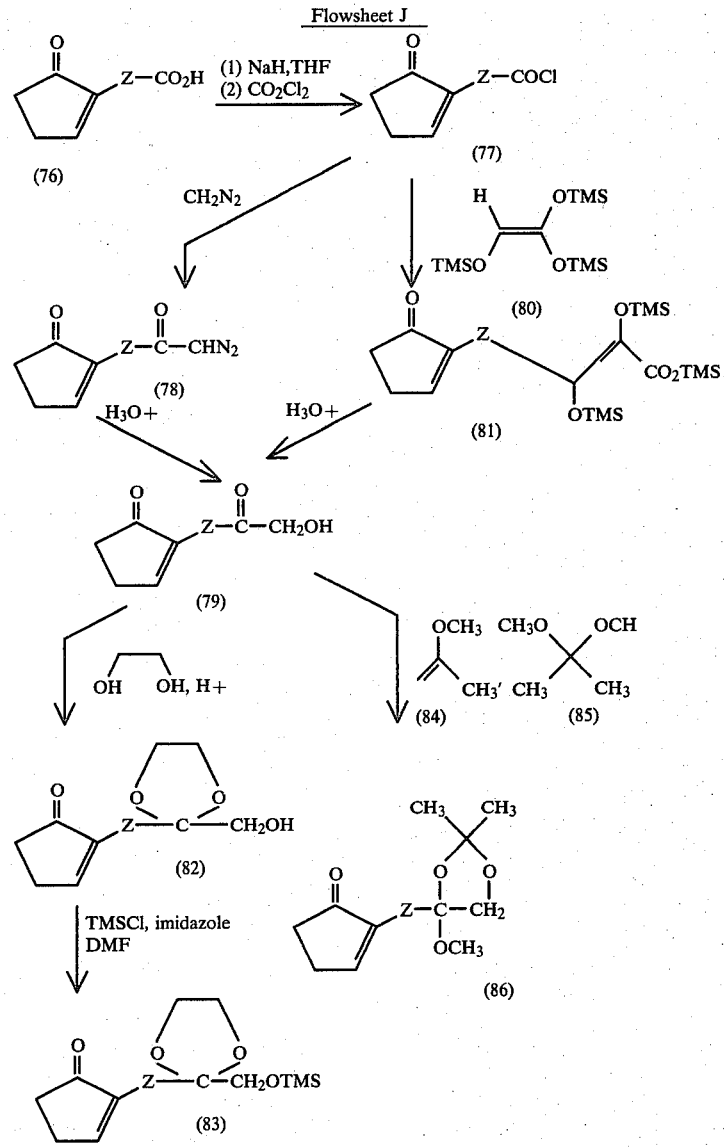

Flowsheet J

The preparation of the 4-hydroxycyclopentenones of this invention (92) wherein Z is hereinabove defined is outlined in Flowsheet K below. The reaction of the hydroxy acid (87) with at least two equivalents of dimethyl-t-butyl-silylchloride in the presence of imidazole in dimethylformamide at 30–40° C. gives the bis-dimethyl-t-butylsilated compound 88. The carboxylate dimethyl-t-butylsilyl group can be selectively removed by treatment with acetic acid, tetrahydrofuran and water (4:2:1) to give the carboxylic acid (89). The acid chloride (90) is prepared by first treating the acid (89) with sodium hydride in tetrahydrofuran to give the sodium salt. The resulting suspension of the sodium salt is then treated with oxalyl chloride in the presence of a catalytic amount of dimethylformamide. Alternatively the acid chloride (90) can be prepared directly by the reaction of the acid (89) or the dimethyl-t-butylsilyl ester (88) with oxalyl chloride in tetrahydrofuran in the presence of a catalytic amount of dimethylformamide at 0° C. The slow addition of an etheral solution of the as p-toluenesulfonic acid to give the bis-ketal (94) which is suitably produced for a conjugate addition reaction.

Flowsheet K

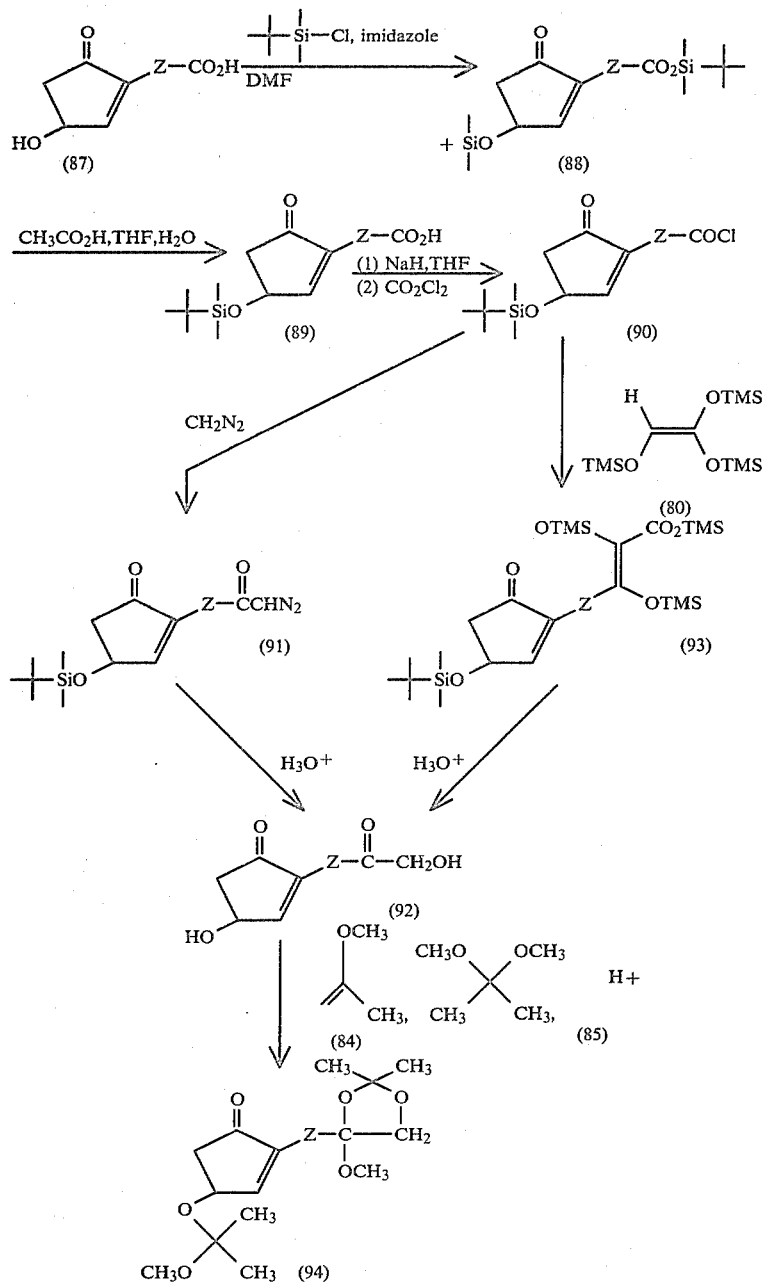

acid chloride (90) to an etheral solution of two to three equivalents of diazomethane gives the diazoketone (91) which on acid hydrolysis gives the 4-hydroxy cyclopentenone (92) containing the hydroxyketone function.

Alternatively the acid chloride (90) can be heated with at least two equivalents of 1,1,2-tris-trimethyl-silylethylene at 90–120° C. in the absence of a solvent to give compound (93) which is readily hydrolized and decarboxylated to give the 4- hydroxycyclopentenone (92) containing the hydroxyketone feature. Protecting of 92 can be accomplished by treatment with an excess of a mixture of 2-methoxy-1-propene (84) and 2,2-dimethoxypropane (85) in benzene with an acid catalyst such Another preparation of the 4-hydroxycyclopentenones of this invention which contain a cis double bond in the potential α chain (109) is shown hereinbelow in Flowsheet L wherein g is as hereinabove defined. As illustrated in Flowsheet L there are three methods available to prepare the important intermediate 98. The reaction of the ω-bromo carboxylic acid (95) with oxalyl chloride in an inert solvent such as benzene gives the acid chloride (96). Addition of the acid chloride (96) in ether to an etheral solution of diazomethane (2 to 3 equivalents) yields the diazoketone (97) which can be hydrolized in a two phase system consisting of ether and dilute sulfuric acid to the hydroxyketone (98). Alternatively the acid chloride (96) can be treated with an excess of 1,1,2-tris-trimethylsilyloxyethylene in the presence of a catalytic amount of stannic chloride in the absence of solvent to give compound (99) which can readily be hydrolized and decarboxylated to the desired hydroxyketone (98) using dilute hydrochloric acid in tetrahydrofuran. An alternate method to prepare (98) involves the reaction of the bromoolefin (100) with aqueous n-bromosuccinimide (NBS) in the presence of a catalytic amount of acetic acid to give a mixture of bromohydrins (101 and 102). Oxidation of the mixture of bromohydrins with an oxidizing agent such as pyridinium chlorochromate in methylene chloride gives a mixture of bromoketone (103) and bromoaldehyde (104). Refluxing this mixture with sodium formate in methanol then gives the desired intermediate (98). Protection of the ketone function of 98 is accomplished using ethylene glycol in refluxing toluene using a catalytic amount of p-toluenesulfonic acid. The ketal (103) is then reacted with dimethyl-t-butylsilylchloride and imidazole in dimethylformamide to give the fully protected compound 104. The phosphonium salt (105) is obtained by refluxing a solution of 104 and triphenylphosphine in acetonitrile. Treatment of the phosphonium salt (105) with sodium methylsulfinylmethide in dimethylsulfoxide generates a phosphonium yield which on reaction with aldehyde 106 gives 107. Refluxing a water-dioxane solution of 107 in the presence of a phosphate buffer (PH 5 to 6) gives the cyclopentenone (108). Treatment of 108 with chloral and triethylamine in ether gives (109) which on hydrolysis in a mixture of tetrahydrofuran and dilute hydrochloric acid at 50–70° C. then gives the desired 4-hydroxycyclopentenone (110) which can be protected as described hereinabove in Flowsheet K.

Treatment of 109 with trimethylsilylchloride and imidazole in DMF gives 111 which is also suitably protected for a conjugate addition reaction.

Flowsheet L

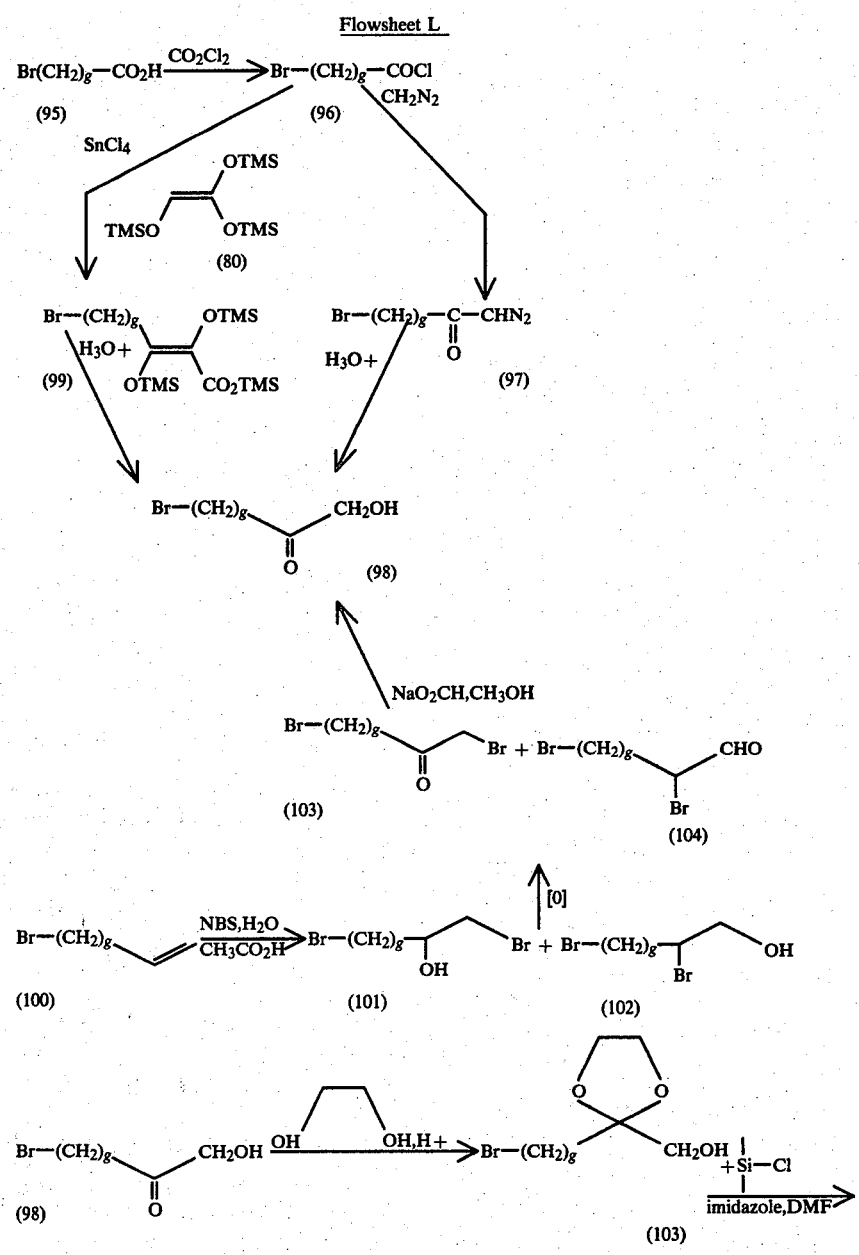

Flowsheet L

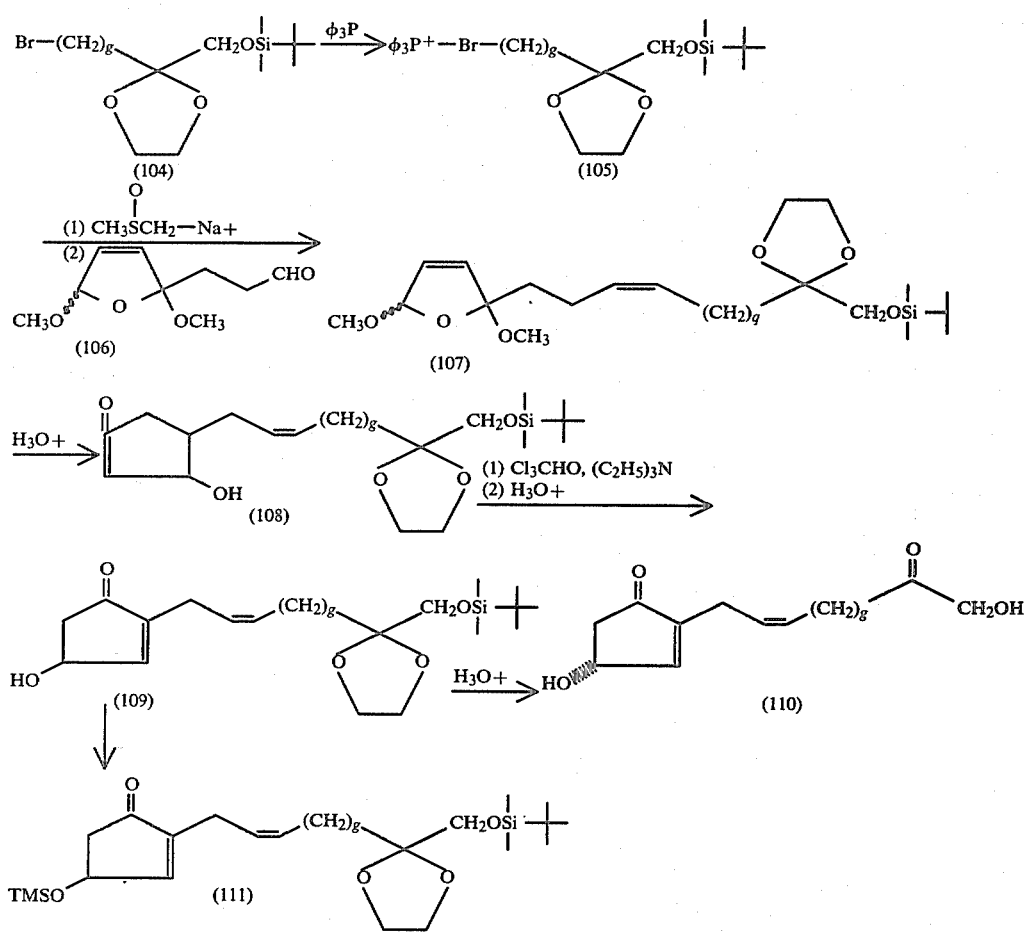

The reagent 1,1,2-tris-trimethylsilyloxyethylene (80) and its use for the conversion of acid chlorides to hydroxyketone (for example 96 to 98 and 90 to 92) are claimed in this invention. The reagent preparation is described hereinbelow in Flowsheet M. The reaction of glycolic acid with 1,1,1,-3,3,3-hexamethyldisilazane and trimethylsilylchloride in pyridine gives bis-trimethylsilated glycolic acid (113). Addition of (113) to a tetrahydrofuran solution of one equivalent of lithium 1,1,1,3,3,3-hexamethyldisilazane amide at −78° C. generates a lithium enolate which is trapped with trimethylsilylchloride to produce the desired reagent (80).

Flowsheet M

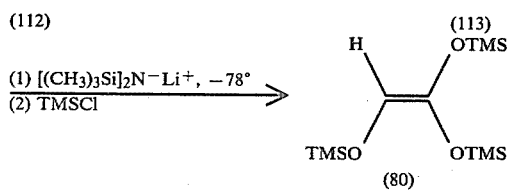

The preparation of the prostaglandin congeners of this invention are described hereinbelow in Flowsheet N wherein Z is as hereinabove defined; $R_3''$ is hydrogen, 2-methoxypropyl-2-oxy ($-OC(CH_3)_2OCH_3$) or trimethylsilyloxy; $R_3'''$ is hydrogen or hydroxy; T' is the radical

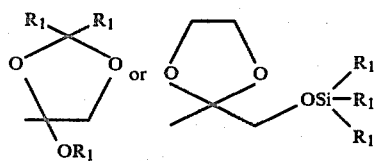

wherein $R_1$ is as hereinabove defined. R' is selected from the group consisting of:

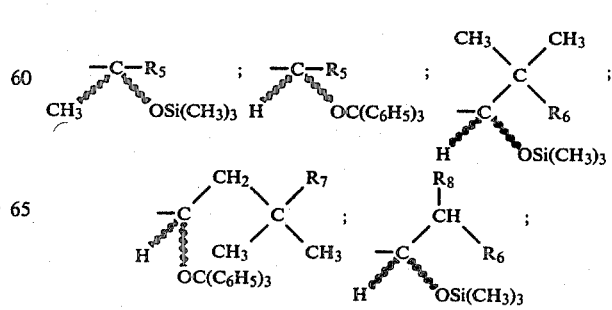

-continued

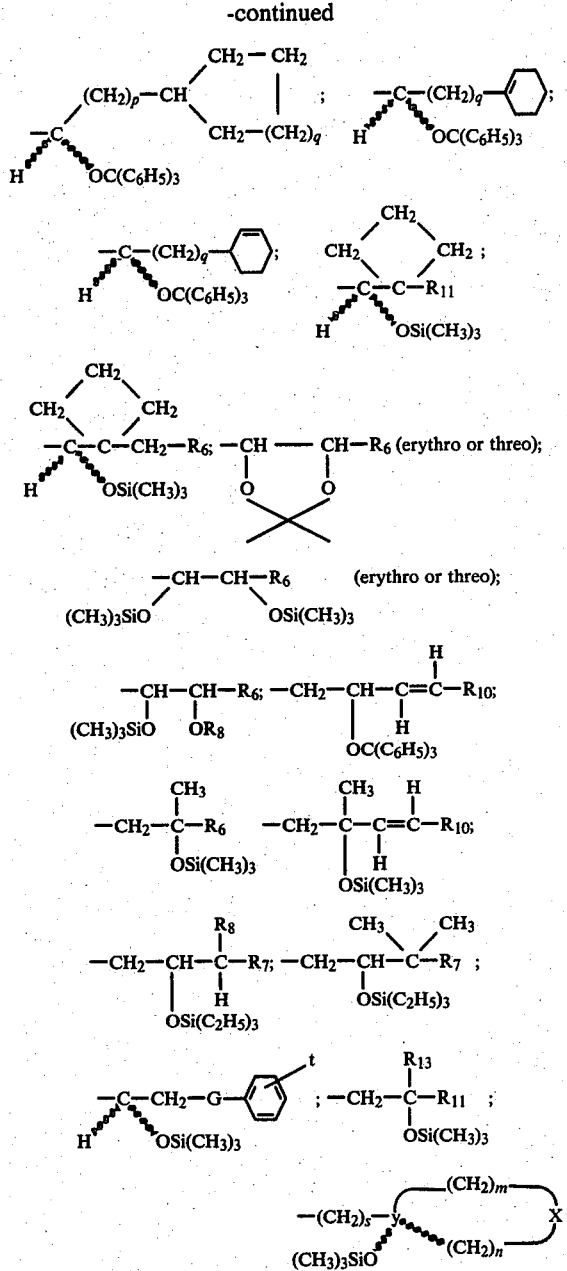

wherein $R_5$, $R_6$, $R_7$, $R_8$, $R_9$, $R_{10}$, $R_{11}$, $R_{13}$, G, p, q, t, s, m, n, y, and X are as hereinabove defined.

In accodance with Flowsheet N the vinyliodide (114) is treated with either one equivalent of n-butyllithium or 2 equivalents of t-butyllithium at low temperature, preferably $-30°$ to $-70°$ C. in an inert solvent, eg. hexane, ether or toluene to provide the trans alkenyl-lithium reagent (116).

Alternatively, the vinyllithium reagent (116) can be prepared by treatment of a vinylstannyl derivative such as (115) with n-butyllithium at $-10°$ to $-78°$ C. in ether or THF.

For the preparation of the asymmetrical lithio cuprate (117) or the like, a solution of one molar equivalent of copper (I)-1-alkyne, preferably copper (I)-1-pentyne in anhydrous hexamethylphosphorous triamide preferably one to five molar equivalents and anhydrous ether is added to one molar equivalent of the aforementioned vinyllithium solution cooled to about $-78°$ C. After about one hour at this temperature, a molar equivalent of the requisite cyclopentenone (120) is added. After several hours at $-78°$ C. to $-20°$ C. the reaction mixture is quenched with aqueous ammonium chloride solution and the blocked product (121) is isolated in the usual manner.

It is also possible to effect conjugate 1,4-addition with the asymmetrical lithio cuprate (119) derived from vinyllithium (116) and cuprous thiophenoxide. A solution of vinyllithium (116) in ether at $-78°$ C. is reacted with an equimolar amount of a reagent prepared by admixture, in ether at a temperature of $0°$ C. to $-78°$ C., of equimolar amounts of cuprous thiophenoxide and copper (I) iodide tributylphosphonium complex. After about 30 minutes at this temperature, the lithio cuprate (119) is treated with the requisite cyclopentenone (II) as described hereinabove for the conjugate addition with 1-alkynyl lithio cuprate (117).

For the preparation of the symmetrical lithio cuprate (118) one molar equivalent of copper (I) iodide tributylphosphine complex, dissolved in anhydrous ether, is added at about $-78°$ C. to two molar equivalents of the aforementioned vinyl lithium (116) solution in hexanes, cooled to $-78°$ C. After about one hour at this temperature, the lithio cuprate (118) is treated with the requisite cyclopentenone (120) as described hereinabove for the conjugate addition with the 1-alkynyl lithio cupate (117).

The procedures for conjugate addition involving organocopper reagents are well known in the art, see for example, C. J. Sih, et al., J. A. C. S., 97, 865 (1975).

All available evidence leads us to believe that the $-CH=CH-R'_2$ function introduced by the cuprate process occupies a position trans to the 11-oxy function. Similarly, we are led to the conclusion that in the product (121) the two side-chains attached to $C_8$ and $C_{12}$ are trans to each other. However, we are not certain of this configurational relationship in the product as it is obtained directly from the cuprate process. These products may have the side-chains in a trans- or cis-relationship or they may be a mixture containing both the trans- and cis-isomers. This is indicated in the nomenclature of the compounds involved by the designation 8ε. In order to ensure a trans-relationship in (121) these products can be submitted to conditions known in the literature to equilibrate the cis-8-iso-PGE$_1$ to a mixture containing about 90% of the trans product. These conditions involve treatment with potassium acetate in aqueous methanol for 96 hours at room temperature.

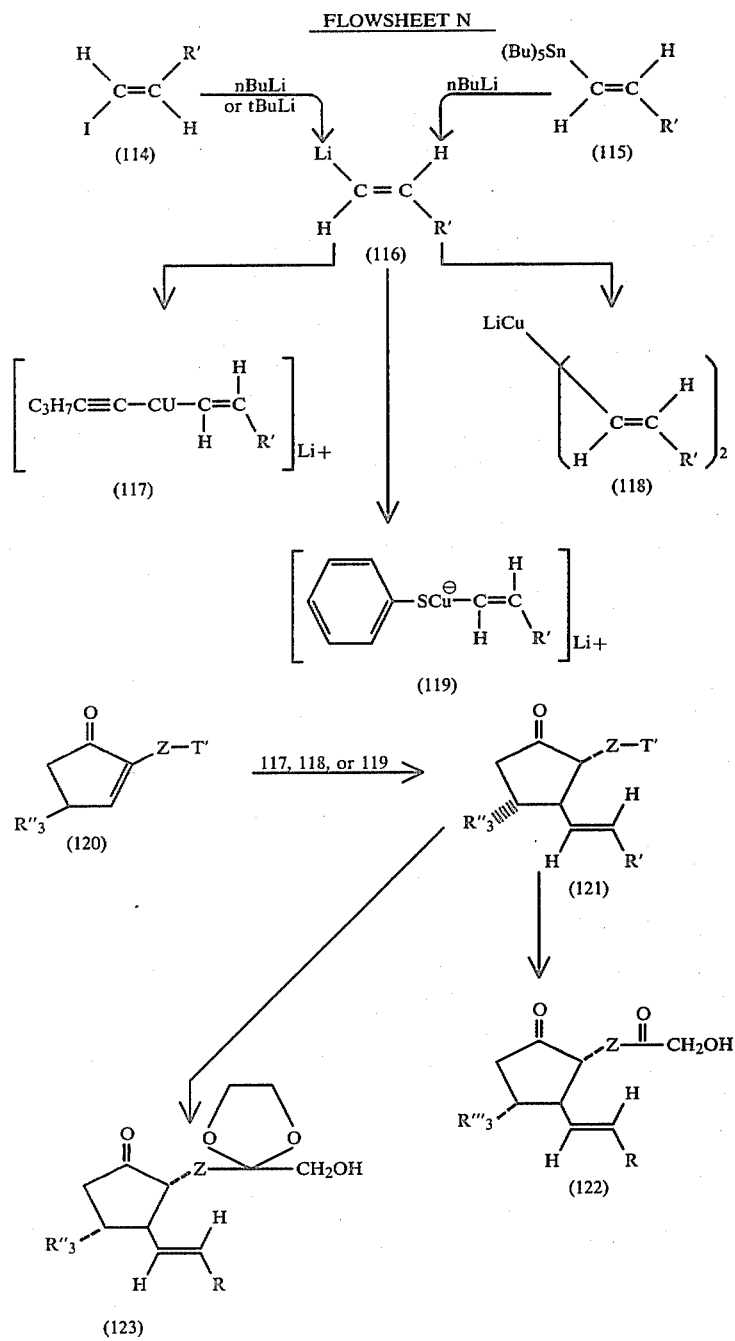

FLOWSHEET N

When T' is

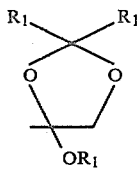

removal of the blocking groups from (121) to give the prostaglandin congener (122) is accomplished by treatment of (121) with a mixture of acetic acid, tetrahydrofuran and water (4:2:1) at 25° to 55° C.

When T' is

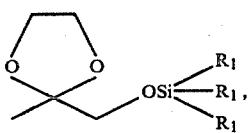

(121) can be partially deblocked to give the ketal (123) by treatment of (121) with 0.6N hydrochloric acid in tetrahydrofuran at room temperature for 4 to 7 hours.

In certain cases it is possible to convert the carboxylic acid function of a prostaglandin congener into a terminal hydroxymethyl ketone function as shown in Flowsheet O hereinbelow wherein Z, $C_{13}$–$C_{14}$, and R is as hereinabove defined. Treatment of a prostaglandin congener (124) in which the hydroxy groups of the β chain are protected with a suitable group such as acetate or a dimethyl-t-butylsilyl ether with oxalyl chloride in benzene for 2 to 5 hours furnishes the acid chloride (125). Addition of the acid chloride (125), dissolved in ether, to an ether solution of at least three equivalents of diazomethane gives the diazoketone (126). Hydrolysis of the diazoketone using aqueous sulfuric acid and tetrahydrofuran at 55° C. gives the hydroxymethyl ketone analog (127). The acetate protecting group can be removed by refluxing with acidified methanol. The dimethyl-t-butylsilyl ether protecting group can be removed by treatment with aqueous hydrochloric acid in tetrahydrofuran at 25 to 60° C.

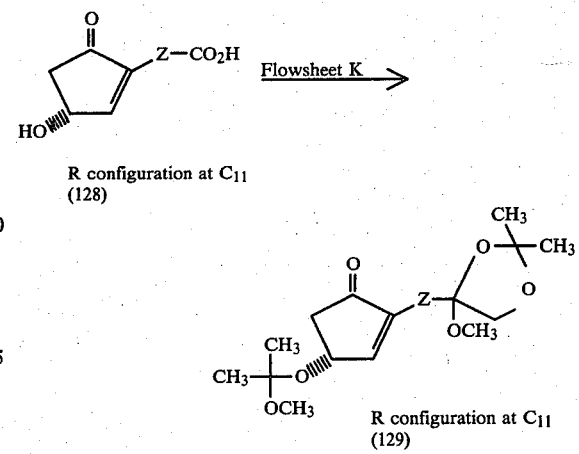

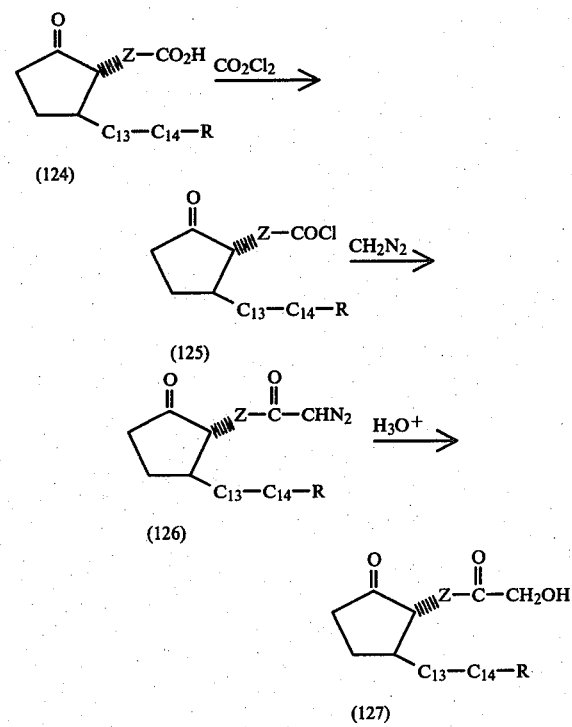

When the compounds of this invention are prepared from racemic starting compounds two racemates are obtained. In appropriate instances these racemates can be separated from each other by careful application of the usual chromatographic procedures. In the more difficult instances it may be necessary to apply high pressure liquid chromatography including recycling techniques. [See G. Fallick, American Laboratory, 19-27 (August, 1973) as well as references cited therein. Additional information concerning high speed liquid chromatography and the instruments necessary for its application is available from Waters Associate, Inc., 60 Maple Street, Milford, Mass.]

It is also possible to prepare the compounds of this invention in their optically active forms by the conversion of the optically active 4-hydroxycyclopent-2-en-1-one carboxylic acids (128) to the optically active protected hydroxy ketone analog (129) using the methods outlined hereinabove in Flowsheet K.

Conjugate addition of the vinyl cuprates to (129) followed by deblocking as described hereinabove in Flowsheet N then gives the compounds of this invention in their optically active forms. Although in some cases two diastereoisomers will be formed, each optically active, they can be separated by chromatographic procedures as described hereinabove.

The preparation of optically active 4-hydroxy-cyclopent-2-en-1-ones such as (128) is described hereinbelow.

The 4-hydroxycyclopentenone racemates may be resolved into their component enantiomers (130) and (131) by derivatizing the ketone function with a reagent having an optically active center. The resulting diastereomeric mixture can then be separated by fractional crystallization, or by chromatography, or by high speed liquid chromatography involving, if necessary, recycling techniques. Among the useful optically active ketone derivatizing reagents are l-α-aminoxy-γ-methylpentanoic acid hydrochloride [to give (132)], (R)-2-aminoxy-3,3-dimethylbutyric acid hydrochloride, and 4-α-methylbenzyl semicarbazide. After separation of the diastereomeric derivatives, reconstitution of the keto function provides the individual 4-hydroxycyclopentenone enantiomers (130) and (131). A useful procedure for the resolution of a 4-hydroxycyclopentenone racemate via an oxime such as (132) is described in the art [R. Pappo, P. Collins and C. Jung, Tetrahedron Letters, 943 (1973)].

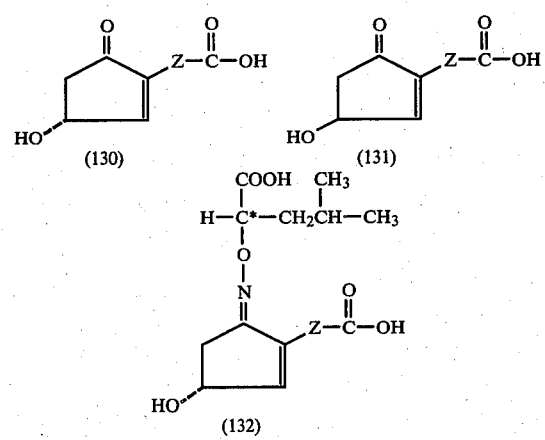

An alternate procedure for the preparation of the 4(R)-hydroxycyclopentenone enantiomers such as (130)

involves as a key step the selective microbiological or chemical reduction of trione (133) to the 4(R)-hydroxycyclopentanedione (134). A wide variety of microorganisms are capable of accomplishing this asymmetric reduction, one of the most useful being *Dipodascus unincleatus*. This step also can be achieved chemically by catalytic hydrogenation in the usual manner (for example, under about one atmosphere of hydrogen in methanol) using a soluble rhodium catalyst with chiral phosphine ligands, such as (1,5-cyclooctadiene)-bis-(o-anisylcyclohexylmethylphosphine)rhodium (I) tetrafluoroborate in the presence of one equivalent of organic base, such as triethylamine.

Conversion of hydroxycyclopentanedione (134) to an enol ether or enol ester, (135, E=alkyl, preferably isopropyl; aroyl such as benzoyl; or arylsulfonyl such as 2-mesitylenesulfonyl), is accomplished by treatment, for example, with isopropyl iodide and a base such as potassium carbonate in refluxing acetone for from 15 to 20 hours, or with a base such as triethylamine and 0.95 equivalents of benzoyl chloride or a slight excess of 2-mesitylenesulfonyl chloride, in a non-prototropic solvent at a temperature of about $-10°$ to $-15°$ C. Reduction of (135) with excess sodium bis(2-methoxyethoxy)aluminum hydride in a solvent such as tetrahydrofuran or toluene at low temperatures, such as $--60°$ to $-78°$ C., followed by mild acid hydrolysis (representative conditions: aqueous dilute hydrochloric acid, pH 2.5; or oxalic acid, sodium oxalate in chloroform) at ambient temperatures from 1 to 3 hours to provides the 4(R)-hydroxycyclopentenone ester (136). The ester (136), can then be hydrolized to acid (130).

For a description of these procedures in the art see: C. J. Sih, et al, J. A. C. S., 95, 1676 (1973); J. B. Heather, et al., *Tetrahedron Letters*, 2213 (1973); R. Pappo and P. W. Collins, *Tetrahedron Letters*, 2627 (1972); and R. Pappo, P. Collins, and C. Jung, Ann. N.Y. Acad. Sci., 180, 64 (1971).

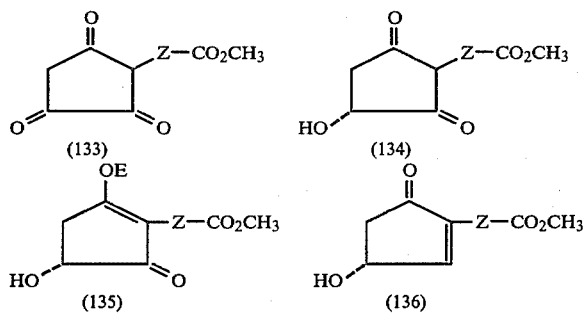

Procedures for the preparation of the requisite cyclopentanetriones (133) are well-established in the art and generally involve the treatment of an ω-1-oxo long chain ester (137) with methyl or ethyl oxalate and a base such as sodium methoxide in methanol, followed by treatment with dilute hydrochloric acid in aqueous methanol to effect the dealkoxalylation of the intermediate (138). See J. Kutsube and M. Matsui, *Agr. Biol. Chem.*, 33 1078 (1969); P. Collins, C. J. Jung and R. Pappo, *Israel Journal of Chemistry*, 6, 839 (1968); R. Pappo, P. Collins and C. Jung, Ann. N.Y. Acad. Sci., 180, 64 (1971); C. J.. Sih, et al., J. A. C. S., 95, 1676 (1973) (see reference 7); and J. B. Heather, et al., *Tetrahedron Letters*, 2313 (1973) por pertinent background literature.

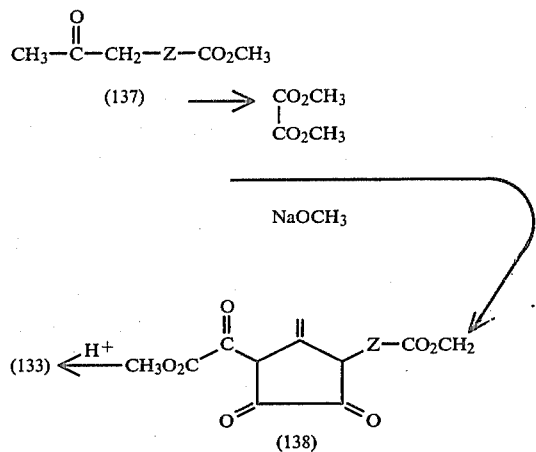

The intermediate keto esters (137) may be prepared by a variety of methods known to the art. One useful procedure is outlined below and involves alkylation of ethyl acetoacetate sodium salt (139) in the usual manner with the appropriate side-chain precursor (140, X=Cl, Br, I, preferably Br or I) followed by decarbethoxylation and reesterification, all in the usual manner.

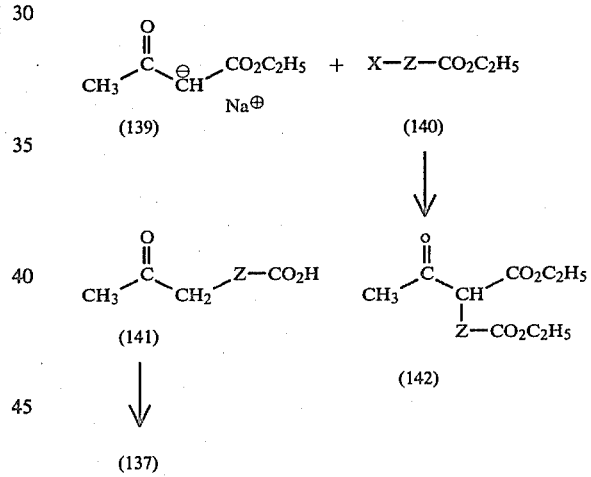

The side-chain precursors (140) are commercially available where Z is $—(CH_2)_p—$, and can be prepared as described in Belgian Patent 786,216 (granted and opened to inspection Jan. 15, 1973).

Those precursors wherein Z is $—(CH_2)_r—O—CH_2—$ can be prepared by the transformation shown directly below starting with the mono-tetrahydropyranyl derivative (143). Thus, (143) is converted to the lithium alcoholate by treatment with butyl lithium, the alcoholate is then O-alkylated with ethyl bromoacetate to provide (144), which on de-O-tetrahydropyranylation, mesylation and reactions with lithium bromide gives the required (145). (These and all the above-described transformations can be effected in the usual manner well-established in the art; pertinent examples for most of the reactions can be found in the above-cited Belgian Pat. No. 786,215).

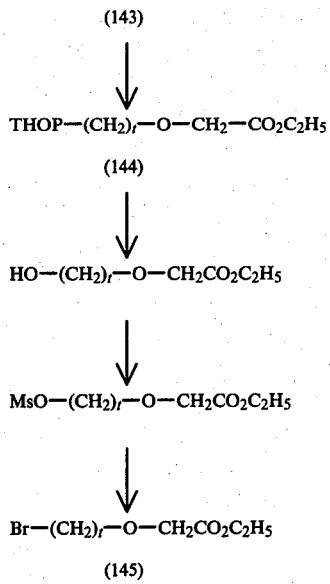

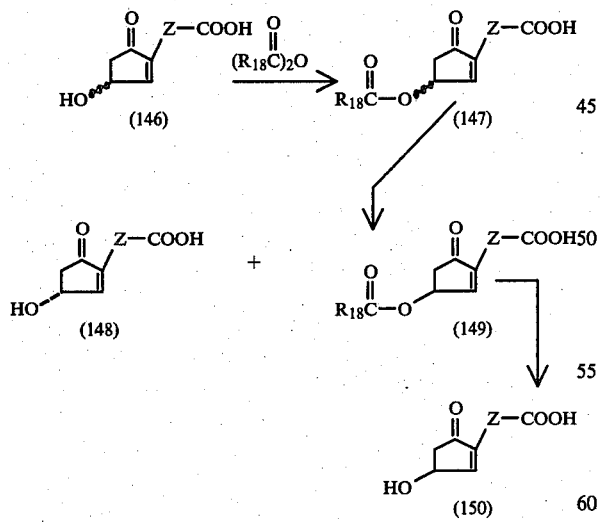

It is also possible to resolve the 4-hydroxycyclopentenone racemate (146) by microbiological means. Thus, treatment of the 4-O-alkanoyl or aroyl derivatives (147, $R_{18}$=aryl or alkyl) of racemate (146) (preferably the 4-O-acetyl and 4-O-propionyl derivatives) with an appropriate microorganism, preferably a Saccharomyces species e.g., 1375-143, affords preferential de-O-acylation of the 4(R)-enantiomer to give (148), which is then separated from the unreacted 4(S)-O-acyl enantiomer (149) by chromatographic procedures. After separation, mild hydrolysis of the 4(S) derivative (149) provides the 4(S)-hydroxycyclopentenone (150). [See N. J. Marsheck and M. Miyano, *Biochima et Biphysica Acta*, 316, 363 (1973) for related examples.]

It is also possible to prepare the individual 4-hydroxycyclopentenones (148) and (150) directly by selective microbial hydroxylations of the corresponding 4-unsubstituted cyclopentenone (151). For example, with *Aspergillus niger* ATCC 9142; a selective 4(R)-hydroxylation of [151, Z=(CH$_2$)$_6$] has been reported; see S. Kurozumi, T. Tora and S. Ishimoto, *Tetrahedron Letters*, 4959 (1973). Other microorganisms can also accomplish this hydroxylation.

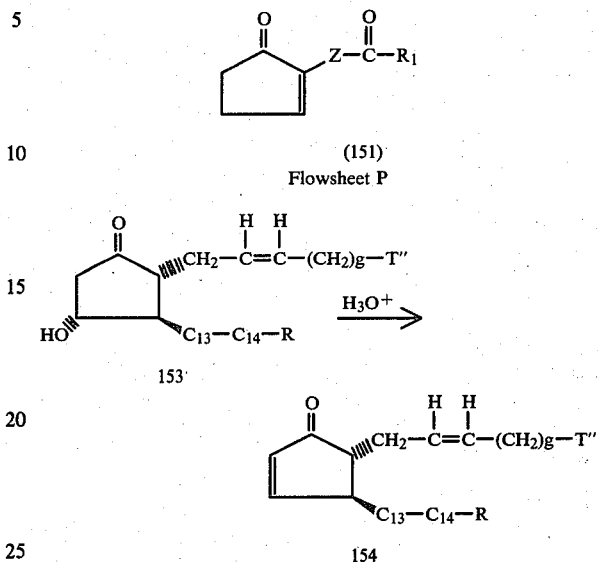

The compounds of this invention (154) are prepared from the corresponding 11α-hydroxy analoge (153) by treatment of 153 with dilute hydrochloric acid in tetrahydrofuran for 2 to 4 days at room temperature as shown hereinabove in Flowsheet P wherein $C_{13}$—$C_{14}$, R, and g are as hereinabove defined and T" is a moiety selected from a group consisting of wherein $R_1$ is hereinabove defined.

As shown in Flowsheet Q hereinbelow, the compounds of this invention wherein T" is (156) can also be prepared by selective esterification of the terminal hydroxyl group of compounds 155 which are also part of this invention.

This esterification can be accomplished by treatment of a pyridine solution of 155 with one equivalent of an anhydride 157 at room temperature for 24 hours.

-continued

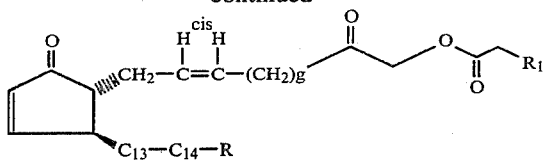

The known PGA compounds are potent in causing multiple biological responses even at low doses. For example, PGA$_1$ and PGA$_2$ are extremely potent in causing vasodepression and smooth muscle stimulation, and also are potent as antilipolytic agents. Moreover, for many applications, these known prostaglandins have an inconveniently short duration of biological activity. In striking contrast, the novel prostaglandin analogs of this invention are substantially more specific with regard to potency in causing prostaglandin-like biological responses, and/or having a substantially, longer duration of biological activity. Therefore, each of these novel prostaglandin analogs is surprisingly and unexpectedly more useful than one of the corresponding above-mentioned known prostaglandins for at least one of the pharmacological purposes indicated below for the latter, either because it has a different and narrower spectrum of biological activity than the known prostaglandins, and therefore is more specific in its activity and causes smaller and fewer undesired side effects than the known prostaglandins, or because of its prolonged activity, fewer and smaller doses of the novel prostaglandin analog can frequently be used to attain the desired result.

Another advantage of the novel compounds of this invention, compared with the known prostaglandins, is that these novel compounds are administered effectively, orally, sublingually, intravaginally, bucally, or rectally, in addition to the usual intravenous, intramusclar, or subcutaneous injection or infusion methods indicated above for the uses of the known prostaglandins. These qualities are advantageous because they facilitate maintaining uniform levels of these compounds in the body with fewer, shorter, or smaller doses, and make possible self-administration by the patient.

PGA compounds, and their esters and pharmacologically acceptable salts, are extremely potent in causing various biological response. For that reason, these compounds are useful for pharmacological purposes. See, for example, Bergstron, et al., Pharmacol. Rev 20, 1 (1968), and references cited therein. A few of those biological responses are systemic arterial blood pressure lowering in the case of the PGA compound as measured, for example, in anesthetized (phenobarbital sodium) pentolinium-treated rats with indwelling aortic and right heart cannulas; stimulation of smooth muscle as shown, for example by tests on strips of guinea pig ileum, rabbit duodenum, or gerbil colon: potentiation of other smooth muscle stimulants; antilipolytic activity as shown by antagonism of epinephrine-induced mobilization of free fatty acids or inhibition of the spontaneous release of glycerol from isolated rat fat pads; inhibition of gastric secretion in the case of the PGA compounds as shown in dogs with secretion stimulated by food or histamine infusion activity on the central nervous system.

Because of these biological responses, these known prostaglandins are useful to study, prevent, control, or alleviate a wide variety of disease and undesirable physiological conditions in birds and mammals, including humans, useful domestic animals, pets, and zoological specimens, and in laboratory animals, for example, mice, rats, rabbits, and monkeys.

For example, these compounds, are useful in mammals, including man, as nasal decongestants. For this purpose, the compounds are used in a dose range of about 10 µg per ml of a pharmacologically suitable liquid vehicle or as an aerosol spray, both for topical application.

The PGA compounds are useful in mammals, including man and certain useful animals, e.g., dogs and pigs, to reduce and control excessive gastric secretion, thereby reducing or avoiding gastric erosion or gastrointestinal ulcer formation, and accelerating the healing of such ulcers already present in the gastrointestinal tract. For this purpose, the compounds are injected or infused intravenously, subcutaneously, or intramuscularly in an infusion dose range of about 0.1 µg per kg of body weight per minute, or in a total daily dose by injection or infusion in the range of about 0.1 mg to about 20 mg per kg of body weight per day, the exact does depending on the age, weight, and condition of the patient or animal, and on the frequency and route of administration. These compounds may also be useful in conjunction with various non-steroidal anti-inflammatory agents, such as aspirin, phenylbutazone, indomethacin and the like, to minimize the well-known ulcerogenic effects of the latter.

The compounds are useful as hypotensive agents to reduce blood pressure in mammals including man. For this purpose, the compounds are administered by intraveneous infusion at the rate of about 0.01 µg to about 50 µg per kg of body weight per minute, or in single or multiple doses of about 25 µg to 2500 µg per kg of body weight total per day.

The PGA compounds and derivatives and salts thereof increase the flow of blood in the mammalian kidney, thereby increasing volume and electrolyte content of the urine. For that reason, PGA compounds are useful in managing cases of renal disfunction, especially in cases of severe impaired renal blood flow, for example, the hepatorena syndrom and early kidney transparent rejection. In case of excessive or inappropriate ADH antidiuretic hormone vasopressin secretion, the diuretic effect of these compounds is even greater. In anephretic states, the vasopressin action of these compounds is especially useful. For that reason, these compounds are useful to promote and accelerate healing of skin which has been damaged, for example, by burns, wounds, and abrasions, and after surgery. These compounds are also useful to promote and accelerate adherence and growth of skin autografts, especially small, deep (Davis) grafts which are intended to cover skinless areas by subsequent outward growth rather than initially, and to retard rejection of homografts.

For these purposes, these compounds are preferably administered topically at or near the site where cell growth and keratin formation is desired, advantageously as an aerosol liquid or micronized powder spray, as an isotonic aqueous solution in the case of wet dressings, or as a lotion, cream, or ointment in combination with the usual pharmaceutically acceptable diluents. In some instances, for example, when there is substantial fluid loss as in the case of extensive burns or skin loss due to other causes, systemic administration is advantageous, for example, by intravenous injection or infusion, separate or in combination with the usual infusions of blood, plasma, or substituents thereof. Alternative routes of administration are subcutaneous or intramuscular near the site, oral, sublingual, buccal, rectal, or vaginal. The exact dose depends on such factors as the route of administration, and the age, weight, and condition of the subject. To illustrate, a wet dressing for topical application to second and/or third degree burns of skin area 5 to 25 square centimeters would advantageously involve use of an isotonic aqueous solution containing 2 to 2000 µg/ml of the PGE compound. Especially for topical use, these prostaglandins are useful in combination with antibiotics, for example, gentamycin, neomycin, polymyxin B, bacitracin, spectinomycin and oxytetracycline, with other antibacterials, for example, mafenide hydrochloride, sulfadiazine, furazolium chloride, and nitrofurazone, and with corticoid steroids, for example hydrocortisone, prednisolone, methylprednisolone, and fluoroprednisoline, each of those being used in combination at the usual concentrations suitable for its use alone.

The novel compounds of this invention induce the biological responses described hereinabove as associated with its particular prostaglandin type. These novel compounds are accordingly used for the above-described corresponding purposes.

The novel PGA compounds of this invention are also useful as bronchodilators for the treatment of asthma and chronic bronchitis. As such they may be conveniently administered by inhalation of aerosol sprays prepared in a dose range of about 10 µg to about 10 mg/ml of a pharmacologically suitable liquid vehicle. Relative to the natural prostaglandins, the PGA compounds in particular have the significant advantage of inducing prolonged effects.

The invention will be described in greater detail in conjunction with the following specific examples.

DETAILED DESCRIPTION OF THE INVENTION

EXAMPLE 1

Preparation of ethyl 2,2-trimethylenehexanoate

To a stirred solution of 27.6 g of freshly distilled N-isopropylcyclohexylamine in 200 ml of dry tetrahydrofuran cooled to −78° C. is added at a fast rate 96 ml of 2.04M n-butyllithium in hexane. To the resulting solution is added dropwise 25 g of ethyl cyclobutanecarboxylate. After 30 minutes the resulting solution is allowed to warm to ambient temperature, is transferred to a dropping funnel under nitrogen and is added dropwise over a period of 1¼ hours to a solution of 54 g of n-butyl iodide in 100 ml of dry dimethylsulfoxide maintaining the temperature at 16°–20° C. Stirring is continued for an additional 30 minutes. The separated salts are removed by filtration, the mother liquor is taken to a small volume and the resulting oil is diluted with hexanes. This solution is washed with 2% hydrochloric acid, saturated sodium chloride soltuion, and dried with anhydrous magnesium sulfate. The solvent is removed and the residual oil is distilled to give 14.6 g (41%) of product, bp 84°–87° C. (10 mm).

EXAMPLE 2

Preparation of ethyl 2,2-tetramethylenehexanoate

In the manner described in Example 1, treatment of the lithium salt of ethyl cyclopentanecarboxylate with n-butyl iodide furnishes the subject product.

EXAMPLE 3

Preparation of 2,2-trimethylenehexan-1-ol

To a stirred solution of 20 g of ethyl 2,2-trimethylenehexanoate (Example 1) in 100 ml of dry toluene,, in an argon atmosphere and cooled in an ice bath, is added dropwise 250 ml (2 molar equivalents) of 0.89 M diisobutlaluminum hydride in toluene. The resulting solution is stirred at ambient temperature for 2 hours and then poured into excess iced 5% hydrochloric acid. The organic phase is separated and washed with 5% hydrochloric acid, saturated sodium chloride solution, dried with anhydrous magnesium sulfate and taken to dryness to give 14.8 g (96%) of oil; bp 92°–93° C. (10 mm).

EXAMPLE 4

Preparation of 2,2-tetramethylenehexan-1-ol

In the manner described in Example 3, treatment of ethyl 2,2,-tetramethylenehexanoate (Example 2) with 0.89 molar diisobutylaluminum hydride furnishes the subject product.

EXAMPLE 5

Preparation of 2,2-trimethylenehexaldehyde

Chromiun trioxide (61.5 g), dried in a vacuum desiccator over phosphorous pentoxide, is added to an ice cold solution of 97 g of dry pyridine in one liter of dry methylene chloride. The deep red suspension is stirred for 15 minutes at 0° C. and then for 45 minutes at ambient temperature. A solution of 14.5 g of 2,2-trimethylenehexanol-1 (Example 3) in 55 ml of methylene chloride is added all at once to the suspension. A black tarry deposit is formed immediately. After stirring at ambient temperature for 15 minutes the solution is decanted from the tarry deposit which is then triturated four times with small portions of methylene chloride. The combined extracts are washed twice with ice cold 5% sodium hydroxide, ice cold 5% hydrochloric acid and finally with saturated sodium chloride solution, dried with magnesium sulfate and taken to dryness. Distillation gives 12.9 g of product; bp 69° C. (11 mm).

EXAMPLE 6

Preparation of 2,2-tetramethylenehexaldehyde

Oxidation of 2,2-tetramethylenehexan-1-ol (Example 4) with chromiun trioxide-pyridine complex in the manner described in Example 5 furnishes the subject product.

EXAMPLE 7

Preparation of 4,4-trimethylene-1-octyn-3-ol

To a solution of lithium acetylide-ethylenediamine complex (9.4 g) in 90 ml of dry dimethylsulfoxide, cooled in an ice bath, is added 12.94 g of 2,2-trimethylenehexaldehyde (Example 5) in 10 ml of dimethylsulfoxide dropwise, at such a rate that the temperature is maintained at 20°–25° C. The solution is stirred at ambient temperature for 12 hours and then poured into a mixture of ice cold 2% hydrochloric acid and ether. The ether layer is separated and the aqueous phase is extracted with ether. The combined ether extracts are washed with saturated sodium chloride solution, dried with anhydrous magnesium sulfate and taken to dryness. Distillation provides 13.53 g of product; bp 108°–109° C. (13 mm).

EXAMPLE 8

Preparation of 4,4-tetramethylene-1-octyn-3-ol

Treatment of 2,2-tetramethylenehexaldehyde (Example 6) with lithium acetylide-ethylenediamine complex in dimethylsulfoxide in the manner described in Example 4 is productive of the subject compound.

EXAMPLE 9

Preparation of 4,4-trimethylene-3-trimethylsilyloxy-1-octyne

To a stirred solution of 5.3 g of 4,4-trimethylene-1-octyn-3-ol (Example 7) and 5.42 g of imidazole in 32 ml of dry dimethylformamide, cooled in an ice bath under argon atmosphere is added 4.35 g of chlorotrimethylsilane. After stirring at 0° C. for 15 minutes, the solution is stirred at ambient temperature for 18 hours and then poured into 200 ml of hexanes. The solution is washed twice with ice cold water, saturated sodium chloride solution, dried with anhydrous magnesium sulfate and taken to dryness. Distillation furnishes 6.02 g (80%) of colorless oil; bp 110°–112° C. (14 mm).

EXAMPLE 10

Preparation of 4,4-tetramethylene-3-trimethylsilyloxy-1-octyne

Treatment of 4,4-tetramethylene-1-octyn-3-ol (Example 8) with chlorotrimethylsilane in dimethylformamide containing imidazole as described in Example 5 furnishes the subject product.

EXAMPLE 11

Preparation of 1-iodo-4,4-trimethylene-3-trimethylsilyloxy-1-octyne

To a solution of 25 g of 4,4-trimethylene-3-trimethylsilyloxy-1-octyne (Example 9), stirred under argon atmosphere at −78° C., is added dropwise 93 ml of 2.3 M n-butyllithium in hexane at a rate to maintain the temperature below −40° C. After stirring for 40 minutes, a solution of iodine is allowed to warm to ambient temperature and 10% aqueous sodium thiosulfate solution is added until the purple color is removed. The organic phase is washed with dilute aqueous sodium thiosulfate solution, saturated sodium chloride solution, dried with anhydrous sodium sulfate and taken to dryness to afford the subject product as an oil.

EXAMPLE 12

Preparation of 1-iodo-4,4-trimethylene-3-trimethylsilyloxy-1-cis-octene

To a solution of 30 g of 1-iodo-4,4-trimethylene-3-trimethylsilyloxy-1-octyne (Example 10) in 100 ml of methanol, under argon atmosphere is added 54 g of potassium azodicarboxylate [J. Thiele, Annalen der Chemie, 271, 127 (1892)]. To this solution is added dropwise 45 ml of acetic acid over a period of about 2 hours. The solids are removed by filtration and the mother liquor is reduced to a small volume; diluted with water and extracted with ether. The ether is evaporated and the residual oil is stirred with 250 ml of 1 M sodium bicarbonate solution. The solution is extracted several times with ether and the combined extracts are washed with saturated sodium chloride solution, dried with anhydrous sodium sulfate and taken to dryness to furnish the subject product as an oil.

EXAMPLE 13

Preparation of 1-iodo-4,4-trimethylene-3-trimethylsilyloxy-1-trans-octene

To a mixture of 4.76 g of sodiumborohydride and 23.6 g of 2-methyl-2-butene in 220 ml of dry tetrahydrofuran at −5° C. is added dropwise 23.8 of freshly distilled borontrifluoride etherate. The resulting mixture is stirred at −5° C. to −0° C. for 2 hours and to it is added dropwise a solution of 20 g of 4,4-trimethylene-3-trimethylsilyloxy-1-octyne (Example 12) in 20 ml of dry tetrahydrofuran. The resulting mixture is stirred at ambient temperature for 2½ hours. The mixture is then cooled to −5° C. and there is added 44 g of trimethylene oxide portionwise over a period of 20 minutes, maintaining the temperature at 15°–20° C. The mixture is stirred at ambient temperature for 2 hours and then poured simultaneously, with a solution of 119 g of iodine in 290 ml of tetrahydrofuran, into 1490 ml of 15% aqueous sodium hydroxide solution. After stirring for 30 minutes the organic phase is separated and the aqueous phase is extracted with ether. The combined organic phase is washed with 5% aqueous sodium thiosulfate solution, saturated sodium chloride solution, dried with anhydrous magnesium sulfate and taken to dryness to give 27 g of oily material. Chromatography on 135 g of florisil and eluting with 500 ml of hexanes furnishes 24 g of oily product which is shown to be contaminated with starting material and iodoform by infrared and thin layer chromatography. The material is purified by removing the trimethylsilyl group in the following manner. The crude product is dissolved in 350 ml of acetic acid-tetrahydrofuran-water (4:2:1) by stirring at ambient temperature for 5 minutes. The solvent is removed under reduced pressure and the residual oil containing mainly 1-iodo-3-hydroxy-4,4-trimethylene-1-trans-octen is applied to a 2″ (flat) dry column containing 1200 g of Woelm silica gel. The column is developed with benzene, cut into one-inch segments and each segment is eluted with chloroform. Combination of the appropriate fractions affords 300 mg of iodomethane, 2.8 g of 4,4-trimethylene-1-octyne-3-ol, and 11.6 g of 1-iodo-3-hydroxy-4,4-trimethylene-1-trans-octene. Silylation of this material in the manner described above followed by distillation of the residual oil furnishes 13 g of pure product; bp 83°–84° C. (0.2 mm).

EXAMPLE 14

Preparation of 1-iodo-4,4-tetramethylene-3-trimethylsilyloxy-1-trans-octene

Treatment of 4,4-tetramethylene-3-trimethylsilyloxy-1-octene (Example 10) in the manner described in Example 13 furnishes the subject product.

EXAMPLES 15–20

Treatment of the lithium salt of ethyl cyclobutanecarboxylate with the alkyl halides listed in Table 1 below by the procedure described in Example 1 furnishes the 2,2-trimethylene esters of the table.

TABLE 1

| Example | Alkyl Halides | Product 2,2-Trimethylene esters |
| --- | --- | --- |
| 15 | propyl iodide | ethyl 2,2-trimethylenepentanoate |
| 16 | amyl iodide | ethyl 2,2-trimethyleneheptanoate |
| 17 | hexyl iodide | ethyl 2,2-trimethyleneoctanoate |
| 18 | benzyl iodide | ethyl 2,2-trimethylene-3-phenylpropionate |
| 19 | 2-cyclopentyl-1-ethyl bromide | ethyl 2,2-trimethylene-4-cyclopentylbutyrate |
| 20 | 1-chloro-2-butyne | ethyl 2,2-trimethylene-4-hexynoate |

EXAMPLES 21-27

Reduction of the various esters listed in Table 2 below with diisobutylaluminum hydride all in the manner described in Example 3 above is productive of the alcohols of the table.

TABLE 2

| Example | Starting Esters of Example | Product Alcohols |
| --- | --- | --- |
| 21 | 15 | 2,2-trimethylenepentan-1-ol |
| 22 | 16 | 2,2-trimethyleneheptan-1-ol |
| 23 | 17 | 2,2-trimethyleneoctan-1-ol |
| 24 | 18 | 2,2-trimethylene-3-phenylpropan-1-ol |
| 25 | 19 | 2,2-trimethylene-4-cyclopentylbutan-1-ol |
| 26 | 20 | 2,2-trimethylene-4-hexyn-1-ol |
| 27 | 55 | 2,2-trimethylene-4-cis-hexen-1-ol |

EXAMPLES 28-34

Oxidation of the alcohols listed in Table 3 below with chromium trioxide-pyridine complex by the procedure described in Example 5 above furnishes the corresponding aldehydes of the table.

TABLE 3

| Example | Starting Alcohols of Example | Product 2,2-Trimethylenealdehydes |
| --- | --- | --- |
| 28 | 21 | 2,2-trimethylenevaleraldehyde |
| 29 | 22 | 2,2-trimethyleneheptaldehyde |
| 30 | 23 | 2,2-trimethyleneoctaldehyde |
| 31 | 24 | 2,2-trimethylene-3-phenylpropionylaldehyde |
| 32 | 25 | 2,2-trimethylene-4-cyclopentylbutyraldehyde |
| 33 | 26 | 2,2-trimethylenehex-4-yn-1-al |
| 34 | 27 | 2,2-trimethylene-4-cis-hexene-1-al |

EXAMPLES 35-41

Treatment of the various aldehydes listed below in Table 4 with lithium acetylide-ethylenediamine complex in the manner described in Example 7 furnishes the hydroxyacetylenes of the table.

TABLE 4

| Example | Starting Aldehyde of Example | Product Hydroxyacetylenes |
| --- | --- | --- |
| 35 | 28 | 4,4-trimethylene-1-heptyn-3-ol |
| 36 | 29 | 4,4-trimethylene-1-nonyn-3-ol |
| 37 | 30 | 4,4-trimethylene-2-decyn-1-ol |
| 38 | 31 | 4,4-trimethylene-5-phenyl-1-pentyn-3-ol |
| 39 | 32 | 4,4-trimethylene-6-cyclopentyl-1-hexyn-3-ol |
| 40 | 33 | 4,4-trimethylene-1,6-octadiyn-3-ol |
| 41 | 34 | 4,4-trimethylene-4-cis-hexene-3-ol |

EXAMPLES 42-48

Treatment of the various alcohols listed below in Table 5 with chlorotrimethylsilane in the manner described in Example 9 furnishes the corresponding trimethylsilyloxy acetylenes of the table.

TABLE 5

| Example | Starting Alcohols of Example | Product Trimethylsilyloxyacetylenes |
| --- | --- | --- |
| 42 | 35 | 4,4-trimethylene-3-trimethylsilyloxy-1-heptyne |
| 43 | 36 | 4,4-trimethylene-3-trimethylsilyloxy-1-nonyne |
| 44 | 37 | 4,4-trimethylene-3-trimethylsilyloxy-1-decyne |
| 45 | 38 | 4,4-trimethylene-3-trimethylsilyloxy-5-phenyl-1-pentyne |
| 46 | 39 | 4,4-trimethylene-3-trimethylsilyloxy-6-cyclopentyl-1-hexyne |
| 47 | 40 | 4,4-trimethylene-3-trimethylsilyloxy-1,6-octadiyne |
| 48 | 41 | 4,4-trimethylene-3-trimethylsilyloxy-4-cis-octene-1-yne |

EXAMPLES 49-54

In the manner described in Example 13 treatment of the various acetylenes of Table 6 below with disiamylborane, made in situ from sodium borohydride and 2-methyl-2-butene, followed by oxidation of the so formed organoborane with trimethylamine oxide followed by treatment of this product with iodine and sodium hydroxide furnishes the trimethylsilyliodovinylcarbinols of the table.

TABLE 6

| Example | Starting Acetylenes of Example | Product Trimethylsilylvinylcarbinols |
| --- | --- | --- |
| 49 | 42 | 1-iodo-4,4-trimethylene-3-trimethylsilyloxy-1-trans-heptene |
| 50 | 43 | 1-iodo-4,4-trimethylene-3-trimethylsilyloxy-1-trans-nonene |
| 51 | 44 | 1-ioso-4,4-trimethylene-3-trimethylsilyloxy-1-trans-decene |
| 52 | 45 | 1-iodo-4,4-trimethylene-3-trimethylsilyloxy-5-phenyl-1-trans-pentene |
| 53 | 46 | 1-iodo-4,4-trimethylene-3-trimethylsilyloxy-6-cyclopentyl-1-trans-hexene |
| 54 | 47 | 1-iodo-4,4-trimethylene-3-trimethylsilyloxy-1-trans-octen-6-yne |

EXAMPLE 55

Preparation of ethyl 2,2-trimethylene-4-cis-hexenoate

A solution of 5 g of ethyl 2,2-trimethylene-4-hexynoate (Example 20 ) in 40 ml of dry pyridine is hydrogenated in a Parr apparatus using 600 mg of 5% palladium on barium sulfate. After one hour when hydrogen uptake is complete, the solution is filtered through celite and the mother liquor is taken to dryness to furnish 4 g of product as an oil.

EXAMPLE 56

Preparation of 3-tetrahydropyranyloxy-1-propyne

To a stirred solution of 112 g (2.0 mol.) of 3-hydroxy-1-propyne and 260 g (3.0 mol.) of dihydropyran in 1.20 liters of methylene chloride cooled to 0° C. in an ice bath, is added a solution of 20 mg of para-toluenesulfonic acid in 100 ml of methylene chloride, dropwise. The reaction mixture is stirred at 0° C. for one-half hour, and at ambient temperature for one hour. It is then poured into 200 ml of a 5% solution of sodium bicarbonate, the organic phase is separated, the aqueous phase extracted with 100 ml of methylene chloride, the combined organic phases washed with 100 ml of a solution of brine, dried over sodium sulfate, and evaporated under vacuum (12 mm) at 45° C. to give 300 g of crude product, which is purified by fractional distillation, bp 71°–73° C. (14 mm) to yield 250 g (89%) of a liquid.

EXAMPLE 57

Preparation of 3-tetrahydropyranyloxy-1-trimethylsilyl-1-propyne

To a stirred −20° C. solution of 125 g (0.89 mol.) of 3-tetrahydropyranyloxy-1-propyne (Example 56) in 450 ml of ether, under a nitrogen atmosphere, is added dropwise, over one hour, a solution of 45 ml (0.89 mol.) of 2.0 N n-butylithium in hexane. After 150 ml of dry ether is added and the mixture stirred at −20° C. for 30 minutes, a solution of 98 g (0.89 mol.) of trimethylchlorosilane in 73 ml of ether is added dropwise. Stirring is continued for 30 minutes at −20° C. and at ambient temperature for 18 hours. The reaction mixture is again cooled to −20° C., and a solution of 90 ml of acetic acid in 300 ml of ether is added dropwise, followed by 90 ml of water. It is then diluted with 500 ml of water, and extracted 3 times with 300 ml of 5% sodium bicarbonate solution. The organic phase is separated, washed with 500 ml of a saturated brine solution, dried over sodium sulfate, and evaporated at 40° C. under vacuum (12 mm.). The crude product is fractionally distilled, bp 120°–125° C. (18 mm.), to yield 120 g of an oil.

EXAMPLE 58

Preparation of d,1-erythro-3-tetrahydropyranyloxy-4-hydroxy-1-trimethylsilyl-1-octyne To a stirred −78° C. solution of 62 ml (124 mmol.) of a 2.0 M solution of n-butyllithium in hexane and 50 ml of dry tetrahydrofuran, under a nitrogen atmosphere is added dropwise, a solution of 24 g (113 mmol.) of 3-tetrahydropyranyloxy-1-trimethylsilyl-1-propyne (Example 57) in 35 ml of tetrahydrofuran. This red solution is stirred one hour at −78° C., then a freshly prepared solution of zinc iodide (135 mmol.) in 125 ml of tetrahydrofuran [F. Mercier, R. Epstein, and S. Holand, Bull. Soc. Chim. France, 2, 690 (1972)] is added dropwise at −78° C., until the mixture turns yellow. After stirring an additional hour at −78° C., a soution of 21 g (250 mmol.) of n-valeraldehyde in 35 ml of tetrahydrofuran is added dropwise and the reaction mixture stirred for one hour at −78° C. and 18 hours at ambient temperature. It is then cooled to 0° C. and a solution of 12 ml of acetic acid in 65 ml of ether is added dropwise, followed by 75 ml of ice-water. The phases are separated and the aqueous phase is extracted twice with ether. The combined organic phases are washed 3 times with saturated sodium bicarbonate solution, until the last wash is basic, then with a saturated brine solution, dried over sodium sulfate, and evaporated to give 40 g of yellow oil. The crude product may be purified on a 4"×40" dry column of alumina, and eluted with chloroform. I.R.: neat; 3550 (OH), 2200 (C≡C), 840, 750 [(CH$_3$)$_3$Si], cm$^{-1}$.

EXAMPLE 59

Preparation of d,1-erythro-3,4-dihydroxy-1-trimethylsilyl-1-octyne

A solution of 19.6 g (0.066 mol) of d,1-erythro-3-tetrahydropyranyloxy-4-hydroxy-1-trimethylsilyl-1-octyne (Example 58) in 55.5 ml of ethanol, 22.2 ml of acetic acid, and 22.2 ml of water is heated at reflux for 3 hours. The cooled mixture is taken to dryness and evaporated twice with benzene. The residue is taken up in hexane, washed 3 times with saturated potassium bicarbonate solution, dried with magnesium sulfate, and evaporated to give 17.0 g of crude product IR: neat, 3500–3400, broad (two OH).

EXAMPLE 60

Preparation of d,1-erythro-3,4-isopropylidenedioxy-1-trimethylsilyl-1-octyne

To a stirred solution of 17.0 g (79.5 mmol.) of crude d,1-erythro-15,16-dihydroxy-1-trimethylsilyl-1-octyne (Example 59) is 33.6 ml of 2,2-dimethoxy propane at 0° C., is added 0.05 ml of 60% perchloric acid. After 30 minutes at ambient temperature, the mixture is shaken with 50 ml of hexane and 25 ml of saturated sodium bicarbonate solution. The hexane phase is separated, dried with magnesium sulfate, and evaporated to give 19.0 g of crude product.

EXAMPLE 61

Preparation of d,1-erythro-3,4-isopropylidenedioxy-1-octyne

A mixture of 19.0 g (75.0 mmol.) of crude d,1-erythro-3,4-isopropylidenedioxy-1-trimethylsilyl-1-octyne (Example 60) with 95 ml of methanol and 3.0 g of potassium carbonate is refluxed for one hour. The mixture is cooled and evaporated at 50° C. (13 mm), taken up in 250 ml of benzene, and washed with 100 ml of water. The water is saturated with salt, the organic phase separated, dried with magnesium sulfate, and evaporated to give 12 g of crude product. Fractional distallation yields 7.0 g of the subject compound as a colorless oil, bp 103°–106° C. (13 mm).

IR: neat; 3300 sharp (H—C≡C), 2100, (C≡C), 780 (erythro configuration) cm$^{-1}$.

nmr: δCDCl$_3$ TMS; 4.75 (dd., 1, C≡C—C$\underline{H}$—CH, J=2 Hz, J=5 Hz), 4.10 (m, 1, C≡C—C$\underline{H}$—CH—CH$_2$, 2.5 (d, 1, $\underline{H}$—C—C—CH), 1.9–1.2 (m, 14, alkyl), 0.90 (m, 3H, CH$_2$C$\underline{H}$$_3$).

EXAMPLE 62

Preparation of d,1-erythro-1-iodo-3,4-isopropylidenedioxy-trans-1-octene

To a stirred 0° C. slurry of 0.852 g (0.023 mol.) of sodium borohydride and 4.21 g (0.060 mol.) of 2-methyl-2-butene in 40 ml of dry tetrahydrofuran, under an argon atmosphere, is added dropwise 4.26 g (0.030 mol.) of boron trifluoride etherate complex. A solution of 2.73 g (0.015 mol.) of d,1-erythro-3,4-isopropylidenedioxy-1-octyne (Example 61) in 5 ml of tetrahydrofuran is added dropwise, the ice bath removed, and the mixture allowed to stir at ambient temperature for two hours. It is then cooled again to 0° C., and 2.88 g (0.105 mol.) of dry trimethylamine oxide is added in portions over 30 minutes. After stirring 3 hours at room temperature, this mixture is poured simultaneously with a 0° C. solution of 2.13 g of iodine in 53 ml of tetrahydrofuran into 766 ml of a 0° C. 15% solution of sodium hydroxide in water and the whole stirred vigorously at 0° C. for 45 minutes. The organic phase is separated, the aqueous phase is extracted twice with ether, the combined organic phases are washed with a 5% solution of sodium thiosulfate, dried with magnesium sulfate, and evaporated. The crude product is chromatographed on a 2" by 40" dry column of silica gel, be eluting with chloroform, to yield 1.2 g (25%) of a yellow oil.

IR: neat; 1599 sharp, 945

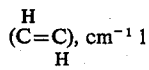

(C=C), cm$^{-1}$ 1

EXAMPLE 63

Preparation of d,1-erythro-3-tetrahydropyranyloxy-4-acetyloxy-1-trimethylsilyl-1-octyne A solution of 3.0 g (13.2 mmol.) of d,1-erythro-3-tetrahydropyranyloxy-4-hydroxy-1-trimethylsilyl-1-octyne is heated at 100° C. for 15 hours with 3 ml of acetic anhydride and 10 ml of pyridien. The mixture is evaporated to dryness, dissolved in ether, washed with sodium bicarbonate solution and water. The organic phase is dried over magnesium sulfate and evaporated to give 2.5 g of the subject compound as an oil IR: neat; 2200 (C C), 1730 (C=O), 830, 760 [(CH$_3$)$_3$Si], cm$^{-1}$.

EXAMPLE 64

Preparation of d,1-erythro-3-hydroxy-4-acetyloxy-1-trimethylsilyl-1-octyne

In the manner of Example 59, 2.5 g (7.4 mmol.) of d,1-erythro-3-tetrahydropyranyloxy-4-acetyloxy-1-trimethylsilyl-1-octyne (Example 63) in a solution of ethanol, acetic acid, and water is heated at 100° C. for 3 hours. After workup, the crude product is chromatographed on a ⅞"×22" dry column of silica gel, and eluted with chloroform to give 1.0 g of a yellow oil.
IR: neat; 3500 (OH), 1730 (C=O), cm$^{-1}$.

EXAMPLE 65

Preparation of d,1-erythro-3-paratoluenesulfonyloxy-4-acetyloxy-1-trimethylsilyl-1-octyne To a solution of 7.5 g (41.0 mmol.) of d,1-erythro-3-hydroxy-4-acetyloxy-1-trimethylsilyl-1-octyne (Example 64) in 41 ml of dry pyridine is added 11.0 g (58 mmol.) of para-toluenesulfonyl chloride and the resulting solution is stirred at 25° C. for 15 hours. The mixture is then warmed at 40° C. for one hour, and after cooling, partitioned between 500 ml of diethyl ether and 100 ml of 1.0 N hydrochloric acid. The organic phase is washed three times with 100 ml of 1.0 N hydrochloric acid, once with dilute sodium bicarbonate solution, dried over magnesium sulfate, and evaporated under reduced pressure to give an oil. The crude product is purified on a 2"×24" dry column of silica gel, and eluted with chloroform to yield a yellow oil.
IR: neat, 1730 (C=O), 1595 (aromatic) cm$^{-1}$.

EXAMPLE 66

Preparation of d,1-threo-3-hydroxy-4-acetyloxy-1-trimethylsilyl-1-octyne

A mixture of 15.5 g (39.0 mmol.) of d,1-erythro-3-para-toluenesulfonyloxy-4-acetyloxy-1-trimethylsilyl-1-octyne (Example 65), 5.0 g of calcium carbonate, 25 ml of water and 250 ml of tetrahydrofuran is refluxed with stirring for 4 days. The mixture is cooled, 100 ml of water added and the organic phase separated. The aqueous phase is extracted with ether, the combined organic phases dried with magnesium sulfate, and evaporated. The crude product is chromatographed on a 3"×30" dry column of silica gel, and eluted with chloroform to give 7.0 g of an oil.
IR: neat; 3500, (OH), cm$^{-1}$.

EXAMPLE 67

Preparation of d,1-threo-3,4-dihydroxy-1-octyne

A solution of 7.0 g (28 mmol.) of d,1-threo-3-hydroxy-4-acetyloxy-1-trimethylsilyl-1-octyne (Example 66) in 50 ml of methanol is stirred at room temperature for 24 hours with a solution of 6.3 g (112 mmol.) of potassium hydroxide in 50 ml of water. The mixture is extracted twice with hexane, washed with 0.5 M hydrochloric acid, brine, and dried with magnesium sulfate. After evaporation, the subject compound is obtained as a yellow oil.
IR: neat, 2500 broad (2-OH), cm$^{-1}$.

EXAMPLE 68

Preparation of d,1-threo-3,4-isopropylidenedioxy-1-octyne

In the manner of Example 60, treatment of a solution of d,1-threo-3,4-dihydroxy-1-octyne (Example 67) in dimethoxypropane with 60% perchloric acid, and fractional distillation (12 mm) is productive of the subject compound as a colorless oil, containing 15% of d,1-erythro-3,4-isopropylidenedioxy-1-octyne (Example 60), as an impurity.
IR: neat; 810 (threo configuration).
nmr: $\delta_{TMS}^{CDCl_3}$; 4.2 (dd, 1, -C≡C-CH-, J's-2H$_z$, 6H$_z$), 4.1-3.9 (m, 1, -C≡C-CH-CH-CH$_2$-), 2.5 (d, 1, H-C≡C-, J=2H$_z$), 1.9-1.2 (m, 14, alkyl), 0.90 (m, 3H, CH$_2$-CH$_3$).

EXAMPLE 69

Preparation of d,1-threo-1-iodo-3,4-isopropylidenedioxy-trans-1-octene

In the manner of Example 62, d,1-threo-3,4-isopropylidenedioxy-trans-1-octyne (Example 68) is treated successively with disiamylborane, trimethylamine oxide, iodine, and sodium hydroxide to give the subject compound.

EXAMPLE 70

Preparative of d,1-erythro-3-tetrahydropyranyloxy-4-hydroxy-1-octyne

Alakline hydrolysis of d,1-erythro-3-tetrahydropyranyloxy-4-hydroxy-1-trimethylsilyl-1-octyne

EXAMPLE 71

Preparation of d,1-erythro-3-tetrahydropyranyloxy-4-methoxy-1-octyne

To a stirred slurry of 6.0 g (150 mmol.) of a 60% oil dispersion of sodium hydride and 96 g of iodomethane, under an argon atmosphere, is added 700 ml of dry tetrahydrofuran. The stirred mixture is cooled to −20° C. and a solution of 30 g (133 mmol.) of d,1-erythro-3-tetrahydropyranyloxy-4-hydroxy-1-octyne (Example 70), is added dropwise, followed by 0.1 ml of methanol. The mixture is stirred at ambient temperature for 24 hours, 10 ml of methanol is added, and evaporated. The residue is taken up in ether, washed 3 times with water, dried over magnesium sulfate, and evaporated. The crude product is purified by fractional distillation to yield 16.3 g of a colorless oil, bp 137°–140° C. (12 mm).

EXAMPLE 72

Preparation of d,1-erythro-3-tetrahydropyranyloxy-4-methoxy-1-iodo-trans-1-octen In the manner of Example 62, 1.20 g (5.0 mmol.) of d,1-erythro-3-tetrahydropyranyloxy-4-methoxy-1-octyne (Example 71) is treated successively with disiamylborane, trimethylamine oxide, iodine, and sodium hydroxide. Chromatography on a 2″×36″ dry column of silica gel and elution with chloroform is productive of 0.80 g (40%) of the subject compound as an oil.

nmr: $\delta_{TMS}^{CDCl_3}$; 7.9–6.1 (m,2, HC=CH), 4.9–4.6 (2 m, 2, c=C-CH, O—CH—O), 4.3–4.0 (m, 1, c=c-CH-C$\underline{H}$-CH$_2$), 3.9–3.0 (m, 6, C$\underline{H}_2$-O-C$\underline{H}$, OCH$_3$), 1.8–1.2 (m, 12 H, alkyl), 0.9 (m, 3, —CH$_3$).

EXAMPLE 73

Preparation of d,1-erythro-3-hydroxy-4-methoxy-1-iodo-trans-1-octene

A solution of 3.10 g (8.24 mmol.) of d,1-erythro-3-tetrahydropyranyloxy-4-methoxy-1-iodo-trans-1-octene (Example 72) in 60 ml of acetic acid, 30 ml of tetrahydrofuran, and 15 ml of water is stirred at ambient temperature for 18 hours. It is then evaporated at 70° C. under high vacuum (1.0 mm), and three times with 40 ml of toluene to give the crude product as an oil.

EXAMPLE 74

Preparation of d,1-erythro-3-trimethylsilyloxy-4-methoxy-1-iodo-trans-1-octene

To a stirred solution of 3.0 g (10.2 mmol.) of d,1-erythro-3-hydroxy-4-methoxy-1-iodo-trans-1-octene (Example 73) in 11.0 ml of dry dimethylformamide and 1.90 g (28.0 mmol.) of imidazole cooled to 0° C. is added, dropwise, 1.35 g (12.5 mmol.) of trimethylsilyl chloride. The reaction mixture is stirred a further 4 hours at room temperature. It is then poured into a mixture of 100 ml of hexane and 25 ml of water, the organic phase is separated, washed twice with water once with a solution of saturated sodium chloride, dried over magnesium sulfate, and evaporated. The crude product is purified by fractional distillation to yield 2.0 g of a colorless oil, bp 82°–83° C. (0.3 mm).

IR: neat; 1602 sharp

840, 750 braod [(CH$_3$)$_3$Si-], cm$^{-1}$.

EXAMPLE 75

Preparation of d,1-erythro-1-iodo-3,4-dihydroxy-trans-1-octene

A solution of 1.40 g (4.50 mmol.) of d,1-erythro-1-iodo-3,4-isopropylidenedioxy-trans-1-octene (Example 62) in 30 ml of acetic acid, 10 ml of tetrahydrofuran and 10 ml of water is stirred and heated at 50° C. for five hours. It is then evaporated at 40° C. under high vacuum (1.0 mm), and twice more with 50 ml of benzene. Crystallization from 10 ml of chloroform at 0° C. is productive of 700 mg of the white crystalline subject product.

EXAMPLE 76

Preparation of d,1-erythro-1-iodo-3,4-bis-trimethylsilyloxy-trans-1-octene

To a stirred solution of 700 mg (2.40 mmol.) of d,1-erythro-1-iodo-3,4-dihydroxy-trans-1-octene (Example 75) and 800 mg (12.0 mmol.) of imidazole, in 10 ml of dry dimethylformamide at 0° C. is added dropwise 1.20 g (11.0 mmol.) of trimethylchlorosilane. The ice bath is removed, and the mixture is stirred and heated at 50° C. for five hours. It is then cooled, shaken with 50 ml of hexane and 50 ml of water, the organic layer separated and washed with 15 ml of 0.5 M hydrochloric acid, 15 ml of a saturated solution of sodium bicarbonate, dried with magnesium sulfate, and evaporated. This crude product is fractionally distilled, bp 90°–92° C. (0.40 mm) to yield 250 mg of a colorless oil.

EXAMPLE 77

Preparation of d,1-erythro-3-trimethylsilyloxy-4-ethoxy-1-iodo-trans-1-octene

Following the procedure of Example 71, ethylation using iodoethane of d,1-erythro-3-tetrahydropyranyloxy-4-hydroxy-1-octyne for a period of 22 hours is productive of the corresponding d,1-erythro-3-tetrahydropyranyloxy-4-ethoxy-1-octyne. This intermediate is converted to d,1-erythro-3-tetrahydropyranyloxy-4-ethoxy-1-iodo-trans-1-octene when treated successively with disiamylborane, trimethylamine oxide iodine, and sodium hydroxide solution after the procedure of Example 72. Acid hydrolysis by the method of Example 18 to d,1-erythro-3-hydroxy-4-ethoxy-1-iodo-trans-1-octene, followed by treatment with chlorotrimethylsilane and imidazole in dimethylformamide using the procedure of Example 74, and subsequent distillation, is productive of the subject compound.

EXAMPLES 78–82

By the method of Example 58 reaction of 1-trimethylsilyl-3-tetrahydropyranyloxy-1-propyne with n-butyllithium and subsequent treatment with the aldehydes listed in Table 7, below, provides the d,1-erythro-1-trimethylsilyl-3-tetrahydropyranyloxy-4-hydroxy-1-alkynes of the table.

TABLE 7

| Example | Starting Aldehyde | Product d,l-erythro-3-tetrahydropyranyloxy-4-hydroxy-1-trimethylsilyl-1-alkyne |
|---|---|---|
| 78 | n-butanol | d,l-erythro-1-trimethylsilyl-3-tetrahydropyranyloxy-4-hydroxy-1-heptyne |
| 79 | n-hexanal | d,l-erythro-1-trimethylsilyl-3-tetrahydropyranyloxy-4-hydroxy-1-nonyne |
| 80 | n-heptanal | d,l-erythro-1-trimethylsilyl-3-tetrahydropyranyloxy-4-hydroxy-1-decyne |
| 81 | 4-methyl-n-pentanal | d,l-erythro-1-trimethylsilyl-3-tetrahydropyranyloxy-4-hydroxy-7-methyl-1-octyne |
| 82 | 2-trans-n-pentenal | d,l-erythro-1-trimethylsilyl-3-tetrahydropyranyloxy-4-hydroxy-5-trans-en |

EXAMPLES 83–87

Hydrolysis of the 3-tetrahydropyranyloxy group of the d,l-erythro-1-trimethylsilyl-3-tetrahydropyranyloxy-4-hydroxy-1-alkynes listed in Table 8 below by the method described in Example 59, followed by conversion of the resulting d,l-erythro-1-trimethylsilyl-3,4-dihydroxy-1-alkyne to the corresponding d,l-erythro-1-trimethylsilyl-3,4-isopropylidenedioxy-1-alkyne by treatment with dimethoxypropane in the presence of perchloric acid by the method described in Example 60, followed by desilylation to the corresponding d,l-erythro-3,4-isopropylidenedioxy-1-alkyne by the procedure of Example 61 followed by treatment with disiamylborane, trimethylamine oxide, iodine, and sodium hydroxide solution by the method described in Example 62 provides the product d,l-erythro-1-iodo-3,4-isopropylidenedioxy-trans-1-alkenes of Table 8, below.

TABLE 8

| Example | Starting d,l-erythro-1-trimethylsilyl-3-tetrahydropyranyloxy-4-hydroxy-1-alkyne of Example | Product d,l-erythro-1-iodo-3,4-isopropylidenedioxy-trans-1-alkene |
|---|---|---|
| 83 | 78 | d,l-erythro-1-iodo-3,4-isopropylidenedioxy-trans-1-heptene |
| 84 | 79 | d,l-erythro-1-iodo-3,4-isopropylidenedioxy-trans-1-nonene |
| 85 | 80 | d,l-erythro-1-iodo-3,4-isopropylidenedioxy-trans-1-decene |
| 86 | 81 | d,l-erythor-1-iodo-3,4-isopropylidenedioxy-7-methyl-trans-octene |
| 87 | 82 | d,l-erythro-1-iodo-3,4-isopropylidenedioxy-trans,trans-1,5-octadiene |

EXAMPLES 88–92

Acetylation of the 4-hydroxy group of the d,l-erythro-1-trimethylsilyl-3-tetrahydropyranyloxy-4-hydroxy-1-alkynes listed in Table 9 below by the method described in Example 63, followed by hydrolysis of the resulting d,l-erythro-1-trimethylsilyl-3-tetrahydropyranyloxy-4-acetyloxy-1-alkynes to the corresponding d,l-erythro-1-trimethylsilyl-3-hydroxy-4-acetyloxy-1-alkynes by the method of Example 65, followed by epimerization to d,l-threo-1-trimethylsilyl-3-hydroxy-4-acetyloxy-1-alkynes by the method of Example 66 followed by hydrolysis by the method of Example 67 to give d,l-threo-3,4-dihydroxy-1-alkynes are converted to the corresponding d,l-threo-3,4-isopropylidenedioxy-1-alkynes by treatment with dimethoxypropane in the presence of perchloric acid by the method described in Example 68 followed by treatment with disiamylborane, trimethylamine oxide, iodine, and sodium hydroxide solution by the method described in Example 62 provides the product d,l-threo-3,4-isopropylidenedioxy-trans-1-alkenes of Table 9 below.

TABLE 9

| Example | Starting d,l-erythro-1-trimethylsilyl-3-tetrahydropyranyloxy-4-hydroxy-1-alkyne of Example | Product d,l-threo-1-iodo-3,4-isopropylidenedioxy-trans-1-alkene |
|---|---|---|
| 88 | 78 | d,l-threo-1-iodo-3,4-isopropylidenedioxy-trans-1-heptene |
| 89 | 79 | d,l-threo-1-iodo-3,4-isopropylidenedioxy-trans-1-nonene |
| 90 | 80 | d,l-threo-1-iodo-3,4-isopropylidenedioxy-trans-1-decene |
| 91 | 81 | d,l-threo-1-iodo-3,4-isopropylidenedioxy-trans-1,7-methyl-1-octene |
| 92 | 82 | d,l-threo-1-iodo-3,4-isopropylidenedioxy trans-1,5-trans-1-octadiene |

EXAMPLE 93

Preparation of 1-octyn-4-ol

A suspension of 24.3 g (1.0 mole) of magnesium in 90 ml of dry ether is stirred at room temperature under nitrogen with 100 mg of mercuric chloride. The reaction is initiated by the addition of 2 ml of propargyl bromide and maintained by the dropwise addition of a solution of 119.5 g (1.0 mole) of propargyl bromide and 107.7 g (1.25 mole) of valenaldehyde in 300 ml of dry ether. While the initial reaction is quite vigorous and is maintained at 30° C. only by cooling in an ice bath it may become necessary to heat the mixture to reflux temperature after about a third of the ether solution is added in order to maintain the reaction. After the addition is complete the reaction mixture is refluxed until most of the magnesium is dissolved (several hours) and the reaction mixture is decanted from excess magnesium into 1500 ml of stirred ice-cold ammonium chloride solution. The ether layer is separated and the aqueous layer is extracted three times with 300 ml portions of ether. The combined ether extract is washed with saturated sodium chloride solution, dried over magnesium sulfate and filtered. Evaporation of the ether under vacuum leaves about 115 g of yellow oil, which is distilled through a 15 cm Vigreaux column at 18 mm. The fraction boiling at 81°–82° C. is collected (36 g) and the higher-boiling and lower-boiling distillates may be redistilled to yield additional product. The infrared absorption spectrum shows at most a trace of allene (5.1 $\mu$) and gas-liquid partition chromatography shows a purity of about 98% for the main fraction.

EXAMPLES 94–97

The product 1-alkyn-4-ols of Table 10 below are prepared by treatment of the aldehydes listed in Table 10 with propargyl magnesium bromide by the procedure described above in Example 93.

TABLE 10

| Example | Starting Aldehyde | Product 1-alkyn-4-ol |
|---|---|---|
| 94 | n-hexaldehyde | 1-nonyn-4-ol |
| 95 | n-heptaldehyde | 1-decyn-4-ol |
| 96 | n-butyraldehyde | 1-heptyn-4-ol |
| 97 | 3-cis-hexenaldehyde* | 4-hydroxy-6-cis-ene-1-nonyne |

*M. Winter, Helv. Chim. Acta, 46, 1792 (1963).

EXAMPLE 98

Preparation of 4-triphenylmethoxy-1-octyne

A mixture of 10 g (0.08 moles) of 4-hydroxy-1-octyne [1. Crombie and A. G. Jacklin, J. Chem. Soc., 1632 (1957), also Example 93] and 30.75 g (0.09 moles) of triphenylmethyl bromide in 85 ml of dry pyridine is heated on the steam bath for 2 hours. The cooled mixture is treated with water and extracted with ether. The extract is washed successively with ice cold 2% hydrochloric acid, saturated sodium chloride solution, dried with magnesium sulfate, and taken to dryness. Column chromatography of the residue on Florisil affords an oil; $\lambda$ max 3.01, 4.72 (acetylenic hydrogen), 6.28, 9.65 and 14.25 $\mu$ (triphenylmethoxy group).

EXAMPLE 99

Preparation of 4-triphenylmethoxy-1-hexyne

A stirred solution of 9.81 g (0.10 moles) of 4-hydroxy-1-hexyne and 33.5 g (0.12 moles) of triphenylmethyl chloride in 100 ml of dry pyridine is heated at reflux for 2 hours. The cooled mixture is treated with water and extracted with a hexane-ether mixture. The extract is washed successively with water and saturated sodium chloride solution, dried over magnesium sulfate, and concentrated. Column chromatography of the residue on Florisil gives an oil, max. 3290 (acetylenic hydrogen), 1600, 1030 and 705 cm-1 (triphenylmethoxy group).

EXAMPLES 100–106

The triphenylmethoxy substituted 1-alkynes listed in Table 11 below are prepared by the method of Example 98 from triphenylmethyl bromide and the corresponding hydroxy substituted 1-alkynes, appropriate literature references to which are provided in the table.

TABLE 11

| Example | Reference to Starting Hydroxy Substituted 1-Alkyne | Product Triphenylmethoxy Substituted 1-Alkyne |
|---|---|---|
| 100 | Reference 1 | 4-triphenylmethoxy-1-pentyne |
| 101 | Reference 1 (Example 96) | 4-triphenylmethoxy-1-heptyne |
| 102 | Reference 1 | 4-triphenylmethoxy-5-methyl-1-hexyne |
| 103 | Reference 2 (Example 94) | 4-triphenylmethoxy-1-nonyne |
| 104 | Reference 3 (Example 95) | 4-triphenylmethoxy-1-decyne |
| 105 | Reference 4 | 4-triphenylmethoxy-5-ethyl-1-heptyne |
| 106 | Example 97 | 4-triphenylmethoxy-6-cis-ene-1-nonyne |

References:
1 G. Fontaine, et al., Bull. Soc. Chem. France, 1447 (1963).
2 S. Abe and K. Sato, Bull. Soc. Chem. Japan, 29, 88 (1956); Chem. Abstr., 50, 13737 (1956).
3 L. Crombie and A. G. Jacklin, J. Chem. Soc., 1622 (1957);
4 Nobuharra, Akio, Chem. Abstr., 70, 3219 (1969).

EXAMPLE 107

Preparation of 1-iodo-4-triphenylmethoxy-trans-1-octene

To a stirred suspension of 1.78 g (0.074 mole) of sodium borohydride in 200 ml of dry glyme at −5° C. under nitrogen is added 15.8 g (0.22 mole) of 2-methyl-2-butene and 16.2 g. (0.11 mole) of boron trifluoride etherate, and the mixture is stirred for 2 hours at −5° C. to 0° C. A solution of 37.5 g (0.10 mole) of 4-trityloxy-1-octyne (Example 98) in 50 ml of glyme is added to the cold solution during 5–10 minutes, and the solution is allowed to warm to 20° C. during 1.5 hours. The reaction mixture is cooled to 0° C. and 30 g. (0.4 mole) of dry trimethylamine-N-oxide is added during 5 minutes. On removing the cooling bath the temperature rises to 40° C. and the mixture is kept between 30°–40° C. for 1.5 hours. The suspension is poured rapidly into one liter of ice cold 15% sodium hydroxide solution during good stirring and a solution of 80 g of iodine in 200 ml of tetrahydrofuran is added immediately. Stirring is continued for 30 minutes without further cooling and the organic layer is separated. The aqueous layer is extracted with three 200 ml protions of ether and the combined organic layers are washed successively with water, 5% sodium thiosulfate solution and saturated sodium chloride, dried over magnesium sulfate, filtered and evaporated to yield 50 g of yellow oil. The bulk of the oil is dissolved in hexane and, after decantation from a gummy solid the hexane solution is percolated through a 5.1 cm diameter column of 1500 g. of alumina with additional hexane. Fractions containing the desired product are concentrated to a pale yellow oil (33 g) which has n.m.r. and infrared spectra characteristics of the desired product.

EXAMPLES 108–115

Treatment of the triphenylmethoxy substituted 1-alkynes listed in Table 12 below the disiamylborane, prepared in situ from 2-methyl-2-butene, boron, trifluoride and sodium borohydride, followed by trimethylamine N-oxide, and then sodium hydroxide and iodine - all by the procedure described in Example 107 above furnishes the product triphenylmethoxy substituted 1-iodo-1-trans-alkenes of the table.

TABLE 12

| Example | Starting Triphenylmethoxy Substituted 1-Alkyne of Example | Product 1-Iodo-triphenylmethoxysubstituted-1-trans-alkene |
| --- | --- | --- |
| 108 | 99 | 1-iodo-4-triphenylmethoxy-1-trans-hexene |
| 109 | 100 | 1-iodo-4-triphenylmethoxy-1-trans-pentene |
| 110 | 101 | 1-iodo-4-triphenylmethoxy-1-trans-heptene |
| 111 | 102 | 1-iodo-4-triphenylmethoxy-5-methyl-1-trans-hexene |
| 112 | 103 | 1-iodo-4-triphenylmethoxy-1-trans-nonene |
| 113 | 104 | 1-iodo-4-triphenylmethoxy-1-trans-decene |
| 114 | 106 | 1-iodo-4-triphenylmethoxy-1-trans-6-cis-nonadiene |

EXAMPLES 116-124

The starting aldehydes or ketones of Table 13 below are converted to the product 1-alkyn-4-ols of the table by the procedure described in Example 93.

TABLE 13

| Example | Starting Aldehyde or Ketone | Product 1-Alkyn-4-ol |
| --- | --- | --- |
| 115 | 2-octanone | 4-methyl-4-hydroxy-1-decyne |
| 116 | trans-2-hexenal | 4-hydroxy-5-trans-nonen-1-yne |
| 117 | 2,2-dimethylhexanal | 5,5-dimethyl-4-hydroxy-1-nonyne |
| 118 | z-heptanone | 4-methyl-4-hydroxy-1-nonyne |
| 119 | 2,2-dimethylpentanal | 5,5-dimethyl-4-hydroxy-1-octyne |
| 120 | 2-methylpentanal | 5-methyl-4-hydroxy-1-octyne |
| 121 | 2-methylhexanal | 5-methyl-4-hydroxy-1-nonyne |
| 122 | 2-hexanone | 4-hydroxy-4-methyl-1-octyne |
| 123 | trans-3-hexen-2-one[a] | 4-hydroxy-4-methyl-5-trans-octen-1-yne |
| 124 | trans-2-pentenal[b] | 4-hydroxy-5-trans-octen-1-yne |
| 124a | trans-2-heptenal[b] | 4-hydroxy-5-trans-decen-1-yne |

[a] G. Sturtz, Bull. Soc. Chim. Fr., 1967, 2477.
[b] R. I. Hoaglin and D. M. Hirsh, U.S. Pat. No. 2,628,257; Chem. Abstr., 48, 1423e (1954).

EXAMPLE 125

Preparation of 4-methyl-4-trimethylsilyloxy-1-octyne

To a stirred solution of 75.4 g (0.537 moles) of 4-hydroxy-4-methyl-1-octyne (Example 122), 104.9 g (1.54 moles) of imidazole, and 325 ml of dimethylformamide is added 65.2 g (0.60 moles) of chlorotrimethylsilane. After standing overnight the mixture is poured into 800 ml of hexane. The mixture is washed thoroughly with water followed by sodium bicarbonate solution and brine. The solution is dried over magnesium sulfate, filtered, and evaporated to give a liquid, p.m.r spectrum, δ 1.26 (singlet, 3, C$\underline{H}_3$), 1.92 (triplet, 1, H$\underline{C}$), 2.30 (doublet, 2, C$\underline{H}_2$).

EXAMPLES 126-129

The 1-alkyn-4-ols of Table 14 are converted to the product trimethylsilyl ethers of the table by treatment with chlorotrimethylsilane according to the procedure described in Example 125.

TABLE 14

| Example | Starting 1-Alkyn-4-ol | Product Trimethylsilyl Ether |
| --- | --- | --- |
| 126 | 5,5-dimethyl-4-hydroxy-1-nonyne (Ex. 117) | 5,5-dimethyl-4-trimethylsilyloxy-1-nonyne |
| 127 | 4-methyl-4-hydroxy-1-nonyne (Ex. 118) | 4-methyl-4-trimethylsilyloxy-1-nonyne |
| 128 | 5,5-dimethyl-4-hydroxy-1-octyne (Ex. 119) | 5,5-dimethyl-4-trimethylsilyloxy-1-octyne |
| 129 | 4-hydroxy-4-methyl-5-trans-octen-1-yne (Ex. 123) | 4-methyl-5-trimethylsilyloxy-5-trans-octen-1-yne |
| 129a | 4-hydroxy-4-methyl-1-decyne (Ex. 124a) | 4-methyl-4-trimethylsilyloxy-1-decyne |

EXAMPLE 130

Preparation of 1-iodo-4-hydroxy-4-methyl-trans-1-octene

To a stirred solution of 400 ml of 0.5 M bis-(3-methyl-2-butyl)borane in glyme, prepared from sodium borohydride, 2-methyl-2-butene, and boronitrifluoride etherate as in Example 107, is added 63.7 g (0.30 moles) of 4-methyl-4-trimethylsilyloxy-1octyne (Example 125) at −10° C. The solution is stirred at ambient temperature for 2.5 hours, cooled to −10° C., and treated during 30 minutes with 158 g (2.1 moles) of solid trimethylamine oxide with cooling. The mixture is stirred at ambient temperature for 2 hours and then poured into a stirred, ice-cold solution of 15% aqueous sodium hydroxide; the stirred mixture is treated immediately with a solution of 426 g (1.68 moles) of iodine in 1100 ml of tetrahydrofuran. After 4 hours the mixture is extracted with ether. The extract is washed successively with water, aqueous sodium thiosulfate, and brine and dried over magnesium sulfate. The extract is concentrated, and the residue is subjected to chromatography on silica gel with hexane to provide an oil, p.m.r. (CDCl$_3$): δ 1.18 (singlet, 4-C$\underline{H}_3$ group).

EXAMPLES 131-134

The 4-trimethylsilyloxy-1-alkynes of Table 15 are converted to the 4-hydroxy-1-iodo-trans-1-octenes of the table by the procedure described in Example 130.

TABLE 15

| Example | Starting 4-Trimethylsilyloxy-1-octyne of Example | Product 4-Hydroxy-1-iodo-trans-1-octene |
| --- | --- | --- |
| 131 | 126 | 1-iodo-5,5-dimethyl-4-hydroxy-trans-1-nonene |
| 132 | 127 | 1-iodo-4-methyl-4-hydroxy-trans-1-nonene |
| 133 | 128 | 1-iodo-5,5-dimethyl-4-hydroxy-trans-1-octene |
| 134 | 129 | 1-iodo-4-methyl-4-hydroxy- |

TABLE 15-continued

| Example | Starting 4-Trimethylsilyloxy-1-octyne of Example | Product 4-Hydroxy-1-iodo-trans-1-octene |
|---|---|---|
| 134a | 129a | trans,trans-1,5-octadiene 1-iodo-4-methyl-4-hydroxy-trans-1-decene |

EXAMPLE 135

Preparation of 1-iodo-4-methyl-4-trimethylsilyloxy-trans-1-octene

To a stirred mixture of 24.5 g (55.6 mmoles) of 1-iodo-4-hydroxy-4-methyl-trans-1-octene (Example 130), 13.6 g (200 mmoles) of imidazole, and 75 ml of dimethylformamide is added 10.9 g (100 mmoles) of chlorotrimethylsilane. After standing overnight the mixture is poured into 250 ml of hexane. The mixture is washed thoroughly with water followed by brine and dried over magnesium sulfate. After removal of the solvent, the product is distilled to give a colorless liquid, bp 67.5°–68° C. (0.07 mm).

EXAMPLES 136–139

The 1-iodo-4-hydroxy-trans-1-alkenes of Table 16 are converted to the product trimethylsilyl ethers of the table according to the procedure described in Example 135.

TABLE 16

| Example | Starting 1-Iodo-4-hydroxy-trans-1-alkene of Example | Product Trimethylsilyl Ether |
|---|---|---|
| 136 | 131 | 1-iodo-5,5-dimethyl-4-trimethylsilyloxy-trans-nonene |
| 137 | 132 | 1-iodo-4-methyl-4-trimethylsilyloxy-trans-1-nonene |
| 138 | 133 | 1-iodo-5,5-dimethyl-4-trimethylsilyloxy-trans-1-octene |
| 139 | 134 | 1-iodo-4-methyl-4-trimethylsilyloxy-trans,trans-1,5-octadiene |
| 139a | 134a | 1-iodo-4-methyl-4-trimethylsilyloxy-trans-1-decene |
| 139b | 134b | 1-iodo-4-methyl-4-trimethylsilyloxy-trans-1-decene |

EXAMPLE 140

Preparation of 4-benzoyloxy-1-octyne

To a stirred solution of 63. g (0.50 moles) of 1-octyn-4-ol (Example 93) in 500 ml of pyridine is added 77 g (0.55 moles) of benzoyl chloride. After stirring for 1.5 hours the mixture is treated with 10 ml of water, allowed to stand for 15 minutes, and concentrated. A solution of the residue in ether is washed successively with ice-cold hydrochloric acid, water, sodium bicarbonate solution, and brine. The solution is dried over magnesium sulfate, filtered through Celite, and concentrated to give an oil, λmax. 3240 (terminal acetylene) and 1730 cm$^{-1}$ (benzyloxy group).

EXAMPLE 141

Stereoselective Hydrolysis of Racemic 4-benzoyloxy-1-octyne by Rhizopus arrhizus An agar slant of R. arrhizus (MUMF 1638) is used to inoculate 7 shake flasks (250 ml Erlenmeyer). Each flask contains 50 ml of a medium consisting of 2% Edamine, 2% glucose, and 0.72% corn steep liquor in water with pH adjusted to 7.0. A total of 14 such flasks are incubated on a rotary shaker at 28° C. After 72 hours incubation, 50 mg of racemic 4-benzoyloxy-1-octyne (Example 135) in 0.1 ml of acetone is added to each flask. After 28 hours the flasks are harvested and worked up by extraction of the whole mash with an equal volume of chloroform. The combined extracts are dried over magnesium sulfate and concentrated. The resulting oil is chromatographed on a column of silica gel with hexane progressively enriched in ethyl acetate.

From fractions 3–6 is obtained 150 mg of colorless oil, identical to 4-benzoyloxy-1-octyne, $[\alpha]_D^{25} = 5 \pm 1.0°$ (C=0.91, ethyl acetate). This compound has the (S)-configuration.

From fractions 13–20 is obtained 75 mg of colorless oil, identical to 4-hydroxy-1-octyne, $[\alpha]_D^{25} = -17 \pm 1.0°$ (C=0.77, ethyl acetate). This compound has the (R)-configuration.

The strain of R. arrhizus utilized in this experiment is a higher fungus which grows steadily on a variety of artificial media at 20°–25° C. In this study of the taxonomic aspects of the culture, Petri dishes of potato-dextrose, malt extract, and cornmeal agars were inoculated and incubated at ambient room temperature for 10 days. Observations of cultural and morphological characteristics are recorded in the description below:

Colonies on Petri dishes of potato-dextrose agar growing rapidly, covering the agar surface in 3–5 days and producing a thick, loose mat of grayish mycelium. Colony surface characterized by abundant black sporangia. Colony reverse grayish white. Colonies on malt extract agar growing rapidly, covering the agar surface in 3–5 days. Mycelial mat thick, grayish-yellow. Colony surface becoming brownish-black from masses of sporangia. Colony reverse yellowish. Colonies on cornmeal agar very thin, whitish; spreading across agar surface. Cultures transparent with relatively few sporangia porduced. Visibility of micromorphology is good on this mediu. Rhizoids produced sparingly along stoloniferous hyphae. Generally two to three sporangiophores arose from rhizoids. Walls of sporangiophores olive brown, 14.0–20.0 μm in width at base, tapering slightly to apex; 0.5–1.5 mm in length. Sporangiophores terminated by spherical sporangia, 130–225 μm in diameter. Columellae hemispherical, 3–50 μm high by 50–70 μm wide. Spores brownish when mature, 6.0–8.5 μm × 4.5–6.0 μm. Spore walls conspicuously marked by longitudinal striations.

EXAMPLE 142

Preparation of (S)-4-hydroxy-1-octyne

A solution of 1.15 g (5.0 mmoles) of (S)-4-benzoyloxy-1-octyne (Example 141) and 1.40 g (25 mmoles) of potassium hydroxide in 50 ml of 10:1 methanol-water is allowed to stand at room temperature for 24 hours. The bulk of the methanol is evaporated at room temperature, and the mixture is extracted with ether. The extract is washed with brime, dried over magnesium sulfate, and evaporated to give a colorless oil, identical to 4-hydroxy-1-octyne $[\alpha]_D^{25} = +17 \pm 1.0°$ (C=0.77, ethyl acetate). This compound has the (S)-configuration.

EXAMPLES 143-148

The starting 1-alkyn-4-ols of Table 17 below are converted to the triphenylmethoxy substituted 1-alkynes by the method of Example 98.

TABLE 17

| Example | Starting 1-Alkyn-4-ol of Example | Product Triphenyl-methoxy Substituted 1-Alkyne |
|---|---|---|
| 143 | 116 | 4-triphenylmethoxy-5-trans-nonen-1-yne |
| 144 | 120 | 5-methyl-4-triphenyl-methoxy-1-octyne |
| 145 | 121 | 5-methyl-4-triphenyl-methoxy-1-nonyne |
| 146 | 124 | 4-triphenylmethoxy-5-trans-octen-1-yne |
| 147 | 141 | (R)-4-triphenylmeth-oxy-1-octyne |
| 148 | 142 | (S)-4-triphenylmeth-oxy-1-octyne |
| 148a | 124a | 4-triphenylmethoxy-5-trans-decen-1-yne |

EXAMPLES 149-154

The product triphenylmethoxy substituted 1-iodo-1-trans-alkenes of Table 18 below are prepared from the starting triphenylmethoxy substituted 1-alkynes of the table by the procedure described in Example 107.

TABLE 18

| Example | Starting Triphenyl-methoxy Substituted 1-Alkyn of Example | Product Triphenylmethoxy Substituted 1-Iodo-trans-1-alkene |
|---|---|---|
| 149 | 143 | 1-iodo-4-triphenylmethoxy-trans,trans-1,5-nonadiene |
| 150 | 144 | 1-iodo-5-methyl-4-triphenylmethoxy-trans-1-octene |
| 151 | 145 | 1-iodo-5-methyl-4-triphenylmethoxy-trans-1-nonene |
| 152 | 146 | 1-iodo-4-triphenylmethoxy-trans,trans-1,5-octadiene |
| 153 | 47 | (R)-1-iodo-4-triphenylmethoxy-1-trans-octene |
| 154 | 148 | (S)-1-iodo-4-triphenylmethoxy-1-trans-octene |
| 154a | 148a | 1-iodo-4-triphenylmethoxy-trans,trans-1,5-decadiene |

EXAMPLE 155

Preparation of ethyl-p-fluorophenoxy-acetate

To a stirred solution of 50 g (0.29 moles) of p-fluorophenoxy acetic acid in one liter of absolute ethanol is added 10 ml of sulfuric acid. The mixture is heated to reflux for 18 hours, cooled to room temperature, and evaporated under vacuum. It is then poured onto 300 g of ice, extracted twice with 500 ml of ether, washed twice with 250 ml of a saturated solution of sodium bicarbonate, 100 ml of saturated sodium chloride solution, dried with magnesium sulfate, filtered and evaporated under vacuum giving 58 g of an oil. This is crystallized from 50 ml of hexane at −25° C. to give 55 g (90%) of the subject product as colorless crystals, mp 32°-33° C.

EXAMPLE 156

Preparation of p-fluorophenoxy acetaldehyde

To a stirred solution of 1.98 g (10 mmoles) of ethyl-p-fluorophenoxy acetate (Example 155) in 15 ml of dry toluene, cooled to −78° C., under argon, is added, dropwise over 30 minutes, 8 ml of a 1.4 M solution of diisobutylaluminum hydride in toluene (11 mmoles). The mixture is stirred for 2 hours at −78° C., 1 ml of methanol is added, followed by 5 ml of water, dropwise. The gel formed is filtered through Celite and washed with 100 ml of ether, portionwise. The organic phase is separated, washed twice with 25 ml of a saturated brine solution, dried with magnesium sulfate, filtered, and evaporated. The oil obtained is distilled at 71°-73° C. (0.1 mm) to give 600 mg (45%) of the subject product as a colorless liquid.

EXAMPLE 157

Preparation of 3-hydroxy-4-p-flurorphenoxy-1-butyne

Acetylene gas, dried by passing through a trap containing sulfuric acid, is bubbled at a moderate rate, through 5 ml of vigorously stirred tetrahydrofuran, for 15 minutes. To this acetylenic solution, is then added dropwise, with continued passage of acetylene, 3.5 ml of a 2.4 M solution of n-butylmagnesium chloride in tetrahydrofuran (8.4 mmoles) over 45 minutes. The mixture is stirred a further 15 minutes, and a solution of 580 mg (3.9 mmoles) of p-fluorophenoxy acetaldehyde (Example 156) in 3 ml of tetrahydrofuran is added dropwise over 15 minutes. This solution is stirred for 2 more hours, with passage of acetylene, poured into 50 ml of a saturated solution of ammonium chloride, extracted twice with 50 ml of ether, washed with 10 ml of ammonium chloride solution, dried with magnesium sulfate, filtered, and evaporated. The crude subject product is purified by sublimation at 75° C. (0.1 mm) for 5 hours to give 330 mg (48%) of white crystals, mp 46°-47° C.

EXAMPLE 158

Preparation of 4-p-fluorophenoxy-3-trimethylsilyloxy-1-butyne

To a 0° C. solution of 10 g (55 mmoles) of 3-hydroxy-4-p-fluorophenoxy-1-butyne (Example 157) in 75 ml of dry dimethylformamide and 88 g (130 mmoles) of imidazole is added dropwise, with stirring, 7.5 g (68 mmoles) of chlorotrimethylsilane. The mixture, while under an argon atmosphere, is stirred at room temperature for 18 hours, and then poured into 150 ml of hexane and 100 ml of ice-water. The organic phase is separated, washed with 50 ml of a brine solution, dried with magnesium sulfate, and evaporated under vacuum. This crude product is distilled under vacuum at 0.1 mm (bp 73°-75° C.), to give 12.2 g (91%) of the subject compound as a colorless oily liquid.

EXAMPLE 159

Preparation of 1-tri-n-butylstannyl-4-p-fluorophenoxy-3-trimethyl-silyloxy-trans-1-butene A mixture of 2.52 g (10 mmoles) of 3-trimethyl-silyloxy-4-p-fluorophenoxy-1-butyne (Example 158), 2.91 g (10 mmoles) of tri-n-butyl-tin hydride, and 10 mg of azobisisobutyronitrile is heated under an argon atmosphere, with stirring, for 2 hours at 140° C. Afer cooling to room temperature, the crude reaction mixture is fractionally distilled at 180°–185° C. (0.05 mm), to give 4.6 g (85%) of the subject product as a colorless liquid.

EXAMPLES 160–162

The product esters of Table 19 below are obtained by the procedure described in Example 155.

TABLE 19

| Example | Starting Aryloxy Acid | Product Aryloxy Ethyl Ester |
|---------|----------------------|------------------------------|
| 160 | m-chlorophenoxy-acetic acid | ethyl-m-chlorophenoxy-acetate |
| 161 | 3,4-dichlorophenoxyacetic acid | ethyl-3,4-dichlorophenoxyacetate |
| 162 | phenoxyacetic acid | ethyl phenoxyacetate |

EXAMPLE 163

Preparation of ethyl-m-trifluoromethylphenoxy-acetate

A mixture of 100 g (0.618 mole) of α,α,α-trifluoro-m-cresol, 106 g (0.632 mole) of ethyl bromoacetate, 87.5 g (0.632 mole) of potassium carbonate, and 1500 ml of acetone is stirred at reflux for 4 hours, and at room temperature for 18 hours. The mixture is filtered, evaporated under vacuum on a rotorary evaporator at 45° C. and at 85° C. (0.1 mm) to remove excess ethyl bromoacetate. The reaction mixture is taken up in 500 ml of ether, washed three times with 100 ml each of 0.1 M potassium carbonate, once with 100 ml of water, 100 ml of 0.01 M hydrochloric acid, and 100 ml of water. It is then dried with magnesium sulfate, filtered and evaporated, giving 142 g of the crude product. This is fractionally distilled at 73°–75° C. (0.1 mm) to give 124 g of the purified subject product as a colorless liquid.

EXAMPLES 164–166

The product esters of Table 20 are obtained by treating the starting phenols with ethyl bromoacetate by the procedure of Example 162.

TABLE 20

| Example | Starting Phenol | Product Ester |
|---------|-----------------|---------------|
| 164 | p-bromophenol | ethyl p-bromophenoxy-acetate |
| 165 | 4-t-butylphenol | ethyl 4-t-butylphenoxy-acetate |
| 166 | p-methoxyphenol | ethyl p-methoxyphenoxy-acetic acid |

EXAMPLES 167–173

Following the procedure of Example 156, the starting esters of Table 21 are treated with diisobutylaluminum hydride to provide the product aldehydes of the table.

TABLE 21

| Example | Starting Ester | Product Aldehyde |
|---------|----------------|------------------|
| 167 | 163 | m-trifluoromethylphenoxy acetaldehyde |
| 168 | 164 | p-bromophenoxy acetaldehyde |
| 169 | 165 | 4-t-butylphenoxy acetaldehyde |
| 170 | 166 | p-methoxyphenoxy acetaldehyde |
| 171 | 160 | m-chlorophenoxy acetaldehyde |
| 172 | 161 | 3,4-dichlorophenoxy acetaldehyde |
| 173 | 162 | phenoxyacetaldehyde |

EXAMPLES 174–180

Following the procedure of Example 156, treatment of the starting aldehyde of Table 22 with acetylene magnesium chloride provides the product alkynes of Table 22.

TABLE 22

| Example | Starting Aldehyde | Product Aryloxy Alkyne |
|---------|-------------------|------------------------|
| 174 | 167 | 3-hydroxy-4-m-trifluoromethyl-phenoxy-1-butyne |
| 175 | 168 | 3-hydroxy-4-p-bromophenoxy-1-butyne |
| 176 | 169 | 3-hydroxy-4-t-butylphenoxy-1-butyne |
| 177 | 170 | 3-hydroxy-4-p-methoxyphenoxy-1-butyne |
| 178 | 171 | 3-hydroxy-4-m-chlorophenoxy-1-butyne |
| 179 | 172 | 3-hydroxy-4-(3,4-dichlorophenoxy)-1-butyne |
| 180 | 173 | 3-hydroxy-4-phenoxy-1-butyne |
| 180a | a | 3-hydroxy-5-phenyl-1-pentyne |
| 180b | b | 3-hydroxy-5-(p-chlorophenyl)-1-pentyne |
| 180c | c | 3-hydroxy-5-(p-methoxyphenyl)-1-pentyne |
| 180d | d | 3-hydroxy-5-(m-trifluoromethylphenyl)-1-pentyne | a hydrocinnamaldehyde[1]
b p-chlorohydrocinnamaldehyde[1]
c p-methoxyhydrocinnamaldehyde[1]
d m-trifluoromethylhydrocinnamaldehyde[2]
[1]Billman, et al., Synthetic Communications, 1, 127–131 (1971).
[2]Lednicer, Journ. Med. Chem., 11, 1258 (1968).

EXAMPLES 181–186

Treatment of the starting alkynes of Table 23 by the procedure of Example 158 followed by treatment of the procedure of Example 159 provides the product (E) 1-tri-n-butyltin-1-alkenes of the table.

TABLE 23

| Example | Starting Alkyne | Product (E)-1-tri-n-butyltin-1-alkene |
|---------|-----------------|---------------------------------------|
| 180 | 174 | (E)-1-tri-n-butylstannyl-3-trimethylsilyloxy-4-m-trifluoromethylphenoxy-1-butene |
| 181 | 175 | (E)-1-tri-n-butylstannyl-3-trimethylsilyloxy-4-p-bromophenoxy-1-butene |
| 182 | 176 | (E)-1-tri-n-butylstannyl-3-trimethylsilyloxy-4-t-butylphenoxy-1-butene |
| 183 | 177 | (E)-1-tri-n-butylstannyl-3-trimethylsilyloxy-4-p-methoxyphenoxy-1-butene |
| 184 | 178 | (E)-1-tri-n-butylstannyl-3-trimethylsilyloxy-4-m-chlorophenoxy-1-butene |
| 185 | 179 | (E)-1-tri-n-butylstannyl-3-trimethylsilyloxy-3,4-dichlorophenoxy-1-butene |
| 186 | 180 | (E)-1-tri-n-butylstannyl-3-trimethylsilyloxy-4-phenoxy-1-butene |
| 186a | 48 | (E)-1-tri-n-butylstannyl-4,4-trimethylene-3-trimethylsilyloxy-(Z)-6-octadiene |
| 186B | 180A | (E)-1-tri-n-butylstannyl-3-trimethylsilyloxy-5-phenyl-1-pentene |
| 186c | 180b | (E)-1-tri-n-butylstannyl-3-trimethylsilyloxy-5-(p-chlorophenyl)-1-pentene |
| 186d | 180c | (E)-1-tri-n-butylstannyl-3-trimethylsilyloxy-5-(p-methoxyphenyl)-1-pentene |
| 186e | 180d | (E)-1-tri-n-butylstannyl-3-trimethylsilyloxy-5-(m-trifluoromethylphenyl)-1-pentene |

EXAMPLE 187

Preparation of 1-chloro-1-octen-3-one

This compound is prepared according to the procedure of Price and Pappalardo [C. C. Price and J. A. Pappalardo, Org. Syn, 32, 27 (1952)] from hexanoyl chloride, acetylene, and aluminum chloride in 94% yield, bp 51°-52° C. (0.1 mm); λ max 1680, 1595, 941 cm$^{-1}$.

EXAMPLE 188

Preparation of 1-iodo-1-octen-3-one

A mixture of 25 g (0.16 moles) of 1-chloro-1-octen-3-one (Example 187) and 35 g (0.23 moles) of sodium iodide in 200 ml of reagent acetone is stirred at the reflux temperature for 18 hours. The cooled mixture is filtered and the mother liquor taken to dryness. The residual oil is dissolved in benzene and the solution is washed with 5% sodium thiosulfate solution, saturated sodium chloride solution, dried and taken to dryness. The residual oil is crystallized from hexane to give 26 g of a white solid, mp 35°-37° C; λ max 1670, 950 cm$^{-1}$.

EXAMPLE 189

Preparation of 3-hydroxy-1-iodo-3-methyl-1-octene

To a Grignard solution prepared from 1.05 g (0.41 moles) of magnesium and 6.2 g (0.435 moles) of methyl iodide in 30 ml of dry ether under argon is added dropwise 10 g of 1-iodo-1-octen-3-one (Example 183) in 45 ml of ether. The resulting solution is stirred at ambient temperature for one hour. After the addition of 75 ml of saturated ammonium chloride the ether layer is separated and the aqueous layer is separated and the aqueous layer is extracted several times with ether. The combined ether extracts are washed successively with ammonium chloride and water, dried and taken to dryness to give 9.24 g of product as an oil; λ max 2.89, 3.23, 6.24 and 10.5.

EXAMPLE 190

Preparation of 1-iodo-3-methyl-3-trimethylsilyloxy-1-octene

To a stirred solution of 11.7 g of 3-hydroxy-1-iodo-3-methyl-1-octene (Example 184) and 7.4 g of imidazole in 45 ml of dry dimethylformamide is added dropwise 5.98 g of trimethylsilylchloride at 0° C. under argon atmosphere. After stirring at 0° C. for an additional 15 minutes, the solution is stirred at ambient temperature for 18 hours. The reaction mixture is poured into 600 ml of hexane and the resulting solution washed with water, saturated sodium chloride solution, dried over anhydrous magnesium sulfate and taken to dryness to furnish 14.7 g of oil. Distillation affords 13.4 g of clear oil; bp 65° C. (0.05 mm); λ max 6.21, 8.00, 9.90, 10.51, 11.90, 13.2μ.

EXAMPLE 190a

Preparation of 1-iodo-3-methyl-3-trimethylsilyloxy-1-decene

Treatment of octanoylchloride by the procedures of Example 187 followed by treatment of the resulting 1-chloro-1-decen-3-one by the procedure of Example 188 followed by treatment according to Examples 189 and 190 is productive of the named compound.

EXAMPLE 191

Preparation of 4-trimethylsiloxy-1-octyne

To a cold solution of 166 g of 4-hydroxy-1-octyne [Prostaglandins, 10, 289 (1975)], and 240 g of imidazole in one liter of dimethylformamide is added dropwise 202 g of chlorotrimethylsilane. The mixture is allowed to stand at room temperature for 2 to 3 days. The mixture is partitioned with water and hexane. The hexane layer is washed with brine dried over magnesium sulfate, and concentrated. Distillation of the residue gives a colorless liquid, bp 38° C. (0.2 mm).

EXAMPLE 192

Preparation of 1-iodo-4-trimethylsiloxy-trans-1-octene

To a stirred solution of 0.20 moles of freshly prepared bis-(3-methyl-2-butyl)borane in 300 ml of tetrahydrofuran at 0°-5° C. is added dropwise a solution of 19.8 g of 4-trimethylsilyloxy-1-octyne in 30 ml of tetrahydrofuran. The resulting mixture is stirred at ambient temperature for several hours, cooled in an ice bath, and treated with 53 g of trimethylamine oxide. The mixture is stirred several hours at 25°-40° C. and then poured into 2 liters of 15% sodium hydroxide. The resulting mixture is treated immediately with a solution of 140 g of iodine in 300 ml of tetrahydrofuran. After 0.5 hour the organic phase is separated and the aqueous phase is extracted with ether. The combined organic layers are washed with water, sodium thiosulfate solution, and brine; dried over magnesium sulfate; and concentrated to give an oil pmr spectrum (CDCl$_3$): 6.2 (d, IC$\underline{H}$=) and 6.7 (quintuplet, =C$\underline{H}$-).

EXAMPLE 193

Preparation of 4-hydroxy-1-iodo-trans-1-octene

A 23 g portion of 1-iodo-4-trimethylsilyloxy-1-octene is dissolved in a mixture of 200 ml of glacial acetic acid, 100 ml of tetrahydrofuran, and 50 ml of water. Concentration provides the named product.

EXAMPLE 194

Preparation of 4-trimethylsiloxy-4-vinyl-1-iodo-trans-1-octene

To a stirred solution of 456 mg of 4-hydroxy-4-vinyl-1-iodo-trans-1-octene and 320 mg of imidazole in 1.0 ml of dimethylformamide is added 0.23 ml of chlorotrimethylsilane during 3 minutes. The mixture is stirred at room temperature for 22 hours and partitioned with a mixture of cold hexane and water. The hexane layer is washed repeatedly with water and then brine, dried over magnesium sulfate, and concentrated to give an oil, pmr spectrum (CDCl$_3$): 0.13 (s, trimethylsiloxy group) and 2.32 (d, =CHCH$_2$).

EXAMPLE 195

Preparation of n-butyl cyclopropyl ketone

To a vigorously-stirred solution of 31.0 g of cyclopropanecarboxylic acid in 330 ml of ether is added a solution of n-butyllithium (748 mmoles) in about 750 ml of 2:1 ether-hexane during one hour at 5°-10° C. The resulting suspension is diluted with 300 ml of ether and stirred at room temperature for 2 hours and at reflux for 2 hours. The mixture is cooled and poured into several portions of 1:1 ice:4 N hydrochloric acid. The ethereal phases are combined and washed with brine, sodium carbonate solution, and brine. The extract is dried over magnesium sulfate and concentrated. The residue is distilled to provide a liquid, bp-102°-104° C. (80 mm), pmr spectrum (CDCl$_3$): δ 2.55 (triplet, -C$\underline{H}_2$CO-).

EXAMPLE 196

Preparation of 4-cyclopropyl-4-hydroxy-1-octyne

To a stirred, refluxing suspension of amalgum prepared from 6.2 g of magnesium and 50 mg of mercuric chloride suspended in 60 ml of ether is added a solution of a mixture of 30.4 g of n-butyl cyclopropyl ketone (Example 189) and 29.8 g of propargyl bromide in 65 ml of ether during 60 minutes. After reaction at reflux temperature for an additional 30 minutes, the mixture is cooled to 0° C. and treated with 35 ml of saturated ammonium chloride. The mixture is diluted with ether and filtered through Celite. The filtrate is washed with brine, dried over potassium carbonate, and concentrated. The residue is distilled to provide a liquid, δ 0.43 (cyclopropyl hydrogens), 2.07 (triplet, $\underline{H}$C≡C), and 2.44 (doublet, C≡CC$\underline{H}_2$).

EXAMPLE 197

Preparation of 4-cyclopropyl-4-trimethylsiloxy-1-octyne

To a stirred solution of 27.8 g of 4-cyclopropyl-4-hydroxy-1-octyne (Example 190) and 33.3 g of imidazole in 130 ml of dimethylformamide at 5° C. is added 24 ml of chlorotrimethylsilane during 5 minutes. The solution is stirred at ambient temperature for 17 hours and then partitioned with 600 ml of hexane and 250 ml of ice water. The hexane phase is separated and washed successively with water and brine. The solution is dried over magnesium sulfate and evaporated to give a liquid, pmr spectrum (CDCl$_3$): δ 0.12 (singlet, trimethylsiloxy group), 2.02 (triplet, $\underline{H}$C≡C), and 2.45 (doublet, C≡C$\underline{H}_2$).

EXAMPLE 198

Preparation of 4-cyclopropyl-4-trimethylsiloxy-1-(tri-n-butylstannyl)-trans-1-octene A stirred mixture of 23.8 g of 4-cyclopropyl-4-trimethylsiloxy-1-octyne (Example 191), 28 ml of tri-n-butyltin hydride, and 50 mg of azobisisobutyronitrile under nitrogen is heated to 85° C. After the resulting exothermic reaction subsides the mixture is heated at 130° C. for one hour. The crude product is evaporatively distilled to give a liquid, pmr spectrum (CDCl$_3$): δ 0.10 (trimethylsiloxy group), 2.33 (doublet, =CHC$\underline{H}_2$), and 6.02 (vinyl hydrogens).

EXAMPLES 199-204

Treatment of the starting carboxylic acids of Table 24 with the appropriate alkyllithium by the method of Example 190 provides the product ketones of the table.

TABLE 24

| Example | Starting Carboxylic Acid | Alkyl Lithium | Product Ketone |
|---|---|---|---|
| 199 | cyclopropane carboxylic acid | n-hexyllithium | n-hexylcyclopropyl ketone |
| 200 | cyclopropane carboxylic acid | n-propyllithium | n-propylcyclopropyl ketone |
| 201 | acrylic acid | n-hexyllithium | n-hexylvinyl ketone |
| 202 | acrylic acid | n-propyllithium | n-propylvinyl ketone |
| 203 | crotonic acid | n-butyllithium | n-butyl-1-propenyl ketone |
| 204 | crotonic acid | n-hexyllithium | n-hexyl-1-propenyl ketone |
| 204a | acrylic acid | n-butyllithium | n-butylvinyl ketone |

EXAMPLES 205-210e

Treatment of the starting ketones of Table 25 with propargymagnesium bromide by the procedure of Example 190 followed by treatment with chlorotrimethylsilane by the procedure of Example 191 followed by treatment with tri-n-butyltin hydride by the method of Example 192 is productive of the vinylstannyl derivatives of the table.

TABLE 25

| Example | Starting Ketone | Product Vinylstannyl Derivative |
|---|---|---|
| 205 | 199 | (E)4-trimethylsilyloxy-4-cyclopropyl-1-tri-n-butylstannyldecene |
| 206 | 200 | (E)4-trimethylsilyloxy-4-cyclopropyl-1-tri-n-butylstannylheptene |
| 207 | 201 | (E)4-trimethylsilyloxy-4-vinyl-1-tri-n-butylstannyldecene |
| 208 | 202 | (E)4-trimethylsilyloxy-4-vinyl-1-tri-n-butylstannylheptene |
| 209 | 203 | (E)4-trimethylsilyloxy-4-(1-propenyl)-1-tri-n-butylstannyloctene |
| 210 | 204 | (E)4-trimethylsilyloxy-4-(1-propenyl)-1-tri-n-butylstannyldecene |
| 210a | 204a | (E)4-trimethylsilyloxy-4-vinyl-1-tri-n-butylstannyloctene |
| 210b | 2-hexanone | (E)-4-trimethylsilyloxy-4-methyl-1-tri-n-butylstannyloctene |
| 210c | 3-heptanone | (E)-4-trimethylsilyloxy-4-ethyl-1-tri-n-butylstannyloctene |
| 210d | 3-octanone | (E)-4-trimethylsilyloxy-4-ethyl-1-tri-n-butylstannylnonene |
| 210e | 3-hexanone | (E)-4-trimethylsilyloxy-4-ethyl-1-tri-n-butylstannylheptene |

EXAMPLE 211

Preparation of trans-1-Hydroxy-2-(3-trifluoromethyl)phenoxycyclopentane

A mixture of 88 g of cyclopentene oxide, 150.7 g of 3-trifluoromethylphenol, 5.0 g of sodium hydroxide in 30 ml of water and 4.0 g of methyltricaprylyl ammonium chloride is stirred at 70°-80° C. for 51 hours and at 25° C. for 96 hours. The mixture is then diluted with methylene chloride and poured into water. The organic layer is washed with dilute sodium hydroxide solution and water. The solution is dried over magnesium sulfate. The solvent is removed giving 221.5 g of a liquid which is distilled (bp 110°-113° C. 0.8 mm) giving trans-1-hydroxy-2-(3-trifluoromethyl)phenoxycyclopentane.

EXAMPLE 212

In the manner described above in Example 211 from 4-fluorophenol and cyclopentane epoxide is prepared trans-1-hydroxy-2-(4-fluoro)phenoxycyclopentane.

EXAMPLE 213

In the manner described above in Example 211 from 3-chlorophenol and cyclopentane epoxide is prepared trans-1-hydroxy-2-(3-chloro)phenoxycyclopentane.

EXAMPLE 214

Preparation of 2-(3-Trifluoromethylphenoxy)cyclopentanone

To a suspension of 327.43 g of pyridinium chlorochromate in one liter of methylene chloride is added 220 g of trans-1-hydroxy-2-(3-trifluoromethylphenoxy)cyclopentane in 500 ml of methylene chloride. The mixture is stirred for 2 hours 15 minutes. Another 50 g of the oxidizing agent is added and the mixture is stirred for 4½ hours. The mixture is diluted with ether and decanted from a black residue which is washed with more ether. The combined solutions are filtered through silica gel. The solvent is removed. The residue is dissolved in ether and again filtered through silica-gel. The solvent is removed and the residue is distilled (bp 113°–116° C., 1.5 mm) to give 188 g of 2-(3-trifluoromethylphenoxy)cyclopentanone.

EXAMPLE 215

In the manner described above for Example 214 is prepared from the product of Example 212; 2-(4-fluorophenoxy)cyclopentanone.

EXAMPLE 216

In the manner described above for Example 214 is prepared from the product of Example 213; 2-(3-chlorophenoxy)cyclopentanone.

EXAMPLE 217

Preparation of 1R,2S(and 1S,2R)-1-Ethynyl-1-hydroxy-2-butylcyclopentane and 1R,2R(and 1S,2S)-1-ethynyl-1-hydroxy-2-butylcyclopentane Into 150 ml of dry tetrahydrofuran is bubbled purified acetylene, as a solution of 2.4 M n-butyl magnesium chloride (92 ml) is added dropwise with stirring over a 2 hour period. To the resulting solution of acetylene magnesium chloride is added 21 g of 2-butylcyclopentanone in 50 ml of tetrahydrofuran dropwise over 15 minutes. The solution is stirred for 30 minutes and then is poured into an ice cold solution of saturated ammonium chloride. The mixture is acidified to pH 5 and extracted with ether. The ether solution is washed with brine and dried over magnesium chloride, the ether is removed and the residue is distilled giving 14.8 g of a colorless liquid. This is chromatographed on a dry column of silica-gel eluting with benzene-ethyl acetate (19:1) to separate isomers giving 1R,2S(and 1S,2R)-1-ethylnyl-1-hydroxy-2-butylcyclopentane and 1R,2R(and 1S,2S)-1-ethynyl-1-hydroxy-2-butylcyclopentane.

EXAMPLE 218

Preparation of 1-propargyl-1-hydroxycyclohexane

A stirred suspension of 121.6 g (5.0 mol) of magnesium in 1-1 of anhydrous ether is treated with 0.6 g of mercuric chloride and about 100 mg of iodine. After several minutes, 3 ml of propargyl bromide is added and if no exotherm is noted, a small amount of reacting propargyl bromide and magnesium in ether is added. When the reaction begins, a mixture of 5.0 mol of cyclohexanone and 595 g (5.0 mol) of propargyl bromide is added dropwise at a rate that produces vigorous refluxing of the solution. (The propargyl bromide must always be present in some excess otherwise the reaction will stop. If this happens, the addition of about 1 ml of propargyl bromide will restart the reaction.) After about half of the propargyl bromide-cyclohexanone mixture has been added, another 500–750 ml of ether is used to dilute the reaction mixture. At the end of the addition, the reaction mixture is refluxed for at least 0.5 hour, cooled and poured into 4 liters of saturated ammonium chloride during good stirring. The ethereal layer is separated and the aqueous layer is washed with ether several times and the combined extract is washed twice with saturated sodium chloride solution and dried over anhydrous magnesium sulfate. Evaporation of the ether yields 583 g (630 g theory) of a dark oil which is distilled giving purified 1-propargyl-1-hydroxycyclohexane.

EXAMPLES 219–238

In the manner of Examples 217 and 218 described above the following acetylenic alcohol listed in Table 26 were prepared from the acetylenic Grignard reagent and ketone specified.

TABLE 26

| Example | Grignard Reagent | Ketone | Acetylenic Alcohol |
|---|---|---|---|
| 219 | acetylene magnesium chloride | cyclohexanone | 1-ethynyl-1-hydroxycyclohexane |
| 220 | acetylene magnesium chloride | cyclopentanone | 1-ethynyl-1-hydroxycyclopentane |
| 221 | acetylene magnesium chloride | cycloheptanone | 1-ethynyl-1-hydroxycycloheptane |
| 222 | acetylene magnesium chloride | 3-propylcyclopentanone | 1R,3S-(and 1S,3R-) 1-ethynyl-1-hydroxy-3-propylcyclopentane |
| 223 | acetylene magnesium chloride | 3-propylcyclopentanone | 1R,3R-(and 1S,3S-) 1-ethynyl-1-hydroxy-3-propylcyclopentane |
| 224 | acetylene magnesium chloride | 2-butylcyclohexanone | 1R,2S-(and 1S,2R-) 1-ethynyl-1-hydroxy-2-butylcyclohexane |
| 225 | acetylene magnesium chloride | 2-butylcyclohexanone | 1R,2R-(and 1S,2S-) 1-ethynyl-1-hydroxy-2-butylcyclohexane |
| 226 | acetylene magnesium chloride | 2-(3-trifluoromethylphenoxy)-cyclopentanone | 1R,2S-(and 1S,2R-) 1-ethynyl-1-hydroxy-2-(3-trifluoromethylphenoxy)cyclopentane |
| 227 | acetylene magnesium chloride | 2-(3-trifluoromethylphenoxy)-cyclopentanone | 1R,2R-(and 1S,2S-) 1-ethynyl-1-hydroxy-2-(3-trifluoromethylphenoxy)cyclopentane |
| 228 | acetylene magnesium chloride | 2-(4-fluorophenoxy)cyclopentanone | 1R,2S-(and 1S,2R-) 1-ethynyl-1-hydroxy-2-(4-fluorophenoxy)cyclopentane |
| 229 | acetylene magnesium chloride | 2-(4-fluorophenoxy)cyclopentanone | 1R,2R-(and 1S,2S-) 1-ethynyl-1-hydroxy-2-(4-fluorophenoxy)cyclopentane |
| 230 | acetylene magnesium chloride | 2-(3-chlorophenoxy)-cyclopentanone | 1R,2S-(and 1S,2R-) 1-ethynyl-1-hydroxy-2-(3-chlorophenoxy)cyclopentane |

TABLE 26-continued

| Example | Grignard Reagent | Ketone | Acetylenic Alcohol |
| --- | --- | --- | --- |
| 231 | acetylene magnesium chloride | 2-(3-chlorophenoxy)-cyclopentanone | 1R,2R-(and 1S,2S-) 1-ethynyl-1-hydroxy-2-(3-chlorophenoxy)cyclopentane |
| 232 | acetylene magnesium chloride | 3-methylcyclohexanone | 1R,3S-(and 1S,3R) 1-ethynyl-1-hydroxy-3-methylcyclohexane |
| 234 | acetylene magnesium chloride | 3-methylcyclohexanone | 1R,3R-(and 1S,3S-) 1-ethynyl-1-hydroxy-3-methylcyclohexane |
| 235 | propargyl magnesium bromide | 2-butylcyclopentanone | 1R,2S-(and 1S,2R-) 1-propargyl-1-hydroxy-2-butylcyclopentane |
| 236 | propargyl magnesium bromide | 2-butylcyclopentanone | 1R,2R-(and 1S,2S-) 1-propargyl-1-hydroxy-2-butylcyclopentane |
| 237 | propargyl magnesium bromide | 2-(3-trifluoromethylphenoxy)-cyclopentanone | 1R,2S-(and 1S,2R-) 1-propargyl-1-hydroxy-2-(3-trifluoromethylphenoxy)cyclopentane |
| 238 | propargyl magnesium bromide | 2-(3-trifluoromethylphenoxy)-cyclopentanone | 1R,2R-(and 1S,2S-) 1-propargyl-1-hydroxy-2-(3-trifluoromethylphenoxy)cyclopentane |

EXAMPLE 239

Preparation of 1R,2S(and 1S,2R)-1-Ethynyl-1-trimethylsilyloxy-2-butylcyclopentane To a solution of 29.4 g of 1R,2S(and 1S,2R)-1-ethynyl-1-hydroxy-2-butylcyclopentane and 30.2 g of imidazole in 180 ml of dimethylformamide is added at 0° C. with stirring 24.1 g of trimethylsilylchloride. The mixture is stirred for 3 hours. The mixture is poured into 700 ml of hexane and washed twice with water and once with brine. The ether solution is dried over magnesium sulfate. The solvent is removed and the residue is distilled (bp 64°–72° C., 0.6 mm) to give 35.8 g of 1R,2S(and 1S,2R)-1-ethynyl-1-trimethylsilyloxy-2-butylcyclopentane.

EXAMPLE 240

Preparation of 1R,2R(and 1S,2S)-1-Ethynyl-1-trimethylsilyloxy-2-butylcyclopentane To a mixture of 45.0 g of 1R,2R(and 1S,2S)-1-ethynyl-1-hydroxy-2-butylcyclopentane and 46.2 g of imidazole in 255 ml of dimethylformamide at 0° C. under nitrogen is added 36.9 g of trimethylsilylchloride. The mixture is stirred at room temperature for 3 hours and then poured into 700 ml of hexane. Water is added, the organic layer is separated and the water layer is extracted with hexane. The combined hexane solutions are washed twice with water and dried over magnesium sulfate. The solvent is removed and the residue is distilled giving the product as 53 g of a colorless oil.

EXAMPLE 241

Preparation of 1-Ethynyl-1-trimethylsilyloxycyclohexane

A 194 g portion of imidazole and 158.2 g of 1-ethynylcyclohexan-1-ol are mixed with 500 g of dimethylformamide with cooling in an ice bath. A 152 g portion of trimethylchlorosilane is added with cooling and stirring in about one minute. The mixture is stirred for one hour and allowed to stand overnight. One liter of hexane is added. The lower layer is separated, diluted with water and extracted with hexane. The hexane layers are washed several times with water and then combined and dried over magnesium sulfate. Filtration and then evaporation of the hexane gives 198.5 g of product which is distilled giving 168 g of the desired product.

EXAMPLE 242

Preparation of 1-Propargyl-1-trimethylsilyloxycyclohexane

To a stirred solution of 55.4 g of 1-(2-propyn-1-yl)cyclohexanol [H. Gutmann, et al., Helv. Chim. Acta, 42, 719 (1959)] and 79 g of imidazole in 240 ml of DMF at 10° C. initially is added 56 ml of chlorodimethylsilane during 10 minutes. The cloudy yellow solution is stirred at room temperature for 26 hours. The resulting mixture is partitioned between 1000 ml of hexane and 400 ml of water at 0°–5° C. The hexane phase is washed successively with 6×200 ml of cold water and 200 ml of brine. The extract is dried over magnesium sulfate, filtered, and evaporated to give 85 g of colorless liquid, i.r. (film): 1240 and 830 cm$^{-1}$ (trimethylsilyloxy group).

EXAMPLE 243

Preparation of 1R,2S(and 1S,2R)-1-(trans-2-Iodovinyl)-1-trimethylsilyloxy-2-butylcyclopentane To a mixture of 9.2 g of sodium borohydride and 45.8 g of 2-methyl-2-butene in 350 ml of dry tetrahydrofuran at 0° C. with stirring under nitrogen is added, over 20 minutes, 41.1 ml of boron trifluoride etherate. After 3 hours, to this resulting solution of diisomaylborane is added 38.8 g of 1R,2S(and 1S,2R)-1-ethynyl-1-trimethylsilyloxy-2-butycyclopentane in 40 ml of tetrahydrofuran in 20 minutes. The mixture is stirred 2 hours and then stored at −20° C. overnight. The mixture is allowed to warm to 0° C. and at 0° C. 85 g of dry trimethylamineoxide is added portionwise over 20 minutes. After stirring at 25° C. for one hour, the mixture is filtered through diatomaceous earth. The filtrate is poured simultaneously with a solution of 230 g of iodine in 250 ml of tetrahydrofuran into a stirred, cold solution of 430 g of sodium hydroxide in 1900 ml of water. After stirring for 30 minutes, the organic layer is separated. The aqueous layer is extracted with ether. The combined organic solution are washed twice with a saturated solution of sodium thiosulfate and once with brine. The solution is dried over magnesium sulfate, the solvent is removed and the residue is dissolved in hexane. The hexane solution is filtered through diatomaceous earth and silica gel. The hexane is removed and the residue is purified by dry column chromatography on silica gel eluting with hexane: 45.35 g of 1R,2S(and 1S,2R)-1-(trans-2-iodovinyl)-1-trimethylsilyloxy-2-butylcyclopentane is obtained.

EXAMPLE 244

Preparation of 1R,2R(and 1S,2S)-1-(trans-2-Iodovinyl)-1-trimethylsilyloxy-2-butylcyclopentane To a mixture of 12.22 g of sodium borohydride and 60.82 g of 2-methyl-2-butene in 450 ml of tetrahydrofuran under nitrogen at 0° C., is added 54.6 ml of boron trifluoride ehterate, dropwise over a 20 minute period. The solution is stirred at 0° C. for 2 hours and then at room temperature for 30 minutes. This solution is cooled to 0° C. and 55.5 g of 1R,2R(and 1S,2S)-1-ethynyl-1-trimethylsilyloxy-2-butylcyclopentane in 50 ml of tetrahydrofuran is added. The mixture is allowed to stand in a cold room overnight. To this mixture at 0° C. is added with stirring 112.8 g of trimethylamine oxide over a 20 minute period. The mixture is stirred at room temperature for 90 minutes and then filtered. To the filtrate is added simultaneously a solution of 565 g of sodium hydroxide in 2000 ml of water and a solution of 300 g of iodine in 300 ml of tetrahydrofuran. The mixture is stirred 30 minutes, the organic layer is separated and the aqueous layer is extracted with ether. The combined organic solutions are washed with saturated sodium thiosulfate solution and with saturated sodium chloride solution. The solution is dried with magnesium sulfate and filtered through a pad of silica gel. The solution is removed giving an orange liquid which is chromatographed on a dry column of silica gel giving 59.5 g of the product as a yellow liquid.

EXAMPLE 245

Preparation of 1-(3-Tri-n-butylstannyl-2-trans-propenyl)-1-trimethylsilyloxycyclohexane To a stirred mixture of 31.5 g of 1-propargyl-1-trimethylsilyloxycyclohexane and 150 mg of azobisisobutyronitrile is added 41 ml of tri-n-butyltin hydride. The stirred mixture is heated to about 80° C. The initial exothermic reaction is moderated, and the temperature is subsequently maintained at 130°–135° C. for one hour.

The product is distilled to afford 56 g of colorless liquid, bp 150°–160° C. (0.15–0.3 mm), pmr (CDCl$_3$): 6.0 (multiplet, vinyl protons).

EXAMPLES 246–265

Using the procedure outlined above for Examples 239–242, the actylenic alcohols listed in Table 27 are converted to their corresponding acetylenic trimethylsilyloxy derivative these in turn using the procedure outlined above for Examples 243 and 244, were converted to their corresponding trans-2-iodovinyl derivatives or using the procedure outlined above for Example 245, were converted to their corresponding trans-2tri-n-butylstannyl derivatives (Table 27).

TABLE 27

| Example | Acetylene of Example | Method of Example | Vinyl Iodide or Vinyl Tin Compound |
|---|---|---|---|
| 246 | 219 | 244 | 1-(trans-2-iodovinyl)-1-trimethylsilyloxycyclohexane |
| 247 | 220 | 244 | 1-(trans-2-iodovinyl)-1-trimethylsilyloxycyclopentane |
| 248 | 221 | 245 | 1-(trans-2-tri-n-butylstannylvinyl)-1-trimethylsilyloxycycloheptane |
| 249 | 222 | 244 | 1R,3S-(and 1S,3R-) 1-(trans-2-iodovinyl)-1-trimethylsilyloxy-3-propylcyclopentane |
| 250 | 223 | 244 | 1R,3R-(and 1S,3S-) 1-(trans-2-iodovinyl)-1-trimethylsilyloxy-3-propylcyclopentane |
| 251 | 217 | 244 | 1R,2R-(and 1S,2S-) 1-(trans-2-iodovinyl)-1-trimethylsilyloxy-2-butylcyclopentane |
| 252 | 224 | 244 | 1R,2S-(and 1S,2R-) 1-(trans-2-iodovinyl)-1-trimethylsilyloxy-2-butylcyclohexane |
| 253 | 225 | 244 | 1R,2R-(and 1S,2S-) 1-(trans-1-iodovinyl)-1-trimethylsilyloxy-2-butylcyclohexane |
| 254 | 226 | 245 | 1R,2S-(and 1S,2R-) 1-(trans-2-tri-n-butylstannylvinyl)-1-trimethylsilyloxy-2-(3-trifluoromethylphenoxy)cyclopentane |
| 255 | 227 | 245 | 1R,2R-(and 1S,2S-) 1-trans-2-tri-n-butylstannylvinyl)-1-trimethylsilyloxy-2-(3-trifluoromethylphenoxy)cyclopentane |
| 256 | 228 | 244 | 1R,2S-(and 1S,2R-( 1-(trans-2-iodovinyl)-1-trimethylsilyloxy-2-(4-fluorophenoxy)cyclopentane |
| 257 | 229 | 244 | 1R,2R-(and 1S,2S-) 1-(trans-2-iodovinyl)-1-trimethylsilyloxy-2-(4-fluorophenoxy)cyclopentane |
| 258 | 230 | 245 | 1R,2S-(and 1S,2R-) 1-(trans-2-tri-n-butylstannylvinyl)-1-trimethylsilyloxy-2-(3-chlorophenoxy)cyclopentane |
| 259 | 231 | 245 | 1R,2R-(and 1S,2S-) 1-(trans-2-tri-n-butylstannylvinyl)-1-trimethylsilyloxy-2-(3-chlorophenoxy)cyclopentane |
| 260 | 232 | 244 | 1R,3S-(and 1S,3R-) 1-(trans-2-iodovinyl)-1-trimethylsilyloxy-2-methylcyclohexnae |
| 261 | 234 | 244 | 1R,3R-(and 1S,3S-) 1-(trans-2-iodovinyl)-1-trimethylsilyloxy-3-methylcyclohexane |
| 262 | 235 | 245 | 1R,2S-(and 1S,2R-) 1-(3-tri-n-butylstannyl-2-trans-propenyl)-1-trimethylsilyloxy-2-butylcyclopentane |
| 263 | 236 | 245 | 1R,2R-(and 1S,2S-) 1-(3-tri-n-butylstannyl-2-trans-propenyl)-1-trimethylsilyloxy-2-butylcyclopentane |
| 264 | 237 | 245 | 1R,2S-(and 1S,2R-) 1-(3-tri-n-butylstannyl-2-trans-propenyl)-1-trimethylsilyloxy-2- |

TABLE 27-continued

| Example | Acetylene of Example | Method of Example | Vinyl Iodide or Vinyl Tin Compound |
| --- | --- | --- | --- |
| 265 | 238 | 245 | (3-trifluoromethylphenoxy)cyclopentane 1R,2R-(and 1S,2S-) 1-(3-tri-n-butylstannyl-2-trans-propenyl)-1-trimethylsilyloxy-2-(3-trifluoromethylphenoxy)cyclopentane |

EXAMPLE 266

Preparation of trimethylsilyl-2-trimethylsilyloxy acetate

To a solution of 15 g (0.197 mol) of glycolic acid in 50 ml of dry pyridine is poured 32.3 g (0.2 mol) of 1,1,1,3,3,3-hexamethyldisilazine. After stirring 15 minutes, 10.86 g (0.1 mol) of trimethylsilyl chloride is added dropwise. The mixture is stirred for one hour and then filtered from a white solid which is washed with petrolium ether. The filtrate and washings are concentrated at reduced pressure at 30° C. The residue is distilled (85°-86°, 15 minutes) to give 38 g of the title compound.

EXAMPLE 267

Preparation of tris-trimethylsilyloxyethylene

To a solution of 50.98 g (0.316 mol) of 1,1,1,3,3,3-hexamethyldisilazine in 250 ml of tetrahydrofuran is added with stirring under argon at 0° C. dropwise 133.3 ml (0.32 mol) of 2.4 M n-butyl lithium in hexane. After addition is completed the solution is maintained at 45° C. for 30 minutes. The solution is cooled to −78° and 58.7 g of trimethylsilyl-2-trimethysilyloxy acetate (Example 266) is added dropwise. After stirring 30 minutes, 43.2 g (0.4 mol) of trimethylsilylchloride is added over 10 minutes. The solution is allowed to warm to room temperature over 30 minutes. The solvent is removed at reduced pressure. The residue is mixed with an equal volume of petrolium ether and filtered from the suspended lithium chloride. The solvent is removed and the residue is distilled (70°-75° C., 1.4 minute) to give 64.65 g of the title compound.

EXAMPLE 268

Preparation of 2-[6-(chloroformyl)hexyl]cyclopent-2-en-1-one

To a suspension of 1.94 g (0.08 mol) of sodium hydric in 100 ml of tetrahydrofuran is added with stirring under argo dropwise a solution of 17 g (0.08 mol) of 2-(6-carboxyhexyl)-cyclopent-2-en-1-one in 160 ml of tetrahydrofuran. After the addition is complete, the mixture is stirred for 1 hour 15 minutes. The mixture is cooled to 0° C. and 13 ml of oxalyl chloride is added. The mixture is stirred at 0° C. for 30 minutes and at room temperature for 30 minutes. The solution is diluted with 500 ml of ether and filtered through Celite. The solvent is removed from the filtrate and the residue is extracted with hot hexane twice. The hexane is removed to give 16.0 g of the title compound.

EXAMPLE 269

Preparation of 2-(8-hydroxy-7-oxo-octyl)cyclopent-2-en-1-one

A mixture of 6.3 g of 2-[6-(chloroformyl)hexyl]cyclopent-2-en-1-one (Example 268) and 16 g of tris-trimethylsilyloxyethylene (Example 267) are stirred at 90° to 100° C. under argon for one hour. To this mixture is added 25 ml of dioxane and 10 ml of 0.6 N hydrochloric acid. The mixture is heated at 80° C. for 30 minutes. The mixture is poured into brine and extracted with ether. The ether solution is washed with saturated sodium bicarbonate and dried over magnesium sulfate. The solvent is removed and the residue is chromatographed on a dry column of silica gel eluting with ether containing 2% acetic acid to give 1.7 g of the title compound ($R_f = 0.45$).

EXAMPLE 270

Preparation of 2-(6-carbodimethyl-t-butylsilyloxyhex-2-cis-en-yl)-4-dimethyl-t-butylsilyloxy-cyclopent-2-en-1-one To 5.0 g of 2-(6-carboxyhex-2-cis-enyl)-4-hydroxycyclopent-2-en-1-one and 7.5 g of imidazole in 24 ml of dimethylformamide is added 10.2 g of dimethyl-t-butylsilylchloride. The mixture is maintained at 37° C. for 4 hours. The mixture is poured into ice water and extracted with hexane. The hexane solution is washed with saturated sodium bicarbonate and dried over magnesium sulfate. The solvent is removed. Toluene is added and removed. The residue is distilled in a Kugelrohr apparatus (165°° C., 0.5–0.1 mm) to give 4.56 g of the title compound.

EXAMPLE 271

Preparation of 1-(6-carboxyhex-2-cis-enyl)-4-dimethyl-t-butylsilyloxycyclopent-2-en-1-one A solution of 1-(6-carbodimethyl-t-butylsilyloxyhex-2-cis-enyl)-4-dimethyl-t-butylsilyloxycyclopent-2-en-1-one (Example 270) in 40 ml of acetic acid - tetrahydrofuran - water (4:2:1) is stirred at room temperature for 1.5 hour. The solvents are removed at reduced pressure at 40° C. The residue is dissolved in ether. The ether solution is washed with water, brine, and dried over magnesium sulfate. The solvent is removed. Toluene is added and removed to give 3.1 g of the title compound.

EXAMPLE 272

Preparation of 1-[6-(chloroformyl)hex-2-cis-enyl]-4-dimethyl-t-butylsilyloxycyclopent-2-en-1-one To 59.66 g of 1-(6-carboxyhex-2-cis-enyl)-4-dimethy-t-butylsilyloxycyclopent-2-en-1-one (Example 271) in 300 ml of tetrahydrofuran containing 0.5 ml of dimethylformamide at 0° C. under argon with stirring is added over 20 minutes 29.2 m of oxalyl chloride in 40 ml of tetrahydrofuran. After 1.5 hour the solvent is removed at reduced pressure at 35° C. The residue is dissolved in petrolium ether and filtered through Celite. The solvent is removed to give 59.3 g of the title compound.

EXAMPLE 273

Preparation of
1-(8-hydroxy-7-oxo-oct-2-cis-enyl)-4-hydroxycyclopent-2-en-1-one

A mixture of 59.3 g of 1-[6-(chloroformyl)hex-2-cis-enyl]-4-dimethyl-t-butylsilyloxycyclopent-2-en-1-one (Example 272) and 101.5 g of tris-trimethylsilyloxyethylene (Example 267) is heated under argon at 90°-95° C. for 3 hours 10 minutes The reaction mixture is poured into a mixture of 300 ml of tetrahydrofuran and 140 ml of 0.6 N hydrochloric acid and the resulting mixture is stirred at 70° C. for 2.5 hours. The mixture is poured in brine and extracted with ethyl acetate. The organic layer is washed with saturated sodium bicarbonate and dried of magnesium sulfate. The solvent is removed and the residue is chromatographed of a dry column of silica gel eluting with ethyl acetate. The product bond ($R_f \approx 0.4$) is extracted to give 6.45 g of the title compound.

EXAMPLE 274

Preparation of 5-bromopentanoylchloride

To a solution of 97 g of 5-bromopentanoic acid in 240 ml of methylene chloride containing 1 ml of dimethylformamide is added dropwise 76.2 g of oxalyl chloride. The mixture is stirred one hour at room temperature and 30 minutes at 50° C. The solvent is removed and the residue is distilled twice (75° C., 0.6 minute) to give 88.2 g of the title compound.

EXAMPLE 275

Preparation of 6-bromo-1-hydroxy-2-hexanone

To 191.4 g of tris-trimethylsilyloxyethylene (Example 267) containing 15 drops of stannic tetrachloride under argon with stirring at 10° C. is added 87 g of 5-bromopentanoyl chloride (Example 274) dropwise. After one-half of the acid chloride is added, the mixture is stirred until an exotherm ensues. The remaining acid chloride is added dropwise maintaining the reaction exotherm at 65° C. The mixture is then stirred for 2.5 hours. The mixture is slowly poured into a stirred mixture of 100 ml of 0.6 N hydrochloric acid and 200 ml of tetrahydrofuran. The mixture is stirred for 30 minutes and poured into brine. The mixture is extracted with ether. The ether solution is washed with saturated sodium bicarbonate and dried over magnesium sulfate. The solvent is removed. The residue is mixed with petrolium ether and cooled in dry-ice-acetone to induce crystallization. The petrolium ether is decanted and the solid is dried at reduced pressure to give 64.72 g of the title compound.

EXAMPLE 276

Preparation of
6-bromo-1-dimethyl-t-butylsilyloxy-2-hexanone ethylene ketal

A mixture of 84 l g of 6-bromo-1-hydroxy-2-hexanone (Example 275), 240 ml of ethylene glycol, and 1.7 g of p-toluenesulfonic acid is refluxed in 1800 ml of toluene using a Dean-Stark trap for 1 hour 45 minutes. The mixture is cooled to room temperature and washed with saturated sodium bicarbonate, water, and brine. The solvent is removed giving 75.17 g of a yellow oil. To a 27.36 g portion of this material and 16.2 g of imidazole in 57 ml of dimethylformamide at 0° with stirring is added 20.55 g of dimethyl-t-butylchlorosilane. The mixture is stirred at room temperature for 1.5 hour and then poured into water. The mixture is extracted with petrolium ether. The organic phase is washed with dilute hydrochloric acid, saturated sodium bicarbonate and dried over magnesium sulfate. The solvent is removed and the residue is distilled in a Klugrohr apparatus (0.5-0.2 mm, 100°-110° C.) to give 35.25 of the title compound.

EXAMPLE 277

Preparation of 1-dimethyl-t-butylsilyloxy-2-hexanone ethylene ketal 6-triphenylphosphonium bromide A mixture of 35.25 g of 6-bromo-1-dimethyl-t-butylsilyloxy-2-hexanone ethylene ketal (Example 276) and 26.2 g of triphenylphosphine in 68 ml of acetonitrile is refluxed 90 hours. The acetonitrile is removed at reduced pressure. The residue is washed three times with ether and dried at reduced pressure to give 53.8 g of the title compound.

EXAMPLE 278

Preparation of
2,5-dihydro-2,5-dimethoxy-2-(9-dimethyl-t-butylsilyloxy-8-oxonon-3-cis-enyl)furan A suspension of 2.3 g (0.096 mol) of oil free sodium hydride is stirred under argon at 65° C. in 75 ml of dimethylsulfoxide. After gas evolution ceased (1 hour), at 0° C. is added 53.8 g (0.086 mol) of 1-dimethyl-t-butylsilyloxy-2-hexanone ethylene ketal 6-triphenylphosphonium bromide (Example 277) in 160 ml of dimethylsulfoxide. After stirring 15 minutes at room temperature, 16.3 g (0.087 mol) of 2,5-dihydro-2,5-dimethoxy-2-(3'-oxopropyl)furan [U.S. Pat. No. 3,952,033] in 40 ml of dimethylsulfoxide is added. After stirring one hour at room temperature, the solvent is removed at reduced pressure at 55° C. The solid residue is extracted with an ether-petroleum ether mixture. The solution is washed with water, saturated sodium bicarbonate and dried over magnesium sulfate. The solvent is removed and petrolium ether is added. After standing 30 minutes, the triphenylphosphine oxide is removed by filtration. The solvent is removed and the residue is chromatographed on a dry column of florisil eluting first with hexane and then with hexane-ether 5:1 to give 13.2 g of the title compound.

EXAMPLE 279

Preparation of
2-(8-dimethyl-t-butylsilyloxy-7-oxo-oct-2-cis-enyl)-4-hydroxycyclopent-2-en-1-one,7-ethylene ketal A mixture of 66.08 g of 2,5-dihydro-2,5-dimethoxy-2-(9-dimethyl-t-butylsilyloxy-8-oxonon-3-cis-enyl)furan (Example 228), 26.4 g of sodium dihydrogen phosphate, 5.2 g of sodium acetate and 0.5 g of hydroquinone in 1320 ml of dioxane and 660 ml of water is stirred at reflux under argon for 22 hours. The mixture is cooled to room temperature, saturated with sodium chloride, and the organic layer is separated. The aqueous layer is extracted with ether. The combined organic solutions are washed with brine and dried over magnesium sulfate. The solvent is removed to give 57.5 g of an oil. To this is added 300 ml of ether, 300 ml of petroleum ether 22 g of anhydrous chloral. The solution is stirred under argon and 23 g of triethylamine is added. After 1 hour 40 minutes the solution is washed with water, dilute hydrochloric acid, saturated sodium bicarbonate, brine, and dried over magnesium sulfate. The solvent is removed and the residue is chromatographed on a dry column of silica gel eluting with ethylacetate-hexane 1:1 to give 14.55 g of the title compound ($R_f=0.4$).

EXAMPLE 280

Preparation of 2-(8-dimethyl-t-butylsilyloxy-7-oxo-oct-2-cis-enyl)-4-trimethylsilyloxycyclopent-2-en-1-one,7-ethylene ketal A mixture of 14.5 g (0.0367 mol) of 2-(8-dimethyl-t-butylsiloxy-7-oxo-oct-2-cis-enyl)-4-hydroxycyclopent-2-en-1-one,7-ethylene ketal (Example 279) and 3.34 g (0.04 mol) of imidazole in 30 ml of dimethylformamide is stirred as 4.98 g (0.046 mol) of trimethylsilylchloride is added. After on hour, the mixture is poured into water and extracted with hexane. The hexane solution is washed with water, saturated sodium bicarbonate, and dried over magnesium sulfate. The solution is filtered through a pad of silica gel. The solvent is removed and the residue is dried at reduced pressure to give 12.5 g of the title compound.

EXAMPLE 281

Preparation of 2-[6-(4-methoxy-2,2-dimethyl-1,3-dioxolan-4-yl)hex-2-cis-enyl]-4-(2-methoxypropyl-2-oxy)cyclopent-2-en-1-one A mixture of 2-(8-hydroxy-7-oxo-oct-2-cis-enyl)-4-hydroxycyclopent-2-en-1-one (Example 273), 14 ml of 2-methoxy propene, and 0.23 g of ammonium nitrate in 35 ml of benzene is added 7 ml of dimethoxypropane. P-toluenesulfonic acid is added in very small portions until TLC indicates the reaction is initiated. The mixture is stirred 1.5 hour at room temperature, 40° C. for 15 minutes, and another 30 minutes at room temperature. To the stirred solution is added 50 g of crushed 4A molecular sieve. After 15 minutes, the solution is filtered, washed with saturated sodium bicarbonate, and dried over sodium sulfate. The solvent is removed and the residue is chromatographed on a dry column of silica gel eluting with ether-hexane 1:1. The product bond ($R_f\approx0.5$) is extracted to give 3.44 g of the title compound.

EXAMPLE 282

Preparation of 2-(8-hydroxy-7-oxo-octyl)cyclopent-2-en-1-one,7-ethylene ketal

A solution of 5.5 g of 2-(8-hydroxy-7-oxo-octyl)cyclopent-2-en-1-one (Example 269), 25 ml of ethylene glycol, and 0.1 g of p-toluenesulfonic acid in 200 ml of toluene is refluxed for 40 minutes using a Dean-Stark trap. The solution is poured in to saturated sodium bicarbonate. The mixture is extracted with benzene. The organic solution is washed three times with water and dried over magnesium sulfate. The solvent is removed to give 6.0 of the title compound.

EXAMPLE 283

Preparation of 2-(8-trimethylsilyloxy-7-oxo-octyl)cyclopent-2-en-1-one,7-ethylene ketal To a solution of 2.2 g of 2-(8-hydroxy-7-oxo-octyl)cyclopent-2-en-1-one,7-ethylene ketal (Example 232) in 20 ml of pyridine is added 4.6 ml of 1,1,1,3,3,3-hexamethyldisilazin and, dropwise, 2.3 ml of trimethylsilylchloride. After 15 minutes, the excess reagents and solvent is removed at reduced pressure. The residue is taken up in ether and filtered through a short pad of silica gel . The solvent is removed. Toluene is added and removed. The residue is dried at reduced pressure to give 2.77 g of the title compound.

EXAMPLES 284–294

By the sequence of reactions described hereinabove for Examples 268 and 269 or 270 to 273 and the protection reaction described hereinabove in Example 281, the protected cyclopent-2-en-1-ones listed in Table 28 hereinbelow and prepared from the indicated carboxylic acids.

TABLE 28

| Example | Carboxylic acid | Protected cyclopent-2-en-1-one |
|---|---|---|
| 284 | 2-(6-carboxyhexyl)cyclopent-2-en-1-one | 2-[6-(4-methoxy-2,2-dimethyl-1,3-dioxolan-4-yl)-hexylcyclopent-2-en-1-one |
| 285 | 2-(5-carboxypentyl)cyclopent-2-en-1-one | 2-[5-(4-methoxy-2,2-dimethyl-1,3-dioxolan-4-yl)-pentylcyclopent-2-en-1-one |
| 286 | 2-(7-carboxyheptyl)cyclopent-2-en-1-one | 2-[7-(4-methoxy-2,2-dimethyl-1,3-dioxolan-4-yl)-heptylcyclopent-2-en-1-one |
| 287 | 2-(6-carboxyhex-2-cis-enyl)-cyclopent-2-en-1-one | 2-[6-(4-methoxy-2,2-dimethyl-1,3-dioxolan-4-yl)-hex-2-cis-enyl]cyclopent-2-en-1-one |
| 288 | 2-(5-carboxypent-2-cis-enyl)-cyclopent-2-en-1-one | 2-[5-(4-methoxy-2,2-dimethyl-1,3-dioxolan-4-yl)-pent-2-cis-enyl]cyclopent-2-en-1-one |
| 289 | 2-(7-carboxyhept-2-cis-enyl)-cyclopent-2-en-1-one | 2-[7-(4-methoxy-2,2-dimethyl-1,3-dioxolan-4-yl)-hept-2-cis-enyl]cyclopent-2-en-1-one |
| 290 | 2-(5-carboxypent-2-cis-enyl)-4-hydroxycyclopent-2-en-1-one | 2-[5-(4-methoxy-2,2-dimethyl-1,3-dioxolan-4-yl)-pent-2-cis-enyl]4-(2-methoxypropyl-2-oxy)cyclopent-2-en-1-one |
| 291 | 2-(7-carboxyhept-2-cis-enyl)-4-hydroxycyclopent-2-en-1-one | 2-[7-(4-methoxy-2,2-dimethyl-1,3-dioxolan-4-yl)-hept-2-cis-enyl]4-(2-methoxypropyl-2-oxy)cyclopent-2-en-1-one |
| 292 | 2-(6-carboxyhexyl)-4-hydroxy-cyclopent-2-en-1-one | 2-[6-(4-methoxy-2,2-dimethyl-1,3-dioxolan-4-yl)-hexyl]-4-(2-methoxypropyl-2-oxy)cyclopent-2-en-1-one |
| 293 | 2-(5-carboxypentyl)-4-hydroxy-cyclopent-2-en-1-one | 2-[5-(4-methoxy-2,2-dimethyl-1,3-dioxolan-4-yl)-pentyl]-4-(2-methoxypropyl-2-oxy)cyclopent-2-en-1-one |
| 294 | 2-(7-carboxyheptyl)-4-hydroxy-cyclopent-2-en-1-one | 2-[7-(4-methoxy-2,2-dimethyl-1,3-dioxolan-4-yl)-heptyl]-4-(2-methoxypropyl-2-oxy)cyclopent-2-en-1-one |
| 295 | 2-(6-carboxyhex-2-cis-enyl)-4(R)-hydroxycyclopent-2-en-1-one | 2-[6-(4-methoxy-2,2-dimethyl-1,3-dioxolan-4-yl)-hex-2-cis-enyl]-4(R)-(2-methoxypropyl-2-oxy)cyclopent-2-en-1-one |

TABLE 28-continued

| Example | Carboxylic acid | Protected cyclopent-2-en-1-one |
|---|---|---|
| 296 | 2-(6-carboxyhexyl)-4(R)-hydroxycyclopent-2-en-1-one | 2-[6-(4-methoxy-2,2-diemthyl-1,3-dioxolan-4-yl)-hexyl]-4(R)-(2-methoxypropyl-2-oxy)cyclopent-2-en-1-one |

EXAMPLES 297–298

By the sequence of reaction given hereinabove in the Examples 274 to 280, the protected cyclopent-2-en-1-ones of Table 29 are prepared from indicated Bromo-carboxylic acid.

TABLE 29

| Example | Bromo-carboxylic acid | Protected Cyclopent-2-en-1-one |
|---|---|---|
| 297 | 4-bromobutanoyl-chloride | 1-(7-dimethyl-t-butylsilyloxy-6-oxohept-2-cis-enyl)-4-trimethylsilyloxycyclopent-2-en-1-one,6-ethylene ketal |
| 298 | 6-bromohexanoyl chloride | 1-(9-dimethyl-t-butylsilyloxy-8-oxonon-2-cis-enyl)-4-trimethylsilyloxycyclopent-2-en-1-one,8-ethylene ketal |

EXAMPLES 299–306

By the methods described hereinabove in Examples 268 and 269 and the ketalization reaction described in Example 282, the cyclopent-2-en-1-ones in Table 30 are prepared from the indicated carboxylic acid. By the methods described hereinabove in the sequence of reactions shown in Examples 270–273 and the ketalization reaction described in Example 282 the 4-hydroxy-cyclopent-2-en-1-ones in Table 30 are prepared from the indicated carboxylic acid.

EXAMPLE 309

Preparation of 2-(8-trimethylsilyloxy-7-oxooctyl)-4-trimethylsilyloxycyclopent-2-en-1-one,7-ethylene ketal To a solution of 2.2 g of 2-(8-hydroxy-7-oxooctyl)-4-hydroxycyclopent-2-en-1-one,7-ethylene ketal (Example 301) in 40 ml of pyridine is added 9.2 ml 1,1,1,3,3,3-hexamethyldisilazine and, dropwise, 4.6 ml of trimethylsilylchloride. After 30 minutes, the excess reagents and pyridine are removed at reduced pressure. The residue is taken up in ether and filtered through a short pad of silica gel. The solvent is removed and the residue is dried at reduced pressure to give the title compound.

EXAMPLES 310–318

By the methods described hereinabove in Examples 283 and 309, the hydroxycyclopent-2-en-1-ones listed in Table 31 are converted to their trimethylsilyl ethers shown.

TABLE 30

| Example | Carboxylic acid | Cyclopent-2-en-1-one |
|---|---|---|
| 299 | 2-(5-carboxypentyl)cyclopent-2-en-1-one | 2-(7-hydroxy-6-oxoheptyl)cyclopent-2-en-1-one,-6-ethylene ketal |
| 300 | 2-(7-carboxyheptyl)cyclopent-2-en-1-one | 2-(9-hydroxy-8-oxononyl)cyclopent-2-en-1-one,-8-ethylene ketal |
| 301 | 2-(6-carboxyhexyl)-4-hydroxycyclopent-2-en-1-one | 2-(8-hydroxy-7-oxooctyl)-4-hydroxycyclopent-2-en-1-one,7-ethylene ketal |
| 302 | 2-(5-carboxypentyl)-4-hydroxycyclopent-2-en-1-one | 2-(7-hydroxy-6-oxoheptyl)-4-hydroxycyclopent-2-en-1-one,6-ethylene ketal |
| 303 | 2-(7-carboxyheptyl)cyclopent-2-en-1-one | 2-(9-hydroxy-8-oxononyl)-4-hydroxycyclopent-2-en-1-one,8-ethylene ketal |
| 304 | 2-(6-carboxyhex-2-cis-enyl)cyclopent-2-en-1-one | 2-(8-hydroxy-7-oxooct-2-cis-enyl)cyclopent-2-en-1-one,7-ethylene ketal |
| 305 | 2-(5-carboxypent-2-cis-enyl)cyclopent-2-en-1-one | 2-(7-hydroxy-7-oxohept-2-cis-enyl)cyclopent-2-en-1-one,6-ethylene ketal |
| 306 | 2-(7-carboxyhept-2-cis-enyl)cyclopent-2-en-1-one | 2-(9-hydroxy-8-oxonon-2-cis-enyl)cyclopent-2-en-1-one,8-ethylene ketal |
| 307 | 2-(6-carboxyhex-2-cis-enyl)-4(R)-hydroxycyclopent-2-en-1-one | 2-(8-hydroxy-7-oxooct-2-cis-enyl)-4(R)-hydroxycyclopent-2-en-1-one,7-ethylene ketal |
| 308 | 2-(6-carboxyhexyl)-4(R)-hydroxycyclopent-2-en-1-one | 2-(8-hydroxy-7-oxooctyl)-4(R)-hydroxycyclopent-2-en-1-one,7-ethylene ketal |

TABLE 31

| Example | Hydroxycyclopent-2-en-1-one of Example | Protected cyclopent-2-en-1-one |
|---|---|---|
| 310 | 299 | 2-(7-trimethylsilyloxy-6-oxoheptyl)cyclopent-2-en-1-one,6-ethylene ketal |
| 311 | 300 | 2-(9-trimethylsilyloxy-8-oxononyl)cyclopent-2-en-1-one,8-ethylene ketal |
| 312 | 302 | 2-(7-trimethylsilyloxy-6-oxoheptyl)-4-trimethylsilyloxycyclopent-2-en-1-one,6-ethylene ketal |
| 313 | 303 | 2-(9-trimethylsilyloxy-8-oxononyl)-4-trimethylsilyloxycyclopent-2-en-1-one,8-ethylene ketal |

TABLE 31-continued

| Example | Hydroxycyclopent-2-en-1-one of Example | Protected cyclopent-2-en-1-one |
|---|---|---|
| 314 | 304 | 2-(8-trimethylsilyloxy-7-oxooct-2-cis-enyl)-cyclopent-2-en-1-one,7-ethylene ketal |
| 315 | 305 | 2-(7-trimethylsilyloxy-6-oxohept-2-cis-enyl)-cyclopent-2-en-1-one,6-ethylene ketal |
| 316 | 306 | 2-(9-trimethylsilyloxy-8-oxonon-2-cis-enyl)-cyclopent-2-en-1-one,8-ethylene ketal |
| 317 | 307 | 2-(8-trimethylsilyloxy-7-oxooct-2-cis-enyl)-4(R)-trimethylsilyloxycyclopent-2-en-1-one,7-ethylene ketal |
| 318 | 308 | 2-(8-trimethylsilyloxy-7-oxooctyl)-4(R)-trimethylsilyloxycyclopent-2-en-1-one,7-ethylene ketal |

EXAMPLE 319

Preparation of
1,9-dioxo-11α,15-dihydroxy-1-hydroxymethyl-16,16-trimethylene-13-trans-5-cis-prostadiene and
1,9-dioxo-11α,15-epi-dihydroxy-1-hydroxymethyl-16,16-trimethylene-13-trans-5-cis-prostadiene To a solution of 1.95 g (0.00533 mol) of 1-iodo-4,4-trimethylene-3-trimethylsilyloxy-1-trans-octene (Example 13) in 6.5 ml of ether is added at −78° C. with stirring under argon 6.66 ml (0.0107 mol) of 1.6M t-butyllithium in pentane. After 15 minutes at −78° C., the mixture is stirred at −10° to −5° C. for 90 minutes. The solution is cooled to −78° C. and a solution of 0.704 g (0.00533 mol) of copper pentyne and 1.75 g (0.0106 mol) of hexamethylphosphoroustriamide in 20 ml of ether is added. After stirring for one hour, 1.7 g (0.0044 mol) of 2-[6-(4-methoxy-2,2-dimethyl-1,3-dioxolan-4-yl)hex-2-cis-enyl]-4-(2-methoxypropyl-2-oxy)cyclopent-2-en-1-one (Example 281) in 13 ml of ether is added. The solution is maintained at −40° to −50° C. for one hour and −30° C. for 30 minutes. A solution of 1 ml of acetic acid in 5 ml of ether is added followed by a saturated solution of ammonium chloride and dilute hydrochloric acid. The solution is filtered and solids are washed with ether. The combined filtrate is extracted with ether. The ether solution is washed with saturated sodium bicarbonate and dried over magnesium sulfate. The ether is removed giving a yellow oil which is dissolved in 60 ml of acetic acid-tetrahydrofuran-water 4:2:1 and heated to 40°–50° C. for 70 minutes. The solvent is removed at reduced pressure at 50° C. The residue is dissolved in ethyl acetate. The ethyl acetate solution is washed with saturated sodium bicarbonate, brine, and dried over magnesium sulfate. The solvent is removed. The residue is chromatographed on a dry column of silica gel eluting with ethyl acetate-benzene 3:2 containing 1% acetic acid to give 0.35 of 1,9-dioxo-11α,15-dihydroxy-1-hydroxymethyl-16,16-trimethylene-13-trans-5-cis-prostadiene and 0.39 g of 1,9-dioxo-11α,15-epi-dihydroxy-1-hydroxymethyl-16,16-trimethylene-13-trans-5-cis-prostadiene.

EXAMPLE 320

Preparation of
1,9-dioxo-11α,16-dihydroxy-1-hydroxymethyl-16-vinyl-5-cis-13-trans-prostadiene To a solution of 2.9 g (5.6 mmol) of (E)4-trimethylsilyloxy-4-vinyl-1-tri-n-butylstannyloctene (Example 210a) in 4 ml of tetrahydrofuran at −78° C. under argon with stirring is added 2.4 ml of 2.4M n-butyllithium in hexane. The solution is stirred at −30° to −20° C. for 2 hours. A solution of 0.74 g (5.6 mmol) of copper pentyne and 2.3 ml of hexamethylphosphorous triamide in 18 ml of ether is added at −78° C. The solution is stirred at −78° C. for 1.5 hour. A solution of 2.0 g (5.2 mmol) of 2-[6-(4-methoxy-2,2-dimethyl-1,3-dioxolan-4yl)hex-2-cis-enyl]-4-(2-methoxypropyl-2-oxy)cyclopent-2-en-1-one (Example 281) in 20 ml of ether is added. The solution is stirred at −30° to −20° C. for 1.5 hour. To the solution is added 100 ml of saturated ammonium chloride. The mixture is extracted with ether and the ether solution is washed with dilute hydrochloric acid, saturated sodium bicarbonate, and dried over magnesium sulfate. The solvent is removed and the residue is dissolved in 90 ml of acetic acid-tetrahydrofuran-water 4:2:1. The solution is stirred at room temperature for 2 hours. The solvents are removed at reduced pressure at 50° C. Toluene was added and removed. The residue is chromatographed on a dry column of silica gel eluting with ethyl acetate to give 0.5 g of the title compound.

EXAMPLES 321–422

By the methods described hereinabove in Examples 319 and 320, the 1,9-dioxo-1-hydroxymethylprostene derivatives shown in Table 32 are prepared by the indicated method from the indicated vinyl iodide or vinyl tin compound and the indicated cyclopent-2-en-1-one. In those cases where isomers are obtained at the C$_{15}$ or C$_{16}$ positions, only the C$_{15}$ or C$_{16}$-normal isomers are listed in Table 32; it should be understood that the corresponding C$_{15}$ or C$_{16}$-epi isomers are also formed and are part of this invention.

In those cases where the initial conjugate addition product contains a triphenylmethoxy blocking group, deblocking is conducted in acetic acid-tetrahydrofuran-water 4:2:1 at 50° C. for 5 hours.

TABLE 32

| Example | Method of Example | Cyclopent-2-en-1-one | Vinyl Iodide or Vinyl Tin of Example | 1,9-dioxo-1-hydroxymethylprostene |
|---|---|---|---|---|
| 321 | 319 | 281 | 49 | 1,9-dioxo-11α,15-dihydroxy-1-hydroxymethyl-16,16-trimethylene-20-nor-5-cis-13-trans-prostadiene |
| 322 | 319 | 281 | 50 | 1,9-dioxo-11α,15-dihydroxy-1-hydroxymethyl-16,16-trimethylene-20-methyl-5- |

TABLE 32-continued

| Example | Method of Example | Cyclopent-2-en-1-one | Vinyl Iodide or Vinyl Tin of Example | 1,9-dioxo-1-hydroxymethylprostene |
|---|---|---|---|---|
| 333 | 319 | 281 | 51 | 1,9-dioxo-11α,15-dihydroxy-1-hydroxymethyl-16,16-trimethylene-20-ethyl-5-cis-13-trans-prostadiene |
| 334 | 320 | 281 | 199 | 1,9-dioxo-11α,16-dihydroxy-16-cyclopropyl-20-ethyl-1-hydroxymethyl-5-cis-13-trans-prostadiene |
| 335 | 320 | 281 | 201 | 1,9-dioxo-11α,16-dihydroxy-16-vinyl-20-ethyl-1-hydroxymethyl-5-cis-13-trans-prostadiene |
| 336a | 320 | 281 | 198 | 1,9-dioxo-11α,16-dihydroxy-16-cyclopropyl-1-hydroxymethyl-5-cis-13-trans-prostadiene |
| 336b | 320 | 281 | 210c | 1,9-dioxo-11α,16-dihydroxy-16-ethyl-1-hydroxymethyl-5-cis-13-trans-prostadiene |
| 337 | 319 | 281 | 74 | dl-erythro-1,9-dioxo-11α,15-dihydroxy-16-methoxy-1-hydroxymethyl-5-cis-13-trans-prostadiene |
| 338 | 319 | 281 | 77 | dl-erythro-1,9-dioxo-11α-15-dihydroxy-16-ethoxy-1-hydroxymethyl-5-cis-13-trans-prostadiene |
| 339 | 319 | 281 | 83 | dl-erythro-1,9-dioxo-11α,15,16-trihydroxy-1-hydroxymethyl-20-nor-5-cis-13-trans-prostadiene |
| 340 | 319 | 281 | 84 | dl-erythro-1,9-dioxo-11α,15,16-trihydroxy-1-hydroxymethyl-20-methyl-5-cis-13-trans-prostadiene |
| 341 | 319 | 281 | 85 | dl-erythro-1,9-dioxo-11α,15,16-trihydroxy-1-hydroxymethyl-20-ethyl-5-cis-13-trans-prostadiene |
| 342 | 319 | 281 | 86 | dl-erythro-1,9-dioxo-11α,15,16-trihydroxy-19-methyl-1-hydroxymethyl-5-cis-13-trans-prostadiene |
| 343 | 319 | 281 | 87 | dl-erythro-1,9-dioxo-11α,15,16-trihydroxy-1-hydroxymethyl-5-cis-13-trans-17-trans-prostatriene |
| 344 | 319 | 281 | 69 | dl-threo-1,9-dioxo-11α,15,16-trihydroxy-1-hydroxymethyl-5-cis-13-trans-prostadiene |
| 345 | 319 | 281 | 88 | dl-threo-1,9-dioxo-11α,15,16-trihydroxy-20-nor-1-hydroxymethyl-5-cis-13-trans-prostadiene |
| 346 | 319 | 281 | 76 | dl-erythro-1,9-dioxo-11α,15,16-trihydroxy-1-hydroxymethyl-5-cis-13-trans-prostadiene |
| 347 | 319 | 281 | 89 | dl-threo-1,9-dioxo-11α,15,16-trihydroxy-20-methyl-1-hydroxymethyl-5-cis-13-trans-prostadiene |
| 348 | 319 | 281 | 90 | dl-threo-1,9-dioxo-11α,15,16-trihydroxy-20-ethyl-1-hydroxymethyl-5-cis-13-trans-prostadiene |
| 349 | 319 | 281 | 91 | dl-threo-1,9-dioxo-11α,15,16-trihydroxy-19-methyl-1-hydroxymethyl-5-cis-13-trans-prostadiene |
| 350 | 319 | 281 | 92 | dl-threo-1,9-dioxo-11α,15,16-trihydroxy-1-hydroxymethyl-5-cis-13-trans-17-trans-prostatriene |
| 351 | 319 | 281 | 107 | 1,9-dioxo-11α,16-dihydroxy-1-hydroxymethyl-5-cis-13-trans-prostadiene |
| 352 | 319 | 281 | 108 | 1,9-dioxo-11α,16-dihydroxy-1-hydroxymethyl-19,20-dinor-5-cis-13-trans-prostadiene |
| 353 | 319 | 281 | 109 | 1,9-dioxo-11α,16-dihydroxy-1-hydroxymethyl-18,19,20-trinor-5-cis-13-trans-prostadiene |
| 354 | 319 | 281 | 110 | 1,9-dioxo-11α,16-dihydroxy-1-hydroxymethyl-20-nor-5-cis-13-trans-prostadiene |
| 355 | 319 | 281 | 144 | 1,9-dioxo-11α,16-dihydroxy-17-methyl-1-hydroxymethyl-5-cis-13-trans-prostadiene |
| 356 | 319 | 281 | 112 | 1,9-dioxo-11α,16-dihydroxy-20-methyl-1-hydroxymethyl-5-cis-13-trans-prostadiene |
| 357 | 319 | 281 | 113 | 1,9-dioxo-11α,16-dihydroxy-20-ethyl-1-hydroxymethyl-5-cis-13-trans-prostadiene |
| 358 | 319 | 281 | 139a | 1,9-dioxo-11α,16-dihydroxy-16-methyl- |

TABLE 32-continued

| Example | Method of Example | Cyclopent-2-en-1-one | Vinyl Iodide or Vinyl Tin of Example | 1,9-dioxo-1-hydroxymethylprostene |
|---|---|---|---|---|
| | | | | 20-ethyl-1-hydroxymethyl-5-cis-13-trans-prostadiene |
| 359 | 319 | 281 | 115 | 1,9-dioxo-11α,16-dihydroxy-1-hydroxymethyl-13-trans-17-cis-5-cis-prostatriene |
| 360 | 319 | 281 | 135 | 1,9-dioxo-11α,16-dihydroxy-16-methyl-1-hydroxymethyl-5-cis-13-trans-prostadiene |
| 361 | 319 | 281 | 136 | 1,9-dioxo-11α,16-dihydroxy-17,17,20-trimethyl-1-hydroxymethyl-5-cis-13-trans-prostadiene |
| 362 | 319 | 281 | 137 | 1,9-dioxo-11α,16-dihydroxy-16,20-dimethyl-1-hydroxymethyl-13-trans-5-cis-prostadiene |
| 363 | 319 | 281 | 138 | 1,9-dioxo-11α,16-dihydroxy-17,17-dimethyl-1-hydroxymethyl-5-cis-13-trans-prostadiene |
| 364 | 319 | 281 | 139 | 1,9-dioxo-11α,16-dihydroxy-16-methyl-1-hydroxymethyl-13-trans-17-trans-5-cis-prostatriene |
| 365 | 319 | 281 | 149 | 1,9-dioxo-11α,16-dihydroxy-20-methyl-1-hydroxymethyl-13-trans-17-trans-5-cis-prostatriene |
| 366 | 319 | 281 | 150 | 1,9-dioxo-11α,16-dihydroxy-16-methyl-1-hydroxymethyl-5-cis-13-trans-prostadiene |
| 367 | 319 | 281 | 151 | 1,9-dioxo-11α,16-dihydroxy-17,20-dimethyl-1-hydroxymethyl-5-cis-13-trans-prostadiene |
| 368 | 319 | 281 | 152 | 1,9-dioxo-11α,16-dihydroxy-1-hydroxymethyl-13-trans-17-trans-5-cis-prostatriene |
| 369 | 319 | 281 | 153 | 1,9-dioxo-11α,16(R)-dihydroxy-1-hydroxymethyl-5-cis-13-trans-prostadiene |
| 370 | 319 | 281 | 154 | 1,9-dioxo-11α,16(S)-dihydroxy-1-hydroxymethyl-5-cis-13-trans-prostadiene |
| 371 | 319 | 281 | 148a | 1,9-dioxo-11α,16-dihydroxy-20-ethyl-1-hydroxymethyl-5-cis-13-trans-17-trans-prostatriene |
| 372 | 319 | 281 | 1-iodo-3-triphenylmethoxy-1-trans-octene (U.S. Pat. No. 3,873,607). | 1,9-dioxo-11α,15α-dihydroxy-1-hydroxymethyl-5-cis-13-trans-prostadiene |
| 373 | 319 | 281 | 1-iodo-3-triphenylmethoxy-1-trans-nonene (U.S. Pat. No. 3,873,607). | 1,9-dioxo-11α,15α-dihydroxy-20-methyl-1-hydroxymethyl-5-cis-13-trans-prostadiene |
| 374 | 319 | 281 | 1-iodo-3-triphenylmethoxy-1-trans-decene (U.S. Pat. No. 3,873,607). | 1,9-dioxo-11α,15α-dihydroxy-20-ethyl-1-hydroxymethyl-5-cis-13-trans-prostadiene |
| 375 | 319 | 281 | 1-iodo-3-triphenylmethoxy-4,4-dimethyl-1-trans-octene (U.S. Pat. No. 3,873,607). | 1,9-dioxo-11α,15α-dihydroxy-16,16-dimethyl-1-hydroxymethyl-5-cis-13-trans-prostadiene |
| 376 | 319 | 281 | 1-iodo-3-triphenylmethoxy-5,5-dimethyl-1-trans-octene (U.S. Pat. No. 3,873,607). | 1,9-dioxo-11α,15α-dihydroxy-17,17-dimethyl-1-hydroxymethyl-5-cis-13-trans-prostadiene |
| 377 | 319 | 281 | 1-iodo-3-triphenylmethoxy-4-methyl-1-trans-octene (U.S. Pat. No. 3,876,690). | 1,9-dioxo-11α,15α-dihydroxy-16-methyl-1-hydroxymethyl-5-cis-13-trans-prostadiene |
| 378 | 319 | 281 | 1-iodo-3-triphenylmethoxy-4-ethyl-1-trans-octene (U.S. Pat. No. 3,876,690). | 1,9-dioxo-11α,15α-dihydroxy-16-ethyl-1-hydroxymethyl-5-cis-13-trans-prostadiene |
| 379 | 319 | 281 | 1-iodo-3-tri- | 1,9-dioxo-11α,15α-dihydroxy-17,20- |

TABLE 32-continued

| Example | Method of Example | Cyclopent-2-en-1-one | Vinyl Iodide or Vinyl Tin of Example | 1,9-dioxo-1-hydroxymethylprostene |
|---|---|---|---|---|
| | | | phenylmethoxy-4-cyclopentyl-1-trans-butene-(U.S. Pat. No. 3,884,969). | tetra-nor-16-cyclopentyl-1-hydroxymethyl-5-cis-13-trans-prostadiene |
| 380 | 319 | 281 | 1-iodo-3-triphenylmethoxy-3-cyclohexyl-1-trans-pentene (U.S. Pat. No. 3,884,969). | 1,9-dioxo-11α,15α-dihydroxy-16,20-pentanor-15-cyclohexyl-1-hydroxymethyl-5-cis-13-trans-prostadiene |
| 381 | 319 | 281 | 1-iodo-3-triphenylmethoxy-5-cyclohexyl-1-trans-pentene (U.S. Pat. No. 3,884,969). | 1,9-dioxo-11α,15α-dihydroxy-18,20-trinor-17-cyclohexyl-1-hydroxymethyl-5-cis-13-trans-prostadiene |
| 382 | 319 | 281 | 1-iodo-3-triphenylmethoxy-6-cyclopentyl-1-trans-hexene (U.S. Pat. No. 3,884,969). | 1,9-dioxo-11α,15α-dihydroxy-19,20-dinor-18-cyclopentyl-1-hydroxymethyl-5-cis-13-trans-prostadiene |
| 383 | 319 | 281 | 1-iodo-3-methyl-3-trimethylsilyloxy-trans-1-octene (Example 125) | 1,9-dioxo-11α,15α-dihydroxy-15-methyl-1-hydroxymethyl-5-cis-13-trans-prostadiene |
| 384 | 319 | 281 | 1-iodo-3-methyl-3-trimethylsilyloxy-trans-1-decene (Example 190a) | 1,9-dioxo-11α,15α-dihydroxy-15-methyl-20-ethyl-1-hydroxymethyl-5-cis-13-trans-prostadiene |
| 385 | 320 | 281 | 159 | 1,9-dioxo-11α,15α-dihydroxy-17,18,19,20-tetranor-16-p-fluorophenoxy-1-hydroxymethyl-5-cis-13-trans-prostadiene |
| 386 | 320 | 281 | 186 | 1,9-dioxo-11α,15α-dihydroxy-17,18,19,20-tetranor-16-phenoxy-1-hydroxymethyl-5-cis-13-trans-prostadiene |
| 387 | 320 | 281 | 181 | 1,9-dioxo-11α,15α-dihydroxy-17,18,19,20-tetranor-16-p-bromophenoxy-1-hydroxymethyl-5-cis-13-trans-prostadiene |
| 388 | 320 | 281 | 182 | 1,9-dioxo-11α,15α-dihydroxy-17,18,19,20-tetranor-16-p-t-butylphenoxy-1-hydroxymethyl-5-cis-13-trans-prostadiene |
| 389 | 320 | 281 | 183 | 1,9-dioxo-11α,15α-dihydroxy-17,18,19,20-tetranor-16-p-methoxyphenoxy-1-hydroxymethyl-5-cis-13-trans-prostadiene |
| 390 | 320 | 281 | 184 | 1,9-dioxo-11α,15α-dihydroxy-17,18,19,20-tetranor-16-m-chlorophenoxy-1-hydroxymethyl-5-cis-13-trans-prostadiene |
| 391 | 320 | 281 | 180 | 1,9-dioxo-11α,15α-dihydroxy-17,18,19,20-tetranor-16-m-trifluorophenoxy-1-hydroxymethyl-5-cis-13-trans-prostadiene |
| 392 | 320 | 281 | 185 | 1,9-dioxo-11α,15α-dihydroxy-17,18,19,20-tetranor-16-(3,4-dichlorophenoxy)-1-hydroxymethyl-5-cis-13-trans-prostadiene |
| 393 | 320 | 281 | 186b | 1,9-dioxo-11α,15α-dihydroxy-18,19,20-trinor-17-phenyl-1-hydroxymethyl-5-cis-13-trans-prostadiene |
| 394 | 320 | 281 | 186e | 1,9-dioxo-11α,15α-dihydroxy-18,19,20-trinor-17-(m-trifluoromethylphenyl)-1-hydroxymethyl-5-cis-13-trans-prostadiene |
| 395 | 320 | 281 | 186d | 1,9-dioxo-11α,15α-dihydroxy-18,19,20-trinor-17-(p-methoxyphenyl)-1-hydroxymethyl-5-cis-13-trans-prostadiene |
| 396 | 319 | 290 | 1-iodo-3-triphenylmethoxy-1-trans-octene (U.S. Pat. 3,873,607) | 1,9-dioxo-11α,15α-dihydroxy-1-hydroxymethyl-2-nor-5-cis-13-trans-prostadiene |
| 397 | 319 | 290 | 190 | 1,9-dioxo-11α,15α-dihydroxy-15-methyl-1-hydroxymethyl-2-nor-5-cis-13-trans-prostadiene |
| 398 | 319 | 290 | 1-iodo-3-triphenylmethoxy-5,5-dimethyl octene (U.S. Pat. 3,873,607) | 1,9-dioxo-11α,15α-dihydroxy-16,16-dimethyl-1-hydroxymethyl-2-nor-5-cis-13-trans-prostadiene |
| 399 | 319 | 290 | 13 | 1,9-dioxo-11α,15α-dihydroxy-16,16-tri- |

TABLE 32-continued

| Example | Method of Example | Cyclopent-2-en-1-one | Vinyl Iodide or Vinyl Tin of Example | 1,9-dioxo-1-hydroxymethylprostene |
|---|---|---|---|---|
| | | | | methylene-1-hydroxymethyl-2-nor-5-cis-13-trans-prostadiene |
| 400 | 319 | 290 | 76 | erythro-1,9-dioxo-11α,15α,16-trihydroxy-1-hydroxymethyl-2-nor-5-cis-13-trans-prostadiene |
| 401 | 319 | 290 | 69 | threo-1,9-dioxo-11α,15α,16-trihydroxy-1-hydroxymethyl-2-nor-5-cis-13-trans-prostadiene |
| 402 | 319 | 290 | 74 | erythro-1,9-dioxo-11α,15α-dihydroxy-16-methoxy-1-hydroxymethyl-2-nor-5-cis-13-trans-prostadiene |
| 403 | 319 | 290 | 107 | 1,9-dioxo-11α,16-dihydroxy-1-hydroxymethyl-2-nor-5-cis-13-trans-prostadiene |
| 404 | 319 | 290 | 130 | 1,9-dioxo-11α,16-dihydroxy-16-methyl-1-hydroxymethyl-2-nor-5-cis-13-trans-prostadiene |
| 405 | 319 | 290 | 134 | 1,9-dioxo-11α,16-dihydroxy-16-methyl-1-hydroxymethyl-2-nor-5-cis-13-trans-prostadiene |
| 406 | 320 | 290 | 186 | 1,9-dioxo-11α,15α-dihydroxy-2,17,18,-19,20-pentanor-16-phenoxy-1-hydroxymethyl-5-cis-13-trans-prostadiene |
| 407 | 320 | 290 | 180 | 1,9-dioxo-11α,15α-dihydroxy-2,17,18,-19,20-pentanor-16-m-trifluoromethyl-phenoxy-1-hydroxymethyl-5-cis-13-trans-prostadiene |
| 408 | 319 | 290 | 194 | 1,9-dioxo-11α,16-dihydroxy-16-vinyl-1-hydroxymethyl-2-nor-5-cis-13-trans-prostadiene |
| 409 | 320 | 290 | 198 | 1,9-dioxo-11α,16-dihydroxy-16-cyclopropyl-1-hydroxymethyl-2-nor-5-cis-13-trans-prostadiene |
| 410 | 320 | 290 | 186b | 1,9-dioxo-11α,15α-dihydroxy-2,18,19,-20-tetranor-17-phenyl-1-hydroxymethyl-5-cis-13-trans-prostadiene |
| 411 | 319 | 290 | 186e | 1,9-dioxo-11α,15α-dihydroxy-2,18,19,-20-tetranor-17-(m-trifluorophenyl)-1-hydroxymethyl-5-cis-13-trans-prostadiene |
| 412 | 319 | 290 | 186d | 1,9-dioxo-11α,15α-dihydroxy-2,18,19,-20-tetranor-17-(p-methoxyphenyl)-1-hydroxymethyl-5-cis-13-trans-prostadiene |
| 413 | 319 | 285 | 125 | 1,9-dioxo-15-hydroxy-15-methyl-1-hydroxymethyl-2-nor-13-trans-prostene |
| 414 | 319 | 289 | 130 | 1,9-dioxo-11α,16-dihydroxy-16-methyl-1-homo-1-hydroxymethyl-5-cis-13-trans-prostadiene |
| 415 | 319 | 289 | 134 | 1,9-dioxo-11α,16-dihydroxy-16-methyl-1-homo-1-hydroxymethyl-5-cis-13-trans-17-trans-prostatriene |
| 416 | 320 | 289 | 186 | 1,9-dioxo-11α,15α-dihydroxy-1-homo-17,-18,19,20-tetranor-16-phenoxy-1-hydroxymethyl-5-cis-13-trans-prostadiene |
| 417 | 320 | 289 | 180 | 1,9-dioxo-11α,15α-dihydroxy-1-homo-17,-18,19,20-tetranor-16-m-trifluoromethyl-phenoxy-1-hydroxymethyl-5-cis-13-trans-prostadiene |
| 418 | 319 | 289 | 194 | 1,9-dioxo-11α,16-dihydroxy-16-vinyl-1-homo-1-hydroxymethyl-5-cis-13-trans-prostadiene |
| 419 | 320 | 289 | 198 | 1,9-dioxo-11α,16-dihydroxy-16-cyclopropyl-1-homo-1-hydroxymethyl-5-cis-13-trans-prostadiene |
| 420 | 320 | 289 | 186b | 1,9-dioxo-11α,15α-dihydroxy-1-homo-18,-19,20-trinor-17-phenyl-1-hydroxymethyl-5-cis-13-trans-prostadiene |
| 421 | 319 | 289 | 186e | 1,9-dioxo-11α,15α-dihydroxy-1-homo-18,-19,20-trinor-17-(m-trifluorophenyl)-13-trans-1-hydroxymethyl-5-cis-prostadiene |
| 422 | 319 | 289 | 186d | 1,9-dioxo-11α,15α-dihydroxy-1-homo-18,-19,20-trinor-17-(p-methoxyphenyl)-13-trans-1-hydroxymethyl-5-cis-prostadiene |

EXAMPLES 423–445

By the methods described hereinabove in Examples 319 and 320, the 1,9-dioxo-1-hydroxymethyl prostene derivatives shown in Table 33 are prepared by the indicated method from the indicated vinyl iodide or vinyl tin compound and the indicated cyclopent-2-en-1-one.

In those cases where two diastereoisomers are formed in the conjugate-addition, only one of the diastereoisomers is listed in Table 33. It should be understood that the other diastereoisomer is also formed which in its nat and ent forms has an opposite (mirror image) configuration at the assymetric carbon atoms on the β-chain (the chain containing $C_{13}$ ... $C_{14}$ etc.) to that of the respective nat and ent forms of the listed diastereoisomer; both of these diastereoisomers are claimed in this invention as well as their component enantiomers.

TABLE 33

| Example | Method of Example | Cyclopent-2-en-1-one of Example | Vinyl Iodide or Vinyl Tin of Example | 1,9-dioxo-1-hydroxymethylprostene and its diastereomer |
|---|---|---|---|---|
| 423 | 319 | 281 | 246 | nat(and ent)-1,9-dioxo-11α,15-dihydroxy-15,16-tetramethylene-17,18,19,20-tetranor-1-hydroxymethyl-5-cis,13-trans-prostadiene |
| 424 | 320 | 281 | 245 | nat(and ent)-1,9-dioxo-11α,16-dihydroxy-16,17-tetramethylene-18,19,20-trinor-1-hydroxymethyl-5-cis-13-trans-prostadiene |
| 425 | 319 | 281 | 243 | nat-15S,16R(and ent-15R,16S)-1,9-dioxo-11α,15-dihydroxy-15,16-trimethylene-1-hydroxymethyl-5-cis-13-trans-prostadiene |
| 426 | 319 | 281 | 243 | nat-15S,16R-(and ent-15R,16S)-1,9-dioxo-11α,15-dihydroxy-15,16-trimethylene-1-hydroxymethyl-13-trans-5-cis-prostadiene |
| 427 | 319 | 281 | 251 | nat-15S,16S-(and ent-15R,16R)-1,9-dioxo-11α,15-dihydroxy-15,16-trimethylene-1-hydroxymethyl-13-trans-5-cis-prostadiene |
| 428 | 319 | 281 | 247 | nat-(and ent)-1,9-dioxo-11α,15-dihydroxy-15,16-trimethylene-17,18,19,20-tetranor-1-hydroxymethyl-13-trans-5-cis-prostadiene |
| 429 | 320 | 281 | 248 | nat-(and ent)-1,9-dioxo-11α,15-dihydroxy-15,16-pentamethylene-17,18,19,20-tetranor-1-hydroxymethyl-13-trans-5-cis-prostadiene |
| 430 | 319 | 281 | 249 | nat-15S,17R-(and ent-15R,17S)-1,9-dioxo-11α,15-dihydroxy-15,17-dimethylene-1-hydroxymethyl-13-trans-5-cis-prostadiene |
| 431 | 319 | 281 | 250 | nat-15S,17S-(and ent-15R,17R)-1,9-dioxo-11α,15-dihydroxy-15,17-dimethylene-1-hydroxymethyl-13-trans-5-cis-prostadiene |
| 432 | 319 | 281 | 252 | nat-15S,16R-(and ent-15R,16S)-1,9-dioxo-11α,15-dihydroxy-15,16-tetramethylene-1-hydroxymethyl-13-trans-5-cis-prostadiene |
| 433 | 319 | 281 | 253 | nat-15S,16S-(and ent-15R,16R)-1,9-dioxo-11α,15-dihydroxy-15,16-tetramethylene-1-hydroxymethyl-13-trans-5-cis-prostadiene |
| 434 | 320 | 281 | 254 | nat-15R,16S-(and ent-15S,16R)-1,9-dioxo-11α,15-dihydroxy-15,16-trimethylene-16-(3-trifluoromethylphenoxy)-17,18,19,20-tetranor-1-hydroxymethyl-13-trans-5-cis-prostadiene |
| 435 | 320 | 281 | 255 | nat-15R,16R-(and ent-15S,16S)-1,9-dioxo-11α,15-dihydroxy-15,16-trimethylene-16-(3-trifluoromethylphenoxy)-17,18,19,20-tetranor-1-hydroxymethyl-13-trans-5-cis-prostadiene |
| 436 | 319 | 281 | 256 | nat-15R,16S-(and ent-15S,16R)-1,9-dioxo-11α,15-dihydroxy-15,16-trimethylene-16-(4-fluorophenoxy)-17,18,19,20-tetranor-1-hydroxymethyl-13-trans-5-cis-prostadiene |
| 437 | 319 | 281 | 257 | nat-15R,16R-(and ent-15S,16S)-1,9-dioxo-11α,15-dihydroxy-15,16-trimethylene-16-(4-fluorophenoxy)-17,18,19,20-tetranor-1-hydroxymethyl-13-trans-5-cis-prostadiene |
| 438 | 320 | 281 | 258 | nat-15R,16S-(and ent-15S,16R)-1,9-dioxo-11α,15-dihydroxy-15,16-trimethylene-16-(3-chlorophenoxy)-17,18,19,20-tetranor-1-hydroxymethyl-13-trans-5-cis-prostadiene |
| 439 | 320 | 281 | 259 | nat-15R,16R-(and ent-15S,16S)-1,9-dioxo-11α,15-dihydroxy-15,16-trimethylene-16-(3-chlorophenoxy)-17,18,19,20-tetranor-1-hydroxymethyl-13-trans-5-cis-prostadiene |
| 440 | 319 | 281 | 260 | nat-15S,17R-(and ent-15R,17S)-1,9-dioxo-11α,15-dihydroxy-15,17-trimethylene-19,20-dinor-1-hydroxymethyl-13-trans-5-cis-prostadiene |

TABLE 33-continued

| Example | Method of Example | Cyclopent-2-en-1-one of Example | Vinyl Iodide or Vinyl Tin of Example | 1,9-dioxo-1-hydroxymethylprostene and its diastereomer |
|---|---|---|---|---|
| 441 | 319 | 281 | 261 | nat-15S,17S-(and ent-15R,17R)-1,9-dioxo-11α,15-dihydroxy-15,17-trimethylene-19,-20-dinor-1-hydroxymethyl-13-trans-5-cis-prostadiene |
| 442 | 320 | 281 | 262 | nat-16R,17S-(and ent-16S,17R)-1,9-dioxo-11α,16-dihydroxy-16,17-trimethylene-20-methyl-1-hydroxymethyl-13-trans-5-cis-prostadiene |
| 443 | 320 | 281 | 263 | nat-16R,17R-(and ent-16S,17S)-1,9-dioxo-11α,16-dihydroxy-16,17-trimethylene-20-methyl-1-hydroxymethyl-13-trans-5-cis-prostadiene |
| 444 | 320 | 281 | 264 | nat-16R,17S-(and ent-16S,17R)-1,9-dioxo-11α,16-dihydroxy-16,17-trimethylene-16-(3-trifluoromethylphenoxy)-18,19,20-trinor-1-hydroxymethyl-13-trans-5-cis-prostadiene |
| 445 | 320 | 281 | 265 | nat-16R,17R-(and ent-16S,17S)-1,9-dioxo-11α,16-dihydroxy-16,17-trimethylene-16-(3-trifluoromethylphenoxy)-18,19,20-trinor-1-hydroxymethyl-13-trans-5-cis-prostadiene |

EXAMPLES 446–530

By the methods described hereinabove in Examples 319 and 320, the 1,9-dioxo-1-hydroxymethyl prostene derivative shown in Table 34 are prepared by the indicated method from the indicated vinyl iodide or vinyl tin compound and the indicated cyclopent-2-en-1-one.

In those cases where isomers are obtained at the $C_{15}$ or $C_{16}$ positions, only the $C_{15}$ or $C_{16}$-normal isomers is listed in Table 34; it should be understood that the corresponding $C_{15}$ or $C_{16}$-epi isomers are also formed and are part of this invention.

In those cases where the initial conjugate addition product contains a triphenylmethoxy blocking group, deblocking is conducted in acetic acid-tetrahydrofuran-water 4:2:1 at 50° C. for 5 hours.

TABLE 34

| Example | Method of Example | Cyclopent-2-en-1-one | Vinyl Iodide or Vinyl Tin of Example | 1,9-dioxo-1-hydroxymethylprostene |
|---|---|---|---|---|
| 446 | 319 | 292 | 49 | 1,9-dioxo-11α,15-dihydroxy-1-hydroxymethyl-16,16-trimethylene-20-nor-13-trans-prostene |
| 447 | 319 | 292 | 50 | 1,9-dioxo-11α,15-dihydroxy-1-hydroxymethyl-16,16-trimethylene-20-methyl-13-trans-prostene |
| 448 | 319 | 292 | 51 | 1,9-dioxo-11α,15-dihydroxy-1-hydroxymethyl-16,16-trimethylene-20-ethyl-13-trans-prostene |
| 449 | 320 | 292 | 193 | 1,9-dioxo-11α,16-dihydroxy-16-cyclopropyl-20-ethyl-1-hydroxymethyl-13-trans-prostene |
| 450 | 320 | 292 | 195 | 1,9-dioxo-11α,16-dihydroxy-16-vinyl-20-ethyl-1-hydroxymethyl-13-trans-prostene |
| 451 | 320 | 292 | 192 | 1,9-dioxo-11α,16-dihydroxy-16-cyclopropyl-1-hydroxymethyl-13-trans-prostene |
| 452 | 319 | 292 | 13 | 1,9-dioxo-11α,15-dihydroxy-1-hydroxymethyl-16,16-trimethylene-13-trans-prostene |
| 453 | 320 | 292 | 210a | 1,9-dioxo-11α,16-dihydroxy-1-hydroxymethyl-16-vinyl-13-trans-prostene |
| 454 | 319 | 292 | 74 | dl-erythro-1,9-dioxo-11α,15-dihydroxy-16-methoxy-1-hydroxymethyl-13-trans-prostene |
| 455a | 319 | 292 | 77 | dl-erythro-1,9-dioxo-11α,15-dihydroxy-16-ethoxy-1-hydroxymethyl-13-trans-prostene |
| 455b | 320 | 292 | 210c | 1,9-dioxo-11α,16-dihydroxy-16-ethyl-1-hydroxymethyl-13-trans-prostene |
| 456 | 319 | 292 | 83 | dl-erythro-1,9-dioxo-11α,15,16-trihydroxy-1-hydroxymethyl-20-nor-13-trans-prostene |
| 457 | 319 | 292 | 84 | dl-erythro-1,9-dioxo-11α,15,16-trihydroxy-1-hydroxymethyl-20-methyl-13-trans-prostene |
| 458 | 319 | 292 | 85 | dl-erythro-1,9-dioxo-11α,15,16-trihydroxy-20-ethyl-1-hydroxymethyl-13-trans-prostene |
| 459 | 319 | 292 | 86 | dl-erythro-1,9-dioxo-11α,15,16-trihydroxy-19-methyl-1-hydroxymethyl-13-trans- |

4,212,969

TABLE 34-continued

| Example | Method of Example | Cyclopent-2-en-1-one | Vinyl Iodide or Vinyl Tin of Example | 1,9-dioxo-1-hydroxymethylprostene |
|---|---|---|---|---|
| 460 | 319 | 292 | 87 | dl-erythro-1,9-dioxo-11α,15,16-trihydroxy-1-hydroxymethyl-13-trans-17-trans-prostadiene |
| 461 | 319 | 292 | 69 | dl-threo-1,9-dioxo-11α,15,16-trihydroxy-1-hydroxymethyl-13-trans-prostene |
| 462 | 319 | 292 | 88 | dl-threo-1,9-dioxo-11α,15,16-trihydroxy-20-nor-1-hydroxymethyl-13-trans-prostene |
| 463 | 319 | 292 | 76 | dl-erythro-1,9-dioxo-11α,15,16-trihydroxy-1-hydroxymethyl-13-trans-prostene |
| 465 | 319 | 292 | 89 | dl-threo-1,9-dioxo-11α,15,16-trihydroxy-20-methyl-1-hydroxymethyl-13-trans-prostene |
| 465 | 319 | 292 | 90 | dl-threo-1,9-dioxo-11α,15,16-trihydroxy-20-ethyl-1-hydroxymethyl-13-trans-prostene |
| 466 | 319 | 292 | 91 | dl-threo-1,9-dioxo-11α,15,16-trihydroxy-19-methyl-1-hydroxymethyl-13-trans-prostene |
| 467 | 319 | 292 | 92 | dl-threo-1,9-dioxo-11α,15,16-trihydroxy-1-hydroxymethyl-13-trans-17-trans-prostadiene |
| 468 | 319 | 292 | 107 | 1,9-dioxo-11α,16-dihydroxy-1-hydroxymethyl-13-trans-prostene |
| 469 | 319 | 292 | 108 | 1,9-dioxo-11α,16-dihydroxy-1-hydroxymethyl-19,20-dinor-13-trans-prostene |
| 470 | 319 | 292 | 109 | 1,9-dioxo-11α,16-dihydroxy-1-hydroxymethyl-18,19,20-trinor-13-trans-prostene |
| 471 | 319 | 292 | 110 | 1,9-dioxo-11α,16-dihydroxy-1-hydroxymethyl-20-nor-13-trans-prostene |
| 472 | 319 | 292 | 144 | 1,9-dioxo-11α,16-dihydroxy-17-methyl-1-hydroxymethyl-13-trans-prostene |
| 473 | 319 | 292 | 112 | 1,9-dioxo-11α,16-dihydroxy-20-methyl-1-hydroxymethyl-13-trans-prostene |
| 474 | 319 | 292 | 113 | 1,9-dioxo-11α,16-dihydroxy-20-ethyl-1-hydroxymethyl-13-trans-prostene |
| 475 | 319 | 292 | 139a | 1,9-dioxo-11α,16-dihydroxy-16-methyl-20-ethyl-1-hydroxymethyl-13-trans-prostene |
| 476 | 319 | 292 | 115 | 1,9-dioxo-11α,16-dihydroxy-1-hydroxymethyl-13-trans-17-cis-prostadiene |
| 477 | 319 | 292 | 135 | 1,9-dioxo-11α,16-dihydroxy-16-methyl-1-hydroxymethyl-13-trans-prostene |
| 478 | 319 | 292 | 136 | 1,9-dioxo-11α,16-dihydroxy-17,17,20-trimethyl-1-hydroxymethyl-13-trans-prostene |
| 479 | 319 | 292 | 137 | 1,9-dioxo-11α,16-dihydroxy-16,20-dimethyl-1-hydroxymethyl-13-trans-prostene |
| 480 | 319 | 292 | 138 | 1,9-dioxo-11α,16-dihydroxy-17,17-dimethyl-1-hydroxymethyl-13-trans-prostene |
| 481 | 319 | 292 | 139 | 1,9-dioxo-11α,16-dihydroxy-16-methyl-1-hydroxymethyl-13-trans-17-trans-prostadiene |
| 482 | 319 | 292 | 149 | 1,9-dioxo-11α,16-dihydroxy-20-methyl-1-hydroxymethyl-13-trans-17-trans-prostadiene |
| 483 | 319 | 292 | 150 | 1,9-dioxo-11α,16-dihydroxy-16-methyl-1-hydroxymethyl-13-trans-prostene |
| 485 | 319 | 292 | 151 | 1,9-dioxo-11α,16-dihydroxy-17,20-dimethyl-1-hydroxymethyl-13-trans-prostene |
| 486 | 319 | 292 | 152 | 1,9-dioxo-11α,16-dihydroxy-1-hydroxymethyl-13-trans-17-trans-prostadiene |
| 487 | 319 | 292 | 153 | 1,9-dioxo-11α,16(R)-dihydroxy-1-hydroxymethyl-13-trans-prostene |
| 488 | 319 | 292 | 154 | 1,9-dioxo-11α,16(S)-dihydroxy-1-hydroxymethyl-13-trans-prostene |
| 489 | 319 | 292 | 148a | 1,9-dioxo-11α,16-dihydroxy-20-ethyl-1-hydroxymethyl-13-trans-17-trans-prostadiene |
| 490 | 319 | 292 | 1-iodo-3-triphenylmethoxy-1-trans-octene (U.S. Pat. No. 3,873,607). | 1,9-dioxo-11α,15α-dihydroxy-1-hydroxymethyl-13-trans-prostadiene |
| 491 | 319 | 292 | 1-iodo-3-triphenylmethoxy-1-trans-nonene (U.S. Pat. No. 3,873,607). | 1,9-dioxo-11α,15α-dihydroxy-20-methyl-1-hydroxymethyl-13-trans-prostene |
| 492 | 319 | 292 | 1-iodo-3-triphenylmethoxy-1-trans-decene | 1,9-dioxo-11α,15α-dihydroxy-20-ethyl-1-hydroxymethyl-13-trans-prostene |

TABLE 34-continued

| Example | Method of Example | Cyclopent-2-en-1-one | Vinyl Iodide or Vinyl Tin of Example | 1,9-dioxo-1-hydroxymethylprostene |
|---|---|---|---|---|
| 493 | 319 | 292 | 1-iodo-3-triphenylmethoxy-4,4-dimethyl-1-trans-octene (U.S. Pat. No. 3,873,607). | 1,9-dioxo-11α,15α-dihydroxy-16,16-dimethyl-1-hydroxymethyl-13-trans-prostene |
| 494 | 319 | 292 | 1-iodo-3-triphenylmethoxy-5,5-dimethyl-1-trans-octene (U.S. Pat. No. 3,873,607). | 1,9-dioxo-11α,15α-dihydroxy-17,17-dimethyl-1-hydroxymethyl-13-trans-prostene |
| 495 | 319 | 292 | 1-iodo-3-triphenylmethoxy-4-methyl-1-trans-octene (U.S. Pat. No. 3,876,690). | 1,9-dioxo-11α,15α-dihydroxy-16-methyl-1-hydroxymethyl-13-trans-prostene |
| 496 | 319 | 292 | 1-iodo-3-triphenylmethoxy-4-ethyl-1-trans-octene (U.S. Pat. No. 3,876,690). | 1,9-dioxo-11α,15α-dihydroxy-16-ethyl-1-hydroxymethyl-13-trans-prostene |
| 497 | 319 | 292 | 1-iodo-3-triphenylmethoxy-4-cyclopentyl-1-trans-butene- (U.S. Pat. No. 3,884,969). | 1,9-dioxo-11α,15α-dihydroxy-17,20-tetranor-16-cyclopentyl-1-hydroxymethyl-13-trans-prostene |
| 498 | 319 | 292 | 1-iodo-3-triphenylmethoxy-3-cyclohexyl-1-trans-pentene (U.S. Pat. No. 3,884,969). | 1,9-dioxo-11α,15α-dihydroxy-16,20-pentanor-15-cyclohexyl-1-hydroxymethyl-13-trans-prostene |
| 499 | 319 | 292 | 1-iodo-3-triphenylmethoxy-5-cyclohexyl-1-trans-pentene (U.S. Pat. No. 3,884,969). | 1,9-dioxo-11α,15α-dihydroxy-18,20-trinor-17-cyclohexyl-1-hydroxymethyl-13-trans-prostene |
| 500 | 319 | 292 | 1-iodo-3-triphenylmethoxy-6-cyclopentyl-1-trans-hexene (U.S. Pat. No. 3,884,969). | 1,9-dioxo-11α,15α-dihydroxy-19,20-dinor-18-cyclopentyl-1-hydroxymethyl-13-trans-prostene |
| 501 | 319 | 292 | 1-iodo-3-trimethylsilyloxy-trans-1-octene (Example 125) | 1,9-dioxo-11α,15α-dihydroxy-15-methyl-1-hydroxymethyl-13-trans-prostene |
| 502 | 319 | 292 | 1-iodo-3-methyl-3-trimethylsilyloxy-trans-1-decene (Example 190a) | 1,9-dioxo-11α,15α-dihydroxy-15-methyl-20-ethyl-1-hydroxymethyl-13-trans-prostene |
| 503 | 320 | 292 | 159 | 1,9-dioxo-11α,15α-dihydroxy-17,18,19,20-tetranor-16-p-fluorophenoxy-1-hydroxymethyl-13-trans-prostene |
| 504 | 320 | 292 | 186 | 1,9-dioxo-11α,15α-dihydroxy-17,18,29,10-tetranor-16-phenoxy-1-hydroxymethyl-13-trans-prostene |
| 505 | 320 | 292 | 181 | 1,9-dioxo-11α,15α-dihydroxy-17,18,19,20-tetranor-16-p-bromophenoxy-1-hydroxymethyl-13-trans-prostene |
| 506 | 320 | 292 | 182 | 1,9-dioxo-11α,15α-dihydroxy-17,18,19,20-tetranor-16-p-t-butylphenoxy-1-hydroxymethyl-13-trans-prostene |
| 507 | 320 | 292 | 183 | 1,9-dioxo-11α,15α-dihydroxy-17,18,19,20-tetranor-16-p-methoxyphenoxy-1-hydroxymethyl-13-trans-prostene |
| 508 | 320 | 292 | 184 | 1,9-dioxo-11α,15α-dihydroxy-17,18,19,20-tetranor-16-m-chlorophenoxy-1-hydroxymethyl-13-trans-prostene |
| 509 | 320 | 292 | 180 | 1,9-dioxo-11α,15α-dihydroxy-17,18,19,20-tetranor-16-m-trifluorophenoxy-1-hydroxymethyl-13-trans-prostene |

TABLE 34-continued

| Example | Method of Example | Cyclopent-2-en-1-one | Vinyl Iodide or Vinyl Tin of Example | 1,9-dioxo-1-hydroxymethylprostene |
|---|---|---|---|---|
| 510 | 320 | 292 | 185 | 1,9-dioxo-11α,15α-dihydroxy-17,18,19,20-tetranor-16-(3,4-dichlorophenoxy)-1-hydroxymethyl-13-trans-prostene |
| 511 | 320 | 292 | 186b | 1,9-dioxo-11α,15α-dihydroxy-18,19,20-trinor-17-phenyl-1-hydroxymethyl-13-trans-prostene |
| 512 | 320 | 292 | 186e | 1,9-dioxo-11α,15α-dihydroxy-18,19,20-trinor-17-(m-trifluoromethylphenyl)-1-hydroxy-13-trans-prostene |
| 513 | 320 | 292 | 186d | 1,9-dioxo-11α,15α-dihydroxy-18,19,20-trinor-17-(p-methoxyphenyl)-1-hydroxymethyl-13-trans-prostene |
| 514 | 319 | 293 | 1-iodo-3-triphenylmethoxy-1-trans-octene (U.S. Pat. No. 3,873,607). | 1,9-dioxo-11α,15α-dihydroxy-1-hydroxymethyl-trans-prostadiene |
| 515 | 319 | 293 | 190 hydroxymethyl-2-nor-13-trans-prostene | 1,9-dioxo-11α,15α-dihydroxy-15-methyl-1- |
| 516 | 319 | 293 | 1-iodo-3-triphenylmethoxy-5,5-dimethyl-octene (U.S. Pat. No. 3,873,607) | 1,9-dioxo-11α,15α-dihydroxy-16,16-dimethyl-1-hydroxymethyl-2-nor-13-trans- |
| 517 | 319 | 293 | 3 | 1,9-dioxo-11α,15α-dihydroxy-16,16-trimethylene-1-hydroxymethyl-2-nor-13-trans-prostene |
| 518 | 319 | 293 | 76 | erythro-1,9-dioxo-11α,15α,16-trihydroxy-1-hydroxymethyl-2-nor-13-trans-prostene |
| 519 | 319 | 293 | 69 | threo-1,9-dioxo-11α,15α,16-trihydroxy-1-hydroxymethyl-2-nor-13-trans-prostene |
| 520 | 319 | 293 | 74 | erythro-1,9-dioxo-11α,15α-dihydroxy-16-methoxy-1-hydroxymethyl-2-nor-13-trans-prostene |
| 521 | 319 | 293 | 107 | 1,9-dioxo-11α,16-dihydroxy-1-hydroxymethyl-2-nor-13-trans-prostene |
| 522 | 319 | 293 | 130 | 1,9-dioxo-11α,16-dihydroxy-16-methyl-1-hydroxymethyl-2-nor-13-trans-prostene |
| 523 | 319 | 293 | 134 | 1,9-dioxo-11α,16-dihydroxy-16-methyl-1-hydroxymethyl-2-nor-13-trans-prostene |
| 524 | 320 | 293 | 186 | 1,9-dioxo-11α,15α-dihydroxy-2,17,18,19,20-pentanor-16-phenoxy-1-hydroxymethyl-13-trans-prostene |
| 525 | 320 | 293 | 180 | 1,9-dioxo-11α,15α-dihydroxy-2,17,18,19,20-pentanor-16-m-trifluoromethylphenoxy-1-hydroxymethyl-13-trans-prostene |
| 526 | 319 | 293 | 194 | 1,9-dioxo-11α,16-dihydroxy-16-vinyl-1-hydroxymethyl-2-nor-13-trans-prostene |
| 527 | 320 | 293 | 198 | 1,9-dioxo-11α,16-dihydroxy-16-cyclopropyl-1-hydroxymethyl-2-nor-13-trans-prostene |
| 528 | 320 | 293 | 186b | 1,9-dioxo-11α,15α-dihydroxy-2,18,19,20-tetranor-17-phenyl-1-hydroxymethyl-13-trans-prostene |
| 529 | 319 | 293 | 186e | 1,9-dioxo-11α,15α-dihydroxy-2,18,19,20-tetranor-17-(m-trifluorophenyl)-1-hydroxymethyl-13-trans-prostene |
| 530 | 319 | 293 | 186d | 1,9-dioxo-11α,15α-dihydroxy-2,18,19,20-tetranor-17-(p-methoxyphenyl)-1-hydroxymethyl-13-trans-prostene |

EXAMPLES 531–553

By the methods described hereinabove in Examples 319 and 320, the 1,9-dioxo-1-hydroxymethyl prostene derivatives shown in Table 35 are prepared by the indicated method from the indicated vinyl iodide or vinyl tin compound and the indicated cyclopent-2-en-1-one.

In those cases where two diastereoisomers are formed in the conjugate-addition, only one of the diastereoisomers is listed in Table 35. It should be understood that the other diastereoisomer is also formed which in its nat and ent forms has an opposite (mirror image) configuration at the assymmetric carbon atoms on the β-chain (the chain containing $C_{13}...C_{14}$ etc.) to that of the respective nat and ent forms of the listed diastereoisomer; both of these diastereoisomers are claimed in this invention as well as their component enantiomers.

TABLE 35

| Example | Method of Example | Cyclopent-2-en-1-one of Example | Vinyl Iodide or Vinyl Tin of Example | 1,9-dioxo-1-hydroxymethylprostene and its diastereomer |
|---|---|---|---|---|
| 531 | 319 | 292 | 246 | nat(and ent)-1,9-dioxo-11α,15-dihydroxy-15,16-tetramethylene-17,18,19,20-tetranor-1-hydroxymethyl-13-trans-prostene |
| 532 | 320 | 292 | 245 | nat(and ent)-1,9-dioxo-11α,16-dihydroxy-16,17-tetramethylene-18,19,20-trinor-1-hydroxymethyl-13-trans-prostene |
| 533 | 319 | 292 | 243 | nat-15S,16R(and ent-15R,16S)-1,9-dioxo-11α,15-dihydroxy-15,16-trimethylene-1-hydroxymethyl-13-trans-prostene |
| 534 | 319 | 292 | 243 | nat-15S,16R-(and ent-15R,16S)-1,9-dioxo-11α,15-dihydroxy-15,16-trimethylene-1-hydroxymethyl-13-trans-prostene |
| 535 | 319 | 292 | 251 | nat-15S,16S-(and ent-15R,16R)-1,9-dioxo-11α,15-dihydroxy-15,16-trimethylene-1-hydroxymethyl-13-trans-prostene |
| 536 | 319 | 292 | 247 | nat-(and ent)-1,9-dioxo-11α,15-dihydroxy-15,16-trimethylene-17,18,19,20-tetranor-1-hydroxymethyl-13-trans-prostene |
| 537 | 320 | 292 | 248 | nat-(and ent)-1,9-dioxo-11α,15-dihydroxy-15,16-pentamethylene-17,18,19,20-tetranor-1-hydroxymethyl-13-trans-prostene |
| 538 | 319 | 292 | 249 | nat-15S,17R-(and ent-15R,17S)-1,9-dioxo-11α,15-dihydroxy-15,17-dimethylene-1-hydroxymethyl-13-trans-prostene |
| 539 | 319 | 292 | 250 | nat-15S,17S-(and ent-15R,17R)-1,9-dioxo-11α,15-dihydroxy-15,17-dimethylene-1-hydroxymethyl-13-trans-prostene |
| 540 | 319 | 292 | 252 | nat-15S,16R-(and ent-15R,16S)-1,9-dioxo-11α,15-dihydroxy-15,16-tetramethylene-1-hydroxymethyl-13-trans-prostene |
| 541 | 319 | 292 | 253 | nat-15S,16S-(and ent-15R,16R)-1,9-dioxo-11α,15-dihydroxy-15,16-tetramethylene-1-hydroxymethyl-13-trans-prostene |
| 542 | 320 | 292 | 254 | nat-15R,16S-(and ent-15S,16R)-1,9-dioxo-11α,15-dihydroxy-15,16-trimethylene-16-(3-trifluoromethylphenoxy)-17,18,19,20-tetranor-1-hydroxymethyl-13-trans-prostene |
| 543 | 320 | 292 | 255 | nat-15R,16R-(and ent-15S,16S)-1,9-dioxo-11α,15-dihydroxy-15,16-trimethylene-16-(3-trifluoromethylphenoxy)-17,18,19,20-tetranor-1-hydroxymethyl-13-trans-prostene |
| 544 | 319 | 292 | 256 | nat-15R,16S-(and ent-15S,16R)-1,9-dioxo-11α,15-dihydroxy-15,16-trimethylene-16-(4-fluorophenoxy)-17,18,19,20-tetranor-1-hydroxymethyl-13-trans-prostene |
| 545 | 319 | 292 | 257 | nat-15R,16R-(and ent-15S,16S)-1,9-dioxo-11α,15-dihydroxy-15,16-trimethylene-16-(4-fluorophenoxy)-17,18,19,20-tetranor-1-hydroxymethyl-13-trans-prostene |
| 546 | 320 | 292 | 258 | nat-15R,16S-(and ent-15S,16R)-1,9-dioxo-11α,15-dihydroxy-15,16-trimethylene-16-(3-chlorophenoxy)-17,18,19,20-tetranor-1-hydroxymethyl-13-trans-prostene |
| 547 | 320 | 292 | 259 | nat-15R,16R-(and ent-15S,16S)-1,9-dioxo-11α,15-dihydroxy-15,16-trimethylene-16-(3-chlorophenoxy)-17,18,19,20-tetranor-1-hydroxymethyl-13-trans-prostene |
| 548 | 319 | 292 | 260 | nat-15S,17R-(and ent-15R,17S)-1,9-dioxo-11α,15-dihydroxy-15,17-trimethylene-19,20-dinor-1-hydroxymethyl-13-trans-prostene |
| 549 | 319 | 292 | 261 | nat-15S,17S-(and ent-15R,17R)-1,9-dioxo-11α,15-dihydroxy-15,17-trimethylene-19,20-dinor-1-hydroxymethyl-13-trans-prostene |
| 550 | 320 | 292 | 262 | nat-16R,17S-(and ent-16S,17R)-1,9-dioxo-11α,16-dihydroxy-16,17-trimethylene-20-methyl-1-hydroxymethyl-13-trans-prostene |
| 551 | 320 | 292 | 263 | nat-16R,17R-(and ent-16S,17S)-1,9-dioxo-11α,16-dihydroxy-16,17-trimethylene-20-methyl-1-hydroxymethyl-13-trans-prostene |
| 552 | 320 | 292 | 264 | nat-16R,17S-(and ent-16S,17R)-1,9-dioxo-11α,17-dihydroxy-16,17-trimethylene-16-(3-trifluoromethylphenoxy)-18,19,20-trinor-1-hydroxymethyl-13-trans-prostene |
| 553 | 320 | 292 | 265 | nat-16R,17R-(and ent-16S,17S)-1,9-dioxo-11α,16-dihydroxy-16,17-trimethylene-16- |

TABLE 35-continued

| Example | Method of Example | Cyclopent-2-en-1-one of Example | Vinyl Iodide or Vinyl Tin of Example | 1,9-dioxo-1-hydroxymethylprostene and its diastereomer |
|---|---|---|---|---|
| | | | | (3-trifluoromethylphenoxy)-18,19,20-trinor-1-hydroxymethyl-13-trans-prostene |

EXAMPLES 554–637

By the methods described hereinabove in Examples 319 and 320, the 1,9-dioxo-1-hydroxymethyl prostene derivatives shown in Table 36 are prepared by the indicated method from the indicated vinyl iodide or vinyl tin compound and the indicated cyclopent-2-en-1-one.

In those cases where isomers are obtained at the $C_{15}$ or $C_{16}$ positions, only the $C_{15}$ or $C_{16}$-normal isomers are listed in Table 36; it should be understood that the corresponding $C_{15}$ or $C_{16}$-epi isomer is also formed and is part of this invention.

In those cases where the initial conjugate addition product contains a tripheylmethoxy blocking group, deblocking is conducted in acetic acid-tetrahydrofuran 4:2:1 at 50° C. for 5 hours.

TABLE 36

| Example | Method of Example | Cyclopent-2-en-1-one | Vinyl Iodide or Vinyl Tin of Example | 1,9-dioxo-1-hydroxymethylprostene |
|---|---|---|---|---|
| 554 | 319 | 287 | 49 | 1,9-dioxo-15-hydroxy-1-hydroxymethyl-16,16-trimethylene-20-nor-5-cis-13-trans-prostadiene |
| 555 | 319 | 287 | 50 | 1,9-dioxo-15-hydroxy-1-hydroxymethyl-16,16-trimethylene-20-methyl-5-cis-13-trans-prostadiene |
| 556 | 319 | 287 | 51 | 1,9-dioxo-15-hydroxy-1-hydroxymethyl-16,16-trimethylene-20-ethyl-5-cis-13-trans-prostadiene |
| 557 | 320 | 287 | 193 | 1,9-dioxo-16-hydroxy-16-cyclopropyl-20-ethyl-1-hydroxymethyl-5-cis-13-trans-prostadiene |
| 558 | 320 | 287 | 195 | 1,9-dioxo-16-hydroxy-16-vinyl-20-ethyl-1-hydroxymethyl-5-cis-13-trans-prostadiene |
| 559 | 320 | 287 | 192 | 1,9-dioxo-11α,16-dihydroxy-16-cyclopropyl-1-hydroxymethyl-5-cis-13-trans-prostadiene |
| 560 | 319 | 287 | 13 | 1,9-dioxo-15-hydroxy-1-hydroxymethyl-16,16-trimethylene-13-trans-5-cis-prostadiene |
| 561 | 320 | 287 | 210a | 1,9-dioxo-16-hydroxy-1-hydroxymethyl-16-vinyl-5-cis-13-trans-prostadiene |
| 562 | 319 | 287 | 74 | dl-erythro-1,9-dioxo-15-hydroxy-16-methoxy-1-hydroxymethyl-5-cis-13-trans-prostadiene |
| 563 | 319 | 287 | 77 | dl-erythro-1,9-dioxo-15-hydroxy-16-ethoxy-1-hydroxymethyl-5-cis-13-trans-prostadiene |
| 564 | 319 | 287 | 83 | dl-erythro-1,9-dioxo-15,16-dihydroxy-1-hydroxymethyl-20-nor-5-cis-13-trans-prostadiene |
| 565 | 319 | 287 | 84 | dl-erythro-1,9-dioxo-15,16-dihydroxy-1-hydroxymethyl-20-methyl-5-cis-13-trans-prostadiene |
| 566 | 319 | 287 | 85 | dl-erythro-1,9-dioxo-15,16-dihydroxy-20-ethyl-1-hydroxymethyl-5-cis-13-trans-prostadiene |
| 567 | 319 | 287 | 86 | dl-erythro-1,9-dioxo-15,16-dihydroxy-19-methyl-1-hydroxymethyl-5-cis-13-trans-prostadiene |
| 568 | 319 | 287 | 87 | dl-erythro-1,9-dioxo-15,16-dihydroxy-1-hydroxymethyl-5-cis-13-trans-17-trans-prostatriene |
| 569 | 319 | 287 | 69 | dl-threo-1,9-dioxo-15,16-dihydroxy-1-hydroxymethyl-5-cis-13-trans-prostadiene |
| 570 | 319 | 287 | 88 | dl-threo-1,9-dioxo-15,16-dihydroxy-20-nor-1-hydroxymethyl-5-cis-13-trans-prostadiene |
| 571 | 319 | 287 | 76 | dl-erythro-1,9-dioxo-11α,15,16-trihydroxy-1-hydroxymethyl-5-cis-13-trans-prostadiene |
| 572 | 319 | 287 | 89 | dl-threo-1,9-dioxo-15,16-dihydroxy-20-methyl-1-hydroxymethyl-5-cis-13-trans-prostadiene |
| 573 | 319 | 287 | 90 | dl-threo-1,9-dioxo-15,16-dihydroxy-20-ethyl-1-hydroxymethyl-5-cis-13-trans-prostadiene |
| 574 | 319 | 287 | 91 | dl-threo-1,9-dioxo-15,16-dihydroxy-19- |

TABLE 36-continued

| Example | Method of Example | Cyclopent-2-en-1-one | Vinyl Iodide or Vinyl Tin of Example | 1,9-dioxo-1-hydroxymethylprostene |
|---------|-------------------|----------------------|--------------------------------------|------------------------------------|
| 575 | 319 | 287 | 92 | methyl-1-hydroxymethyl-5-cis-13-trans-prostadiene dl-threo-1,9-dioxo-15,16-dihydroxy-1-hydroxymethyl-5-cis-13-trans-17-trans-prostatriene |
| 576 | 319 | 287 | 107 | 1,9-dioxo-16-hydroxy-1-hydroxymethyl-5-cis-13-trans-prostadiene |
| 577 | 319 | 287 | 108 | 1,9-dioxo-16-hydroxy-1-hydroxymethyl-19,20-dinor-5-cis-13-trans-prostadiene |
| 578 | 319 | 287 | 109 | 1,9-dioxo-16-hydroxy-1-hydroxymethyl-18,19,20-trinor-5-cis-13-trans-prostadiene |
| 579 | 319 | 287 | 110 | 1,9-dioxo-16-hydroxy-1-hydroxymethyl-20-nor-5-cis-13-trans-prostadiene |
| 580 | 319 | 287 | 144 | 1,9-dioxo-16-hydroxy-17-methyl-1-hydroxymethyl-5-cis-13-trans-prostadiene |
| 581 | 319 | 287 | 112 | 1,9-dioxo-16-hydroxy-20-methyl-1-hydroxymethyl-5-cis-13-trans-prostadiene |
| 582 | 319 | 287 | 113 | 1,9-dioxo-16-hydroxy-20-ethyl-1-hydroxymethyl-5-cis-13-trans-prostadiene |
| 583 | 319 | 287 | 139a | 1,9-dioxo-16-hydroxy-16-methyl-20-ethyl-1-hydroxymethyl-5-cis-13-trans-prostadiene |
| 584 | 319 | 287 | 115 | 1,9-dioxo-16-hydroxy-1-hydroxymethyl-13-trans-17-cis-5-cis-prostatriene |
| 585 | 319 | 287 | 135 | 1,9-dioxo-16-hydroxy-16-methyl-1-hydroxymethyl-5-cis-13-trans-prostadiene |
| 586 | 319 | 287 | 136 | 1,9-dioxo-16-hydroxy-17,17,20-trimethyl-1-hydroxymethyl-5-cis-13-trans-prostadiene |
| 587 | 319 | 287 | 137 | 1,9-dioxo-16-hydroxy-16,20-dimethyl-1-hydroxymethyl-13-trans-5-cis-prostadiene |
| 588 | 319 | 287 | 138 | 1,9-dioxo-16-hydroxy-17,17-dimethyl-1-hydroxymethyl-5-cis-13-trans-prostadiene |
| 589 | 319 | 287 | 139 | 1,9-dioxo-16-hydroxy-16-methyl-1-hydroxymethyl-13-trans-17-trans-5-cis-prostatriene |
| 590 | 319 | 287 | 149 | 1,9-dioxo-16-hydroxy-20-methyl-1-hydroxymethyl-13-trans-17-trans-5-cis-prostatriene |
| 591 | 319 | 287 | 150 | 1,9-dioxo-16-hydroxy-16-methyl-1-hydroxymethyl-5-cis-13-trans-prostadiene |
| 592 | 319 | 287 | 151 | 1,9-dioxo-16-hydroxy-17,20-dimethyl-1-hydroxymethyl-5-cis-13-trans-prostadiene |
| 593 | 319 | 287 | 152 | 1,9-dioxo-16-hydroxy-1-hydroxymethyl-13-trans-17-trans-5-cis-prostatriene |
| 594 | 319 | 287 | 153 | 1,9-dioxo-16(R)-hydroxy-1-hydroxymethyl-5-cis-13-trans-prostadiene |
| 595 | 319 | 287 | 154 | 1,9-dioxo-16(S)-hydroxy-1-hydroxymethyl-5-cis-13-trans-prostadiene |
| 596 | 319 | 287 | 148a | 1,9-dioxo-16-hydroxy-20-ethyl-1-hydroxymethyl-5-cis-13-trans-17-trans-prostatriene |
| 597 | 319 | 287 | 1-iodo-3-triphenylmethoxy-1-trans-octene (U.S. Pat. No. 3,873,607). | 1,9-dioxo-15α-hydroxy-1-hydroxymethyl-6-cis-13-trans-prostadiene |
| 598 | 319 | 287 | 1-iodo-3-triphenylmethoxy-1-trans-nonene (U.S. Pat. No. 3,873,607). | 1,9-dioxo-15α-hydroxy-20-methyl-1-hydroxymethyl-5-cis-13-trans-prostadiene |
| 599 | 319 | 287 | 1-iodo-3-triphenylmethoxy-1-trans-decene (U.S. Pat. No. 3,873,607). | 1,9-dioxo-15α-hydroxy-20-ethyl-1-hydroxymethyl-5-cis-13-trans-prostadiene |
| 600 | 319 | 287 | 1-iodo-3-triphenylmethoxy-4,4-dimethyl-1-trans-octene (U.S. Pat. No. 3,873,607). | 1,9-dioxo-15α-hydroxy-16,16-dimethyl-1-hydroxymethyl-5-cis-13-trans-prostadiene |
| 601 | 319 | 287 | 1-iodo-3-triphenylmethoxy-5,5-dimethyl-1-trans-octene (U.S. Pat. No. 3,873,607). | 1,9-dioxo-15α-hydroxy-17,17-dimethyl-1-hydroxymethyl-5-cis-13-trans-prostadiene |
| 602 | 319 | 287 | 1-iodo-3-triphenylmethoxy-4-methyl-1-trans-octene (U.S. Pat. No. 3,876,690). | 1,9-dioxo-15α-hydroxy-16-methyl-1-hydroxymethyl-5-cis-13-trans-prostadiene |

TABLE 36-continued

| Example | Method of Example | Cyclopent-2-en-1-one | Vinyl Iodide or Vinyl Tin of Example | 1,9-dioxo-1-hydroxymethylprostene |
|---|---|---|---|---|
| 603 | 319 | 287 | 1-iodo-3-triphenylmethoxy-4-ethyl-1-trans-octene (U.S. Pat. No. 3,876,690). | 1,9-dioxo-15α-hydroxy-16-ethyl-1-hydroxymethyl-5-cis-13-trans-prostadiene |
| 604 | 319 | 287 | 1-iodo-3-triphenylmethoxy-4-cyclopentyl-1-transbutene (U.S. Pat. No. 3,884,969). | 1,9-dioxo-15α-hydroxy-17,20-tetranor-16-cyclopentyl-1-hydroxymethyl-5-cis-13-trans-prostadiene |
| 605 | 319 | 287 | 1-iodo-3-triphenylmethoxy-3-cyclohexyl-1-transpentene (U.S. Pat. No. 3,884,969). | 1,9-dioxo-15α-hydroxy-16,20-pentanor-15-cyclohexyl-1-hydroxymethyl-5-cis-13-trans-prostadiene |
| 606 | 319 | 287 | 1-iodo-3-triphenylmethoxy-5-cyclohexyl-1-transpentene (U.S. Pat. No. 3,884,969). | 1,9-dioxo-15α-hydroxy-18,20-trinor-17-cyclohexyl-1-hydroxymethyl-5-cis-13-trans-prostadiene |
| 607 | 319 | 287 | 1-iodo-3-triphenylmethoxy-6-cyclopentyl-1-transhexene (U.S. Pat. No. 3,884,969). | 1,9-dioxo-15α-hydroxy-19,20-dinor-18-cyclopentyl-1-hydroxymethyl-5-cis-13-trans-prostadiene |
| 608 | 319 | 287 | 1-iodo-3-methyl-3-trimethylsilyloxy-trans-1-octene (Example 125) | 1,9-dioxo-15α-hydroxy-15-methyl-1-hydroxymethyl-5-cis-13-trans-prostadiene |
| 609 | 319 | 287 | 1-iodo-3-methyl-3-trimethylsilyloxy-trans-1-decene (Example 190a) | 1,9-dioxo-15α-hydroxy-15-methyl-20-ethyl-1-hydroxymethyl-5-cis-13-trans-prostadiene |
| 610 | 320 | 287 | 159 | 1,9-dioxo-15α-hydroxy-17,18,19,20-tetranor-16-p-fluorophenoxy-1-hydroxymethyl-5-cis-13-trans-prostadiene |
| 611 | 320 | 287 | 186 | 1,9-dioxo-15α-hydroxy-17,18,19,20-tetranor-16-phenoxy-1-hydroxymethyl-5-cis-13-trans-prostadiene |
| 612 | 320 | 287 | 181 | 1,9-dioxo-15α-hydroxy-17,18,19,20-tetranor-16-p-bromophenoxy-1-hydroxymethyl-5-cis-13-trans-prostadiene |
| 613 | 320 | 287 | 182 | 1,9-dioxo-15α-hydroxy-17,18,19,20-tetranor-16-p-t-butylphenoxy-1-hydroxymethyl-5-cis-13-trans-prostadiene |
| 614 | 320 | 287 | 183 | 1,9-dioxo-15α-hydroxy-17,18,19,20-tetranor-16-p-methoxyphenoxy-1-hydroxymethyl-5-cis-13-trans-prostadiene |
| 615 | 320 | 287 | 184 | 1,9-dioxo-15α-hydroxy-17,18,19,20-tetranor-16-p-chlorophenoxy-1-hydroxymethyl-5-cis-13-trans-prostadiene |
| 616 | 320 | 287 | 180 | 1,9-dioxo-11α,15α-dihydroxy-17,18,19,20-tetranor-m-trifluorophenoxy-1-hydroxymethyl-5-cis-13-trans-prostadiene |
| 617 | 320 | 287 | 185 | 1,9-dioxo-15α-hydroxy-17,18,19,20-tetranor-16-(3,4-dichlorophenoxy)-1-hydroxymethyl-5-cis-13-trans-prostadiene |
| 618 | 320 | 287 | 186b | 1,9-dioxo-15α-hydroxy-18,19,20-trinor-17-phenyl-1-hydroxymethyl-5-cis-13-trans-prostadiene |
| 619 | 320 | 287 | 186e | 1,9-dioxo-15α-hydroxy-18,19,20-trinor-17-(m-trifluoromethylphenyl)-1-hydroxymethyl-5-cis-13-trans-prostadiene |
| 620 | 320 | 287 | 186d | 1,9-dioxo-15α-hydroxy-18,19,20-trinor-17-(p-methoxyphenyl)-1-hydroxymethyl-5-cis-13-trans-prostadiene |
| 621 | 319 | 288 | 1-iodo-3-triphenylmethoxy-1-transoctene (U.S. Pat. No. 3,873,607). | 1,9-dioxo-15α-dihydroxy-1-hydroxymethyl-2-nor-5-cis-13-trans-prostadiene |
| 622 | 319 | 288 | 190 | 1,9-dioxo-15α-hydroxy-15-methyl-1-hydroxymethyl-2-nor-5-cis-13-trans-prostadiene |
| 623 | 319 | 288 | 1-iodo-3-triphenylmethoxy-5,5-dimethyl octene (U.S. Pat. No. 3,873,607). | 1,9-dioxo-15α-hydroxy-16,16-dimethyl-1-hydroxymethyl-2-nor-5-cis-13-trans-prostadiene |
| 624 | 319 | 288 | 13 | 1,9-dioxo-15α-hydroxy-16,16-trimethylene- |

TABLE 36-continued

| Example | Method of Example | Cyclopent-2-en-1-one | Vinyl Iodide or Vinyl Tin of Example | 1,9-dioxo-1-hydroxymethylprostene |
|---|---|---|---|---|
| 625 | 319 | 288 | 76 | 1-hydroxymethyl-2-nor-5-cis-13-trans-prostadiene erythro-1,9-dioxo-15α,16-dihydroxy-1-hydroxymethyl-2-nor-5-cis-13-trans-prostadiene |
| 626 | 319 | 288 | 69 | threo-1,9-dioxo-15α,16-dihydroxy-1-hydroxymethyl-2-nor-5-cis-13-trans-prostadiene |
| 627 | 319 | 288 | 74 | erythro-1,9-dioxo-15α-hydroxy-16-methoxy-1-hydroxymethyl-2-nor-5-cis-13-trans-prostadiene |
| 628 | 319 | 288 | 107 | 1,9-dioxo-16-hydroxy-1-hydroxymethyl-2-nor-5-cis-13-trans-prostadiene |
| 629 | 319 | 288 | 130 | 1,9-dioxo-16-hydroxy-16-methyl-1-hydroxymethyl-2-nor-5-cis-13-trans-prostadiene |
| 630 | 319 | 288 | 134 | 1,9-dioxo-16-hydroxy-16-methyl-1-hydroxymethyl-2-nor-5-cis-13-trans-17-trans-prostatriene |
| 631 | 320 | 288 | 186 | 1,9-dioxo-15αhydroxy-2,17,18,19,20-pentanor-16-phenoxy-1-hydroxymethyl-5-cis-13-trans-prostadiene |
| 632 | 320 | 288 | 180 | 1,9-dioxo-15α-hydroxy-2,17,18,19,20-pentanor-16-m-trifluoromethylphenoxy-1-hydroxymethyl-5-cis-13-trans-prostadiene |
| 633 | 319 | 288 | 194 | 1,9-dioxo-16-hydroxy-16-vinyl-1-hydroxymethyl-2-nor-5-cis-13-trans-prostadiene |
| 634 | 320 | 288 | 198 | 1,9-dioxo-16-hydroxy-16-cyclopropyl-1-hydroxymethyl-2-nor-5-cis-13-trans-prostadiene |
| 635 | 320 | 288 | 186b | 1,9-dioxo-15α-hydroxy-2,18,19,20-tetranor-17-phenyl-1-hydroxymethyl-5-cis-13-trans-prostadiene |
| 636 | 319 | 288 | 186e | 1,9-dioxo-15α-hydroxy-2,18,19,20-tetranor-17-(m-trifluorophenyl)-1-hydroxymethyl-5-cis-13-trans-prostadiene |
| 637a | 319 | 288 | 186d | 1,9-dioxo-15α-hydroxy-2,18,19,20-tetranor-17-(p-methoxyphenyl)-1-hydroxymethyl-5-cis-13-trans-prostadiene |
| 637b | 320 | 288 | 210c | 1,9-dioxo-16-hydroxy-16-ethyl-1-hydroxymethyl-2-nor-5-cis-13-trans-prostadiene |

EXAMPLES 638–660

By the methods described hereinabove in Examples 319 and 320, the 1,9-dioxo-1-hydroxymethyl prostene derivatives shown in Table 37 are prepared by the indicated method from the indicated vinyl iodide or vinyl tin compound and the indicated cyclopent-2-en-1-one.

In those cases where two diastereoisomers are formed in the conjugate-addition, only one of the idastereoisomers is listed in Table 37. It should be understood that the other diastereoisomer is also formed which in its nat and ent forms has an opposite (mirror image) configuration at the assymmetric carbon atoms on the β-chain (the chain containing $C_{13}$ ... $C_{14}$ etc.) to that of the respective nat and ent forms of the listed diastereoisomer; both of these diastereoisomers are claimed in this invention as well as their componenet enantiomers.

EXAMPLE 661–749

By the methods described hereinabove in Examples 319 and 320, the 1,9-dioxo-1-hydroxymethyl prostene derivatives shown in Table 38 are prepared by the indicated method from the indicated vinyl idoide or vinyl tin compound and the indicated cyclopent-2-en-1-one.

In those cases where isomers are obtained at the $C_{15}$ or $C_{16}$ positions, only the $C_{15}$ or $C_{16}$-normal isomers are listed in Table 38; it should be understood that the corresponding $C_{15}$ or $C_{16}$-epi isomers are also formed and are part of this invention.

In those cases where the initial conjugate-addition product contains a triphenylmethoxy blocking group, deblocking is conducted in acetic acid-tetrahydrofuran-water 4:2:1 at 50° C. for 5 hours.

TABLE 37

| Example | Method of Example | Cyclopent-2-en-1-one of Example | Vinyl Iodide or Vinly Tin of Example | 1,9-dioxo-1-hydroxymethylprostene and its diastereomer |
|---|---|---|---|---|
| 638 | 319 | 287 | 246 | nat-(and ent)-1,9-dioxo-15-hydroxy-15,16-tetramethylene-17,18,19,20-tetranor-1-hydroxymethyl-5-cis-13-trans-prostadiene |
| 639 | 320 | 287 | 245 | nat-(and ent)-1,9-dioxo-16-hydroxy-16,17-tetramethylene-18,19,20-trinor-1-hydroxymethyl-5-cis-13-trans-prostadiene |
| 640 | 319 | 287 | 243 | nat-15S,16R(and ent-15R,16S)-1,9-dioxo-15-hydroxy-15,16-trimethylene-1-hydroxymethyl-5-cis-13-trans-prostadiene |
| 641 | 319 | 287 | 243 | nat-15S,16R-(and ent-15R,16S)-1,9-dioxo- |

TABLE 37-continued

| Example | Method of Example | Cyclopent-2-en-1-one of Example | Vinyl Iodide or Vinly Tin of Example | 1,9-dioxo-1-hydroxymethylprostene and its diastereomer |
|---|---|---|---|---|
| 642 | 319 | 287 | 251 | 15-hydroxy-15,16-trimethylene-1-hydroxymethyl-13-trans-5-cis-prostadiene nat-15S,16S-(and ent-15R,16R)-1,9-dioxo-15-hydroxy-15,16-trimethylene-1-hydroxymethyl-13-trans-5-cis-prostadiene |
| 643 | 319 | 287 | 247 | nat-(and ent)-1,9-dioxo-15-hydroxy-15,16-trimethylene-17,18,19,20-tetranor-1-hydroxymethyl-13-trans-5-cis-prostadiene |
| 644 | 320 | 287 | 248 | nat-(and ent)-1,9-dioxo-15-hydroxy-15,16-pentamethylene-17,18,19,20-tetranor-1-hydroxymethyl-13-trans-5-cis-prostadiene |
| 645 | 319 | 287 | 249 | nat-15S,17R-(and ent-15R,17S)-1,9-dioxo-15-hydroxy-15,17-dimethylene-1-hydroxymethyl-13-trans-5-cis-prostadiene |
| 646 | 319 | 287 | 250 | nat-15S,17S-(and ent-15R,17R)-1,9-dioxo-15-hydroxy-15,17-dimethylene-1-hydroxymethyl-13-trans-5-cis-prostadiene |
| 647 | 319 | 287 | 252 | nat-15S,16R-(and ent-15R,16S)-1,9-dioxo-15-hydroxy-15,16-tetramethylene-1-hydroxymethyl-13-trans-5-cis-prostadiene |
| 648 | 319 | 287 | 253 | nat-15S,16S-(and ent-15R,16R)-1,9-dioxo-15-hydroxy-15,16-tetramethylene-1-hydroxymethyl-13-trans-5-cis-prostadiene |
| 649 | 320 | 287 | 254 | nat-15R,16S-(and ent-15S,16R)-1,9-dioxo-15-hydroxy-15,16-trimethylene-16-(3-trifluoromethylphenoxy)-17,18,19,20-tetranor-1-hydroxymethyl-13-trans-5-cis-prostadiene |
| 650 | 320 | 287 | 255 | nat-15R,16R-(and ent-15S,16S)-1,9-dioxo-15-hydroxy-15,16-trimethylene-16-(3-trifluoromethylphenoxy)17,18,19,20-tetranor-1-hydroxymethyl-13-trans-5-cis-prostadiene |
| 651 | 319 | 287 | 256 | nat-15R,16S-(and ent-15S,16R)-1,9-dioxo-15-hydroxy-15,16-trimethylene-16-(4-fluorophenoxy)-17,18,19,20-tetranor-1-hydroxymethyl-13-trans-5-cis-prostadiene |
| 652 | 319 | 287 | 257 | nat-15R,16R-(and ent-15S,16S)-1,9-dioxo-15-hydroxy-15,16-trimethylene-16-(4-fluorophenoxy)-17,18,19,20-tetranor-1-hydroxymethyl-13-trans-5-cis-prostadiene |
| 653 | 320 | 287 | 258 | nat-15R,16S-(and ent-15S,16R)-1,9-dioxo-15-hydroxy-15,16-trimethylene-16-(3-chlorophenoxy)-17,18,19,20-tetranor-1-hydroxymethyl-13-trans-5-cis-prostadiene |
| 654 | 320 | 287 | 259 | nat-15R,16R-(and ent-15S,16S)-1,9-dioxo-15-hydroxy-15,16-trimethylene-16-(3-chlorophenoxy)-17,18,19,20-tetranor-1-hydroxymethyl-13-trans-5-cis-prostadiene |
| 655 | 319 | 287 | 260 | nat-15S,17R-(and ent-15R,17S)-1,9-dioxo-15-hydroxy-15,17-trimethylene-19,20-dinor-1-hydroxymethyl-13-trans-5-cis-prostadiene |
| 656 | 319 | 287 | 261 | nat-15S,17S-(and ent-15R,17R)-1,9-dioxo-15-hydroxy-15,17-trimethylene-19,20-dinor-1-hydroxymethyl-13-trans-5-cis-prostadiene |
| 657 | 320 | 287 | 262 | nat-16R,17S-(and ent-16S,17R)-1,9-dioxo-16-hydroxy-16,17-trimethylene-20-methyl-1-hydroxymethyl-13-trans-5-cis-prostadiene |
| 658 | 320 | 287 | 263 | nat-16R,17R-(and ent-16S,17S)-1,9-dioxo-16-hydroxy-16,17-trimethylene-20-methyl-1-hydroxymethyl-13-trans-5-cis-prostadiene |
| 659 | 320 | 287 | 264 | nat-16R,17S-(and ent-16S,17R)-1,9-dioxo-16-hydroxy-16,17-trimethylene-16-(3-trifluoromethylphenoxy)-18,19,20-trinor-1-hydroxymethyl-13-trans-5-cis-prostadiene |
| 660 | 320 | 287 | 265 | nat-16R,17R-(and ent-16S,17S)-1,9-dioxo-16-hydroxy-16,17-trimethylene-16-(3-trifluoromethylphenoxy)-18,19,20-trinor-1-hydroxymethyl-13-trans-5-cis-prostadiene |

TABLE 38

| Example | Method of Example | Cyclopent-2-en-1-one | Vinyl Iodide or Vinyl Tin of Example | 1,9-dioxo-1-hydroxymethylprostene |
|---|---|---|---|---|
| 662 | 319 | 284 | 49 | 1,9-dioxo-15-hydroxy-1-hydroxymethyl-16,-16-trimethylene-20-nor-13-trans-prostene |
| 663 | 319 | 284 | 50 | 1,9-dioxo-15-hydroxy-1-hydroxymethyl-16,-16-trimethylene-20-methyl-13-trans-prostene |
| 664 | 319 | 284 | 51 | 1,9-dioxo-15-hydroxy-1-hydroxymethyl-16,-16-trimethylene-20-ethyl-13-trans-prostene |
| 665 | 320 | 284 | 193 | 1,9-dioxo-16-hydroxy-16-cyclopropyl-20-ethyl-1-hydroxymethyl-13-trans-prostene |
| 666 | 320 | 284 | 195 | 1,9-dioxo-16-hydroxy-16-vinyl-20-ethyl-1-hydroxymethyl-13-trans-prostene |
| 667 | 320 | 284 | 192 | 1,9-dioxo-16-hydroxy-16-cyclopropyl-1-hydroxymethyl-13-trans-prostene |
| 668 | 319 | 284 | 13 | 1,9-dioxo-15-hydroxy-1-hydroxymethyl-16,-16-trimethylene-13-trans-prostene |
| 669 | 320 | 284 | 210a | 1,9-dioxo-15-hydroxy-1-hydroxymethyl-16-vinyl-13-trans-prostene |
| 670 | 319 | 284 | 74 | dl-erythro-1,9-dioxo-15-dihydroxy-16-methoxy-1-hydroxymethyl-13-trans-prostene |
| 671 | 319 | 284 | 77 | dl-erythro-1,9-dioxo-16-dihydroxy-16-ethoxy-1-hydroxymethyl-13-trans-prostene |
| 672 | 319 | 284 | 83 | dl-erythro-1,9-dioxo-15,16-dihydroxy-1-hydroxymethyl-20-nor-13-trans-prostene |
| 673 | 319 | 284 | 84 | dl-erythro-1,9-dioxo-15,16-dihydroxy-1-hydroxymethyl-20-methyl-13-trans-prostene |
| 674 | 319 | 284 | 85 | dl-erythro-1,9-dioxo-15,16-dihydroxy-20-ethyl-1-hydroxymethyl-13-trans-prostene |
| 675 | 319 | 284 | 86 | dl-erythro-1,9-dioxo-15,16-dihydroxy-19-methyl-1-hydroxymethyl-13-trans-prostene |
| 676 | 319 | 284 | 87 | dl-erythro-1,9-dioxo-15,16-dihydroxy-1-hydroxymethyl-13-trans-17-trans-prostadiene |
| 677 | 319 | 284 | 69 | dl-threo-1,9-dioxo-15,16-dihydroxy-1-hydroxymethyl-13-trans-prostene |
| 678 | 319 | 284 | 88 | dl-threo-1,9-dioxo-15,16-dihydroxy-20-nor-1-hydroxymethyl-13-trans-prostene |
| 679 | 319 | 284 | 76 | dl-erythro-1,9-dioxo-15,16-dihydroxy-1-hydroxymethyl-13-trans-prostene |
| 680 | 319 | 284 | 89 | dl-threo-1,9-dioxo-15,16-dihydroxy-20-methyl-1-hydroxymethyl-13-trans-prostene |
| 681 | 319 | 284 | 90 | dl-threo-1,9-dioxo-15,16-dihydroxy-20-ethyl-1-hydroxymethyl-13-trans-prostene |
| 682 | 319 | 284 | 91 | dl-threo-1,9-dioxo-15,16-dihydroxy-19-methyl-1-hydroxymethyl-13-trans-prostene |
| 683 | 319 | 284 | 92 | dl-threo-1,9-dioxo-15,16-dihydroxy-1-hydroxymethyl-13-trans-17-trans-prostadiene |
| 684 | 319 | 284 | 107 | 1,9-dioxo-16-hydroxy-1-hydroxymethyl-13-trans-prostene |
| 685 | 319 | 284 | 108 | 1,9-dioxo-16-hydroxy-1-hydroxymethyl-19,-20-dinor-13-trans-prostene |
| 687 | 319 | 284 | 109 | 1,9-dioxo-16-hydroxy-1-hydroxymethyl-18,-19,20-trinor-13-trans-prostene |
| 688 | 319 | 284 | 110 | 1,9-dioxo-16-hydroxy-1-hydroxymethyl-20-nor-13-trans-prostene |
| 689 | 319 | 284 | 144 | 1,9-dioxo-16-hydroxy-17-methyl-1-hydroxymethyl-13-trans-prostene |
| 690 | 319 | 284 | 112 | 1,9-dioxo-16-hydroxy-20-methyl-1-hydroxymethyl-13-trans-prostene |
| 691 | 319 | 284 | 113 | 1,9-dioxo-16-hydroxy-20-ethyl-1-hydroxymethyl-13-trans-prostene |
| 692 | 319 | 284 | 139a | 1,9-dioxo-16-hydroxy-16-methyl-20-ethyl-1-hydroxymethyl-13-trans-prostene |
| 693 | 319 | 284 | 115 | 1,9-dioxo-16-hydroxy-1-hydroxymethyl-13-trans-17-cis-prostadiene |
| 694 | 319 | 284 | 135 | 1,9-dioxo-16-hydroxy-16-methyl-1-hydroxymethyl-13-trans-prostene |
| 695 | 319 | 284 | 136 | 1,9-dioxo-16-hydroxy-17,17,20-trimethyl-1-hydroxymethyl-13-trans-prostene |
| 696 | 319 | 284 | 137 | 1,9-dioxo-16-hydroxy-16,20-dimethyl-1-hydroxymethyl-13-trans-prostene |
| 697 | 319 | 284 | 138 | 1,9-dioxo-16-hydroxy-17,17-dimethyl-1-hydroxymethyl-13-trans-prostene |
| 698 | 319 | 284 | 139 | 1,9-dioxo-16-hydroxy-16-methyl-1-hydroxymethyl-13-trans-17-trans-prostadiene |
| 699 | 319 | 284 | 149 | 1,9-dioxo-16-hydroxy-20-methyl-1-hydroxymethyl-13-trans-17-trans-prostadiene |
| 700 | 319 | 284 | 150 | 1,9-dioxo-16-hydroxy-16-methyl-1-hydr- |

TABLE 38-continued

| Example | Method of Example | Cyclopent-2-en-1-one | Vinyl Iodide or Vinyl Tin of Example | 1,9-dioxo-1-hydroxymethylprostene |
|---|---|---|---|---|
| | | | | oxymethyl-13-trans-prostene |
| 701 | 319 | 284 | 151 | 1,9-dioxo-16-hydroxy-17,20-dimethyl-1-hydroxymethyl-13-trans-prostene |
| 702 | 319 | 284 | 152 | 1,9-dioxo-16-hydroxy-1-hydroxymethyl-13-trans-17-trans-prostadiene |
| 703 | 319 | 284 | 153 | 1,9-dioxo-16(R)-hydroxy-1-hydroxymethyl-13-trans-prostene |
| 704 | 319 | 284 | 154 | 1,9-dioxo-16(S)-hydroxy-1-hydroxymethyl-13-trans-prostene |
| 705 | 319 | 284 | 148a | 1,9-dioxo-16-hydroxy-20-ethyl-1-hydroxymethyl-13-trans-17-trans-prostadiene |
| 706 | 319 | 284 | 1-iodo-3-triphenylmethoxy-1-trans-octene (U.S. Pat. No. 3,873,607). | 1,9-dioxo-15α-hydroxy-1-hydroxymethyl-13-trans-prostadiene |
| 707 | 319 | 284 | 1-iodo-3-triphenylmethoxy-1-trans-nonene (U.S. Pat. No. 3,873,607). | 1,9-dioxo-15α-hydroxy-20-methyl-1-hydroxymethyl-13-trans-prostene |
| 708 | 319 | 284 | 1-iodo-3-triphenylmethoxy-1-trans-decene (U.S. Pat. No. 3,873,607). | 1,9-dioxo-15α-hydroxy-20-ethyl-1-hydroxymethyl-13-trans-prostene |
| 709 | 319 | 284 | 1-iodo-3-triphenylmethoxy-4,4-dimethyl-1-trans-octene (U.S. Pat. No. 3,873,607). | 1,9-dioxo-15α-hydroxy-16,16-dimethyl-1-hydroxymethyl-13-trans-prostene |
| 710 | 319 | 284 | 1-iodo-3-triphenylmethoxy-5,5-dimethyl-1-trans-octene (U.S. Pat. No. 3,873,607). | 1,9-dioxo-15α-hydroxy-17,17-dimethyl-1-hydroxymethyl-13-trans-prostene |
| 711 | 319 | 284 | 1-iodo-3-triphenylmethoxy-4-methyl-1-trans-octene (U.S. Pat. No. 3,876,690). | 1,9-dioxo-15α-hydroxy-16-methyl-1-hydroxymethyl-13-trans-prostene |
| 712 | 319 | 284 | 1-iodo-3-triphenylmethoxy-4-ethyl-1-trans-octene (U.S. Pat. No. 3,876,690). | 1,9-dioxo-15α-hydroxy-16-ethyl-1-hydroxymethyl-13-trans-prostene |
| 713 | 319 | 284 | 1-iodo-3-triphenylmethoxy-4-cyclopentyl-1-trans-butene (U.S. Pat. No. 3,884,969). | 1,9-dioxo-15α-hydroxy-17,20-tetranor-16-cyclopentyl-1-hydroxymethyl-13-trans-prostene |
| 714 | 319 | 284 | 1-iodo-3-triphenylmethoxy-3-cyclohexyl-1-trans-pentene (U.S. Pat. No. 3,884,969). | 1,9-dioxo-15α-hydroxy-16,20-pentanor-15-cyclohexyl-1-hydroxymethyl-13-trans-prostene |
| 715 | 319 | 284 | 1-iodo-3-triphenylmethoxy-5-cyclohexyl-1-trans-pentene (U.S. Pat. No. 3,884,969). | 1,9-dioxo-15α-hydroxy-18,20-trinor-17-cyclohexyl-1-hydroxymethyl-13-trans-prostene |
| 716 | 319 | 284 | 1-iodo-3-triphenylmethoxy-6-cyclopentyl-1-trans-hexene (U.S. Pat. No. 3,884,969). | 1,9-dioxo-15α-hydroxy-19,20-dinor-18-cyclopentyl-1-hydroxymethyl-13-trans-prostene |
| 717 | 319 | 284 | 1-iodo-3-methyl-3-trimethylsilyloxy-trans-1-octene (Example 125). | 1,9-dioxo-15α-hydroxy-15-methyl-1-hydroxymethyl-13-trans-prostene |
| 718 | 319 | 284 | 1-iodo-3-methyl-3-trimethylsilyloxy-trans-1-decene (Example 190a). | 1,9-dioxo-15α-hydroxy-15-methyl-20-ethyl-1-hydroxymethyl-13-trans-prostene |
| 719 | 319 | 284 | 159 | 1,9-dioxo-15α-hydroxy-17,18,19,20-tetranor-16-p-fluorophenoxy-1-hydroxymethyl-13-trans-prostene |
| 720 | 320 | 284 | 186 | 1,9-dioxo-15α-hydroxy-17,18,19,20-tetranor-16-phenoxy-1-hydroxymethyl-13-trans-prostene |
| 721 | 320 | 284 | 181 | 1,9-dioxo-15α-hydroxy-17,18,19,20-tetranor-16-p-bromophenoxy-1-hydroxymethyl-13- |

TABLE 38-continued

| Example | Method of Example | Cyclopent-2-en-1-one | Vinyl Iodide or Vinyl Tin of Example | 1,9-dioxo-1-hydroxymethylprostene |
|---|---|---|---|---|
| 722 | 320 | 284 | 182 | trans-prostene 1,9-dioxo-15α-hydroxy-17,18,19,20-tetra-nor-16-p-t-butylphenoxy-1-hydroxymethyl-13-trans-prostene |
| 723 | 320 | 284 | 183 | 1,9-dioxo-15α-hydroxy-17,18,19,20-tetra-nor-16-p-methoxyphenoxy-1-hydroxymethyl-13-trans-prostene |
| 724 | 320 | 284 | 184 | 1,9-dioxo-15α-hydroxy-17,18,19,20-tetra-nor-16-m-chlorophenoxy-1-hydroxymethyl-13-trans-prostene |
| 725 | 320 | 284 | 180 | 1,9-dioxo-15α-hydroxy-17,18,19,20-tetra-nor-16-m-trifluorophenoxy-1-hydroxymethyl-13-trans-prostene |
| 726 | 320 | 284 | 185 | 1,9-dioxo-15α-hydroxy-17,18,19,20-tetra-nor-16-(3,4-dichlorophenoxy)-1-hydroxymethyl-13-trans-prostene |
| 727 | 320 | 284 | 186b | 1,9-dioxo-15α-hydroxy-18,19,20-trinor-17-phenyl-1-hydroxymethyl-13-trans-prostene |
| 728 | 320 | 284 | 186e | 1,9-dioxo-15α-hydroxy-18,19,20-trinor-17-(m-trifluoromethylphenyl)-1-hydroxymethyl-13-trans-prostene |
| 729 | 320 | 284 | 186d | 1,9-dioxo-15α-hydroxy-18,19,20-trinor-17-(p-methoxyphenyl)-1-hydroxymethyl-13-trans-prostene |
| 730 | 319 | 285 | 1-iodo-3-triphen-ylmethoxy-1-trans-octene (U.S. Pat. No. 3,873,607). | 1,9-dioxo-15α-hydroxy-1-hydroxymethyl-2-nor-13-trans-prostadiene |
| 731 | 319 | 285 | 190 | 1,9-dioxo-15α-hydroxy-15-methyl-1-hydroxymethyl-2-nor-13-trans-prostene |
| 732 | 319 | 285 | 1-iodo-3-triphen-ylmethoxy-5,5-dimethyl-octene (U.S. Pat. No. 3,873,607). | 1,9-dioxo-15α-hydroxy-16,16-dimethyl-1-hydroxymethyl-2-nor-13-trans-prostene |
| 733 | 319 | 285 | 13 | 1,9-dioxo-15α-hydroxy-16,16-trimethylene-1-hydroxymethyl-2-nor-13-trans-prostene |
| 734 | 319 | 285 | 76 | erythro-1,9-dioxo-15α,16-dihydroxy-1-hydroxymethyl-2-nor-13-trans-prostene |
| 735 | 319 | 285 | 69 | threo-1,9-dioxo-15α,16-dihydroxy-1-hydroxymethyl-2-nor-13-trans-prostene |
| 736 | 319 | 285 | 74 | erythro-1,9-dioxo-15α-hydroxy-16-methoxy-1-hydroxymethyl-2-nor-13-trans-prostene |
| 737 | 319 | 285 | 107 | 1,9-dioxo-16-hydroxy-1-hydroxymethyl-2-nor-13-trans-prostene |
| 738 | 319 | 285 | 130 | 1,9-dioxo-16-hydroxy-16-methyl-1-hydroxymethyl-2-nor-13-trans-prostene |
| 739 | 319 | 285 | 134 | 1,9-dioxo-16-hydroxy-16-methyl-1-hydroxymethyl-2-nor-13-trans-17-trans-prostadiene |
| 740 | 320 | 285 | 186 | 1,9-dioxo-15α-hydroxy-2,17,18,19,20-penta-nor-16-phenoxy-1-hydroxymethyl-13-trans-prostene |
| 741 | 320 | 285 | 180 | 1,9-dioxo-15α-hydroxy-2,17,18,19,20-penta-nor-16-m-trifluoromethylphenoxy-1-hydroxymethyl-13-trans-prostene |
| 742 | 319 | 285 | 194 | 1,9-dioxo-16-hydroxy-16-vinyl-1-hydroxymethyl-2-nor-13-trans-prostene |
| 743 | 320 | 285 | 198 | 1,9-dioxo-16-hydroxy-16-cyclopropyl-1-hydroxymethyl-2-nor-13-trans-prostene |
| 744 | 320 | 285 | 186b | 1,9-dioxo-15α-hydroxy-2,18,19,20-tetranor-17-phenyl-1-hydroxymethyl-13-trans-prostene |
| 745 | 319 | 285 | 186e | 1,9-dioxo-15α-hydroxy-2,18,19,20-tetranor-17-(m-trifluorophenyl)-1-hydroxymethyl-13-trans-prostene |
| 746 | 319 | 285 | 186d | 1,9-dioxo-15α-hydroxy-2,18,19,20-tetranor-17-(p-methoxyphenyl)-1-hydroxymethyl-13-trans-prostene |

EXAMPLES 747–769

By the methods described hereinabove in Examples 319 and 320, the 1,9-dioxo-1-hydroxymethyl prostene derivatives shown in Table 39 are prepared by the indicated method from the indicated vinyl iodide or vinyl tin compound and the indicated cyclopent-2-en-1-one.

In those cases where two diastereoisomers are formed in the conjugate-addition, only one of the diastereoisomers is listed in Table 39. It should be understood that the other diastereoisomer is also formed which in its nat and ent forms has an opposite (mirror image) configuration at the assymmetric carbon atoms on the β-chain (the chain containing $C_{13}...C_{14}$ etc.) to that of the respective nat and ent forms of the listed diastereoisomer; both of these diastereoisomers are claimed in this invention as well as their component enantiomers.

TABLE 39

| Example | Method of Example | Cyclopent-2-en-1-one of Example | Vinyl Iodide or Vinyl Tin of Example | 1,9-dioxo-1-hydroxymethylprostene and its diastereomer |
|---|---|---|---|---|
| 747 | 319 | 284 | 246 | nat-(and ent)-1,9-dioxo-15-hydroxy-15,-16-tetramethylene-17,18,19,20-tetranor-1-hydroxymethyl-13-trans-prostene |
| 748 | 320 | 284 | 245 | nat-(and ent)-1,9-dioxo-16-hydroxy-16,17-tetramethylene-18,19,20-trinor-1-hydroxymethyl-13-trans-prostene |
| 749 | 319 | 284 | 243 | nat-15S,16R(and ent-15R,16S)-1,9-dioxo-15-hydroxy-15,16-trimethylene-1-hydroxymethyl-13-trans-prostene |
| 750 | 319 | 284 | 243 | nat-15S,16R-(and ent-15R,16S)-1,9-dioxo-15-hydroxy-15,16-trimethylene-1-hydroxymethyl-13-trans-prostene |
| 751 | 319 | 284 | 251 | nat-15S,16S-(and ent-15R,16R)-1,9-dioxo-15-hydroxy-15,16-trimethylene-1-hydroxymethyl-13-trans-prostene |
| 752 | 319 | 284 | 247 | nat-(and ent)-1,9-dioxo-15-hydroxy-15,16-trimethylene-17,18,19,20-tetranor-1-hydroxymethyl-13-tans-prostene |
| 753 | 320 | 284 | 248 | nat-(and ent)-1,9-dioxo-15-hydroxy-15,16-pentamethylene-17,18,19,20-tetranor-1-hydroxymethyl-13-trans-prostene |
| 754 | 319 | 284 | 249 | nat-15S,17R-(and ent-15R,17S)-1,9-dioxo-15-hydroxy-15,17-dimethylene-1-hydroxymethyl-13-trans-prostene |
| 755 | 319 | 284 | 250 | nat-15S,17S-(and ent-15R,17R)-1,9-dioxo-15-hydroxy-15,17-dimethylene-1-hydroxymethyl-13-trans-prostene |
| 756 | 319 | 284 | 252 | nat-15S,16R-(and ent-15R,16S)-1,9-dioxo-15-hydroxy-15,16-tetramethylene-1-hydroxymethyl-13-trans-prostene |
| 757 | 319 | 284 | 253 | nat-15S,16S-(and ent-15R,16R)-1,9-dioxo-15-hydroxy-15,16-tetramethylene-1-hydroxymethyl-13-trans-prostene |
| 758 | 320 | 284 | 254 | nat-15R,16S-(and ent-15S,16R)-1,9-dioxo-15-hydroxy-15,16-trimethylene-16-(3-trifluoromethylphenoxy)-17,18,19,20-tetranor-1-hydroxymethyl-13-trans-prostene |
| 759 | 320 | 284 | 255 | nat-15R,16R-(and ent-15S,16S)-1,9-dioxo-15-hydroxy-15,16-trimethylene-16-(3-trifluoromethylphenoxy)-17,18,19,20-tetranor-1-hydroxymethyl-13-trans-prostene |
| 760 | 319 | 284 | 256 | nat-15R,16S-(and ent-15S,16R)-1,9-dioxo-15-hydroxy-15,16-trimethylene-16-(4-fluorophenoxy)-17,18,19,20-tetranor-1-hydroxymethyl-13-trans-prostene |
| 761 | 319 | 284 | 257 | nat-15R,16R-(and ent-15S,16S)-1,9-dioxo-15-hydroxy-15,16-trimethylene-16-(4-fluorophenoxy)-17,18,19,20-tetranor-1-hydroxymethyl-13-trans-prostene |
| 762 | 320 | 284 | 258 | nat-15R,16S-(and ent-15S,16R)-1,9-dioxo-15-hydroxy-15,16-trimethylene-16-(3-chlorophenoxy)-17,18,19,20-tetranor-1-hydroxymethyl-13-trans-prostene |
| 763 | 320 | 284 | 259 | nat-15R,16R-(and ent-15S,16S)-1,9-dioxo-15-hydroxy-15,16-trimethylene-16-(3-chlorophenoxy)-17,18,19,20-tetranor-1-hydroxymethyl-13-trans-prostene |
| 764 | 319 | 284 | 260 | nat-15S,17R-(and ent-15R,17S)-1,9-dioxo-15-hydroxy-15,17-trimethylene-19,20-dinor-1-hydroxymethyl-13-trans-prostene |
| 765 | 319 | 284 | 261 | nat-15S,17S-(and ent-15R,17R)-1,9-dioxo-15-hydroxy-15,17-trimethylene-19,20-dinor-1-hydroxymethyl-13-trans-prostene |
| 766 | 320 | 284 | 262 | nat-16R,17S-(and ent-16S,17R)-1,9-dioxo-16-hydroxy-16,17-trimethylene-20-methyl-1-hydroxymethyl-13-trans-prostene |
| 767 | 320 | 284 | 263 | nat-16R,17R-(and ent-16S,17S)-1,9-dioxo-16-hydroxy-16,17-trimethylene-20-methyl-1-hydroxymethyl-13-trans-prostene |
| 768 | 320 | 284 | 264 | nat-16R,17S-(and ent-16S,17R)-1,9-dioxo-16-hydroxy-16,17-trimethylene-16-(3-trifluoromethylphenoxy)-18,19,20-trinor-1-hydroxymethyl-13-trans-prostene |
| 769 | 320 | 284 | 265 | nat-16R,17R-(and ent-16S,17S)-1,9-dioxo-16-hydroxy-16,17-trimethylene-16-(3-trifluoromethylphenoxy)-18,19,20-trinor-1- |

TABLE 39-continued

| Example | Method of Example | Cyclopent-2-en-1-one of Example | Vinyl Iodide or Vinyl Tin of Example | 1,9-dioxo-1-hydroxymethylprostene and its diastereomer |
|---|---|---|---|---|
| | | | | hydroxymethyl-13-trans-prostene |

EXAMPLE 770

Preparation of 1-9-oxo-15(S)-acetoxy prostanoyl chloride

To a solution of 0.5 g of 1-9-oxo-15(S)-acetoxy prostanoic acid in 10 ml of benzene at 0° C. with stirring is added 0.5 ml of oxalyl chloride. The mixture is stirred at room temperature for 2 ½ hours. The solvent and excess oxalyl chloride is removed at reduced pressure. The residue is dissolved in hexane and filtered. The solvent is removed giving the title compound.

EXAMPLE 771

Preparation of 1-1,9-dioxo-15(S)-acetoxy-1-hydroxymethyl-prostene

To a solution of 11.9 mmol of diazomethane in ether at 0° C. with stirring is added dropwise a solution of 2.99 mmol of 1-9-oxo-15(S)-acetoxy prostanoyl chloride (Example 770) in 10 ml of ether. After 10 minutes the solution is warmed to room temperature and the solvent and excess diazomethane is removed in a stream of nitrogen. The residue is stirred at 55° C. in 15 ml of tetrahydrofuran containing 5.75 ml of 2 M sulfuric acid for 30 minutes. The mixture is poured into water and extracted with ether. The ether solution is washed with saturated sodium bicarbonate, brine, and dried over magnesium sulfate. The ether is removed and the residue is chromatographed on a dry column of silica gel eluting with hexane-ethyl acetate 3:2 to give the title compound.

EXAMPLE 772

Preparation of 1-1,9-dioxo-15(S)-hydroxy-1-hydroxymethyl prostane

A solution of 0.41 g of 1-1,9-dioxo-15(S)-acetoxy-1-hydroxymethyl prostane (Example 771) in 8 ml of methanol containing 1 ml of water and 0.19 ml of concentrated sulfuric acid is refluxed for 5 hours. The methanol is removed at reduced pressure and water and tetrahydrofuran is added. The mixture is then refluxed for 1 hour. The mixture is poured into dilute sodium bicarbonate and extracted with ether. The ether solution is washed with brine and dried over magnesium sulfate. The solvent is removed giving 0.34 g of the title compound.

EXAMPLE 773

Preparation of 1,9-dioxo-11α,16-dihydroxy-1-hydroxymethyl-20-nor-5-cis-13-trans-prostadiene, 1-ethylene ketal To a solution of 3.58 g (7.0 mmol) of 1-iodo-4-triphenylmethoxy-1-trans-nonene (Example 112) in 8.0 ml of ether is added 8.9 ml of 1.6 M t-butyllithium solution (14.1 mmol) with stirring under argon at −78° C. The solution is allowed to warm to −30° C. over a 2 hour period. The solution is recooled to −78° C. and a solution of 7.0 mmol of copper pentyne and 2.9 ml of hexamethylphosphorous triamide in 20 ml of ether is added. After 1 hour, 3.28 g (7.0 mmol) of 2-(8-dimethyl-t-butylsilyloxy-7-oxooct-2-cis-enyl)-4-trimethylsilyloxycyclopent-2-en-1-one, 7-ethylene ketal (Example 280) in 5 ml of ether is added. The mixture is stirred at −30° C. for 2 hours and at 0° C. for 30 minutes. The mixture is poured into 150 ml of saturated ammonium chloride and extracted with ether. The ether solution is washed with dilute hydrochloric acid and dried over magnesium sulfate to give 6.0 g of an oil. A 3.0 g portion of this oil is stirred in 40 ml of tetrahydrofuran-0.6 N Hydrochloric acid 5:1 for 5 hours at room temperature.

The mixture is poured into water and extracted with ether. The ether is removed and the residue is heated in 70 ml of acetic acid-tetrahydrofuran-water 4:2:1 at 60° C. for 4 hours. The solvent is removed at reduced pressure. Toluene is added and removed. The residue is chromatographed on a silica gel column eluting with ethyl acetate giving 0.1 g of the title compound.

EXAMPLE 774

Preparation of 1,9-dioxo-11α,16-dihydroxy-16-methyl-1-hydroxy methyl-5-cis-13-trans-prostadiene,1-ethylene ketal To a solution of 3.4 g (6.75 mmol) of (E)-4-trimethylsilyloxy-4-methyl-1-tri-n-butylstannyloctene (Example 210b) in 3.5 ml of tetrahydrofuran with stirring at −78° C. under argon is added 2.8 ml (6.75 mmol) of 2.4 M n-butyllithium in hexane. The solution is maintained at −20° to −15° C. for 2½ hours. A solution of 0.89 g (6.75 mmol) of copper pentyne and 2.2 g of hexamethylphosphorous triamide in 25 ml of ether is added at −78° C. After 1 hour, a solution of 2.3 g (5.0 mmol) of 2-(8-dimethyl-t-butylsilyloxy-7-oxooct-2-cis-enyl)-4-trimethylsilyloxycyclopent-2-en-1-one,7-ethylene ketal (Example 280) in 20 ml of ether is added. The solution is stirred at −45° C. for 30 minutes and at −45° to −20° C. over 30 minutes. To the solution is added 3 ml of acetic acid followed by saturated ammonium chloride. The mixture is poured into water and extracted with ether. The ether solution is washed with dilute hydrochloric acid, saturated sodium bicarbonate and dried over magnesium sulfate. The solvent is removed and the residue is stirred in 75 ml of tetrahydrofuran containing 15 ml of 0.6 N hydrochloric acid and 1 ml of acetic acid at room temperature for 5 hours. The solution is saturated with sodium chloride and extracted with ethyl acetate. The ethyl acetate solution is washed with saturated sodium bicarbonate and dried over magnesium sulfate. The solvent is removed and the residue is chromatographed on a dry column of silica gel eluting with ethyl acetate containing 0.5% acetic acid (1000 ml) to give 0.65 g of the title compound.

EXAMPLES 776–868

By the methods described hereinabove in Examples 773 and 774, the 1,9-dioxo-1-hydroxymethylprostene derivatives shown in Table 40 are prepared by the indicated method from the indicated cyclopent-2-en-1-one.

In those cases where isomers are obtained at the $C_{15}$ or $C_{16}$ positions, only the $C_{15}$ or $C_{16}$-normal isomers are listed in Table 40; it should be understood that the corresponding $C_{15}$ or $C_{16}$-epi isomers are also formed and are part of this invention.

TABLE 40

| Example | Method of Example | Cyclopent-2-en-1-one | Vinyl Iodide or Vinyl Tin of Example | 1,9-dioxo-1-hydroxymethylprostene |
|---|---|---|---|---|
| 775 | 773 | 280 | 49 | 1,9-dioxo-11α,15-dihydroxy-1-hydroxymethyl-16,16-trimethylene-20-nor-5-cis-13-trans-prostadiene, 1-ethylene ketal |
| 776 | 773 | 280 | 50 | 1,9-dioxo-11α,15-dihydroxy-1-hydroxymethyl-16,16-trimethylene-20-methyl-5-cis-13-trans-prostadiene,1-ethylene ketal |
| 777 | 773 | 280 | 51 | 1,9-dioxo-11α,15-dihydroxy-1-hydroxymethyl-16,16-trimethylene-20-ethyl-5-cis-13-trans-prostadiene,1-ethylene ketal |
| 778 | 773 | 280 | 13 | 1,9-dioxo-11α,15-dihydroxy-1-hydroxymethyl-16,16-trimethylene-13-trans-5-cis-prostadiene,1-ethylene ketal |
| 779 | 774 | 280 | 210a | 1,9-dioxo-11α,16-dihydroxy-1-hydroxymethyl-16-vinyl-5-cis-13-trans-prostadiene, 1-ethylene ketal |
| 780 | 774 | 280 | 199 | 1,9-dioxo-11α,16-dihydroxy-16-cyclopropyl-20-ethyl-1-hydroxymethyl-5-cis-13-trans-prostadiene, 1-ethylene ketal |
| 781 | 774 | 280 | 201 | 1,9-dioxo-11α,16-dihydroxy-16-vinyl-20-ethyl-1-hydroxymethyl-5-cis-13-trans-prostadiene, 1-ethylene ketal |
| 782 | 774 | 280 | 198 | 1,9-dioxo-11α,16-dihydroxy-16-cyclopropyl-1-hydroxymethyl-5-cis-13-trans-prostadiene, 1-ethylene ketal |
| 783a | 773 | 280 | 74 | dl-erythro-1,9-dioxo-11α,15-dihydroxy-16-methoxy-1-hydroxymethyl-5-cis-13-trans-prostadiene, 1-ethylene ketal |
| 783b | 774 | 280 | 210c | 1,9-dioxo-11α,16-dihydroxy-16-ethyl-1-hydroxymethyl-5-cis-13-trans-prostadiene, 1-ethylene ketal |
| 784 | 773 | 280 | 77 | dl-erythro-1,9-dioxo-11α,15-dihydroxy-16-ethoxy-1-hydroxymethyl-5-cis-13-trans-prostadiene, 1-ethylene ketal |
| 785 | 773 | 280 | 83 | dl-erythro-1,9-dioxo-11α,15,16-trihydroxy-1-hydroxymethyl-20-nor-5-cis-13-trans-prostadiene, 1-ethylene ketal |
| 786 | 773 | 280 | 84 | dl-erythro-1,9-dioxo-11α,15,16-trihydroxy-20-methyl-1-hydroxymethyl-5-cis-13-trans-prostadiene, 1-ethylene ketal |
| 787 | 773 | 280 | 85 | dl-erythro-1,9-dioxo-11α,15,16-trihydroxy-20-ethyl-1-hydroxymethyl-5-cis-13-trans-prostadiene, 1-ethylene ketal |
| 788 | 773 | 280 | 86 | dl-erythro-1,9-dioxo-11α,15,16-trihydroxy-19-methyl-1-hydroxymethyl-5-cis-13-trans-prostadiene, 1-ethylene ketal |
| 789 | 773 | 280 | 87 | dl-erythro-1,9-dioxo-11α,15,16-trihydroxy-1-hydroxymethyl-5-cis-13-trans-17-trans-prostatriene, 1-ethylene ketal |
| 790 | 773 | 280 | 69 | dl-threo-1,9-dioxo-11α,15,16-trihydroxy-1-hydroxymethyl-5-cis-13-trans-hydroxymethyl, 1-ethylene ketal |
| 791 | 773 | 280 | 88 | dl-threo-1,9-dioxo-11α,15,16-trihydroxy-20-nor-1-hydroxymethyl-5-cis-13-trans-prostadiene, 1-ethylene ketal |
| 792 | 773 | 280 | 76 | dl-erythro-1,9-dioxo-11α,15,16-trihydroxy-1-hydroxymethyl-5-cis-13-trans-prostadiene, 1-ethylene ketal |
| 793 | 773 | 280 | 89 | dl-threo-1,9-dioxo-11α,15,16-trihydroxy-20-methyl-1-hydroxymethyl-5-cis-13-trans-prostadiene, 1-ethylene ketal |
| 794 | 773 | 280 | 90 | dl-threo-1,9-dioxo-11α,15,16-trihydroxy-20-ethyl-1-hydroxymethyl-5-cis-13-trans-prostadiene, 1-ethylene ketal |
| 795 | 773 | 280 | 91 | dl-threo-1,9-dioxo-11α,15,16-trihydroxy-19-methyl-1-hydroxymethyl-5-cis-13-trans-prostadiene, 1-ethylene ketal |
| 796 | 773 | 280 | 92 | dl-threo-1,9-dioxo-11α,15,16-trihydroxy-1-hydroxymethyl-5-cis-13-trans-17-trans-prostatriene, 1-ethylene ketal |
| 797 | 773 | 280 | 107 | 1,9-dioxo-11α,16-dihydroxy-1-hydroxymethyl-5-cis-13-trans-prostadiene, 1-ethylene ketal |
| 798 | 773 | 280 | 108 | 1,9-dioxo-11α,16-dihydroxy-1-hydroxymethyl-19,20-dinor-5-cis-13-trans-prostadiene-1-ethylene ketal |
| 799 | 773 | 280 | 109 | 1,9-dioxo-11α,16-dihydroxy-1-hydroxymeth- |

TABLE 40-continued

| Example | Method of Example | Cyclopent-2-en-1-one | Vinyl Iodide or Vinyl Tin of Example | 1,9-dioxo-1-hydroxymethylprostene |
|---|---|---|---|---|
| | | | | yl-18,19,20-trinor-5-cis-13-trans-prostadiene, 1-ethylene ketal |
| 800 | 773 | 280 | 110 | 1,9-dioxo-11α,16-dihydroxy-1-hydroxymethyl-20-nor-5-cis-13-trans-prostadiene,1-ethylene ketal |
| 801 | 773 | 280 | 144 | 1,9-dioxo-11α,16-dihydroxy-17-methyl-1-hydroxymethyl-5-cis-13-trans-prostadiene, 1-ethylene ketal |
| 802 | 773 | 280 | 112 | 1,9-dioxo-11α,16-dihydroxy-20-methyl-1-hydroxymethyl-5-cis-13-trans-prostadiene, 1-ethylene ketal |
| 803 | 773 | 280 | 113 | 1,9-dioxo-11α,16-dihydroxy-20-ethyl-1-hydroxymethyl-5-cis-13-trans-prostadiene, 1-ethylene ketal |
| 804 | 773 | 280 | 139a | 1,9-dioxo-11α,16-dihydroxy-16-methyl-20-ethyl-1-hydroxymethyl-5-cis-13-trans-prostadiene, 1-ethylene ketal |
| 805 | 773 | 280 | 115 | 1,9-dioxo-11α,16-dihydroxy-1-hydroxymethyl-13-trans-17-cis-5-cis-prostatriene, 1-ethylene ketal |
| 806 | 773 | 280 | 135 | 1,9-dioxo-11α,16-dihydroxy-16-methyl-1-hydroxymethyl-5-cis-13-trans-prostadiene, 1-ethylene ketal |
| 807 | 773 | 280 | 136 | 1,9-dioxo-11α,16-dihydroxy-17,17,20-trimethyl-1-hydroxymethyl-5-cis-13-trans-prostadiene, 1-ethylene ketal |
| 808 | 773 | 280 | 137 | 1,9-dioxo-11α,16-dihydroxy-16,20-dimethyl-1-hydroxymethyl-13-trans-5-cis-prostadiene, 1-ethylene ketal |
| 809 | 773 | 280 | 138 | 1,9-dioxo-11α,16-dihydroxy-17,17-dimethyl-1-hydroxymethyl-5-cis-13-trans-prostadiene, 1-ethylene ketal |
| 810 | 773 | 280 | 139 | 1,9-dioxo-11α,16-dihydroxy-16-methyl-1-hydroxymethyl-13-trans-17-trans-5-cis-prostatriene, 1-ethylene ketal |
| 811 | 773 | 280 | 149 | 1,9-dioxo-11α,16-dihydroxy-20-methyl-1-hydroxymethyl-13-trans-17-trans-5-cis-prostratriene, 1-ethylene ketal |
| 812 | 773 | 280 | 150 | 1,9-dioxo-11α,16-dihydroxy-16-methyl-1-hydroxymethyl-5-cis-13-trans-prostadiene, 1-ethylene ketal |
| 813 | 773 | 280 | 151 | 1,9-dioxo-11α,16-dihydroxy-17,20-dimethyl-1-hydroxymethyl-5-cis-13-trans-prostadiene, 1-ethylene ketal |
| 814 | 773 | 280 | 152 | 1,9-dioxo-11α,16-dihydroxy-1-hydroxymethyl-13-trans-17-trans-5-cis-prostatriene,-1-ethylene ketal |
| 815 | 773 | 280 | 153 | 1,9-dioxo-11α,16(R)-dihydroxy-1-hydroxymethyl-5-cis-13-trans-prostadiene, 1-ethylene ketal |
| 816 | 773 | 280 | 154 | 1,9-dioxo-11α,16(S)-dihydroxy-1-hydroxymethyl-5-cis-13-trans-prostadiene, 1-ethylene ketal |
| 817 | 773 | 280 | 148a | 1,9-dioxo-11α,16-dihydroxy-20-ethyl-1-hydroxymethyl-5-cis-13-trans-17-trans-prostatriene, 1-ethylene ketal |
| 818 | 773 | 280 | 1-iodo-3-triphenylmethoxy-1-trans-octene (U.S. Pat. No. 3,873,607). | 1,9-dioxo-11α,15α-dihydroxy-1-hydroxymethyl-5-cis-13-trans-prostadiene, 1-ethylene ketal |
| 819 | 773 | 280 | 1-iodo-3-triphenylmethoxy-1-trans-nonene (U.S. Pat. No. 3,873,607). | 1,9-dioxo-11α,15α-dihydroxy-20-methyl-1-hydroxymethyl-5-cis-13-trans-prostadiene 1-ethylene ketal |
| 820 | 773 | 280 | 1-iodo-3-triphenylmethoxy-1-trans-decene (U.S. Pat. No. 3,873,607). | 1,9-dioxo-11α,15α-dihydroxy-20-ethyl-1-hydroxymethyl-5-cis-13-trans-prostadiene 1-ethylene ketal |
| 821 | 773 | 280 | 1-iodo-3-triphenylmethoxy-4,4-dimethyl-1-trans-octene (U.S. Pat. No. 3,873,607). | 1,9-dioxo-11α,15α-dihydroxy-16,16-dimethyl-1-hydroxymethyl-5-cis-13-trans-prostadiene, 1-ethylene ketal |
| 822 | 773 | 280 | 1-iodo-3-triphenylmethoxy-5,5-dimethyl-1-trans-octene (U.S. Pat. No. 3,873,607). | 1,9-dioxo-11α,15α-dihydroxy-17,17-dimethyl-5-cis-13-trans-prostadiene, 1-ethylene ketal |
| 823 | 773 | 280 | 1-iodo-3-triphen- | 1,9-dioxo-11α,15α-dihydroxy-16-methyl-1- |

TABLE 40-continued

| Example | Method of Example | Cyclopent-2-en-1-one | Vinyl Iodide or Vinyl Tin of Example | 1,9-dioxo-1-hydroxymethylprostene |
|---|---|---|---|---|
| | | | ylmethoxy-4-methyl-1-trans-octene (U.S. Pat. No. 3,876,690). | hydroxymethyl-5-cis-13-trans-prostadiene, 1-ethylene ketal |
| 824 | 773 | 280 | 1-iodo-3-triphenylmethoxy-4-ethyl-1-trans-octene (U.S. Pat. No. 3,876,690). | 1,9-dioxo-11α,15α-dihydroxy-16-ethyl-1-hydroxymethyl-5-cis-13-trans-prostadiene, 1-ethylene ketal |
| 825 | 773 | 280 | 1-iodo-3-triphenylmethoxy-3-cyclopentyl-1-trans-butene (U.S. Pat. No. 3,884,969). | 1,9-dioxo-11α,15α-dihydroxy-17,20-tetranor-16-cyclopentyl-1-hydroxymethyl-5-cis-13-trans-prostadiene, 1-ethylene ketal |
| 826 | 773 | 280 | 1-iodo-3-triphenylmethoxy-3-cyclohexyl-1-trans-pentene (U.S. Pat. No. 3,884,969). | 1,9-dioxo-11α,15α-dihydroxy-16,20-pentanor-15-cyclohexyl-1-hydroxymethyl-5-cis-13-trans-prostadiene, 1-ethylene ketal |
| 827 | 773 | 280 | 1-iodo-3-triphenylmethoxy-5-cyclohexyl-1-trans-pentene (U.S. Pat. No. 3,884,969). | 1,9-dioxo-11α,15α-dihydroxy-18,20-trinor-17-cyclohexyl-1-hydroxymethyl-5-cis-13-trans-prostadiene, 1-ethylene ketal |
| 828 | 773 | 280 | 1-iodo-3-triphenylmethoxy-6-cyclopentyl-1-trans-hexene (U.S. Pat. No. 3,884,969). | 1,9-dioxo-11α,15α-dihydroxy-19,20-dinor-18-cyclopentyl-1-hydroxymethyl-5-cis-13-trans-prostadiene, 1-ethylene ketal |
| 829 | 773 | 280 | 1-iodo-3-methyl-3-trimethylsilyloxy-trans-1-octene (Example 125) | 1,9-dioxo-11α,15α-dihydroxy-15-methyl-1-hydroxymethyl-5-cis-13-trans-prostadiene, 1-ethylene ketal |
| 830 | 773 | 280 | 1-iodo-3-methyl-3-trimethylsilyloxy-trans-1-decene (Example 190a) | 1,9-dioxo-11α,15α-dihydroxy-15-methyl-20-ethyl-1-hydroxymethyl-5-cis-13-trans-prostadiene, 1-ethylene ketal |
| 831 | 774 | 280 | 159 | 1,9-dioxo-11 α,15α-dihydroxy-17,18,19,20-tetranor-16-p-fluorophenoxy-1-hydroxymethyl-5-cis-13-trans-prostadiene, 1-ethylene ketal |
| 832 | 774 | 280 | 186 | 1,9-dioxo-11α,15α-dihydroxy-17,18,19,20-tetranor-16-phenoxy-1-hydroxymethyl-5-cis-13-trans-prostadiene, 1-ethylene ketal |
| 833 | 774 | 280 | 181 | 1,9-dioxo-11α,15α-dihydroxy-17,18,19,20-tetranor-16-p-bromophenoxy-1-hydroxymethyl-5-cis-13-trans-prostadiene, 1-ethylene ketal |
| 834 | 774 | 280 | 182 | 1,9-dioxo-11 α,15α-dihydroxy-17,18,19,20-tetranor-16-p-t-butylphenoxy-1-hydroxymethyl-5-cis-13-trans-prostadiene, 1-ethylene ketal |
| 835 | 774 | 280 | 183 | 1,9-dioxo-11α,15α-dihydroxy-17,18,19,20-tetranor-16-p-methoxyphenoxy-1-hydroxymethyl-5-cis-13-trans-prostadiene, 1-ethylene ketal |
| 836 | 774 | 280 | 184 | 1,9-dioxo-11α,15α-dihydroxy-17,18,19,20-tetranor-16-p-chlorophenoxy-1-hydroxymethyl-5-cis-13-trans-prostadiene, 1-ethylene ketal |
| 837 | 774 | 280 | 180 | 1,9-dioxo-11α,15α-dihydroxy-17,18,19,20-tetranor-m-trifluorophenoxy-1-hydroxymethyl-5-cis-13-trans-prostadiene, 1-ethylene ketal |
| 838 | 774 | 280 | 185 | 1,9-dioxo-11α,15α-dihydroxy-17,18,19,20-tetranor-16-(3,4-dichlorophenoxy)-1-hydroxymethyl-5-cis-13-trans-prostadiene, 1-ethylene ketal |
| 839 | 774 | 280 | 186b | 1,9-dioxo-11α,15α-dihydroxy-18,19,20-trinor-17-phenyl-1-hydroxymethyl-5-cis-13-trans-prostadiene, 1-ethylene ketal |
| 840 | 774 | 280 | 186e | 1,9-dioxo-11 α,15α-dihydroxy-18,19,20-trinor-17-(m-trifluoromethylphenyl)-1-hydroxymethyl-5-cis-13-trans-prostadiene, 1-ethylene ketal |
| 841 | 774 | 280 | 186d | 1,9-dioxo-11α,15α-dihydroxy-18,19,20-trinor-17-(p-methoxyphenyl)-1-hydroxymethyl-5-cis-13-trans-prostadiene, 1-ethylene ketal |

TABLE 40-continued

| Example | Method of Example | Cyclopent-2-en-1-one | Vinyl Iodide or Vinyl Tin of Example | 1,9-dioxo-1-hydroxymethylprostene |
|---|---|---|---|---|
| 842 | 773 | 297 | 1-iodo-3-triphenylmethoxy-1-trans-octene (U.S. Pat. No. 3,873,607). | 1,9-dioxo-11α,15α-dihydroxy-1-hydroxymethyl-2-nor-5-cis-13-trans-prostadiene, 1-ethylene ketal |
| 843 | 773 | 297 | 185 | 1,9-dioxo-11α,15α-dihydroxy-15-methyl-1-hydroxymethyl-2-nor-5-cis-13-trans-prostadiene, 1-ethylene ketal |
| 844 | 773 | 297 | 1-iodo-3-triphenylmethoxy-5,5-dimethyl octene (U.S. Pat. No. 3,873,607). | 1,9-dioxo-11α,15α-dihydroxy-16,16-dimethyl-1-hydroxymethyl-2-nor-5-cis-13-trans-prostadiene, 1-ethylene ketal |
| 845 | 773 | 297 | 13 | 1,9-dioxo-11α,15α-dihydroxy-16,16-trimethylene-1-hydroxymethyl-2-nor-5-cis-13-trans-prostadiene, 1-ethylene ketal |
| 846 | 773 | 297 | 76 | erythro-1,9-dioxo-11α,15α,16-trihydroxy-1-hydroxymethyl-2-nor-5-cis-13-trans-prostadiene, 1-ethylene ketal |
| 847 | 773 | 297 | 69 | threo-1,9-dioxo-11α,15α,16-trihydroxy-1-hydroxymethyl-2-nor-5-cis-13-trans-prostadiene, 1-ethylene ketal |
| 848 | 773 | 297 | 74 | erythro-1,9-dioxo-11α,15α,16-dihydroxy-16-methoxy-1-hydroxymethyl-5-cis-13-trans-prostadiene, 1-ethylene ketal |
| 849 | 773 | 297 | 107 | 1,9-dioxo-11α,16-dihydroxy-1-hydroxymethyl-2-nor-5-cis-13-trans-prostadiene, 1-ethylene ketal |
| 850 | 773 | 297 | 130 | 1,9-dioxo-11α,16-dihydroxy-16-methyl-1-hydroxymethyl-2-nor-5-cis-13-trans-prostadiene, 1-ethylene ketal |
| 851 | 773 | 297 | 134 | 1,9-dioxo-11α,16-dihydroxy-16-methyl-1-hydroxymethyl-2-nor-5-cis-13-trans-17-trans-prostadiene, 1-ethylene ketal |
| 852 | 774 | 297 | 186 | 1,9-dioxo-11α,15α-dihydroxy-2,17,18,19,20-pentanor-16-phenoxy-1-hydroxymethyl-5-cis-13-trans-prostadiene, 1-ethylene ketal |
| 853 | 774 | 297 | 180 | 1,9-dioxo-11α,15α-dihydroxy-2,17,18,19,20-pentanor-16-m-trifluoromethylphenoxy-1-hydroxymethyl-5-cis-13-trans-prostadiene, 1-ethylene ketal |
| 854 | 773 | 297 | 194 | 1,9-dioxo-11α,16-dihydroxy-16-vinyl-1-hydroxymethyl-2-nor-5-cis-13-trans-prostadiene, 1-ethylene ketal |
| 855 | 774 | 297 | 198 | 1,9-dioxo-11α,16-dihydroxy-16-cyclopropyl-1-hydroxymethyl-2-nor-5-cis-13-trans-prostadiene, 1-ethylene ketal |
| 856 | 774 | 297 | 186b | 1,9-dioxo-11α,15α-dihydroxy-2,18,19,20-tetranor-17-phenyl-1-hyroxymethyl-5-cis-13-trans-prostadiene, 1-ethylene ketal |
| 857 | 773 | 297 | 186e | 1,9-dioxo-11α,15α-dihydroxy-2,18,19,20-tetranor-17-(m-trifluorophenyl)-1-hydroxymethyl-5-cis-13-trans-prostadiene, 1-ethylene ketal |
| 858 | 773 | 297 | 186d | 1,9-dioxo-11α,15α-dihydroxy-2,18,19,20-tetranor-17-(p-methoxyphenyl)-1-hydroxymethyl-5-cis-13-trans-prostadiene, 1-ethylene ketal |
| 859 | 773 | 310 | 125 | 1,9-dioxo-15-hydroxy-15-methyl-1-hydroxymethyl-2-nor-13-trans-prostene, 1-ethylene ketal |
| 860 | 773 | 298 | 130 | 1,9-dioxo-11α,16-dihydroxy-16-methyl-1-homo-1-hydroxymethyl-5-cis-13-trans-prostadiene, 1-ethylene ketal |
| 861 | 773 | 298 | 134 | 1,9-dioxo-11α,16-dihydroxy-16-methyl-1-homo-1-hydroxymethyl-5-cis-13-trans-17-trans-prostatriene, 1-ethylene ketal |
| 862 | 774 | 298 | 186 | 1,9-dioxo-11α,15α-dihydroxy-17,18,19,20-tetranor-16-phenoxy-1-hydroxymethyl-5-cis-13-trans-prostadiene, 1-ethylene ketal |
| 863 | 774 | 298 | 180 | 1,9-dioxo-11α,15α-dihydroxy-17,18,19,20-tetranor-16-m-trifluoromethylphenoxy-1-hydroxmethyl-5-cis-13-trans-prostadiene, 1-ethylene ketal |
| 864 | 773 | 298 | 194 | 1,9-dioxo-11α,16-dihydroxy-16-vinyl-1-homo-1-hydroxymethyl-5-cis-13-trans-prostadiene, 1-ethylene ketal |
| 865 | 774 | 298 | 198 | 1,9-dioxo-11α,16-dihydroxy-16-cyclopropyl-1-homo-1-hydroxymethyl-5-cis-13-trans-prostadiene, 1-ethylene ketal |

TABLE 40-continued

| Example | Method of Example | Cyclopent-2-en-1-one | Vinyl Iodide or Vinyl Tin of Example | 1,9-dioxo-1-hydroxymethylprostene |
|---|---|---|---|---|
| 866 | 774 | 298 | 186b | 1,9-dioxo-11α,15α-dihydroxy-1-homo-18,19,20-trinor-17-phenyl-1-hydroxymethyl-5-cis-13-trans-prostadiene, 1-ethylene ketal |
| 867 | 773 | 298 | 186e | 1,9-dioxo-11α,15α-dihydroxy-1-homo-18,19,20-trinor-17-(m-trifluorophenyl)-1-hydroxymethyl-13-trans-5-cis-prostadiene, 1-ethylene ketal |
| 868 | 773 | 298 | 186d | 1,9-dioxo-11α,15α-dihydroxy-1-homo-18,19,20-trinor-17-(p-methoxyphenyl)-1-hydroxymethyl-13-tans-5-cis-prostadiene, 1-ethylene ketal |

EXAMPLES 869–891

By the methods described hereinabove in Examples 773 and 774, the 1,9-dioxo-1-hydroxymethyl prostene derivatives shown in Table 41 are prepared by the indicated method from the indicated vinyl iodide or vinyl tin compound and the indicated cyclopent-2-en-1-one.

In those cases where two diastereoisomers are formed in the conjugate-addition, only one of the diastereoisomers is listed in Table 41. It should be understood that the other diastereoisomer is also formed which in its nat and ent forms has an opposite (mirror image) configuration at the assymmetric carbon atoms on the β-chain (the chain containing $C_{13}$....$C_{14}$ etc.) to that of the respective nat and ent forms of the listed diastereoisomer; both of these diastereoisomers are claimed in this invention as well as their component enantiomers.

TABLE 41

| Example | Method of Example | Cyclopent-2-en-1-one of Example | Vinyl Iodide or Vinyl Tin of Example | 1,9-dioxo-1-hydroxymethylprostene and its diastereomer |
|---|---|---|---|---|
| 869 | 773 | 280 | 246 | nat-(and ent)-1,9-dioxo-11α,15-dihydroxy-15,16-tetramethylene-17,18,19,20-tetranor-1-hydroxymethyl-5-cis-13-trans-prostadiene, 1-ethylene ketal |
| 870 | 774 | 280 | 245 | nat-(and ent)-1,9-dioxo-11α,16-dihydroxy-16,17-tetramethylene-18,19,20-trinor-1-hydroxymethyl-5-cis-13-trans-prostadiene, 1-ethylene ketal |
| 871 | 773 | 280 | 243 | nat-15S,16R-(and ent-15R,16S)-1,9-dioxo-11α,15-dihydroxy-15,16-trimethylene-1-hydroxymethyl-5-cis-13-trans-prostadiene, 1-ethylene ketal |
| 872 | 773 | 280 | 243 | nat-15S,16R-(and ent-15R,16S)-1,9-dioxo-11α,15-dihydroxy-15,16-trimethylene-1-hydroxymethyl-13-trans-5-cis-prostadiene, 1-ethylene ketal |
| 873 | 773 | 280 | 251 | nat-15S,16S-(and ent-15R,16R)-1,9-dioxo-11α,15-dihydroxy-15,16-trimethylene-1-hydroxymethyl-13-trans-5-cis-prostadiene, 1-ethylene ketal |
| 874 | 773 | 280 | 247 | nat-(and ent)-1,9-dioxo-11α,15-dihydroxy-15,16-trimethylene-17,18,19,20-tetranor-1-hydroxymethyl-13-trans-5-cis-prostadiene, 1-ethylene ketal |
| 875 | 774 | 280 | 248 | nat-(and ent)-1,9-dioxo-11α,15-dihydroxy-15,16-pentamethylene-17,18,19,20-tetranor-1-hydroxymethyl-13-trans-5-cis-prostadiene, 1-ethylene ketal |
| 876 | 773 | 280 | 249 | nat-15S,17R-(and ent-15R,17S)-1,9-dioxo-11α,15-dihydroxy-15,17-dimethylene-1-hydroxymethyl-13-trans-5-cis-prostadiene,1-ethylene ketal |
| 877 | 773 | 280 | 250 | nat-15S,17S-(and ent-15R,17R)-1,9-dioxo-11α,15-dihydroxy-15,17-dimethylene-1-hydroxymethyl-13-trans-5-cis-prostadiene,1-ethylene ketal |
| 878 | 773 | 280 | 252 | nat-15S,16R-(and ent-15R,16S)-1,9-dioxo-11α,15-dihydroxy-15,16-tetramethylene-1-hydroxymethyl-13-trans-5-cis-prostadiene, 1-ethylene ketal |
| 879 | 773 | 280 | 253 | nat-15S,16S-(and ent-15R,16R)-1,9-dioxo-11α,15-dihydroxy-15,16-tetramethylene-1-hydroxymethyl-13-trans-5-cis-prostadiene, 1-ethylene ketal |
| 880 | 774 | 280 | 254 | nat-15R,16S-(and ent-15S,16R)-1,9-dioxo-11α,15-dihydroxy-15,16-trimethylene-16-(3-trifluoromethylphenoxy)-17,18,19,20-tetranor-1-hydroxymethyl-13-trans-5-cis-prostadiene, 1-ethylene ketal |

TABLE 41-continued

| Example | Method of Example | Cyclopent-2-en-1-one of Example | Vinyl Iodide or Vinyl Tin of Example | 1,9-dioxo-1-hydroxymethylprostene and its diastereomer |
|---|---|---|---|---|
| 881 | 774 | 280 | 255 | nat-15R,16R-(and ent-15S,16S)-1,9-dioxo-11α,15-dihydroxy-15,16-trimethylene-16-(3-trifluoromethylphenoxy)-17,18,19,20-tetranor-1-hydroxymethyl-13-trans-5-cis-prostadiene, 1-ethylene ketal |
| 882 | 773 | 280 | 256 | nat-15R,16S-(and ent-15S,16R)-1,9-dioxo-11α,15-dihydroxy-15,16-trimethylene-16-(4-fluorophenoxy)-17,18,19,20-tetranor-1-hydroxymethyl-13-trans-5-cis-prostadiene, 1-ethylene ketal |
| 883 | 773 | 280 | 257 | nat-15R,16R-(and ent-15S,16S)-1,9-dioxo-11α,15-dihydroxy-15,16-trimethylene-16-(4-fluorophenoxy)-17,18,19,20-tetranor-1-hydroxymethyl-13-trans-5-cis-prostadiene, 1-ethylene ketal |
| 884 | 774 | 280 | 258 | nat-15R,16S-(and ent-15S,16R)-1,9-dioxo-11α,15-dihydroxy-15,16-trimethylene-16-(3-chlorophenoxy)-17,18,19,20-tetranor-1-hydroxymethyl-13-trans-5-cis-prostadiene, 1-ethylene ketal |
| 885 | 774 | 280 | 259 | nat-15R,16R-(and ent-15S,16S)-1,9-dioxo-11α,15-dihydroxy-15,16-trimethylene-16-(3-chlorophenoxy)-17,18,19,20-tetranor-1-hydroxymethyl-13-trans-5-cis-prostadiene, 1-ethylene ketal |
| 886 | 773 | 280 | 260 | nat-15S,17R-(and ent-15R,17S)-1,9-dioxo-11α,15-dihydroxy-15,17-trimethylene-19,20-dinor-1-hydroxymethyl-13-trans-5-cis-prostadiene, 1-ethylene ketal |
| 887 | 773 | 280 | 261 | nat-15S,17S-(and ent-15R,17R)-1,9-dioxo-11α,15-dihydroxy-15,17-trimethylene-19,20-dinor-1-hydroxymethyl-13-trans-5-cis-prostadiene, 1-ethylene ketal |
| 888 | 774 | 280 | 262 | nat-16R,17S-(and ent-16S,17R)-1,9-dioxo-11α,16-dihydroxy-16,17-trimethylene-20-methyl-1-hydroxymethyl-13-trans-5-cis-prostadiene, 1-ethylene ketal |
| 889 | 774 | 280 | 263 | nat-16R,17R-(and ent-16S,17S)-1,9-dioxo-11α,16-dihydroxy-16,17-trimethylene-20-methyl-1-hydroxymethyl-13-trans-5-cis-prostadiene, 1-ethylene ketal |
| 890 | 774 | 280 | 264 | nat-16R,17S-(and ent-16S,17R)-1,9-dioxo-11α,16-dihydroxy-16,17-trimethylene-16-(3-trifluoromethylphenoxy)-18,19,20-trinor-1-hydroxymethyl-13-trans-5-cis-prostadiene, 1-ethylene ketal |
| 891 | 774 | 280 | 265 | nat-16R,17R-(and ent-16S,17S)-1,9-dioxo-11α,16-dihydroxy-16,17-trimethylene-16-(3-trifluoromethylphenoxy)-18,19,20-trinor-1-hydroxymethyl-13-trans-5-cis-prostadiene, 1-ethylene ketal |

EXAMPLES 892–975

By the methods described hereinabove in Examples 773 and 774, the 1,9-dioxo-hydroxymethyl prostene derivatives shown in Table 42 are prepared by the indicated method from the indicated vinyl iodide or vinyl tin compound and the indicated cyclopent-2-en-1-one.

In those cases where isomers are obtained at the $C_{15}$ or $C_{16}$ positions, only the $C_{15}$ or $C_{16}$-normal isomers are listed in Table 42; it should be understood that the corresponding $C_{15}$ or $C_{16}$-epi isomers are also formed and are part of this invention.

In those cases where the initial conjugate-addition product contains a triphenylmethoxy blocking group, deblocking is conducted in acetic acid-tetrahydrofuran-water 4:2:1 at 50° C. for 5 hours.

TABLE 42

| Example | Method of Example | Cyclopent-2-en-1-one | Vinyl Iodide or Vinyl Tin of Example | 1,9-dioxo-1-hydroxymethylprostene |
|---|---|---|---|---|
| 892 | 773 | 309 | 49 | 1,9-dioxo-11α,15-dihydroxy-1-hydroxymethyl-16,16-trimethylene-20-nor-13-trans-prostene,1-ethylene ketal |
| 893 | 773 | 309 | 50 | 1,9-dioxo-11α,15-dihydroxy-1-hydroxymethyl-16,16-trimethylene-20-methyl-13-trans-prostene,1-ethylene ketal |
| 894 | 773 | 309 | 51 | 1,9-dioxo-11α,15-dihydroxy-1-hydroxymethyl-16,16-trimethylene-20-ethyl-13-trans-prostene, 1-ethylene ketal |

TABLE 42-continued

| Example | Method of Example | Cyclopent-2-en-1-one | Vinyl Iodide or Vinyl Tin of Example | 1,9-dioxo-1-hydroxymethylprostene |
|---|---|---|---|---|
| 895 | 774 | 309 | 193 | 1,9-dioxo-11α,16-dihydroxy-16-cyclopropyl-20-ethyl-1-hydroxymethyl-13-trans-prostene,1-ethylene ketal |
| 896 | 774 | 309 | 195 | 1,9-dioxo-11α,16-dihydroxy-16-vinyl-20-ethyl-1-hydroxymethyl-13-trans-prostene, 1-ethylene ketal |
| 897 | 774 | 309 | 192 | 1,9-dioxo-11α,16-dihydroxy-16-cyclopropyl-1-hydroxymethyl-13-trans-prostene,1-ethylene ketal |
| 898 | 773 | 309 | 13 | 1,9-dioxo-11α,15-dihydroxy-1-hydroxymethyl-16,16-trimethylene-13-trans-prostene,-1-ethylene ketal |
| 899 | 773 | 309 | 210a | 1,9-dioxo-11α,16-dihydroxy-1-hydroxymethyl-16-vinyl-13-trans-prostene,1-ethylene ketal |
| 900 | 773 | 309 | 74 | dl-erythro-1,9-dioxo-11α,15-dihydroxy-16-methoxy-1-hydroxymethyl-13-trans-prostene,1-ethylene ketal |
| 901 | 773 | 309 | 77 | dl-erythro-1,9-dioxo-11α,15-dihydroxy-16-ethoxy-1-hydroxymethyl-13-trans-prostene,1-ethylene ketal |
| 902 | 773 | 309 | 83 | dl-erythro-1,9-dioxo-11α,15,16-trihydroxy-1-hydroxymethyl-20-nor-13-trans-prostene,1-ethylene ketal |
| 903 | 773 | 309 | 84 | dl-erythro-1,9-dioxo-11α,15,16-trihydroxy-1-hydroxymethyl-20-methyl-13-trans-prostene,1-ethylene ketal |
| 904 | 773 | 309 | 85 | dl-erythro-1,9-dioxo-11α,15,16-trihydroxy-1-hydroxymethyl-20-ethyl-13-trans-prostene,1-ethylene ketal |
| 905 | 773 | 309 | 86 | dl-erythro-1,9-dioxo-11α,15,16-trihydroxy-19-methyl-1-hydroxymethyl-13-trans-prostene,1-ethylene ketal |
| 906 | 773 | 309 | 87 | dl-erythro-1,9-dioxo-11α,15,16-trihydroxy-13-trans-17-trans-prostadiene,1-ethylene ketal |
| 907 | 773 | 309 | 69 | dl-threo-1,9-dioxo-11α,15,16-trihydroxy-1-hydroxymethyl-13-trans-prostene,1-ethylene ketal |
| 908 | 773 | 309 | 88 | dl-threo-1,9-dioxo-11α,15,16-trihydroxy-20-nor-1-hydroxymethyl-13-trans-prostene,1-ethylene ketal |
| 909 | 773 | 309 | 76 | dl-erythro-1,9-dioxo-11α,15,16-trihydroxy-1-hydroxymethyl-13-trans-prostene,1-ethylene ketal |
| 910 | 773 | 309 | 89 | dl-threo-1,9-dioxo-11α,15,16-trihydroxy-20-methyl-1-hydroxymethyl-13-trans-prostene, 1-ethylene ketal |
| 911 | 773 | 309 | 90 | dl-threo-1,9-dioxo-11α,15,16-trihydroxy-20-ethyl-1-hydroxymethyl-13-trans-prostene,1-ethylene ketal |
| 912 | 773 | 309 | 91 | dl-threo-1,9-dioxo-11α,15,16-trihydroxy-19-methyl-1-hydroxymethyl-13-trans-prostene,1-ethylene ketal |
| 913 | 773 | 309 | 92 | dl-threo-1,9-dioxo-11α,15,16-trihydroxy-1-hydroxymethyl-13-trans-17-trans-prostadiene, 1-ethylene ketal |
| 914 | 773 | 309 | 107 | 1,9-dioxo-11α,16-dihydroxy-1-hydroxymethyl-13-trans-prostene, 1-ethylene ketal |
| 915 | 773 | 309 | 108 | 1,9-dioxo-11α,16-dihydroxy-1-hydroxymethyl-19,20-dinor-13-trans-prostene, 1-ethylene ketal |
| 916 | 773 | 309 | 109 | 1,9-dioxo-11α,16-dihydroxy-1-hydroxymethyl-18,19,20-trinor-13-trans-prostene,1-ethylene ketal |
| 917 | 773 | 309 | 110 | 1,9-dioxo-11α,16-dihydroxy-1-hydroxymethyl-20-nor-13-trans-prostene, 1-ethylene ketal |
| 918 | 773 | 309 | 144 | 1,9-dioxo-11α,16-dihydroxy-17-methyl-1-hydroxymethyl-13-trans-prostene, 1-ethylene ketal |
| 919 | 773 | 309 | 112 | 1,9-dioxo-11α,16-dihydroxy-20-methyl-1-hydroxymethyl-13-trans-prostene, 1-ethylene ketal |
| 920 | 773 | 309 | 113 | 1,9-dioxo-11α,16-dihydroxy-20-ethyl-1-hydroxymethyl-13-trans-prostene,1-ethylene ketal |
| 921 | 773 | 309 | 139a | 1,9-dioxo-11α,16-dihydroxy-16-methyl-20-ethyl-1-hydroxymethyl-13-trans-prostene, |

TABLE 42-continued

| Example | Method of Example | Cyclopent-2-en-1-one | Vinyl Iodide or Vinyl Tin of Example | 1,9-dioxo-1-hydroxymethylprostene |
|---|---|---|---|---|
| 922 | 773 | 309 | 115 | 1,9-dioxo-11α,16-dihydroxy-1-hydroxymethyl-13-trans-17-cis-prostadiene, 1-ethylene ketal |
| 923 | 773 | 309 | 135 | 1,9-dioxo-11α,16-dihydroxy-16-methyl-1-hydroxymethyl-13-trans-prostene, 1-ethylene ketal |
| 924 | 773 | 309 | 136 | 1,9-dioxo-11α,16-dihydroxy-17,17,20-trimethyl-1-hydroxymethyl-13-trans-prostene, 1-ethylene ketal |
| 925 | 773 | 309 | 137 | 1,9-dioxo-11α,16-dihydroxy-16,20-dimethyl-1-hydroxymethyl-13-trans-prostene,1-ethylene ketal |
| 926 | 773 | 309 | 138 | 1,9-dioxo-11α,16-dihydroxy-17,17-dimethyl-1-hydroxymethyl-13-trans-prostene,1-ethylene ketal |
| 927 | 773 | 309 | 139 | 1,9-dioxo-11α,16-dihydroxy-16-methyl-1-hydroxymethyl-13-trans-17-trans-prostadiene,1-ethylene ketal |
| 928 | 773 | 309 | 149 | 1,9-dioxo-11α,16-dihydroxy-20-methyl-1-hydroxymethyl-13-trans-17-trans-prostadiene,1-ethylene ketal |
| 929 | 773 | 309 | 150 | 1,9-dioxo-11α,16-dihydroxy-16-methyl-1-hydroxymethyl-13-trans-prostene, 1-ethylene ketal |
| 930 | 773 | 309 | 151 | 1,9-dioxo-11α,16-dihydroxy-17,20-dimethyl-1-hydroxymethyl-13-trans-prostene,1-ethylene ketal |
| 931 | 773 | 309 | 152 | 1,9-dioxo-11α,16-dihydroxy-1-hydroxymethyl-13-trans-17-trans-prostadiene,1-ethylene ketal |
| 932 | 773 | 309 | 153 | 1,9-dioxo-11α,16(R)-dihydroxy-1-hydroxymethyl-13-trans-prostene, 1-ethylene ketal |
| 933 | 773 | 309 | 154 | 1,9-dioxo-11α,16(S)-dihydroxy-1-hydroxymethyl-13-trans- prostene,1-ethylene ketal |
| 934 | 773 | 309 | 148a | 1,9-dioxo-11α,16-dihydroxy-20-ethyl-1-hydroxymethyl-13-trans-17-trans-prostadiene,1-ethylene ketal |
| 935 | 773 | 309 | 1-iodo-3-triphenylmethoxy-1-trans-octene (U.S. Pat. No. 3,873,607). | 1,9-dioxo-11α,15α-dihydroxy-1-hydroxymethyl-13-trans-prostadiene, 1-ethylene ketal |
| 936 | 773 | 309 | 1-iodo-3-triphenylmethoxy-1-trans-nonene (U.S. Pat. No. 3,873,607). | 1,9-dioxo-11α,15α-dihydroxy-20-methyl-1-hydroxymethyl-13-trans-prostene,1-ethylene ketal |
| 937 | 773 | 309 | 1-iodo-3-triphenylmethoxy-1-trans-decene (U.S. Pat. No. 3,873,607). | 1,9-dioxo-11α,15α-dihydroxy-20-ethyl-1-hydroxymethyl-13-trans-prostene, 1-ethylene ketal |
| 938 | 773 | 309 | 1-iodo-3-triphenylmethoxy-4,4-dimethyl-1-trans-octene (U.S. Pat. No. 3,873,607). | 1,9-dioxo-11α,15α-dihydroxy-16,16-dimethyl-1-hydroxymethyl-13-trans-prostene,1-ethylene ketal |
| 939 | 773 | 309 | 1-iodo-3-triphenylmethoxy-5,5-dimethyl-1-trans-octene (U.S. Pat. No. 3,873,607). | 1,9-dioxo-11α,15α-dihydroxy-17,17-dimethyl-1-hydroxymethyl-13-trans-prostene,1-ethylene ketal |
| 940 | 773 | 309 | 1-iodo-3-triphenylmethoxy-4-methyl-1-trans-octene (U.S. Pat. No. 3,876,690). | 1,9-dioxo-11α,15α-dihydroxy-16-methyl-1-hydroxymethyl-13-trans-prostene, 1-ethylene ketal |
| 941 | 773 | 309 | 1-iodo-3-triphenylmethoxy-4-ethyl-1-trans-octene (U.S. Pat. No. 3,876,690). | 1,9-dioxo-11α,15α-dihydroxy-16-ethyl-1-hydroxymethyl-13-trans-prostene, 1-ethylene ketal |
| 942 | 773 | 309 | 1-iodo-3-triphenylmethoxy-4-cyclopentyl-1-trans-butene (U.S. Pat. No. 3,884,969). | 1,9-dioxo-11α,15α-dihydroxy-17,20-tetranor-16-cyclopentyl-1-hydroxymethyl-13-trans-prostene, 1-ethylene ketal |
| 943 | 773 | 309 | 1-iodo-3-triphenylmethoxy-3-cyclohexyl-1-trans-pentene (U.S. Pat. | 1,9-dioxo-11α,15α-dihydroxy-16,20-pentanor-15-cyclohexyl-1-hydroxymethyl-13-trans-prostene,1-ethylene ketal |

TABLE 42-continued

| Example | Method of Example | Cyclopent-2-en-1-one | Vinyl Iodide or Vinyl Tin of Example | 1,9-dioxo-1-hydroxymethylprostene |
|---|---|---|---|---|
| | | | No. 3,884,969). | |
| 944 | 773 | 309 | 1-iodo-3-triphen-ylmethoxy-5-cyclo-hexyl-1-trans-pentene (U.S. Pat. No. 3,884,969). | 1,9-dioxo-11α,15α-dihydroxy-18,20-trinor-17-cyclohexyl-1-hydroxymethyl-13-trans-prostene, 1-ethylene ketal |
| 945 | 773 | 309 | 1-iodo-3-triphen-ylmethoxy-6-cyclo-pentyl-1-trans-hexene (U.S. Pat. No. 3,884,969). | 1,9-dioxo-11α,15α-dihydroxy-19,20-dinor-18-cyclopentyl-1-hydroxymethyl-13-trans-prostene, 1-ethylene ketal |
| 946 | 773 | 309 | 1-iodo-3-methyl-3-trimethylsilyl-oxy-trans-1-octene (Example 125) | 1,9-dioxo-11α,15α-dihydroxy-15-methyl-1-hydroxymethyl-13-trans-prostene,1-ethylene ketal |
| 947 | 773 | 309 | 1-iodo-3-methyl-3-trimethylsilyl-oxy-trans-1-decene (Example 190a) | 1,9-dioxo-11α,15α-dihydroxy-15-methyl-20-ethyl-1-hydroxymethyl-13-trans-prostene, 1-ethylene ketal |
| 948 | 774 | 309 | 159 | 1,9-dioxo-11α,15α-dihydroxy-17,18,19,20-tetranor-16-p-fluorophenoxy-1-hydroxymethyl-13-trans-prostene, 1-ethylene ketal |
| 949 | 774 | 309 | 186 | 1,9-dioxo-11α,15α-dihydroxy-17,18,19,20-tetranor-16-phenoxy-1-hydroxymethyl-13-trans-prostene, 1-ethylene ketal |
| 950 | 774 | 309 | 181 | 1,9-dioxo-11α,15α-dihydroxy-17,18,19,20-tetranor-16-p-bromophenoxy-1-hydroxy-methyl-13-trans-prostene, 1-ethylene ketal |
| 951 | 774 | 309 | 182 | 1,9-dioxo-11α,15α-dihydroxy-17,18,19,20-tetranor-16-p-t-butylphenoxy-1-hydroxy-methyl-13-trans-prostene, 1-ethylene ketal |
| 952 | 774 | 309 | 183 | 1,9-dioxo-11α,15α-dihydroxy-17,18,19,20-tetranor-16-p-methoxyphenoxy-1-hydroxy-methyl-13-trans-prostene,1-ethylene ketal |
| 953 | 774 | 309 | 184 | 1,9-dioxo-11α,15α-dihydroxy-17,18,19,20-tetranor-16-p-chlorophenoxy-1-hydroxy-methyl-13-trans-prostene, 1-ethylene ketal |
| 954 | 774 | 309 | 180 | 1,9-dioxo-11α,15α-dihydroxy-17,18,19,20-tetranor-m-trifluorophenoxy-1-hydroxy-methyl-13-trans-prostene,1-ethylene ketal |
| 955 | 774 | 309 | 185 | 1,9-dioxo-11α,15α-dihydroxy-17,18,19,20-tetranor-16-(3,4-dichlorophenoxy)-1-hy-droxymethyl-13-trans-prostene,1-ethylene ketal |
| 956 | 774 | 309 | 186b | 1,9-dioxo-11α,15α-dihydroxy-18,19,20-tri-nor-17-phenyl-1-hydroxymethyl-13-trans-prostene,1-ethylene ketal |
| 957 | 774 | 309 | 186e | 1,9-dioxo-11α, 15α-dihydroxy-18,19,20-tri-nor-17-(m-trifluoromethylphenyl)-1-hydr-oxymethyl-13-trans-prostene,1-ethylene ketal |
| 958 | 774 | 309 | 186d | 1,9-dioxo-11α,15α-dihydroxy-18,19,20-tri-nor-17-(p-methoxyphenyl)-1-hydroxymethyl-13-trans-prostene, 1-ethylene ketal |
| 959 | 773 | 312 | 1-iodo-3-triphen-ylmethoxy-1-trans-octene (U.S. Pat. No. 3,873,607). | 1,9-dioxo-11α,15α-dihydroxy-1-hydroxy-methyl-2-nor-13-trans-prostadiene,1-ethylene ketal |
| 960 | 773 | 312 | 185 | 1,9-dioxo-11α,15α-dihydroxy-15-methyl-1-hydroxymethyl-2-nor-13-trans-prostene,1-ethylene ketal |
| 961 | 773 | 312 | 1-iodo-3-triphen-ylmethoxy-5,5-di-methyl-octene (U.S. Pat. No. 3,873,607). | 1,9-dioxo-11α,15α-dihydroxy-16,16-dimeth-yl-1-hydroxymethyl-2-nor-13-trans-prost-ene,1-ethylene ketal |
| 962 | 773 | 312 | 13 | 1,9-dioxo-11α,15α-dihydroxy-16,16-tri-methylene-1-hydroxymethyl-2-nor-13-trans-prostene, 1-ethylene ketal |
| 963 | 773 | 312 | 76 | erythro-1,9-dioxo-11α,15α,16-trihydroxy-1-hydroxymethyl-2-nor-13-trans-prostene, 1-ethylene ketal |
| 964 | 773 | 312 | 69 | threo-1,9-dioxo-11α,15α,16-trihydroxy-1-hydroxymethyl-2-nor-13-trans-prostene,-1-ethylene ketal |
| 965 | 773 | 312 | 74 | erythro-1,9-dioxo-11α,15α-dihydroxy-16-methoxy-1-hydroxymethyl-2-nor-13-trans-prostene, 1-ethylene ketal |
| 966 | 773 | 312 | 107 | 1,9-dioxo-11α,16-dihydroxy-1-hydroxymeth- |

TABLE 42-continued

| Example | Method of Example | Cyclopent-2-en-1-one | Vinyl Iodide or Vinyl Tin of Example | 1,9-dioxo-1-hydroxymethylprostene |
|---|---|---|---|---|
| | | | | yl-2-nor-13-trans-prostene, 1-ethylene ketal |
| 967 | 773 | 312 | 130 | 1,9-dioxo-11α,16-dihydroxy-16-methyl-1-hydroxymethyl-2-nor-13-trans-prostene,-1-ethylene ketal |
| 968 | 773 | 312 | 134 | 1,9-dioxo-11α,16-dihydroxy-16-methyl-1-hydroxymethyl-2-nor-13-trans-17-trans-prostadiene, 1-ethylene ketal |
| 969 | 774 | 312 | 186 | 1,9-dioxo-11α,15α-dihydroxy-2,17,18,19,-20-pentanor-16-phenoxy-1-hydroxymethyl-13-trans-prostene, 1-ethylene ketal |
| 970 | 774 | 312 | 180 | 1,9-dioxo-11α,15α-dihydroxy-2,17,18,19,-20-pentanor-16-m-trifluoromethylphenoxy-1-hydroxymethyl-13-trans-prostene, 1-ethylene ketal |
| 971 | 773 | 312 | 194 | 1,9-dioxo-11α,16-dihydroxy-16-vinyl-1-hydroxymethyl-2-nor-13-trans-prostene,1-ethylene ketal |
| 972 | 774 | 312 | 198 | 1,9-dioxo-11α,16-dihydroxy-16-cyclopropyl-1-hydroxymethyl-2-nor-13-trans-prostene, 1-ethylene ketal |
| 973 | 774 | 312 | 186b | 1,9-dioxo-11α,15α-dihydroxy-2,18,19,20-tetranor-17-phenyl-1-hydroxymethyl-13-trans-prostene, 1-ethylene ketal |
| 974 | 773 | 312 | 186e | 1,9-dioxo-11α,15α-dihydroxy-2,18,19,20-tetranor-17-(m-trifluorophenyl)-1-hydrooxymethyl-13-trans-prostene, 1-ethylene ketal |
| 975 | 773 | 312 | 186d | 1,9-dioxo-11α,15α-dihydroxy-2,18,19,20-tetranor-17-(p-methoxyphenyl)-1-hydroxymethyl-13-trans-prostene,1-ethylene ketal |

EXAMPLES 976–998

By the methods described hereinabove in Examples 773 and 774, the 1,9-dioxo-1-hydroxymethyl prostene derivative shown in Table 43 are prepared by the indicated method from the indicated vinyl iodide or vinyl tin compound and the indicated cyclopent-2-en-1-one.

In those cases where two diastereoisomers are formed in the conjugate-addition, only one of the diastereoisomers is listed in Table 43. It should be understood that the other diastereoisomers is also formed which in its nat and ent forms has an opposite (mirror image) configuration at the assymmetricarbon atoms on the β-chain (the chain containing $C_{13}$ .... $C_{14}$ etc.) to that of the respective nat and ent forms of the listed diastereoisomer; both of these diastereoisomers are claimed in this invention as well as their componenet enantiomers.

TABLE 43

| Example | Method of Example | Cyclopent-2-en-1-one of Example | Vinyl Iodide or Vinyl Tin of Example | 1,9-dioxo-hydroxymethylprostene and its diastereomer |
|---|---|---|---|---|
| 976 | 773 | 309 | 246 | nat-(and ent)-1,9-dioxo-11α,15-dihydroxy-15,16-tetramethylene-17,18,19,20-tetranor-1-hydroxymethyl-13-trans-prostene,1-ethylene ketal |
| 977 | 774 | 309 | 245 | nat-(and ent)-1,9-dioxo-11α,16-dihydroxy-16,17-tetramethylene-18,19,20-trinor-1-hydroxymethyl-13-trans-prostene,1-ethylene ketal |
| 978 | 773 | 309 | 243 | nat-15S,16R-(and ent-15R,16S)-1,9-dioxo-11α,15-dihydroxy-15,16-trimethylene-1-hydroxymethyl-13-trans-prostene,1-ethylene ketal |
| 979 | 773 | 309 | 243 | nat-15S,16R-(and ent-15R,16S)-1,9-dioxo-11α,15-dihydroxy-15,16-trimethylene-1-hydroxymethyl-13-trans-prostene,1-ethylene ketal |
| 980 | 773 | 309 | 251 | nat-15S,16S-(and ent-15R,16R)-1,9-dioxo-11α,15-dihydroxy-15,16-trimethylene-1-hydroxymethyl-13-trans-prostene,1-ethylene ketal |
| 981 | 773 | 309 | 247 | nat-(and ent)-1,9-dioxo-11α,15-dihydroxy-15,16-trimethylene-17,18,19,20-tetranor-1-hydroxymethyl-13-trans-prostene,1-ethylene ketal |
| 982 | 774 | 309 | 248 | nat-(and ent)-1,9-dioxo-11α,15-dihydroxy-15,16-pentamethylene-17,18,19,20-tetranor-1-hydroxymethyl-13-trans-prostene,1-ethylene ketal |
| 983 | 773 | 309 | 249 | nat-15S,17R-(and ent-15R,17S)-1,9-dioxo- |

TABLE 43-continued

| Example | Method of Example | Cyclopent-2-en-1-one of Example | Vinyl Iodide or Vinyl Tin of Example | 1,9-dioxo-hydroxymethylprostene and its diastereomer |
|---|---|---|---|---|
| | | | | 11α,15-dihydroxy-15,17-dimethylene-1-hydroxymethyl-13-trans-prostene,1-ethylene ketal |
| 984 | 773 | 309 | 250 | nat-15S,17S-(and ent-15R,17R)-1,9-dioxo-11α,15-dihydroxy-15,17-dimethylene-1-hydroxymethyl-13-trans-prostene,1-ethylene ketal |
| 985 | 773 | 309 | 252 | nat-15S,16R-(and ent-15R,16S)-1,9-dioxo-11α,15-dihydroxy-15,16-trimethylene-1-hydroxymethyl-13-trans-prostene,1-ethylene ketal |
| 986 | 773 | 309 | 253 | nat-15S,16S-(and ent-15R,16R)-1,9-dioxo-11α,15-dihydroxy-15,16-tetramethylene-1-hydroxymethyl-13-trans-prostene,1-ethylene ketal |
| 987 | 774 | 309 | 254 | nat-15R,16S-(and ent-15S,16R)-1,9-dioxo-11α,15-dihydroxy-15,16-trimethylene-16-(3-trifluoromethylphenoxy)-17,18,19,20-tetranor-1-hydroxymethyl-13-trans-prostene,1-ethylene ketal |
| 988 | 774 | 309 | 255 | nat-15R,16R-(and ent-15S,16S)-1,9-dioxo-11α,15-dihydroxy-15,16-trimethylene-16-(3-trifluoromethylphenoxy)-17,18,19,20-tetranor-1-hydroxymethyl-13-trans-prostene,1-ethylene ketal |
| 989 | 773 | 309 | 256 | nat-15R,16S-(and ent-15S,16R)-1,9-dioxo-11α,15-dihydroxy-15,16-trimethylene-16-(4-fluorophenoxy)-17,18,19,20-tetranor-1-hydroxymethyl-13-trans-prostene,1-ethylene ketal |
| 990 | 773 | 309 | 257 | nat-15R,16R-(and ent-15S,16S)-1,9-dioxo-11α,15-dihydroxy-15,16-trimethylene-16-(4-fluorophenoxy)-17,18,19,20-tetranor-1-hydroxymethyl-13-trans-prostene,1-ethylene ketal |
| 991 | 774 | 309 | 258 | nat-15R,16S-(and ent-15S,16R)-1,9-dioxo-11α,15-dihydroxy-15,16-trimethylene-16-(3-chlorophenoxy)-17,18,19,20-tetranor-1-hydroxymethyl-13-trans-prostene,1-ethylene ketal |
| 992 | 774 | 309 | 259 | nat-15R,16R-(and ent-15S,16S)-1,9-dioxo-11α,15-dihydroxy-15,16-trimethylene-16-(3-chlorophenoxy)-17,18,19,20-tetranor-1-hydroxymethyl-13-trans-prostene,1-ethylene ketal |
| 993 | 773 | 309 | 260 | nat-15S,17R-(and ent-15R,17S)-1,9-dioxo-11α,15-dihydroxy-15,17-trimethylene-19,-2-dinor-1-hydroxymethyl-13-trans-prostene,1-ethylene ketal |
| 994 | 773 | 309 | 261 | nat-15S,17S-(and ent-15R,17R)-1,9-dioxo-11α,15-dihydroxy-15,17-trimethylene-19,-20-dinor-1-hydroxymethyl-13-trans-prostene,1-ethylene ketal |
| 995 | 774 | 309 | 262 | nat-16R,17S-(and ent-16S,17R)-1,9-dioxo-11α,16-dihydroxy-16,17-trimethylene-20-methyl-1-hydroxymethyl-13-trans-prostene,1-ethylene ketal |
| 996 | 774 | 309 | 263 | nat-16R,17R-(and ent-16S,17S)-1,9-dioxo-11α,16-dihydroxy-16,17-trimethylene-20-methyl-1-hydroxymethyl-13-trans-prostene,1-ethylene ketal |
| 997 | 774 | 309 | 264 | nat-16R,17S-(and ent-16S,17R)-1,9-dioxo-11α,16-dihydroxy-16,17-trimethylene-16-(3-trifluoromethylphenoxy)-18,19,20-trinor-1-hydroxymethyl-13-trans-prostene,1-ethylene ketal |
| 998 | 774 | 309 | 265 | nat-16R,17R-(and ent-16S,17S)-1,9-dioxo-11α,16-dihydroxy-16,17-trimethylene-16-(3-trifluoromethylphenoxy)-18,19,20-trinor-1-hydroxymethyl-13-trans-prostene,1-ethylene ketal |

EXAMPLES 994-1082

By the methods described hereinabove in Examples 773 and 774, the 1,9-dioxo-1-hydroxymethyl prostene derivative shown in Table 44 are prepared by the indicated method from the indicated vinyl iodide or vinyl tin compound and the indicated cyclopent-2-en-1-one.

In those cases where isomers are obtained at the $C_{15}$ or $C_{16}$ positions, only the $C_{15}$ or $C_{16}$-normal isomers are listed in Table 44; it should be understood that the corresponding $C_{15}$ or $C_{16}$-epi isomer is also formed and is part of this invention.

In those cases where the initial conjugate-addition product contains a triphenylmethoxy blocking group, deblocking is conducted in acetic acid-tetrahydrofuran-water 4:2:1 at 50° C. for 5 hours.

TABLE 44

| Example | Method of Example | Cyclopent-2-en-1-one | Vinyl Iodide or Vinyl Tin of Example | 1,9-dioxo-1-hydroxymethylprostene |
|---|---|---|---|---|
| 999 | 773 | 314 | 49 | 1,9-dioxo-15-hydroxy-hydroxymethyl-16,16-trimethylene-20-nor-5-cis-13-trans-prostadiene,1-ethylene ketal |
| 1000 | 773 | 314 | 50 | 1,9-dioxo-15-hydroxy-1-hydroxymethyl-16,16-trimethylene-20-methyl-5-cis-13-trans-prostadiene,1-ethylene ketal |
| 1001 | 773 | 314 | 51 | 1,9-dioxo-15-hydroxy-1-hydroxymethyl-16,16-trimethylene-20-ethyl-5-cis-13-trans-prostadiene,1-ethylene ketal |
| 1002 | 774 | 314 | 193 | 1,9-dioxo-16-hydroxy-16-cyclopropyl-20-ethyl-1-hydroxymethyl-5-cis-13-trans-prostadiene,1-ethylene ketal |
| 1003 | 774 | 314 | 195 | 1,9-dioxo-16-hydroxy-16-vinyl-20-ethyl-1-hydroxymethyl-5-cis-13-trans-prostadiene,1-ethylene ketal |
| 1004 | 774 | 314 | 192 | 1,9-dioxo-16-hydroxy-16-cyclopropyl-1-hydroxymethyl-5-cis-13-trans-prostadiene,1-ethylene ketal |
| 1005 | 773 | 314 | 13 | 1,9-dioxo-15-hydroxy-1-hydroxymethyl-16,16-trimethylene-13-trans-5-cis-prostadiene,1-ethylene ketal |
| 1006 | 774 | 314 | 210a | 1,9-dioxo-16-hydroxy-1-hydroxymethyl-16-vinyl-5-cis-13-trans-prostadiene,1-ethylene ketal |
| 1007 | 773 | 314 | 74 | dl-erythro-1,9-dioxo-15-hydroxy-16-methoxy-1-hydroxymethyl-5-cis-13-trans-prostadiene,1-ethylene ketal |
| 1008 | 773 | 314 | 77 | dl-erythro-1,9-dioxo-15-hydroxy-16-ethoxy-1-hydroxymethyl-5-cis-13-trans-prostadiene,1-ethylene ketal |
| 1009 | 773 | 314 | 83 | dl-erythro-1,9-dioxo-15,16-dihydroxy-1-hydroxymethyl-20-nor-5-cis-13-trans-prostadiene,1-ethylene ketal |
| 1010 | 773 | 314 | 84 | dl-erythro-1,9-dioxo-15,16-dihydroxy-1-hydroxymethyl-20-methyl-5-cis-13-trans-prostadiene,1-ethylene ketal |
| 1011 | 773 | 314 | 85 | dl-erythro-1,9-dioxo-15,16-dihydroxy-1-hydroxymethyl-20-ethyl-5-cis-13-trans-prostadiene,1-ethylene ketal |
| 1012 | 773 | 314 | 86 | dl-erythro-1,9-dioxo-15,16-dihydroxy-1-hydroxymethyl-19-methyl-5-cis-13-trans-prostadiene,1-ethylene ketal |
| 1013 | 773 | 314 | 87 | dl-erythro-1,9-dioxo-15,16-dihydroxy-1-hydroxymethyl-5-cis-13-trans-17-trans-prostratriene,1-ethylene ketal |
| 1014 | 773 | 314 | 69 | dl-threo-1,9-dioxo-15,16-dihydroxy-1-hydroxymethyl-5-cis-13-trans-prostadiene,1-ethylene ketal |
| 1015 | 773 | 314 | 88 | dl-threo-1,9-dioxo-15,16-dihydroxy-20-nor-1-hydroxymethyl-5-cis-13-trans-prostadiene,1-ethylene ketal |
| 1016 | 773 | 314 | 76 | dl-erythro-1,9-dioxo-11α,15,16-trihydroxy-1-hydroxymethyl-5-cis-13-trans-prostadiene,1-ethylene ketal |
| 1017 | 773 | 314 | 89 | dl-threo-1,9-dioxo-15,16-dihydroxy-20-methyl-1-hydroxymethyl-5-cis-13-trans-prostadiene,1-ethylene ketal |
| 1018 | 773 | 314 | 90 | dl-threo-1,9-dioxo-15,16-dihydroxy-20-ethyl-1-hydroxymethyl-5-cis-13-trans-prostadiene,1-ethylene ketal |
| 1019 | 773 | 314 | 91 | dl-threo-1,9-dioxo-15,16-dihydroxy-19-methyl-1-hydroxymethyl-5-cis-13-trans-prostadiene,1-ethylene ketal |
| 1020 | 773 | 314 | 92 | dl-threo-1,9-dioxo-15,16-dihydroxy-1-hydroxymethyl-5-cis-13-trans-17-trans-prostratriene,1-ethylene ketal |
| 1021 | 773 | 314 | 107 | 1,9-dioxo-16-hydroxy-1-hydroxymethyl-5-cis-13-trans-prostadiene,1-ethylene ketal |
| 1022 | 773 | 314 | 108 | 1,9-dioxo-16-hydroxy-1-hydroxymethyl-19,20-dinor-5-cis-13-trans-prostadiene,1-ethylene ketal |
| 1023 | 773 | 314 | 109 | 1,9-dioxo-16-hydroxy-1-hydroxymethyl-18,19,20-trinor-5-cis-13-trans-prostadiene,1-ethylene ketal |

TABLE 44-continued

| Example | Method of Example | Cyclopent-2-en-1-one | Vinyl Iodide or Vinyl Tin of Example | 1,9-dioxo-1-hydroxymethylprostene |
|---|---|---|---|---|
| 1024 | 773 | 314 | 110 | 1,9-dioxo-16-hydroxy-1-hydroxymethyl-20-nor-5-cis-13-trans-prostadiene,1-ethylene ketal |
| 1025 | 773 | 314 | 144 | 1,9-dioxo-16-hydroxy-17-methyl-1-hydroxymethyl-5-cis-13-trans-prostadiene,1-ethylene ketal |
| 1026 | 773 | 314 | 112 | 1,9-dioxo-16-hydroxy-20-methyl-1-hydroxymethyl-5-cis-13-trans-prostadiene,1-ethylene ketal |
| 1027 | 773 | 314 | 113 | 1,9-dioxo-16-hydroxy-20-ethyl-1-hydroxymethyl-5-cis-13-trans-prostadiene,1-ethylene ketal |
| 1028 | 773 | 314 | 139a | 1,9-dioxo-16-hydroxy-16-methyl-20-ethyl-1-hydroxymethyl-5-cis-13-trans-prostadiene,1-ethylene ketal |
| 1029 | 773 | 314 | 115 | 1,9-dioxo-16-hydroxy-1-hydroxymethyl-13-trans-17-cis-5-cis-prostatriene,1-ethylene ketal |
| 1030 | 773 | 314 | 135 | 1,9-dioxo-16-hydroxy-16-methyl-1-hydroxymethyl-5-cis-13-trans-prostadiene,1-ethylene ketal |
| 1031 | 773 | 314 | 136 | 1,9-dioxo-16-hydroxy-17,17,20-trimethyl-1-hydroxymethyl-5-cis-13-trans-prostadiene,1-ethylene ketal |
| 1032 | 773 | 314 | 137 | 1,9-dioxo-16-hydroxy-16,20-dimethyl-1-hydroxymethyl-13-trans-5-cis-prostadiene,1-ethylene ketal |
| 1033 | 773 | 314 | 138 | 1,9-dioxo-16-hydroxy-17,17-dimethyl-1-hydroxymethyl-5-cis-13-trans-prostadiene,1-ethylene ketal |
| 1034 | 773 | 314 | 139 | 1,9-dioxo-16-hydroxy-16-methyl-1-hydroxymethyl-13-trans-17-trans-5-cis-prostatriene,1-ethylene ketal |
| 1035 | 773 | 314 | 149 | 1,9-dioxo-16-hydroxy-20-methyl-1-hydroxymethyl-13-trans-17-trans-5-cis-prostatriene,1-ethylene ketal |
| 1036 | 773 | 314 | 150 | 1,9-dioxo-16-hydroxy-16-methyl-1-hydroxymethyl-5-cis-13-trans-prostadiene,1-ethylene ketal |
| 1037 | 773 | 314 | 151 | 1,9-dioxo-16-hydroxy-17,20-dimethyl-1-hydroxymethyl-5-cis-13-trans-prostadiene,1-ethylene ketal |
| 1038 | 773 | 314 | 152 | 1,9-dioxo-16-hydroxy-1-hydroxymethyl-13-trans-17-trans-5-cis-prostatriene,1-ethylene ketal |
| 1039 | 773 | 314 | 153 | 1,9-dioxo-16-(R)-hydroxy-1-hydroxymethyl-5-cis-13-trans-prostadiene,1-ethylene ketal |
| 1040 | 773 | 314 | 154 | 1,9-dioxo-16(S)-hydroxy-1-hydroxymethyl-5-cis-13-trans-prostadiene,1-ethylene ketal |
| 1041 | 773 | 314 | 148a | 1,9-dioxo-16-hydroxy-20-ethyl-1-hydroxymethyl-5-cis-13-trans-17-prostatriene,1-ethylene ketal |
| 1042 | 773 | 314 | 1-iodo-3-triphenylmethoxy-1-trans-octene (U.S. Pat. No. 3,873,607). | 1,9-dioxo-15α-hydroxy-1-5-cis-13-trans-prostadiene,1-ethylene ketal |
| 1043 | 773 | 314 | 1-iodo-3-triphenylmethoxy-1-trans-nonene (U.S. Pat. No. 3,873,607). | 1,9-dioxo-15α-hydroxy-20-methyl-1-hydroxymethyl-5-cis-13-trans-prostadiene,1-ethylene ketal |
| 1044 | 773 | 314 | 1-iodo-3-triphenylmethoxy-1-trans-decene (U.S. Pat. No. 3,873,607). | 1,9-dioxo-15α-hydroxy-20-ethyl-1-hydroxymethyl-5-cis-13-trans-prostadiene,1-ethylene ketal |
| 1045 | 773 | 314 | 1-iodo-3-triphenylmethoxy-4,4-dimethyl-1-trans-octene (U.S. Pat. No. 3,873,607). | 1,9-dioxo-15α-hydroxy-16,16-dimethyl-1-hydroxymethyl-5-cis-13-trans-prostadiene,1-ethylene ketal |
| 1046 | 773 | 314 | 1-iodo-3-triphenylmethoxy-5,5-dimethyl-1-trans-octene (U.S. Pat. No. 3,873,607). | 1,9-dioxo-15α-hydroxy-17,17-dimethyl-1-hydroxymethyl-5-cis-13-trans-prostadiene,1-ethylene ketal |
| 1047 | 773 | 314 | 1-iodo-3-triphenylmethoxy-4-methyl-1-trans-octene | 1,9-djioxo-15α-hydroxy-16-methyl-1-hydroxymethyl-5-cis-13-trans-prostadiene,1-ethylene ketal |

TABLE 44-continued

| Example | Method of Example | Cyclopent-2-en-1-one | Vinyl Iodide or Vinyl Tin of Example | 1,9-dioxo-1-hydroxymethylprostene |
|---|---|---|---|---|
| 1048 | 773 | 314 | 1-iodo-3-triphenylmethoxy-4-ethyl-1-trans-octene (U.S. Pat. No. 3,876,690). | 1,9-dioxo-15α-hydroxy-16-ethyl-1-hydroxymethyl-5-cis-13-trans-prostadiene,1-ethylene ketal |
| 1049 | 773 | 314 | 1-iodo-3-triphenylmethoxy-4-cyclopentyl-1-trans-butene (U.S. Pat. No. 3,884,969). | 1,9-dioxo-15α-hydroxy-17,20-tetranor-16-cyclopetnyl-1-hydroxymethyl-5-cis-13-trans-prostadiene,1-ethylene ketal |
| 1050 | 773 | 314 | 1-iodo-3-triphenylmethoxy-3-cyclohexyl-1-trans-pentene (U.S. Pat. No. 3,884,969). | 1,9-dioxo-15α-hydroxy-16,20-pentanor-15-cyclohexyl-1-hydroxymethyl-5-cis-13-trans-prostadiene,1-ethylene ketal |
| 1051 | 773 | 314 | 1-iodo-3-triphenylmethoxy-5-cyclohexyl-1-trans-pentene (U.S. Pat. No. 3,884,969). | 1,9-dioxo-15α-hydroxy-18,20-trinor-17-cyclohexyl-1-hydroxymethyl-5-cis-13-trans-prostadiene,1-ethylene ketal |
| 1052 | 773 | 314 | 1-iodo-3-triphenylmethoxy-6-cyclopentyl-1-trans-hexene (U.S. Pat. No. 3,884,969). | 1,9-dioxo-15α-hydroxy-19,20-dinor-18-cyclopentyl-1-hydroxymethyl-5-cis-13-trans-prostadiene,1-ethylene ketal |
| 1053 | 773 | 314 | 1-iodo-3-methyl-3-trimethylsilyloxy-trans-1-octene (Example 125) | 1,9-dioxo-15α-hydroxy-15-methyl-1-hydroxymethyl-5-cis-13-trans-prostadiene,1-ethylene ketal |
| 1054 | 773 | 314 | 1-iodo-3-methyl-3-trimethylsilyloxy-trans-1-decene (Example 190a) | 1,9-dioxo-15α-hydroxy-15-methyl-20-ethyl-1-hydroxymethyl-5-cis-13-trans-prostadiene,1-ethylene ketal |
| 1055 | 774 | 314 | 159 | 1,9-dioxo-15α-hydroxy-17,18,19,20-tetranor-16-p-fluorophenoxy-1-hydroxymethyl-5-cis-13-trans-prostadiene,1-ethylene ketal |
| 1056 | 774 | 314 | 186 | 1,9-dioxo-15α-hydroxy-17,18,19,20-tetranor-16-phenoxy-1-hydroxymethyl-5-cis-3-trans-prostadiene,1-ethylene ketal |
| 1057 | 774 | 314 | 181 | 1,9-dioxo-15α-hydroxy-17,18,19,20-tetranor-16-p-bromophenoxy-1-hydroxymethyl-5-cis-13-trans-prostadiene,1-ethylene ketal |
| 1058 | 774 | 314 | 182 | 1,9-dioxo-15α-hydroxy-17,18,19,20-tetranor-16-p-t-butylphenoxy-1-hydroxymethyl-5-cis-13-trans-prostadiene,1-ethylene ketal |
| 1059 | 774 | 314 | 183 | 1,9-dioxo-15α-hydroxy-17,18,19,20-tetranor-16-methoxyphenoxy-1-hydroxymethyl-5-cis-13-trans-prostadiene,1-ethylene ketal |
| 1060 | 774 | 314 | 184 | 1,9-dioxo-15α-hydroxy-17,18,19,20-tetranor-16-p-chlorophenoxy-1-hydroxymethyl-5-cis-13-trans-prostadiene,1-ethylene ketal |
| 1061 | 774 | 314 | 180 | 1,9-dioxo-15α-hydroxy-17,18,19,20-tetranor-m-trifluorophenoxy-1-hydroxymethyl-cis-13-trans-prostadiene,1-ethylene ketal |
| 1062 | 774 | 314 | 185 | 1,9-dioxo-15α-hydroxy-17,18,19,20-tetranor-16-(3,4-dichlorophenoxy)-1-hydroxymethyl-5-cis-13-trans-prostadiene,1-ethylene ketal |
| 1063 | 774 | 314 | 186b | 1,9-dioxo-15α-hydroxy-18,19,20-trinor-17-phenyl-1-hydroxymethyl-5-cis-13-trans-prostadiene,1-ethylene ketal |
| 1064 | 774 | 314 | 186e | 1,9-dioxo-15α-hydroxy-18,19,20-trinor-17-(m-trifluoromethylphenyl)-1-hydroxymethyl-5-cis-13-trans-prostadiene,1-ethylene ketal |
| 1065 | 774 | 314 | 186d | 1,9-dioxo-15α-hydroxy-18,19,20-trinor-17-(p-methoxyphenyl)-1-hydroxymethyl-5-cis-13-trans-prostadiene,1-ethylene ketal |
| 1066 | 773 | 315 | 1-iodo-3-triphenylmethoxy-1-trans-octene (U.S. Pat. No. 3,873,607). | 1,9-dioxo-15α-hydroxy-1-hydroxymethyl-2-nor-5-cis-13-trans-prostadiene,1-ethylene ketal |
| 1067 | 773 | 315 | 185 | 1,9-dioxo-15α-hydroxy-15-methyl-1-hydroxymethyl-2-nor-5-cis-13-trans-prostadiene,-1-ethylene ketal |

TABLE 44-continued

| Example | Method of Example | Cyclopent-2-en-1-one | Vinyl Iodide or Vinyl Tin of Example | 1,9-dioxo-1-hydroxymethylprostene |
|---|---|---|---|---|
| 1068 | 773 | 315 | 1-iodo-3-triphenylmethoxy-5,5-dimethyl-octene (U.S. Pat. No. 3,873,607). | 1,9-dioxo-15α-hydroxy-16,16-dimethyl-1-hydroxymethyl-2-nor-5-cis-13-trans-prostadiene,1-ethylene ketal |
| 1069 | 773 | 315 | 13 | 1,9-dioxo-15α-hydroxy-16,16-trimethylene-1-hydroxymethyl-2-nor-5-cis-13-trans-prostadiene,1-ethylene ketal |
| 1070 | 773 | 315 | 76 | erythro-1,9-dioxo-15α,16-dihydroxy-1-hydroxymethyl-2-nor-5-cis-13-trans-prostadiene,1-ethylene ketal |
| 1071 | 773 | 315 | 69 | threo-1,9-dioxo-15α,16-dihydroxy-1-hydroxymethyl-2-nor-5-cis-13-trans-prostadiene,1-ethylene ketal |
| 1072 | 773 | 315 | 74 | erythro-1,9-dioxo-15α-hydroxy-16-methoxy-1-hydroxymethyl-2-nor-5-cis-13-trans-prostadiene,1-ethylene ketal |
| 1073 | 773 | 315 | 107 | 1,9-dioxo-16-hydroxy-1-hydroxymethyl-2-nor-5-cis-13-trans-prostdiene,1-ethylene ketal |
| 1074 | 773 | 315 | 130 | 1,9-dioxo-16-hydroxy-16-methyl-1-hydroxymethyl-2-nor-5-cis-13-trans-prostadiene,1-ethylene ketal |
| 1075 | 773 | 315 | 134 | 1,9-dioxo-16-hydroxy-16-methyl-1-hydroxymethyl-2-nor-5-cis-13-trans-17-trans-prostatriene,1-ethylene ketal |
| 1076 | 774 | 315 | 186 | 1,9-dioxo-15α-hydroxy-2,17,18,19,20-pentanor-16-phenoxy-5-cis-13-trans-prostadiene,1-ethylene ketal |
| 1077 | 774 | 315 | 180 | 1,9-dioxo-15α-hydroxy-2,17,18,19,20-pentanor-16-m-trifluoromethylphenoxy-1-hydroxy-5-cis-13-trans-prostadiene,1-ethylene ketal |
| 1078 | 774 | 315 | 194 | 1,9-dioxo-16-hydroxy-16-vinyl-1-hydroxymethyl-2-nor-5-cis-13-trans-prostadiene,-1-ethylene ketal |
| 1079 | 774 | 315 | 198 | 1,9-dioxo-16-hydroxy-16-cyclopropyl-1-hydroxymethyl-2-nor-5-cis-13-trans-prostadiene,1-ethylene ketal |
| 1080 | 774 | 315 | 186b | 1,9-dioxo-15α-hydroxy-2,18,19,20-tetranor-17-phenyl-1-hydroxymethyl-5-cis-13-trans-prostadiene,1-ethylene ketal |
| 1081 | 773 | 315 | 186e | 1,9-dioxo-15α-hydroxy-2,18,19,20-tetranor-17-(m-trifluorophenyl)-1-hydroxymethyl-5-cis-13-trans-prostdiene,1-ethylene ketal |
| 1082 | 773 | 315 | 186d | 1,9-dioxo-15α-hydroxy-2,18,19,20-tetranor-17-(p-methoxyphenyl)-1-hydroxymethyl-5-cis-13-trans-prostadiene,1-ethylene ketal |

EXAMPLES 1083–1105

By the methods described hereinabove in Examples 773 and 774, the 1,9-dioxo-1-hydroxymethyl prostene derivative shown in Table 45 are prepared by the indicated method from the indicated vinyl iodide or vinyl tin compound and the indicated cyclopent-2-en-1-one.

In those cases where two diastereoiosmers are formed in the conjugate-addition, only one of the diastereoisomers is listed in Table 45. It should be understood that the other diastereoiosmer is also formed which in its nat and ent forms has an opposite (mirror image) configuration at the assymmetri carbon atoms on the β-chain (the chain containing $C_{13}$....$C_{14}$ etc.) to that of the respective nat and ent forms of the listed diastereoisomer; both of these diastereoisomers are claimed in this invention as well as their component enantiomers.

Table 45

| Example | Method of Example | Cyclopent-2-en-1-one of Example | Vinyl Iodide or Vinyl Tin of Example | 1,9-dioxo-1-hydroxymethylprostene and its diastereomer |
|---|---|---|---|---|
| 1083 | 773 | 314 | 246 | nat-(and ent)-1,9-dioxo-15-hydroxy-15,16-tetramethylene-17,18,19,20-tetranor-1-hydroxymethyl-5-cis-13-trans-prostadiene,1-ethylene ketal |
| 1084 | 774 | 314 | 245 | nat-(and ent)-1,9-dioxo-16-hydroxy-16,17-tetramethylene-18,19,20-trinor-1-hydroxymethyl-5-cis-13-trans-prostadiene,1-ethylene ketal |
| 1085 | 773 | 314 | 243 | nat-15S,16R-(and ent-15R,16S)-1,9-dioxo-15-hydroxy-15,16-trimethylene-1-hydroxy- |

Table 45-continued

| Example | Method of Example | Cyclopent-2-en-1-one of Example | Vinyl Iodide or Vinyl Tin of Example | 1,9-dioxo-1-hydroxymethylprostene and its diastereomer |
|---|---|---|---|---|
| | | | | methyl-5-cis-13-trans-prostadiene,1-ethylene ketal |
| 1086 | 773 | 314 | 243 | nat-15S,16R-(and ent-15R,16S)-1,9-dioxo-15-hydroxy-15,16-trimethylene-1-hydroxymethyl-13-trans-5-cis-prostadiene,1-ethylene ketal |
| 1087 | 773 | 314 | 251 | nat-15S,16S-(and ent-15R,16R)-1,9-dioxo-15-hydroxy-15,16-trimethylene-1-hydroxymethyl-13-trans-5-cis-prostadiene,1-ethylene ketal |
| 1088 | 773 | 314 | 247 | nat-(and ent)-1,9-dioxo-15-hydroxy-15,16-trimethylene-17,18,19,20-tetranor-1-hydroxymethyl-13-trans-5-cis-prostadiene,-1-ethylene ketal |
| 1089 | 774 | 314 | 248 | nat-(and ent)-1,9-dioxo-15-hydroxy-15,16-pentamethylene-17,18,19,20-tetranor-1-hydroxymethyl-13-trans-5-cis-prostadiene,1-ethylene ketal |
| 1090 | 773 | 314 | 249 | nat-15S,17R-(and ent-15R,17S)-1,9-dioxo-15-hydroxy-15,17-dimethylene-1-hydroxymethyl-13-trans-5-cis-prostadiene,1-ethylene ketal |
| 1091 | 773 | 314 | 250 | nat-15S,17S-(and ent-15R,17R)-1,9-dioxo-15-hydroxy-15,17-dimethylene-1-hydroxymethyl-13-trans-5-cis-prostadiene,1-ethylene ketal |
| 1092 | 773 | 314 | 252 | nat-15S,16R-(and ent-15R,16S)-1,9-dioxo-15-hydroxy-15,16-tetramethylene-1-hydroxymethyl-13-trans-5-cis-prostadiene,1-ethylene ketal |
| 1093 | 773 | 314 | 253 | nat-15S,16S-(and ent-15R,16R)-1,9-dioxo-15-hydroxy-15,16-tetramethylene-1-hydroxymethyl-13-trans-5-cis-prostadiene,1-ethylene ketal |
| 1094 | 774 | 314 | 254 | nat-15R,16S-(and ent-15S,16R)-1,9-dioxo-15-hydroxy-15,16-trimethylene-16-(3-trifluoromethylphenoxy)-17,18,19,20-tetranor-1-hydroxymethyl-13-trans-5-cis-prostadiene,1-ethylene ketal |
| 1095 | 774 | 314 | 255 | nat-15R,16R-(and ent-15S,16S)-1,9-dioxo-15-hydroxy-15,16-trimethylene-16-(3-trifluoromethylphenoxy)-17,18,19,20-tetranor-1-hydroxymethyl-13-trans-5-cis-prostadiene,1-ethylene ketal |
| 1096 | 774 | 314 | 256 | nat-15R,16S-(and ent-15S,16R)-1,9-dioxo-15-hydroxy-15,16-trimethylene-16-(4-fluorophenoxy)-17,18,19,20-tetranor-1-hydroxymethyl-13-trans-5-cis-prostadiene,1-ethylene ketal |
| 1097 | 774 | 314 | 257 | nat-15R,16R-(and ent-15S,16S)-1,9-dioxo-15-hydroxy-15,16-trimethylene-16-(4-fluorophenoxy)-17,18,19,20-tetranor-1-hydroxymethyl-13-trans-5-cis-prostadiene,1-ethylene ketal |
| 1098 | 774 | 314 | 258 | nat-15R,16S-(and ent-15S,16R)-1,9-dioxo-15-hydroxy-15,16-trimethylene-16-(3-chlorophenoxy)-17,18,19,20-tetranor-1-hydroxymethyl-13-trans-5-cis-prostadiene,1-ethylene ketal |
| 1099 | 774 | 314 | 259 | nat-15R,16R-(and ent-15S,16S)-1,9-dioxo-15-hydroxy-15,16-trimethylene-16-(3-chlorophenoxy)-17,18,19,20-tetranor-1-hydroxymethyl-13-trans-5-cis-prostadiene,1-ethylene ketal |
| 1100 | 773 | 314 | 260 | nat-15S,17R-(and ent-15R,17S)-1,9-dioxo-15-hydroxy-15,17-trimethylene-19,20-dinor-1-hydroxymethyl-13-trans-5-cis-prostadiene,1-ethylene ketal |
| 1101 | 773 | 314 | 261 | nat-15S,17S-(and ent-15R,17R)-1,9-dioxo-15-hydroxy-15,17-trimethylene-19,20-dinor-1-hydroxymethyl-13-trans-5-cis-prostadiene,1-ethylene ketal |
| 1102 | 774 | 314 | 262 | nat-16R,17S-(and ent-16S,17R)-1,9-dioxo-16-hydroxy-16,17-trimethylene-20-methyl-1-hydroxymethyl-13-trans-5-cis-prostadiene,1-ethylene ketal |
| 1103 | 774 | 314 | 263 | nat-16R,17R-(and ent-16S,17S)-1,9-dioxo-16-hydroxy-16,17-trimethylene-20-methyl-1-hydroxymethyl-13-trans-5-cis-prostadi- |

Table 45-continued

| Example | Method of Example | Cyclopent-2-en-1-one of Example | Vinyl Iodide or Vinyl Tin of Example | 1,9-dioxo-1-hydroxymethylprostene and its diastereomer |
|---|---|---|---|---|
| 1104 | 774 | 314 | 264 | nat-16R,17S-(and ent-16S,17R)-1,9-dioxo-16-hydroxy-16,17-trimethylene-16-(3-trifluoromethylphenoxy)-18,19,20-trinor-1-hydroxymethyl-13-trans-5-cis-prostadiene,1-ethylene ketal |
| 1105 | 774 | 314 | 265 | nat-16R,17R-(and ent-16S,17S)-1,9-dioxo-16-hydroxy-16,17-trimethylene-16-(3-trifluoromethylphenoxy)-18,19,20-trinor-1-hydroxymethyl-13-trans-5-cis-prostadiene,1-ethylene ketal |

EXAMPLES 1106–1189

By the methods described hereinabove in Examples 773 and 774, the 1,9-dioxo-1-hydroxymethylprostene derivatives shown in Table 46 are prepared by the indicated method from the indicated vinyl iodide or vinyl tin compound and the indicated cyclopent-2-en-1-one.

In those cases where isomers are obtained at the $C_{15}$ or $C_{16}$ positions, only the $C_{15}$ or $C_{16}$-normal isomers are listed in Table 46 ; it should be understood that the corresponding $C_{15}$ or $C_{16}$-epi isomers are also formed and are part of this invention.

In those cases where the initial conjugate-addition product contains a triphenylmethoxy blocking group, deblocking is conducted in acetic acid-tetrahydrofuran-water 4:2:1 at 50° C. for 5 hours.

TABLE 46

| Example | Method of Example | Cyclopent-2-en-1-one | Vinyl Iodide or Vinyl Tin of Example | 1,9-dioxo-1-hydroxymethylprostene |
|---|---|---|---|---|
| 1106 | 773 | 283 | 49 | 1,9-dioxo-15-hydroxy-1-hydroxymethyl-16,16-trimethylene-20-nor-13-trans-prostadiene,1-ethylene ketal |
| 1107 | 773 | 283 | 50 | (1,9-dioxo-15-hydroxy-1-hydroxymethyl-16,16-trimethylene-20-methyl-13-trans-prostadiene,1-ethylene ketal |
| 1108 | 773 | 283 | 51 | 1,9-dioxo-15-hydroxy-1-hydroxymethyl-16-16-trimethylene-20-ethyl-13-trans-prostadiene,1-ethylene ketal |
| 1109 | 774 | 283 | 193 | 1,9-dioxo-16-hydroxy-16-cyclopropyl-20-ethyl-1-hydroxymethyl-13-trans-prostene,-1-ethylene ketal |
| 1110 | 774 | 283 | 195 | 1,9-dioxo-16-hydroxy-16-vinyl-20-ethyl-1-hydroxymethyl-13-trans-prostene,1-ethylene ketal |
| 1111 | 774 | 283 | 192 | 1,9-dioxo-16-hydroxy-16-cyclopropyl-1-hydroxymethyl-13-trans-prostene,1-ethylene ketal |
| 1112 | 773 | 283 | 13 | (1,9-dioxo-15-hydroxy-1-hydroxymethyl-16,16-trimethylene-13-trans-prostene,1-ethylene ketal |
| 1113 | 774 | 283 | 210a | 1,9-dioxo-16-hydroxy-1-hydroxymethyl-16-vinyl-13-trans-prostene,1-ethylene ketal |
| 1114 | 773 | 283 | 74 | dl-erythro-1,9-dioxo-15-hydroxy-16-methoxy-1-hydroxymethyl-13-trans-prostene,1-ethylene ketal |
| 1115 | 773 | 283 | 77 | dl-erythro-1,9-dioxo-15-hydroxy-16-ethoxy-1-hydroxymethyl-13-trans-prostene,1-ethylene ketal |
| 1116 | 773 | 283 | 83 | dl-erythro-1,9-dioxo-15,16-dihydroxy-1-hydroxymethyl-20-nor-13-trans-prostene,-1-ethylene ketal |
| 1117 | 773 | 283 | 84 | dl-erythro-1,9-dioxo-15,16-dihydroxy-1-hydroxymethyl-20-methyl-13-trans-prostene,1-ethylene ketal |
| 1118 | 773 | 283 | 85 | dl-erythro-1,9-dioxo-15,16-dihydroxy-1-hydroxymethyl-20-ethyl-13-trans-prostene,1-ethylene ketal |
| 1119 | 773 | 283 | 86 | dl-erythro-1,9-dioxo-15,16-dihydroxy-19-methyl-1-hydroxymethyl-13-trans-prostene,1-ethylene ketal |
| 1120 | 773 | 283 | 87 | dl-erythro-1,9-dioxo-15,16-dihydroxy-1-hydroxymethyl-13-trans-17-trans-prostadiene,1-ethylene ketal |
| 1121 | 773 | 283 | 69 | dl-threo-1,9-dioxo-15,16-dihydroxy-1-hydroxymethyl-13-trans-prostene,1-ethylene ketal |
| 1122 | 773 | 283 | 88 | dl-threo-1,9-dioxo-15,16-dihydroxy-20-nor-1-hydroxymethyl-13-trans-prostene,- |

TABLE 46-continued

| Example | Method of Example | Cyclopent-2-en-1-one | Vinyl Iodide or Vinyl Tin of Example | 1,9-dioxo-1-hydroxymethylprostene |
|---|---|---|---|---|
| 1123 | 773 | 283 | 76 | dl-erythro-1,9-dioxo-15,16-dihydroxy-1-hydroxymethyl-13-trans-prostene,1-ethylene ketal |
| 1124 | 773 | 283 | 89 | dl-threo-1,9-dioxo-15,16-dihydroxy-20-methyl-1-hydroxymethyl-13-trans-prostene,1-ethylene ketal |
| 1125 | 773 | 283 | 90 | dl-threo-1,9-dioxo-15,16-dihydroxy-20-ethyl-1-hydroxymethyl-13-trans-prostene,1-ethylene ketal |
| 1126 | 773 | 283 | 91 | dl-threo-1,9-dioxo-15,16-dihydroxy-19-methyl-1-hydroxymethyl-13-trans-prostene,1-ethylene ketal |
| 1127 | 773 | 283 | 92 | dl-threo-1,9-dioxo-15,16-dihydroxy-1-hydroxymethyl-13-trans-17-prostadiene,1-ethylene ketal |
| 1128 | 773 | 283 | 107 | 1,9-dioxo-16-hydroxy-1-hydroxymethyl-13-trans-prostene,1-ethylene ketal |
| 1129 | 773 | 283 | 108 | 1,9-dioxo-hydroxy-1-hydroxymethyl-19,-20-dinor-13-trans-prostene,1-ethylene ketal |
| 1130 | 773 | 283 | 109 | 1,9-dioxo-16-hydroxy-1-hydroxymethyl-18,-19,20-trinor-13-trans-prostene,1-ethylene ketal |
| 1131 | 773 | 283 | 110 | 1,9-dioxo-16-hydroxy-1-hydroxymethyl-20-nor-13-trans-prostene,1-ethylene ketal |
| 1132 | 773 | 283 | 144 | 1,9-dioxo-16-hydroxy-17-methyl-1-hydroxymethyl-13-trans-prostene,1-ethylene ketal |
| 1133 | 773 | 283 | 112 | 1,9-dioxo-16-hydroxy-20-methyl-1-hydroxymethyl-13-trans-prostene,1-ethylene ketal |
| 1134 | 773 | 283 | 113 | 1,9-dioxo-16-hydroxy-20-ethyl-1-hydroxymethyl-13-trans-prostene,1-ethylene ketal |
| 1135 | 773 | 283 | 139a | 1,9-dioxo-16-hydroxy-16-methyl-20-ethyl-1-hydroxymethyl-13-trans-prostene,1-ethylene ketal |
| 1136 | 773 | 283 | 115 | 1,9-dioxo-16-hydroxy-1-hydroxymethyl-13-trans-17-cis-prostadiene,1-ethylene ketal |
| 1137 | 773 | 283 | 135 | 1,9-dioxo-16-hydroxy-16-methyl-1-hydroxymethyl-13-trans-prostene,1-ethylene ketal |
| 1138 | 773 | 283 | 136 | 1,9-dioxo-16-hydroxy-17,17,20-trimethyl-1-hydroxymethyl-13-trans-prostene,1-ethylene ketal |
| 1139 | 773 | 283 | 137 | 1,9-dioxo-16-hydroxy-16,20-dimethyl-1-hydroxymethyl-13-trans-prostene,1-ethylene ketal |
| 1140 | 773 | 283 | 138 | 1,9-dioxo-16-hydroxy-17,17-dimethyl-1-hydroxymethyl-13-trans-prostene,1-ethylene ketal |
| 1141 | 773 | 283 | 139 | 1,9-dioxo-16-hydroxy-16-methyl-1-hydroxymethyl-13-trans-17-trans-prostadiene,1-ethylene ketal |
| 1142 | 773 | 283 | 149 | 1,9-dioxo-16-hydroxy-20-methyl-1-hydroxymethyl-13-trans-17-trans-prostadiene,1-ethylene ketal |
| 1143 | 773 | 283 | 150 | 1,9-dioxo-16-hydroxy-16-methyl-1-hydroxymethyl-13-trans-prostene,1-ethylene ketal |
| 1144 | 773 | 283 | 151 | 1,9-dioxo-16-hydroxy-17,20-dimethyl-1-hydroxymethyl-13-trans-prostene,1-ethylene ketal |
| 1145 | 773 | 283 | 152 | 1,9-dioxo-16-hydroxy-1-hydroxymethyl-13-trans-17-trans-prostadiene,1-ethylene ketal |
| 1146 | 773 | 283 | 153 | 1,9-dioxo-16(R)-hydroxy-1-hydroxymethyl-13-trans-prostene,1-ethylene ketal |
| 1147 | 773 | 283 | 154 | 1,9-dioxo-16(S)-hydroxy-1-hydroxymethyl-13-trans-prostene,1-ethylene ketal |
| 1148 | 773 | 283 | 148a | 1,9-dioxo-16-hydroxy-20-ethyl-1-hydroxymethyl-13-trans-17-trans-prostadiene,1-ethylene ketal |
| 1149 | 773 | 283 | 1-iodo-3-triphenylmethoxy-1-trans-octene (U.S. Pat. No. 3,873,607). | 1,9-dioxo-15α-hydroxy-1-hydroxymethyl-13-trans-prostadiene,1-ethylene ketal |
| 1150 | 773 | 283 | 1-iodo-3-triphenylmethoxy-1-trans-nonene (U.S. Pat. No. 3,873,607). | 1,9-dioxo-15α-hydroxy-20-methyl-1-hydroxymethyl-13-trans-prostene,1-ethylene ketal |
| 1151 | 773 | 283 | 1-iodo-3-triphenylmethoxy-1-trans- | 1,9-dioxo-15α-hydroxy-20-ethyl-1-hydroxymethyl-13-trans-prostene,1-ethylene |

TABLE 46-continued

| Example | Method of Example | Cyclopent-2-en-1-one | Vinyl Iodide or Vinyl Tin of Example | 1,9-dioxo-1-hydroxymethylprostene |
|---|---|---|---|---|
| | | | decene (U.S. Pat. No. 3,873,607). | ketal |
| 1152 | 773 | 283 | 1-iodo-3-triphenylmethoxy-4,4-dimethyl-1-trans-octene (U.S. Pat. No. 3,873,607). | 1,9-dioxo-15α-hydroxy-16,16-dimethyl-1-hydroxymethyl-13-trans-prostene,1-ethylene ketal |
| 1153 | 773 | 283 | 1-iodo-3-triphenylmethoxy-5,5-dimethyl-1-trans-octene (U.S. Pat. No. 3,873,607). | 1,9-dioxo-15α-hydroxy-17,17-dimethyl-1-hydroxymethyl-13-trans-prostene,1-ethylene ketal |
| 1154 | 773 | 283 | 1-iodo-3-triphenylmethoxy-4-methyl-1-trans-octene (U.S. Pat. No. 3,876,690). | 1,9-dioxo-15α-hydroxy-16-methyl-1-hydroxymethyl-13-trans-prostene,1-ethylene ketal |
| 1155 | 773 | 283 | 1-iodo-3-triphenylmethoxy-4-ethyl-1-trans-octene (U.S. Pat. No. 3,876,690). | 1,9-dioxo-15α-hydroxy-16-ethyl-1-hydroxymethyl-13-trans-prostene,1-ethylene ketal |
| 1156 | 773 | 283 | 1-iodo-3-triphenylmethoxy-4-cyclopentyl-1-trans-butene (U.S. Pat. No. 3,884,969). | 1,9-dioxo-15α-hydroxy-17,20-tetranor-16-cyclopentyl-1-hydroxymethyl-13-trans-prostene,1-ethylene ketal |
| 1157 | 773 | 283 | 1-iodo-3-triphenylmethoxy-3-cyclohexyl-1-trans-pentene (U.S. Pat. No. 3,884,969). | 1,9-dioxo-15α-hydroxy-16,20-pentanor-15-cyclohexyl-1-hydroxymethyl-13-trans-prostene,1-ethylene ketal |
| 1158 | 773 | 283 | 1-iodo-3-triphenylmethoxy-5-cyclohexyl-1-trans-pentene (U.S. Pat. No. 3,884,969). | 1,9-dioxo-15α-hydroxy-18,20-trinor-17-cyclohexyl-1-hydroxymethyl-13-trans-prostene,1-ethylene ketal |
| 1159 | 773 | 283 | 1-iodo-3-triphenylmethoxy-6-cyclopentyl-1-trans-hexene (U.S. Pat. No. 3,884,969). | 1,9-dioxo-15α-hydroxy-19,20-dinor-18-cyclopentyl-1-hydroxymethyl-13-trans-prostene,1-ethylene ketal |
| 1160 | 773 | 283 | 1-iodo-3-methyl-3-trimethylsilyloxy-trans-1-octene (Example 125). | 1,9-dioxo-15α-hydroxy-15-methyl-1-hydroxymethyl-13-trans-prostene,1-ethylene ketal |
| 1161 | 773 | 283 | 1-iodo-3-methyl-3-trimethylsilyl oxy-trans-1-decene (Example 190a). | 1,9-dioxo-15α-hydroxy-15-methyl-20-ethyl-1-hydroxymethyl-13-trans-prostene,1-ethylene ketal |
| 1162 | 774 | 283 | 159 | 1,9-dioxo-15α-hydroxy-17,18,19,20-tetranor-16-p-fluorophenoxy-1-hydroxymethyl-13-trans-prostene,1-ethylene ketal |
| 1163 | 774 | 283 | 186 | 1,9-dioxo-15α-hydroxy-17,18,19,20-tetranor-16-phenoxy-1-hydroxymethyl-13-trans-prostene,1-ethylene ketal |
| 1164 | 774 | 283 | 181 | 1,9-dioxo-15α-hydroxy-17,18,19,20-tetranor-16-p-bromophenoxy-1-hydroxymethyl-13-trans-prostene,1-ethylene ketal |
| 1165 | 774 | 283 | 182 | 1,9-dioxo-15α-hydroxy-17,18,19,20-tetranor-16-p-t-butylphenoxy-1-hydroxymethyl-13-trans-prostene,1-ethylene ketal |
| 1166 | 774 | 283 | 183 | 1,9-dioxo-15α-hydroxy-17,18,19,20-tetranor-16-p-methoxyphenoxy-1-hydroxymethyl-13-trans-prostene,1-ethylene ketal |
| 1167 | 774 | 283 | 184 | 1,9-dioxo-15α-hydroxy-17,18,19,20-tetranor-16-p-chlorophenoxy-1-hydroxymethyl-13-trans-prostene,1-ethylene ketal |
| 1168 | 774 | 283 | 180 | 1,9-dioxo-15α-hydroxy-17,18,19,20-tetranor-m-trifluorophenoxy-1-hydroxymethyl-13-trans-prostene,1-ethylene ketal |
| 1169 | 774 | 283 | 185 | 1,9-dioxo-15α-hydroxy-17,18,19,20-tetranor-16-(3,4-dichlorophenoxy)-1-hydroxymethyl-13-trans-prostene,1-ethylene ketal |
| 1170 | 774 | 283 | 186b | 1,9-dioxo-15α-hydroxy-18,19,20-trinor-17-phenyl-1-hydroxymethyl-13-trans-prostene,1-ethylene ketal |
| 1171 | 774 | 283 | 186e | 1,9-dioxo-15α-hydroxy-18,19,20-trinor-17-(m-trifluoromethylphenyl)-1-hydroxymethyl- |

TABLE 46-continued

| Example | Method of Example | Cyclopent-2-en-1-one | Vinyl Iodide or Vinyl Tin of Example | 1,9-dioxo-1-hydroxymethylprostene |
|---|---|---|---|---|
| 1172 | 774 | 283 | 186d | yl-13-trans-prostene,1-ethylene ketal 1,9-dioxo-15α-hydroxy-18,19,20-trinor-17-(p-methoxyphenyl)-1-hydroxymethyl-13-trans-prostene,1-ethylene ketal |
| 1173 | 773 | 310 | 1-iodo-3-triphenylmethoxy-1-trans-octene (U.S. Pat.). No. 3,873,607). | 1,9-dioxo-15α-hydroxy-1-hydroxymethyl-2-nor-13-trans-prostene,1-ethylene ketal |
| 1174 | 773 | 310 | 185 | 1,9-dioxo-15α-hydroxy-15-methyl-1-hydroxymethyl-2-nor-13-trans-prostene,1-ethylene ketal |
| 1175 | 773 | 310 | 1-iodo-3-triphenylmethoxy-5,5-dimethyl-octene (U.S. Pat. No. 3,873,607). | 1,9-dioxo-15α-hydroxy-16,16-dimethyl-1-hydroxymethyl-2-nor-13-trans-prostene,-1-ethylene ketal |
| 1176 | 773 | 310 | 13 | 1,9-dioxo-hydroxy-16,16-trimethylene-1-hydroxymethyl-2-nor-13-trans-prostene, 1-ethylene ketal |
| 1177 | 773 | 310 | 76 | erythro-1,9-dioxo-15α,16-dihydroxy-1-hydroxymethyl-2-nor-13-trans-prostene,1-ethylene ketal |
| 1178 | 773 | 310 | 69 | threo-1,9-dioxo-15α,16-dihydroxy-1-hydroxymethyl-2-nor-13-trans-prostene,1-ethylene ketal |
| 1179 | 773 | 310 | 74 | erythro-1,9-dioxo-15α-hydroxy-16-methoxy-1-hydroxymethyl-2-nor-13-trans-prostene-1-ethylene ketal |
| 1180 | 773 | 310 | 107 | 1,9-dioxo-16-hydroxy-1-hydroxymethyl-2-nor-13-trans-prostene,1-ethylene ketal |
| 1181 | 773 | 285 | 130 | 1,9-dioxo-16-hydroxy-16-methyl-1-hydroxymethyl-2-nor-13-trans-prostene,1-ethylene ketal |
| 1182 | 773 | 285 | 134 | 1,9-dioxo-16-hydroxy-16-methyl-1-hydroxymethyl-2-nor-13-trans-17-trans-prostadiene,1-ethylene ketal |
| 1183 | 774 | 285 | 186 | 1,9-dioxo-15α-hydroxy-2,17,18,19,20-pentanor-16-phenoxy-1-hydroxymethyl-13-trans-prostene,1-ethylene ketal |
| 1184 | 774 | 285 | 180 | 1,9-dioxo-15α-hydroxy-2,17,18,19,20-pentanor-16-m-trifluoromethylphenoxy-1-hydroxymethyl-13-trans-prostene,1-ethylene ketal |
| 1185 | 773 | 285 | 194 | 1,9-dioxo-16-hydroxy-16-vinyl-1-hydroxymethyl-2-nor-13-trans-prostene,1-ethylene ketal |
| 1186 | 774 | 285 | 198 | 1,9-dioxo-16-hydroxy-16-cyclopropyl-1-hydroxymethyl-2-nor-13-trans-prostene,-1-ethylene ketal |
| 1187 | 774 | 285 | 186b | 1,9-dioxo-15α-hydroxy-2,18,19,20-tetranor-17-phenyl-1-hydroxymethyl-13-trans-prostene,1-ethylene ketal |
| 1188 | 773 | 285 | 186e | 1,9-dioxo-15α-hydroxy-2,18,19,20-tetranor-17-(m-trifluorophenyl)-1-hydroxymethyl-13-trans-prostene,1-ethylene ketal |
| 1189 | 773 | 285 | 186d | 1,9-dioxo-15α-hydroxy-2,18,19,20-tetranor-17-(p-methoxyphenyl)-1-hydroxymethyl-13-trans-prostene,1-ethylene ketal |

EXAMPLES 1190–1212

By the methods described hereinabove in Examples 773 and 774, the 1,9-dioxo-1-hydroxymethyl prostene derivative shown in Table 47 are prepared by the indicated method from the indicated vinyl iodide or vinyl tin compound and the indicated cyclopent-2-en-1-one.

In those cases where two diastereoisomers are formed in the conjugate-addition, only one of the diastereoisomers is listed in Table 47. It should be understood that the other diastereoisomer is also formed which in its nat and ent forms has an opposite (mirror image) configuration at the assymmetri carbon atoms on the β-chain (the chain containing $C_{13}$....$C_{14}$ etc.) to that of the respective nat and ent forms of the listed diastereoisomer; both of these diastereoisomers are claimed in this invention as well as their component enantiomers.

TABLE 47

| Example | Method of Example | Cyclopent-2-en-1-one of Example | Vinyl Todide or Vinyl Tin of Example | 1,9-dioxo-1-hydroxymethylprostene and its diastereomer |
|---|---|---|---|---|
| 1190 | 773 | 283 | 246 | nat-(and ent)-1,9-dioxo-16-hydroxy-15,16-tetramethylene-17,18,19,20-tetranor-1- |

TABLE 47-continued

| Example | Method of Example | Cyclopent-2-en-1-one of Example | Vinyl Iodide or Vinyl Tin of Example | 1,9-dioxo-1-hydroxymethylprostene and its diastereomer |
|---|---|---|---|---|
| | | | | hydroxymethyl-13-trans-prostene,1-ethylene ketal |
| 1191 | 774 | 283 | 245 | nat-(and ent)-1,9-dioxo-16-hydroxy-16,17-tetramethylene-18,19,20-trinor-1-hydroxymethyl-13-trans-prostene, 1-ethylene ketal |
| 1192 | 773 | 283 | 243 | nat-15S, 116R-(and ent-15R,16S)-1,9-dioxo-15-hydroxy-15,16-trimethylene-1-hydroxymethyl-13-trans-prostene,1-ethylene ketal |
| 1193 | 773 | 283 | 243 | nat-15S,16R-(and ent-15R,16S)-1,9-dioxo-15-hydroxy-15,16-trimethylene-1-hydroxymethyl-13-trans-prostene,1-ethylene ketal |
| 1194 | 773 | 283 | 251 | nat-15S,16S-(and ent-15R,16R)-1,9-dioxo-15-hydroxy-15,16-trimethylene-1-hydroxymethyl-13-trans-prostene,1-ethylene ketal |
| 1195 | 773 | 283 | 247 | nat-(and ent)-1,9-dioxo-15-hydroxy-15,16-trimethylene-17,18,19,20-tetranor-1-hydroxymethyl-13-trans-prostene,1-ethylene ketal |
| 1196 | 773 | 283 | 248 | nat-(and ent)-1,9-dioxo-15-hydroxy-15,16-pentamethylene-17,18,19,20-tetranor-1-hydroxymethyl-13-trans-prostene, 1-ethylene ketal |
| 1197 | 773 | 283 | 249 | nat-15S,17R-(and ent-15R, 17S)-1,9-dioxo-15-hydroxy-15,17-dimethylene-1-hydroxymethyl-13-trans-prostene,1-ethylene ketal |
| 1198 | 773 | 283 | 250 | nat-15S,17S-(and ent-15R, 17R)-1,9-dioxo-15-hydroxy-15,17-dimethylene-1-hydroxymethyl-13-trans-prostene, 1-ethylene ketal |
| 1199 | 773 | 283 | 252 | nat-15S,16R-(and ent-15R,16S)-1,9-dioxo-15-hydroxy-15,16-tetramethylene-1-hydroxymethyl-13-trans-prostene, 1-ethylene ketal |
| 1200 | 773 | 283 | 253 | nat-15S,16S-(and ent-15R,16R)-1,9-dioxo-15-hydroxy-15,16-tetramethylene-1-hydroxymethyl-13-trans-prostene,1-ethylene ketal |
| 1201 | 774 | 283 | 254 | nat-15R,16S-(and ent-15S,16R)-1,9-dioxo-15-hydroxy-15,16-trimethylene-16-(3-trifluoromethylphenoxy)-17,18,19,20-tetranor-1-hydroxymethyl-13-trans-prostene, 1-ethylene ketal |
| 1202 | 774 | 283 | 255 | nat-15R,16R-(and ent-15S,16S)-1,9-dioxo-15-hydroxy-15,16-trimethylene-16-(3-trifluoromethylphenoxy)-17,18,19,20-tetranor-1-hydroxymethyl-13-trans-prostene,1-ethylene ketal |
| 1203 | 773 | 283 | 256 | nat-15R,16S-(and ent-15S,16R)-1,9-dioxo-15-hydroxy-15,16-trimethylene-16-(4-fluorophenoxy)-17,18,19,20-tetranor-1-hydroxymethyl-13-trans-prostene,1-ethylene ketal |
| 1204 | 773 | 283 | 257 | nat-15R,16R-(and ent-15S,16S)-1,9-dioxo-15-hydroxy-15,16-trimethylene-16-(4-fluorophenoxy)-17,18,19,20-tetranor-1-hydroxymethyl-13-trans-prostene,1-ethylene ketal |
| 1205 | 774 | 283 | 258 | nat-15R,16S-(and ent-15S,16R)-1,9-dioxo-15-hydroxy-15,16-trimethylene-16-(3-chlorophenoxy)-17,18,19,20-tetranor-1-hydroxymethyl-13-trans-prostene,1-ethylene ketal |
| 1206 | 774 | 283 | 259 | nat-15R,16R-(and ent-15S,16S)-1,9-dioxo-15-hydroxy-15,16-trimethylene-16-(3-chlorophenoxy)-17,18,19,20-tetranor-1-hydroxymethyl-13-trans-prostene,1-ethylene ketal |
| 1207 | 773 | 283 | 260 | nat-15S,17R-(and ent-15R,17S)-1,9-dioxo-15-hydroxy-15,17-trimethylene-19,20-dinor-1-hydroxymethyl-13-trans-prostene,1-ethylene ketal |
| 1208 | 773 | 283 | 261 | nat-15S,17S-(and ent-15R,17R)-1,9-dioxo-15-hydroxy-15,17-trimethylene-19,20-dinor-1-hydroxymethyl-13-trans-prostene,1-ethylene ketal |
| 1209 | 774 | 283 | 262 | nat-16R,17S-(and ent-16S,17R)-1,9-dioxo-16-hydroxy-16,17-trimethylene-20-methyl-1-hydroxymethyl-13-trans-prostene,1-ethylene ketal |
| 1210 | 774 | 283 | 263 | nat-16R,17R-(and ent-16S,17S)-1,9-dioxo- |

TABLE 47-continued

| Example | Method of Example | Cyclopent-2-en-1-one of Example | Vinyl Todide or Vinyl Tin of Example | 1,9-dioxo-1-hydroxymethylprostene and its diastereomer |
|---------|-------------------|----------------------------------|--------------------------------------|--------------------------------------------------------|
| 1211 | 774 | 283 | 264 | 16-hydroxy-16,17-trimethylene-20-methyl-1-hydroxymethyl-13-trans-prostene,1-ethylene ketal nat-16R,17S-(and ent-16S,17R)-1,9-dioxo-16-hydroxy-16,17-trimethylene-16-(3-trifluoromethylphenoxy)-18,19,20-trinor-1-ene ketal |
| 1212 | 774 | 283 | 265 | nat-16R,17R-(and ent-16S,17S)-1,9-dioxo-16-hydroxy-16,17-trimethylene-16-(3-trifluoromethylphenoxy)-18,19,20-trinor-1-hydroxymethyl-13-trans-prostene,1-ethylene ketal |

EXAMPLE 1213

1,9-Dioxo-11α,16-dihydroxy-16-vinyl-1-acetoxymethyl-5-cis-13-trans prostadiene

To a solution of 0.1 g of 1,9-dioxo-11α,16-dihydroxy) 16-vinyl-1-hydroxymethyl-5-cis-13-trans prostadiene in 0.75 ml of pyridine is added 0.026 g of acetic anhydride. After standing overnight, the pyridine is removed at reduced pressure. The residue is chromatographed on a dry column of silica gel eluting with benzene-ethylacetate 1:1 to give 0.049 g of the product.

In accordance with the above example 1213 the 1-hydroxymethyl analogs of Examples 319-769 are treated with acetic anhydride, propionic anhydride, n-butyric anhydride and n-valeric anhydride to give the respective 1-acetoxymethyl, 1-propoxymethyl, 1-n-butoxymethyl and 1-n-peutoxymethyl analogs.

EXAMPLE 1214

Preparation of 1-oxo-9β,11α,16-trihydroxy-1-hydroxymethyl-16-vinyl-5-cis-13-trans-prostadiene and 1-oxo-9α,11α,16-trihydroxy-1-hydroxymethyl-16-vinyl-5-cis-13-trans prostadiene To a solution of 2.9 g. (5.6 mmol) of (E) 4-trimethyl-silyloxy-4-vinyl-1-tri-n-butylstannyloctene (Ex. 210a) in 4 ml. of tetrahydrofuran at 78° C. under argon with stirring is added 2.4 ml of 2.4 M n-butyllithium in hexane. The solution is stirred at −30° to −20° C. for 2 hr. A solution of 0.74 g (5.6 mmol) of copper pentyne and 2.3 ml of hexaethylphosphoroustriamide in 18 ml of ether is added at −78° C. The solution is stirred at −78° C. for 1.5 hr. A solution of 2.0 g (5.2 mmol) of 1-[6-(4-methoxy-2,2-dimethyl-1,3-dioxolan-4-yl(hex-2-enyl]-4-(2-methoxypropyl-2-oxy)cyclopent-2-en-1-one in 20 ml of ether is added. The solution is stirred at −30° to −20° for 1.5 hr. To the solution is added 100 ml of saturated ammonium chloride. The mixture is extracted with ether and the ether solution is washed with dilute hydrochloric acid, saturated sodium bicarbonate, and dried over magnesium sulfate. Dry solvent is removed and the residue is dissolved in 30 Ml of ethanol and 0.37 g of sodium borohydride is added. The mixture is stirred for 8 hr. The solvent is removed. The residue is dissolved in 90 ml of acetic acid-tetrahydrofuran - water 4:2:1. The solution is stirred at room temperature for 2 hr. The solvents are moved at reduced pressure. The residue is chromatographed on silica gel to give 1-oxo-9β,11α,16-trihydroxy-1-hydroxymethyl 16-vinyl-5-cis-3 trans-prostadiene and 1-oxo-9α,11α,16-trihydroxy-1-hydroxymethyl-16-vinyl-5-cis 13 trans-prostadiene.

By the methods described hereinabove in Example 1214 the vinyl iodides or vinyl tin compounds used in Examples 319-772 are exchanged with t-butyl lithium or n-butyllithium respectively to give the vinyl lithium reagents which on reaction with copper pentyne and hexamethyl phosphorous triamide give the cuprate reagents. Addition of the cyclopent-2-en-1-ones used in Example 319 −772 at −78° followed by warming to −20° as described hereinabove in Example 1214 gives the 9-oxo analogs in which the 1-oxo feature is still protected. The reaction of these with sodium borohydride in ethanol followed by deblocking with acetic acid tetrahydrofuran-water 4:2:1 or with dilute hydrochoric acid in tetrahydrofuran gives 1-oxo-9β-hydroxy and 1-oxo-9α-hydroxy analogs corresponding to the 1,9-droxo analogs of Examples 319-772.

EXAMPLE 1215

Preparation of 1-oxo-9α,11α,16-trihydroxy-1-hydroxymethyl-16-methyl-b 5-cis-13-trans prostadiene To a solution of 3.4 (0.00675 mol) of (E) 4-trimethylsilyloxy 4-methyl-1-tri-n-butylstannyloctene (Example 210b) in 3.5 ml of tetrahydrofuran at −78° under argon, with stirring is added 2.8 ml. (0.00675 mol) of 2.4 M n-butyllithium in hexane. The solution is maintained at −15° to −20° for 2.5 hr. A solution of 0.89 g (0.00675 mol) of copper pentyne and 2.2 g of hexamethyl phosphorous triamide in 25 ml of ether is added at −78°. After 1 hr, a solution of 2.4 g (0.005 mol) of 1-(8-dimethyl-t-butylsilyloxy-7-oxooct-2-enyl)-4-trimethylsilyloxycyclopent-2-en-1-one, 7-ethylene ketal in 10 ml of ether is added. The mixture is stirred at −45° for 0.5 hr. and allowed to warm to −20° over 40 min. The solution is recooled to −30° and 2.5 ml. of acetic acid followed by saturated ammonium chloride is added. The mixture is extracted with ether. The ether layer is worked with dilute hydrochloric acid followed by saturated sodium bicarbonate. The solution is dried over magnesium sulfate. The solvent is removed. The residue is dissolved in 10 ml of ether at −78° under argon with stirring is added 20 ml. (0.01 mol) of 0.5 M lithium perhydro-96-borophenolylhydride in tetrahydrofuran. The solution is allowed to warm to 0° over 35 min. At 0° is added 8 g of sodium carbonate in 60 ml of water followed by 13 ml. of 30% hydrogen peroxide. The mixture is stirred for 10 min. and then extracted with ether. The ether solution is washed with water, saturated sodium bisulfite, and saturated sodium bicarbonate. The solution is dried of magnesium sulfate. The residue is dissolved in 60 ml of tetrahydrofuran containing 9.6 ml of water and 1.2 ml of concentrated hydrochloric acid. The solution is stirred at 55°-60° for 4 hr. 45 min. The mixture is saturated with sodium chloride and extracted with ethyl acetate. The organic layer is washed with saturated sodium bicarbonate and dried over magnesium sulfate. The solvent is removed. The residue is chromatographed on a dry column of silica gel eluting with ethyl acetate containing 4° of methanol to give the title compound.

By the methods described hereinabove in Example 1215 the vinyl iodides or vinyl tin compounds used in Examples b 319–772 are exchanged with 5-butyllithium or n-butyl lithium respectively to give the vinyl lithium reagents which on reaction with copper pentyne and hexamethyl phosphorous triamide give the cuprate reagents. Addition of the cyclopent-2-en-1-ones used in Examples 319–772 at −78° followed by warming to −20° as described hereinabove in Example 1214 gives the 9-oxo analogs in which the 1-oxo feature is still protected. The reaction of these with lithium perhydro-9b-boraphenolylhydride at −78° followed by warming to 0°, quenching with sodium carbonate and hydrogen peroxide and deblocking with acetic acid-tetrahydrofuran-water 4:2:1 or with dilute hydrochloric acid in tetrahydrofuran gives the 1-oxo-9 hydroxy analogs corresponding to the 1,9-dioxo analogs of Examples 319–772.

EXAMPLE 1216

Preparation of 1-oxo-9α,11α,16-trihydroxy-1-hydroxymethyl-16 methyl-5-cis-13-trans prostadiene, 1-ethylene ketal and 1-oxo-9β,11α,16-trihydroxy-1-hydroxymethyl-5-cis-16-methyl-13-trans prostadiene, 1-ethylene ketal To a solution of 0.1 g. of 1,9-dioxo-11,16-dihydroxy-1-hydroxymethyl-16-methyl-5-cis-13-trans prostadiene, 1-ethylene ketal (Example 774) in 25 ml of ethanol is added 0.1 g. of sodium borohydride. After stirring 3 hr. the mixture is poured into water and extracted with ethyl acetate. The ethyl acetate solution is dried over magnesium sulfate. The solvent is removed and the title compounds are separated by silica gel chromatography.

By the method described hereinabove in Example 1216 the 1,9-dioxo,1-ethylene ketal analogs of Examples 775–1212 are reacted with an excess of sodium borohydride in ethanol to give the corresponding 9α-hydroxy-1-ethylene ketal and 9-hydroxy-1-ethylene ketal analogs.

EXAMPLE 1217

Preparation of 1,9-dioxo-16-hydroxy-1-hydroxymethyl-16 methyl-5-cis-10,13-trans-prostatriene To a solution of 0.1 g of 1,9-dioxo-11α,16-dihydroxy-1-hydroxymethyl-1b methyl-5-cis-13-trans prostadiene in 4 ml of tetrahydrofuran is added 2 ml of 1.5 N hydrochloric acid. After 2 days the mixture is poured into water and extracted with ether. The ether solution is dried over magnesium sulfate and the ether is removed to give the title compound.

EXAMPLE 1218

Preparation of 1,9-dioxo-16-hydroxy-1-hydroxymethyl-16-methyl-5-cis-10,13-trans-prostatriene-1-ethylene ketal To a solution of 0.1 g of 1,9-dioxo-11α,16-dihydroxy-1-hydroxymethyl-16-methyl-5-cis-13-trans prostadiene-1-ethylene ketal in 4 ml of tetrahydrofuran is added 2 ml of 1.5 N hydrochloric acid. After 2 days the mixture is poured into water and extracted with ether. The ether solution is dried over magnesium sulfate and the ether is removed to give the title compound.

EXAMPLE 1219

Preparation of 1,9-dioxo-16-hydroxy-1-acetoxymethyl 16 methyl-5-cis-10,13-trans-prostatriene To a solution of 0.1 g of 1,9-dioxo-16-hydroxy-1-hydroxymethyl-16-methyl-5-cis-10,13-trans-prostatriene in 0.75 ml of pyridine is added 0.026 g of acetic anhydride. After 18 hr. at room temperature, the solvent is removed at reduced pressure and the residue is chromatographed on silica gel to give the title compound.

By the method described hereinabove in Examples 1214 and 1215 the 11α-hydroxy analogs of Examples 319–1213 were treated with 1.5 N hydrochloric acid in tetrahydrofuran for 2 days to give the corresponding Δ10 compounds of this invention.

I claim:

1. An optically active compound of the formula:

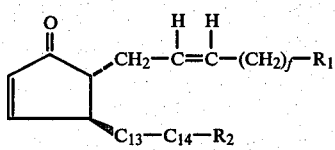

wherein f is an integer from 2 to 4, inclusive; $C_{13}$–$C_{14}$ is selected from the group consisting of ethylene and trans-vinylene; $R_1$ is a radical selected from the group consisting of

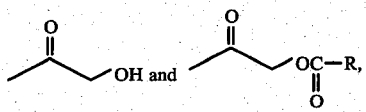

wherein R is selected from the group consisting of $C_1$–$C_4$ alkyl; $R_2$ is a moiety selected from the group consisting of

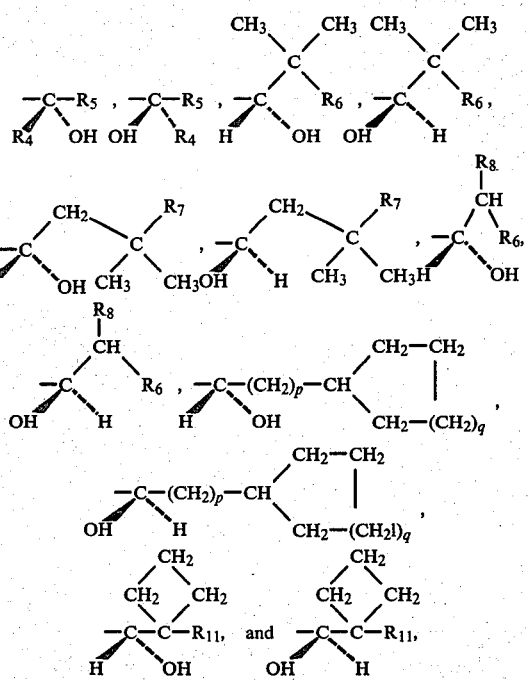

wherein $R_4$ is selected from the group consisting of hydrogen and methyl, $R_5$ is selected from the group consisting of $C_4$–$C_7$ alkyl, $R_6$ is selected from the group consisting of $C_3$–$C_5$ alkyl, $R_7$ is selected from the group consisting of $C_2$–$C_4$, $R_8$ is selected from the group consisting of $C_1$–$C_2$ alkyl, $R_{11}$ is selected from the group consisting of $C_3$–$C_7$ alkyl, p is an integer from 0 to 3, and q is 1 or 2; the racemic mixture thereof; and the mirror image thereof.

2. An optically active compound according to claim 1, wherein f, and $R_2$ are as previously defined; $C_{13}$–$C_{14}$ is trans-vinylene; and $R_1$ is the moiety

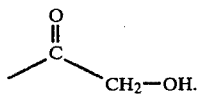

3. An optically active compound according to claim 1, wherein f, and $R_2$ are as previously defined; $C_{13}$–$C_{14}$ is trans-vinylene; and $R_1$ is the moiety

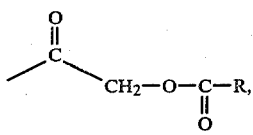

wherein R is as previously defined.

4. An optically active compound according to claim 2, wherein $R_1$, $C_{13}$–$C_{14}$ and f are as previously defined; and $R_2$ is a moiety selected from the group consisting of

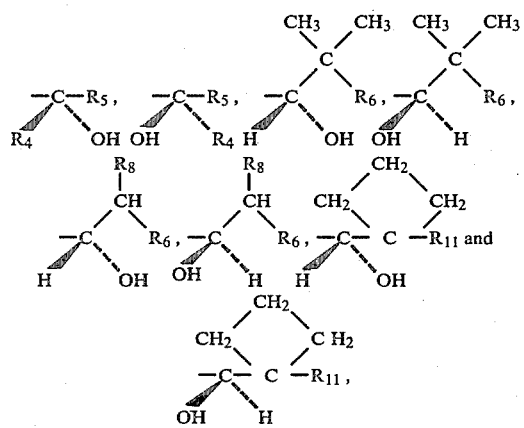

wherein $R_4$, $R_5$, $R_6$, $R_8$ and $R_{11}$ are as previously defined.

5. An optically active compound according to claim 2, wherein $R_1$, $C_{13}$–$C_{14}$ and f are as previously defined; and $R_2$ is a moiety selected from the group consisting of

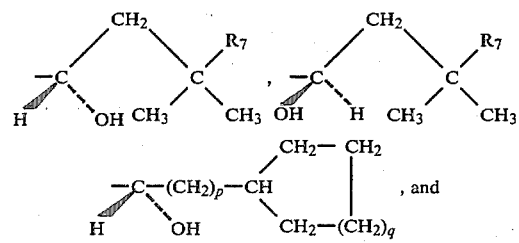

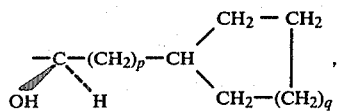

wherein $R_7$, p and q are as previously defined.

6. An optically active compound according to claim 5, wherein $R_1$, $C_{13}$–$C_{14}$ and f are as previously defined; and $R_2$ is a moiety selected from the group consisting of

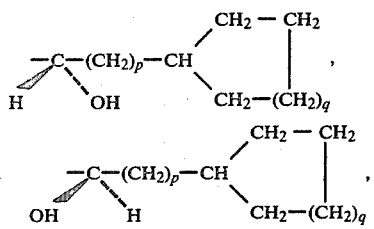

wherein p and q are as previously defined.

7. The racemic compound according to claim 4, dl-1,9-dioxo-15α-hydroxy-1-hydroxymethyl-10,5-cis,13-trans-prostatriene.

8. The racemic compound according to claim 4, dl-1,9-dioxo-15α-hydroxy-1-hydroxymethyl-20-ethyl-10,5-cis,13-trans-prostatriene.

9. The racemic compound according to claim 4, dl-1,9-dioxo-15α-hydroxy-1-hydroxymethyl-16,16-dimethyl-10,5-cis,13-trans-prostatriene.

10. The racemic compound according to claim 4, dl-1,9-dioxo-15α-hydroxy-1-hydroxymethyl-16-methyl-10,5-cis,13-trans-prostatriene.

11. The racemic compound according to claim 4, dl-1,9-dioxo-15α-hydroxy-1-hydroxymethyl-16,16-trimethylene-10,5-cis,13-trans-prostatriene.

12. The racemic compound according to claim 4, dl-1,9-dioxo-15α-hydroxy-1-hydroxymethyl-16,16-trimethylene-20-ethyl-10,5-cis,13-trans-prostatriene.

13. The racemic compound according to claim 4, dl-1,9-dioxo-15α-hydroxy-1-hydroxymethyl-15-methyl-10,5-cis,13-trans-prostatriene.

14. The racemic compound according to claim 4, dl-1,9-dioxo-15α-hydroxy-1-hydroxymethyl-15-methyl-20-ethyl-10,5-cis,13-trans-prostatriene.

15. The racemic compound according to claim 4, dl-1,9-dioxo-15α-hydroxy-1-hydroxymethyl-15-methyl-10,5-cis,13-trans-prostatriene.

16. The racemic compound according to claim 4, dl-1,9-dioxo-15α-hydroxy-1-hydroxymethyl-16,16-trimethylene-10,5-cis,13-trans-prostatriene.

17. The racemic compound according to claim 4, dl-1,9-dioxo-15α-hydroxy-1-hydroxymethyl-10,5-cis,13-trans-prostatriene.

18. The racemic compound according to claim 5, dl-1,9-dioxo-15α-hydroxy-1-hydroxymethyl,17,17-dimethyl-10,5-cis,13-trans-prostatriene.

19. An optically active compound according to claim 3 wherein $R_1$, $C_{13}$–$C_{14}$ and f are as previously defined; and $R_2$ is a moiety selected from the group consisting of

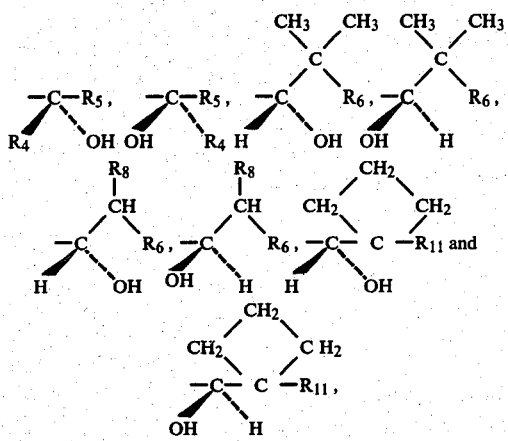

wherein $R_4$, $R_5$, $R_6$, $R_8$ and $R_{11}$ are as previously defined.

20. An optically active compound according to claim 3, wherein $R_1$, $C_{13}$–$C_{14}$ and f are as previously defined; and $R_2$ is a moiety selected from the group consisting of

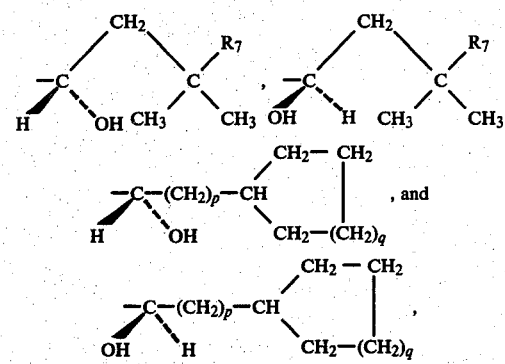

wherein $R_7$, p and q are as previously defined.

21. An optically active compound according to claim 20, wherein $R_1$, $C_{13-14}$ and f are as previously defined; and R is a moiety selected from the group consisting of

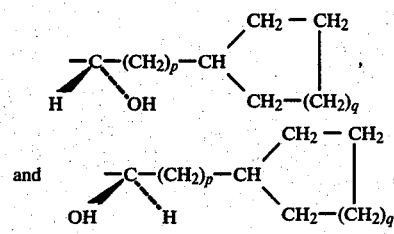

wherein p and q are as previously defined.

22. The racemic compound according to claim 19, dl-1,9-dioxo-15α-hydroxy-1-acetoxymethyl-10,5-cis,13-trans-prostatriene.

23. The racemic compound according to claim 19, dl-1,9-dioxo-15α-hydroxy-1-acetoxymethyl-20-ethyl-10,5-cis,13-trans-prostatriene.

24. The racemic compound according to claim 19, dl-1,9-dioxo-15α-hydroxy-1-propoxymethyl-16,16-trimethylene-20-ethyl-10,5-cis,13-trans-prostatriene.

25. The racemic compound according to claim 19, dl-1,9-dioxo-15α-hydroxy-1-acetoxymethyl-15-methyl-10,5-cis,13-trans-prostatriene.

26. The racemic compound according to claim 19, dl-1,9-dioxo-15α-hydroxy-1-butoxymethyl-15-methyl-20-ethyl-10,5-cis,13-trans-prostatriene.

27. The racemic compound according to claim 19, dl-1,9-dioxo-15α-hydroxy-1-acetoxymethyl-15-methyl-10,5-cis,13-trans-prostatriene.

28. The racemic compound according to claim 19, dl-1,9-dioxo-15α-hydroxy-1-acetoxymethyl-16,16-trimethylene-10,5-cis,13-trans-prostatriene.

29. The racemic compound according to claim 19, dl-1,9-dioxo-15α-hydroxy-1-acetoxymethyl-16,16-dimethyl10,5-cis,13-trans-postatriene.

30. The racemic compound according to claim 19, dl-1,9-dioxo-15α-hydroxy-1-acetoxymethyl-16-methyl-10,5-cis, 13-trans-prostatriene.

31. The racemic compound according to claim 19, dl-1,9-dioxo-15α-hydroxy-1-acetoxymethyl-1616-trimethylene10,5-cis,13-trans-prostatriene.

32. The racemic compound according to claim 19, dl-1,9-dioxo-15α-hydroxy-1-acetoxymethyl-10,5-cis,13-transprostatriene.

33. The racemic compound according to claim 20, dl-1,9-dioxo-11α, 15α-dihydroxy-1-n-pentoxymethyl-17-17-dimethyl-10,5-cis,13-trans-prostatriene.

34. An optically active compound of the formula:

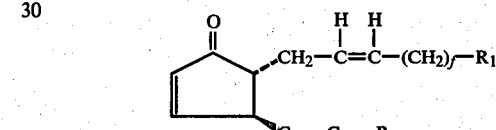

wherein f is an integer from 2 to 4, inclusive; $C_{13}$–$C_{14}$ is selected from the group consisting of ethylene and transvinylene; $R_1$ is a radical selected from the group consisting of

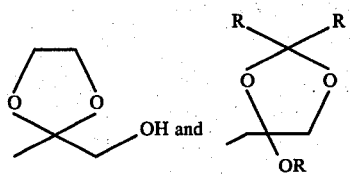

wherein R is selected from the group consisting of $C_1$–$C_4$ alkyl; $R_2$ is a moiety selected from the group consisting of

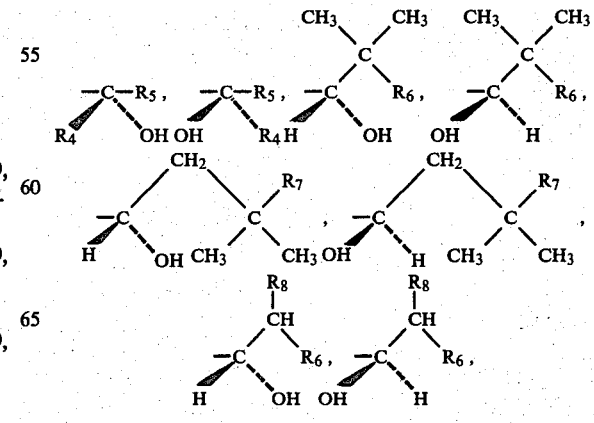

-continued

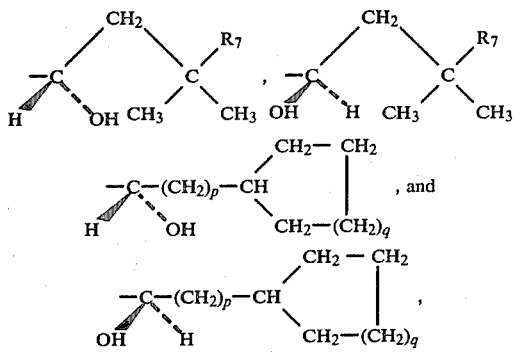

wherein $R_4$, $R_5$, $R_6$, $R_8$ and $R_{11}$ are as previously defined.

38. An optically active compound according to claim 35 wherein $R_1$, $C_{13}$–$C_{14}$ and f are as previously defined; and $R_2$ is a moiety selected from the group consisting of

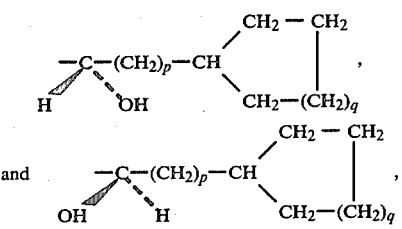

wherein $R_7$, p and q are as previously defined.

39. An optically active compound according to claim 38 wherein $R_1$, $C_{13}$–$C_{14}$ and f are as previously defined; and $R_2$ is a moiety selected from the group consisting of wherein $R_4$ is selected from the group consisting of hydrogen and methyl, $R_5$ is selected from the group consisting of $C_4$–$C_7$ alkyl, $R_6$ is selected from the group consisting of $C_3$–$C_5$ alkyl, $R_7$ is selected from the group consisting of $C_2$–$C_4$, $R_8$ is selected from the group consisting of $C_1$–$C_2$ alkyl, $R_{11}$ is selected from the group consisting of $C_3$–$C_7$ alkyl, p is an integer from 0 to 3, and q is 1 or 2; the racemic mixture thereof and the mirror image thereof.

35. An optically active compound according to claim 34 wherein f, and $R_2$ are as previously defined; $C_{13}C_{14}$ is trans-vinylene; and $R_1$ is the moiety

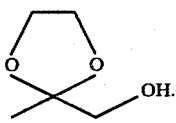

36. An optically active compound according to claim 34 wherein f, and $R_2$ are as previously defined; $C_{13}$–$C_{14}$ is trans-vinylene; and $R_1$ is the moiety

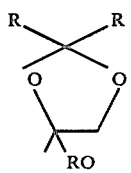

wherein R is as previously defined.

37. An optically active compound according to claim 35 wherein $R_1$, $C_{13}$–$C_{14}$ and f are as previously defined; and $R_2$ is a moiety selected from the group consisting of

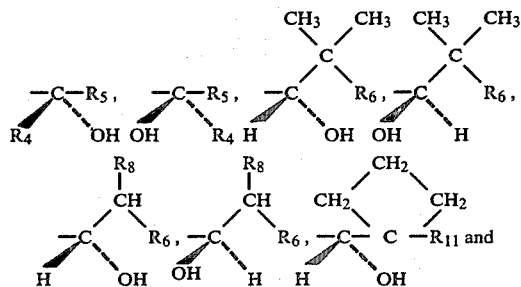

wherein p and q are as previously defined.

40. The racemic compound according to claim 37, dl-1,9-dioxo-15α-hydroxy-1-hydroxymethyl-10,5-cis,13-trans-prostatriene-1-ethylene ketal.

41. The racemic compound according to claim 37, dl-1,9-dioxo-15α-hydroxy-1-hydroxymethyl-20-ethyl-10,5-cis, 13-trans-prostatriene-1-ethylene ketal.

42. The racemic compound according to claim 37, dl-1,9dioxo-15α-hydroxy-1-hydroxymethyl-16,16-dimethyl10,5-cis,13-trans-prostatriene-1-ethylene ketal.

43. The racemic compound according to claim 37, dl-1,9-dioxo-15α-hydroxy--1-hydroxymethyl-16-methyl-10,5-cis, 13-trans-prostatriene-1-ethylene ketal.

44. The racemic compound according to claim 37, dl-1,9-dioxo-15α-hydroxy-1-hydroxymethyl-16,16-trimethylene10,5-cis,13-trans-prostatriene-1-ethylene ketal.

45. The racemic compound according to claim 37, dl-1,9-dioxo-15α-hydroxy-1-hydroxymethyl-16,16-trimethylene20-ethyl-10,5-cis,13-trans-prostatriene-1-ethylene ketal.

46. The racemic compound according to claim 37, dl-1,9-dioxo-15α-hydroxy-1-hydroxymethyl-15-methyl-10,5-cis,13-trans-prostatriene-1-ethylene ketal.

47. The racemic compound according to claim 37, dl-1,9-dioxo-15α-hydroxy-1-hydroxymethyl-15-methyl-20-ethyl10,5-cis,13-trans-prostatriene-1-ethylene ketal.

48. The racemic compound according to claim 37, dl-1,9-dioxo-15α-hydroxy-1-hydroxymethyl-15-methyl-10,5-cis, 13-trans-prostatriene-1-ethylene ketal.

49. The racemic compound according to cliam 37, dl-1,9-dioxo-15α-hydroxy-1-hydroxymethyl-16,16-trimethylene10,5-cis,13-trans-prostatriene-1-ethylene ketal.

50. The racemic compound according to claim 37, dl-1,9-dioxo-15α-hydroxy-1-hydroxymethyl-10,5-cis,13-trans-prostatriene-1-ethylene ketal.

51. The racemic compound according to claim 38, dl-1,9-dioxo-15α-hydroxy-1-hydroxymethyl-17,17-dimethyl-10,5-cis,13-trans-prostatriene-1-ethylene ketal.

52. An optically active compound of the formula:

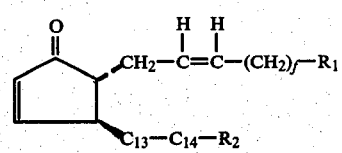

wherein f is an integer from 2 to 4, inclusive, $C_{13}$–$C_{14}$ is selected from the group consisting of ethylene and trans-vinylene; R is a radical selected from the group consisting of

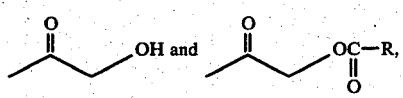

wherein R is selected from the group consisting of $C_1$–$C_4$ alkyl; $R_2$ is a moiety selected from the group consisting of

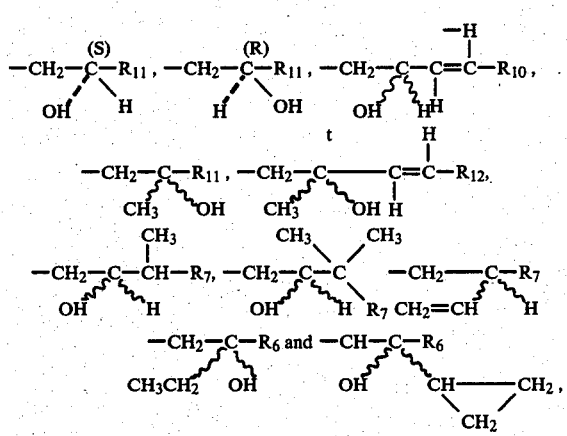

wherein $R_6$ is selected from the group consisting of $C_3$–$C_6$ alkyl, $R_7$ is selected from the group consisting of $C_2$–$C_4$ alkyl, $R_{10}$ is selected from the group consisting of $C_1$–$C_4$ alkyl, $R_{11}$ is selected from the group consisting of $C_3$–$C_7$ alkyl and $R_{12}$ is selected from the group consisting of $C_1$–$C_4$ alkyl; the racemic mixture thereof; and the mirror image thereof.

53. An optically active compound according to claim 5; wherein f, and $R_2$ are as previously defined; $C_{13}$–$C_{14}$ is trans-vinylene; and $R_1$ is the moiety

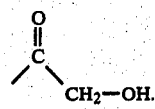

54. An optically active compound according to claim 5, wherein f, and $R_2$ are as previously defined; $C_{13}$–$C_{14}$ is trans-vinylene; and $R_1$ is the moiety

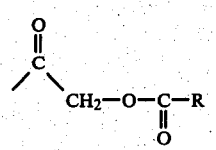

wherein R is as previously defined.

55. An optically active compound according to claim 53, wherein $R_1$, $C_{13}$–$C_{14}$ and f are as previously defined, and $R_2$ is a moiety selected from the group consisting of

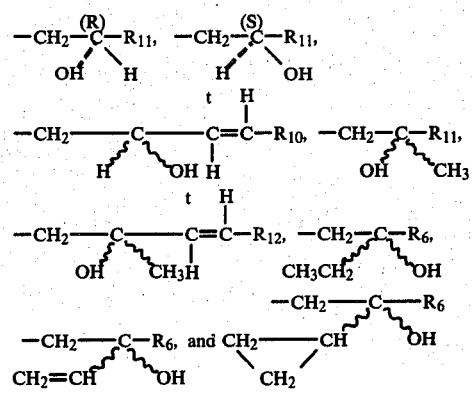

wherein $R_6$, $R_{10}$, $R_{11}$ and $R_{12}$ are as previously defined.

56. An optically active compound according to claim 53 wherein $R_1$, $C_{13}$–$C_{14}$ and f are as previously defined; and $R_2$ is a moiety selected from the group consisting of

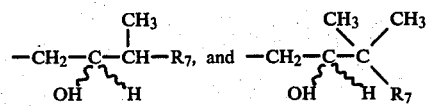

wherein $R_7$ is as previously defined.

57. An optically active compound according to claim 56, wherein $R_1$, $C_{13}$–$C_{14}$ and f are as previously defined; and $R_2$ is a moiety selected from the group consisting of

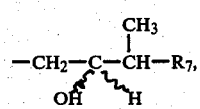

wherein $R_7$ is as previously defined.

58. An optically active compound according to claim 55, wherein $R_1$, $C_{13}$–$C_{14}$ and f are as previously defined;

and R$_2$ is a moiety selected from the group consisting of

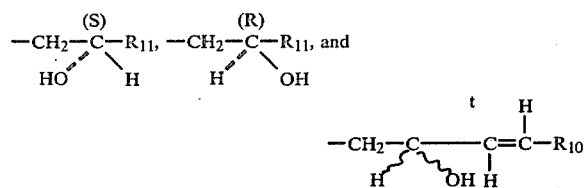

wherein R$_6$, R$_{11}$ and R$_{12}$ are as previously defined.

59. An optically active compound according to claim 55, wherein R$_1$, C$_{13}$–C$_{14}$ and f are as previously defined; and R$_2$ is a moiety selected from the group consisting of

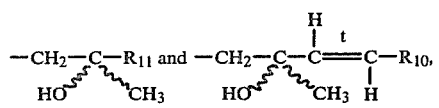

wherein R$_{10}$ and R$_{11}$ are as previously defined.

60. The racemic compound according to claim 55, dl-1,9-dioxo-16-hydroxy-1-hydroxymethyl-16-vinyl-10,5-cis,13-trans-prostatriene.

61. The racemic compound according to claim 55, dl-1,9-dioxo-16-hydroxy-1-hydroxymethyl-16-vinyl-20-ethyl-10,5-cis,13-trans-prostatriene.

62. The racemic compound according to claim 55, dl-1,9-dioxo-16-hydroxy-1-hydroxymethyl-16-cyclopropyl-10,5-cis,13-trans-prostatriene.

63. The racemic compound according to claim 55, dl-1,9-dioxo-16-hydroxy-1-hydroxymethyl-16-cyclopropyl-20-ethyl-10,5-cis,13-trans-prostatriene.

64. The racemic compound according to claim 55, dl-1,9-dioxo-16-hydroxy-1-hydroxymethyl-16-ethyl-10,5-cis,13-trans-prostatriene.

65. The racemic compound according to claim 55, dl-1,9-dioxo-16-hydroxy-1-hydroxymethyl-16,20-diethyl-10,5-cis,13-trans-prostatriene.

66. The racemic compound according to claim 55, dl-1,9-dioxo-16-hydroxy-1-hydroxymethyl-16-vinyl-10,5-cis,13-trans-prostatriene.

67. The racemic compound according to claim 57, dl-1,9-dioxo-16-dihydroxy-1-hydroxymethyl-17-methyl-10,5-cis,13-trans-prostatriene.

68. The racemic compound according to claim 57, dl-1,9-dioxo-16-hydroxy-1-hydroxymethyl-17,2-dimethyl-10,5-cis,13-trans-prostatriene.

69. The racemic compound according to claim 57, dl-1,9-dioxo-16-hydroxy-1-hydroxymethyl-17-methyl-20-ethyl-10,5-cis,13-trans-prostatriene.

70. The racemic compound according to claim 58, dl-1,9-dioxo-16-hydroxy-1-hydroxymethyl-10,5-cis,13-trans-prostatriene.

71. The racemic compound according to claim 58, dl-1,9-dioxo-16-hydroxy-1-hydroxymethyl-20-ethyl-10,5-cis,13-trans-prostatriene.

72. The racemic compound according to claim 58, dl-1,9-dioxo-16(R)-hydroxy-1-hydroxymethyl-10,5-cis,13-trans-prostatriene.

73. The racemic compound according to claim 58, dl-1,9-dioxo-16(S)-hydroxy-1-hydroxymethyl-10,5-cis,13-trans-prostatriene.

74. The racemic compound according to claim 58, dl-1,9-dioxo-16-dihydroxy-1-hydroxymethyl-17-trans-10,5-cis,13-trans-prostatetraene.

75. The racemic compound according to claim 58, dl-1,9-dioxo-16-hydroxy-1-hydroxymethyl-20-ethyl-17-trans-10,5-cis,13-trans-prostatetraene.

76. The racemic compound according to claim 59, dl-1,9-dioxo-16-hydroxy-1-hydroxymethyl-16-methyl-10,5-cis,13-trans-prostatriene.

77. The racemic compound according to claim 59, dl-1,9-dioxo-16-hydroxy-1-hydroxymethyl-16-methyl-20-ethyl-10,5-cis,13-trans-prostatriene.

78. The racemic compound according to claim 59, dl-1,9-dioxo-16-hydroxy-1-hydroxymethyl-16-methyl-17-trans-10,5-cis,13-trans-prostatetraene.

79. The racemic compound according to claim 59, dl-1,9-dioxo-16-hydroxy-1-hydroxymethyl-16-methyl-20-ethyl-17-trans-10,5-cis,13-trans-prostatetraene.

80. An optically active compound according to claim 59, wherein R$_1$, C$_{13}$–C$_{14}$ and f are as previously defined, and R$_2$ is a moiety selected from the group consisting of

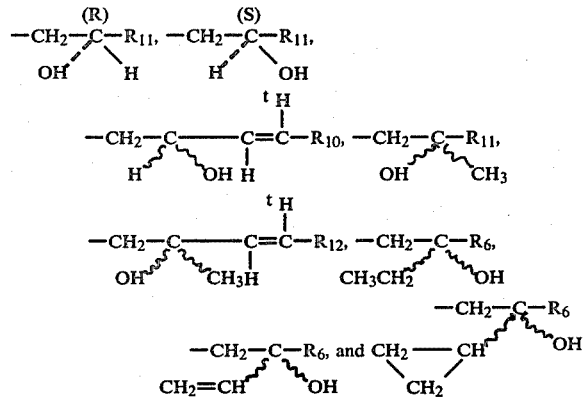

wherein R$_6$, R$_{10}$, R$_{11}$ and R$_{12}$ are as previously defined.

81. An optically active compound according to claim 54, wherein R$_1$, C$_{13}$–C$_{14}$ and f are as previously defined; and R$_2$ is a moiety selected from the group consisting of

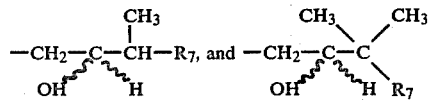

wherein R$_7$ is as previously defined.

82. An optically active compound according to claim 81, wherein R$_1$, C$_{13}$–C$_{14}$ and f are as previously defined; and R$_2$ is a moiety selected from the group consisting of

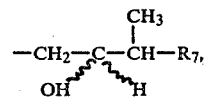

wherein R$_7$ is as previously defined.

83. An optically active compound according to claim 80, wherein R$_1$, C$_{12}$–C$_{14}$ and f are as previously defined; and R$_2$ is a moiety selected from the group consisting of

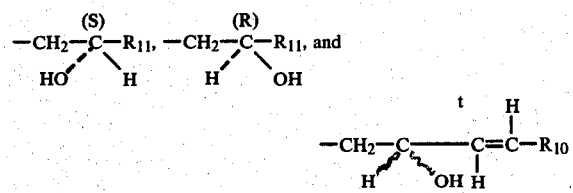

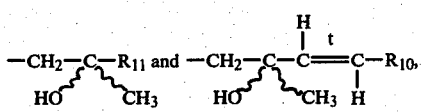

wherein $R_6$, $R_{11}$ and $R_{12}$ are as previously defined.

84. An optically active compound according to claim 80, wherein $R_1$, $C_{13}$–$C_{14}$ and f are as previously defined; and $R_2$ is a moiety selected from the group consisting of

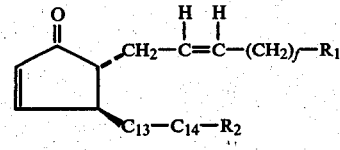

wherein $R_{10}$ and $R_{11}$ are as previously defined.

85. The racemic compound according to claim 80, dl-1,9-dioxo-16-hydroxy-1-acetoxymethyl-16-vinyl-10,5-cis,13-trans-prostatriene.

86. The racemic compound according to claim 80, dl-1,9-dioxo-16-hydroxy-1-aceoxymethyl-16-vinyl-20-ethyl-10,5-cis,13-trans-prostatriene.

87. The racemic compound according to claim 80, dl-1,9-dioxo-16-dihydroxy-1-acetoxymethyl-16-cyclopropyl-10,5-cis,13-trans-prostatriene.

88. The racemic compound according to claim 83, dl-1,9-dioxo-16(R)-hydroxy-1-acetoxymethyl-10,5-cis,13-trans-prostatriene.

89. The racemic compound according to claim 83, dl-1,9-dioxo-16(S)-hydroxy-1-acetoxymethyl-10,5-cis,13-trans-prostatriene.

90. The racemic compound according to claim 83, dl-1,9-dioxo-16-hydroxy-1-acetoxymethyl-17-trans-10,5-cis,13-trans-prostatetraene.

91. The racemic compound according to claim 83, dl-1,9-dioxo-16-hydroxy-1-acetoxymethyl-20-ethyl-17-trans-10,5-cis,13-trans-prostatetraene.

92. The racemic compound according to claim 84, dl-1,9-dioxo-16-hydroxy-1-acetoxymethyl-16-methyl-10,5-cis,13-trans-prostatriene.

93. The racemic compound according to claim 84, dl-1,9-dioxo-16-hydroxy-1-acetoxymethyl-16-methyl-20-ethyl-10,5-cis,13-trans-prostatriene.

94. The racemic compound according to claim 84, dl-1,9-dioxo-16-hydroxy-1-acetoxymethyl-16-methyl-17-trans-10,5-cis,13-trans-prostatetraene.

95. The racemic compound according to claim 84, dl-1,9-dioxo-16-hydroxy-1-acetoxymethyl-16-methyl-20-ethyl-17-trans-10,5-cis,13-trans-prostatetraene.

96. An optically active compound of the formula:

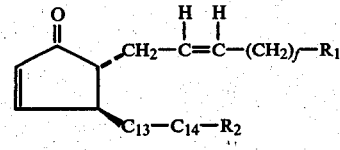

wherein f is an integer from 2 to 4, inclusive; $C_{13}$–$C_{14}$ is selected from the group consisting of ethylene and trans-vinylene; $R_1$ is a radical selected from the group consisting of

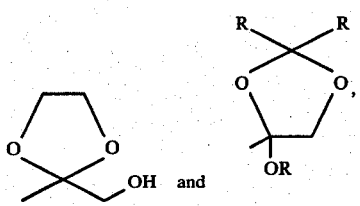

wherein R is selected from the group consisting of $C_1$–$C_4$ alkyl; $R_2$ is a moiety selected from the group consisting of

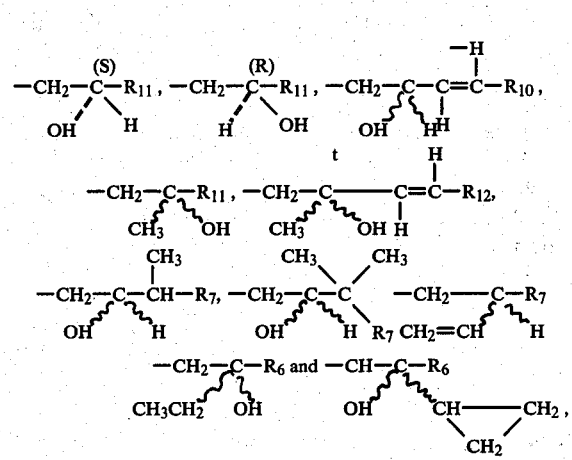

wherein $R_6$ is selected from the group consisting of $C_3$–$C_6$ alkyl, $R_7$ is selected from the group consisting of $C_2$–$C_4$ alkyl, $R_{10}$ is selected from the group consisting of $C_1$–$C_4$ alkyl, $R_{11}$ is selected from the group consisting of $C_3$–$C_7$ alkyl and $R_{12}$ is selected from the group consisting of $C_1$–$C_4$ alkyl; the racemic mixture thereof; and the mirror image thereof.

97. An optically active compound according to claim 96, wherein f, and $R_2$ are as previously defined; $C_{13}$–$C_{14}$ is trans-vinylene; and $R_1$ is the moiety

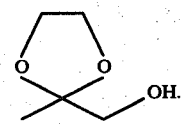

98. An optically active compound according to claim 96, wherein f, and $R_2$ are as previously defined; $C_{13}$–$C_{14}$ is trans-vinylene; and $R_1$ is the moiety

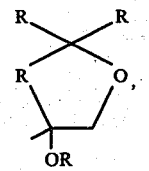

wherein R is as previously defined.

99. An optically active compound according to claim 97, wherein $R_1$, $C_{13}$–$C_{14}$ and f are as previously defined, and $R_2$ is a moiety selected from the group consisting of

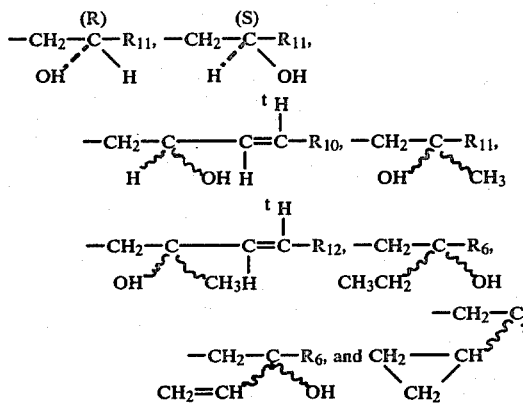

wherein $R_6$, $R_{10}$, $R_{11}$ and $R_{12}$ are as previously defined.

100. An optically active compound according to claim 97, wherein $R_1$, $C_{13}$–$C_{14}$ and f are as previously defined; and $R_2$ is a moiety selected from the group consisting of

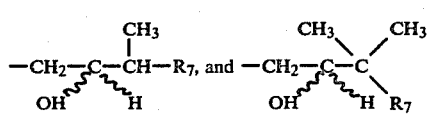

wherein $R_7$ is as previously defined.

101. An optically active compound according to claim 100, wherein $R_1$, $C_{13}$–$C_{14}$ and f are as previously defined; and $R_2$ is a moiety selected from the group consisting of

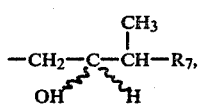

wherein $R_7$ is as previously defined.

102. An optically active compound according to claim 99, wherein $R_1$, $C_{13}$–$C_{14}$ and f are as previously defined; and $R_2$ is a moiety selected from the group consisting of

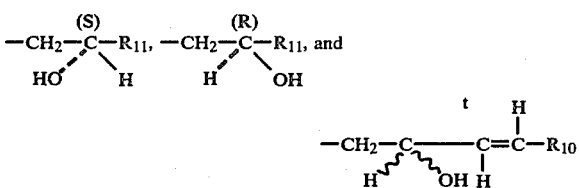

wherein $R_6$, $R_{11}$ and $R_{12}$ are as previously defined.

103. An optically active compound according to claim 99, wherein $R_1$, $C_{13}$–$C_{14}$ and f are as previously defined; and $R_2$ is a moiety selected from the group consisting of

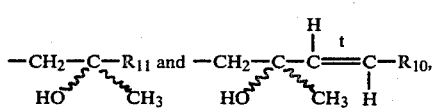

wherein $R_{10}$ and $R_{11}$ are as previously defined.

104. The racemic compound according to claim 99, dl-1,9-dioxo-16-hydroxy-1-hydroxymethyl-16-vinyl-10,5-cis, 13-trans-prostatriene-1-ethylene ketal.

105. The racemic compound according to claim 99, dl-1,9-dioxo-16-hydroxy-1-hydroxymethyl-16-vinyl-20-ethyl-10,5-cis,13-trans-prostatriene-1-ethylene ketal.

106. The racemic compound according to claim 99, dl-1,9-dioxo-16-hydroxy-1-hydroxymethyl-16-cyclopropyl-10,5-cis,13-trans-prostatriene-1-ethylene ketal.

107. The racemic compound according to claim 99, dl-1,9-dioxo-16-hydroxy-1-hydroxymethyl-16-cyclopropyl-20-ethyl-10,5-cis, 13-trans-prostatriene-1-ethylene ketal.

108. The racemic compound according to claim 99, dl-1,9-dioxo-16-hydroxy-1-hydroxymethyl-16-cyclopropyl-20-ethyl-10,5-cis, 13-trans-prostatriene-1ethylene ketal.

109. The racemic compound according to claim 99, dl-1,9-dioxo-16-hydroxy-1-hydroxymethyl-16-20-diethyl-10,5-cis, 13-trans-prostatriene-1-ethylene ketal.

110. The racemic compound according to claim 99; dl-1,9-dioxo-16-hydroxy-1-hydroxymethyl-16-vinyl-10,5-cis,13-trans-prostatriene-1-ethylene ketal.

111. The racemic compound according to claim 101, dl-1,9-dioxo-16-hydroxy-1-hydroxymethyl-17-methyl-10,5-cis,13-trans-prostatriene-1-ethylene ketal.

112. The racemic compound according to claim 101, dl-1,9-dioxo-16-hydroxy-1-hydroxymethyl-17,20-dimethyl-10,5-cis,13-trans-prostatriene-1-ethylene ketal.

113. The racemic compound according to claim 101, dl-1,9-dioxo-16-hydroxy-1-hydroxymethyl-17-methyl-20-ethyl-10,5-cis, 13-trans-prostatriene-1-ethylene ketal.

114. The racemic compound according to claim 102, dl-1,9-dioxo-16-hydroxy-1-hydroxymethyl-10,5-cis,13-transprostatriene-1-ethylene ketal.

115. The racemic compound according to claim 102, dl-1,9-dioxo-16-hydroxy-1-hydroxymethyl-20-ethyl-10,5-cis, 13-trans-prostatriene-1-ethylene ketal.

116. The racemic compound according to claim 102, dl-1,9-dioxo-16(R)-hydroxy-1-hydroxymethyl-10,5-cis,13-trans-prostatriene-1-ethylene ketal.

117. The racemic compound according to claim 102, dl-1,9-dioxo-16(S)-hydroxy-1-hydroxymethyl-10,5-cis,13-trans-prostatriene-1-ethylene ketal.

118. The racemic compound according to claim 102, dl-1,9-dioxo-16-hydroxy-1-hydroxymethyl-17-trans-10,5-cis,13-trans-prostatetraene-1-ethylene ketal.

119. The racemic compound according to claim 102, dl-1,9-dioxo-16-hydroxy-1-hydroxymethyl-20-ethyl-17-trans-10,5-cis,13-trans-prostatetraene-1-ethylene ketal.

120. The racemic compound according to claim 103, dl-1,9-dioxo-16-hydroxy-1-hydroxymethyl-16-methyl-10,5-cis,13-trans-prostatriene-1-ethylene ketal.

121. The racemic compound according to claim 103, dl-1,9-dioxo-16-hydroxy-1-hydroxymethyl-16-methyl-20-ethyl-10,5-cis,13-trans-prostatriene-1-ethylene ketal.

122. The racemic compound according to claim 103, dl-1,9-dioxo-16-hydroxy-1-hydroxymethyl-16-methyl-17-trans-10,5-cis,13-trans-prostatetraene-1-ethylene ketal.

123. The racemic compound according to claim 103, dl-1,9-dioxo-16-hydroxy-1-hydroxymethyl-16-methyl-20-ethyl-17-trans-10,5-cis,13-trans-prostatriene-1-ethylene ketal.

124. An optically active compound of the formula:

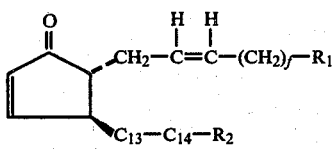

wherein f is an integer from 2 to 4, inclusive; $C_{13}$–$C_{14}$ is selected from the group consisting of ethylene and trans-vinylene; R is a radical selected from the group consisting of

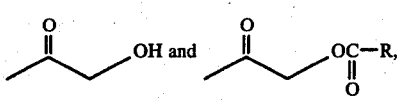

wherein R is selected from the group consisting of $C_1$–$C_4$ alkyl; $R_2$ is a moiety selected from the group consisting of

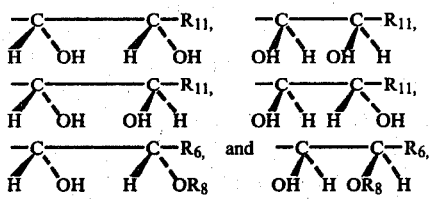

wherein $R_6$ is selected from the group consisting of $C_3$–$C_5$ alkyl, $R_8$ is selected from the group consisting of $C_1$–$C_2$ alkyl and $R_{11}$ is selected from the group consisting of $C_3$–$C_7$ alkyl; the racemic mixture thereof; and the mirror image thereof.

125. An optically active compound according to claim 1, wherein f, and $R_2$ are as previously defined; $C_{13}$–$C_{14}$ is trans-vinylene; and $R_1$ is the moiety

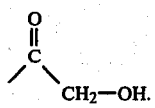

126. An optically active compound according to claim 1, wherein f, and $R_2$ are as previously defined; $C_{13}$–$C_{14}$ is trans-vinylene; and $R_1$ is the moiety

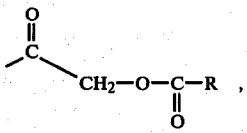

wherein R is as previously defined.

127. An optically active compound according to claim 125, wherein $R_1$, $C_{13}$–$C_{14}$ and f are as previously defined; and $R_2$ is a moiety selected from the group consisting of

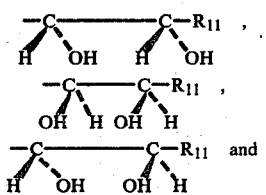

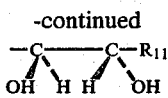

wherein $R_{11}$ is as previously defined.

128. An optically active compound according to claim 125, wherein $R_1$, $C_{13}$–$C_{14}$ and f are as previously defined; and $R_2$ is a moiety selected from the group consisting of

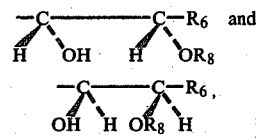

wherein $R_6$ and $R_8$ are as previously defined.

129. The racemic compound according to claim 127, dl-erythro-15α,16-dihydroxy-1,9-dioxo-1-hydroxymethyl-10,5-cis, 13-trans-prostatriene.

130. The racemic compound according to claim 127, dl-erythro-15α,16-dihydroxy-1,9-dioxo-1-hydroxymethyl-20-ethyl-10,5-cis,13-trans-prostatriene.

131. The racemic compound according to claim 127, dl-threo-15α,16-dihydroxy-1,9-dioxo-1-hydroxymethyl-10,5-cis, 13-trans-prostatriene.

132. The racemic compound according to claim 127, dl-threo-15α,16-dihydroxy-1,9-dioxo-1-hydroxymethyl-20-ethyl-10,5-cis,13-trans-prostatriene.

133. The racemic compound according to claim 128, dl-erythro-15α -hydroxy-1,9-dioxo-1-hydroxymethyl-16-methoxy-10,5-cis,13-trans-prostatriene.

134. An optically active compound according to claim 126 wherein $R_1$, $C_{13}$–$C_{14}$ and f are as previously defined; and $R_2$ is a moiety selected from the group consisting of

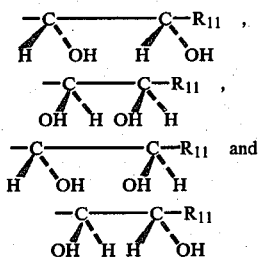

wherein $R_{11}$ is as previously defined.

135. An optically active compound according to claim 126, wherein $R_1$, $C_{13}$–$C_{14}$ and f are as previously defined; and $R_2$ is a moiety selected from the group consisting of

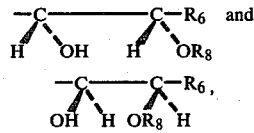

wherein $R_6$ and $R_8$ are as previously defined.

136. The racemic compound according to claim 134, dl-erythro-15α,16-dihydroxy-1,9-dioxo-1-n-propoxymethyl-10,5-cis,13-trans-prostatriene.

137. The racemic compound according to claim 134, dl-erythro-15α,16-dihydroxy-19-dioxo-1-acetoxymethyl-20-ethyl-10,5-cis,13-trans-prostatriene.

138. The racemic compound according to claim 134, dl-threo-15α,16-dihydroxy-1,9-dioxo-1-acetoxymethyl-10,5-cis,13-trans-prostatriene.

139. The racemic compound according to claim 134, dl-threo-15α,16-dihydroxy-1,9-dioxo-1-acetoxymethyl-20-ethyl-10,5-cis,13-trans-prostatriene.

140. The racemic compound according to claim 135, dl-erythro-15α-hydroxy-1,9-dioxo-1-acetoxymethyl-16-methoxy-10,5-cis,13-trans-prostatriene.

141. An optically active compound of the formula:

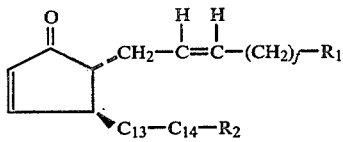

wherein f is an integer from 2 to 4, inclusive; $C_{13}-C_{14}$ is selected from the group consisting of ethylene and trans-vinylene; $R_1$ is a radical selected from the group consisting of

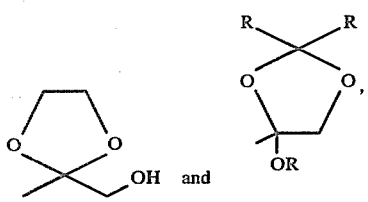

wherein R is selected from the group consisting of $C_1-C_4$ alkyl; $R_2$ is a moiety selected from the group consisting of

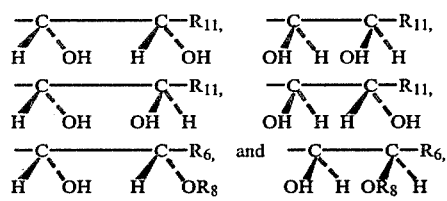

wherein $R_6$ is selected from the group consisting of $C_3-C_5$ alkyl, $R_8$ is selected from the group consisting of $C_1-C_2$ alkyl and $R_{11}$ is selected from the group consisting of $C_3-C_7$ alkyl; the racemic mixture thereof; and the mirror image thereof.

142. An optically active compound according to claim 141, wherein f, and $R_2$ are as previously defined; $C_{13}-C_{14}$ is trans-vinylene; and $R_1$ is the moiety

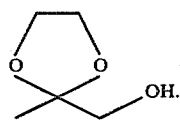

143. An optically active compound according to claim 141 wherein f, and $R_2$ are as previously defined; $C_{13}-C_{14}$ is trans-vinylene; and $R_1$ is the moiety

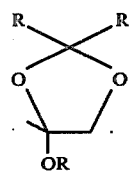

wherein R is as previously defined.

144. An optically active compound according to claim 142, wherein $R_1$, $C_{13}-C_{14}$ and f are as previously defined; and $R_2$ is a moiety selected from the group consisting of

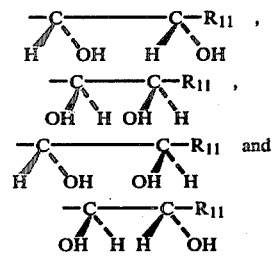

wherein $R_{11}$ is as previously defined.

145. An optically active compound according to claim 142, wherein $R_1$, $C_{13}-C_{14}$ and f are as previously defined; and $R_2$ is a moiety selected from the group consisting of

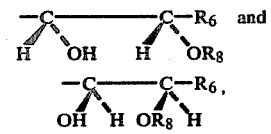

wherein $R_6$ and $R_8$ are as previously defined.

146. The racemic compound according to claim 144, dl-erythro-15α,16-dihydroxy-1,9-dioxo-1-hydroxymethyl-10,5-cis,13-trans-prostatriene-1-ethylene ketal.

147. The racemic compound according to claim 144, dl-erythro-15α,16-dihydroxy-1,9-dioxo-1-hydroxymethyl-20-ethyl-10,5-cis,-13-trans-prostatriene-1-ethylene ketal.

148. The racemic compound according to claim 144, dl-threo-15α,16-dihydroxy-1,9-dioxo-1-hydroxymethyl-10,5-cis,13-trans-prostatriene-1-ethylene ketal.

149. The racemic compound according to claim 144, dl-threo-15α,16-dihydroxy-1,9-dioxo-1-hydroxymethyl-20-ethyl-10,5-cis,-13-trans-prostatriene-1-ethylene ketal.

150. The racemic compound according to claim 145, dl-erythro-15α-hydroxy-1,9-dioxo-1-hydroxymethyl-16-methoxy-10,5-cis,-13-trans-prostatriene-1-ethylene ketal.

151. An optically active compound of the formula:

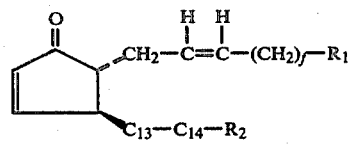

wherein f is an integer from 2 to 4, inclusive; $C_{13}-C_{14}$ is selected from the group consisting of ethylene and trans-vinylene; R is a radical selected from the group consisting of

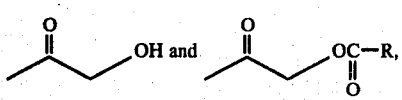

wherein R is selected from the group consisting of $C_1-C_4$ alkyl; $R_2$ is a moiety selected from the group consisting of

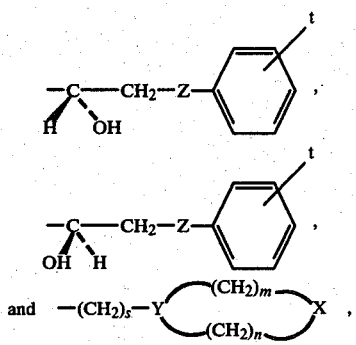

wherein X is a divalent radical selected from the group consisting of

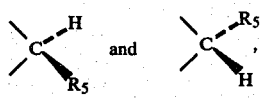

wherein $R_5$ is selected from the group consisting of $C_1-C_7$ alkyl, hydrogen and a phenoxy group optionally substituted from the group consisting of halogen, trifluoromethyl and $C_1-C_4$ alkyloxy, Y is a trivalent radical selected from the group consisting of

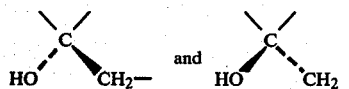

Z is a divalent radical selected from the group consisting of —O— and —$CH_2$—, m is zero or an integer from 1 to 4, inclusive, n is zero or an integer from 1 to 4, inclusive, with the proviso that the sum of m and n has the value of 1 to 4, s is zero or the integer 1, t is selected from the group consisting of hydrogen, chloro, fluoro, dichloro, trifluoro-methyl, methoxy and t-butyl; the racemic mixture thereof; and the mirror image thereof.

152. An optically active compound according to claim 151, wherein f, and $R_2$ are as previously defined; $C_{13}-C_{14}$ is trans-vinylene; and $R_1$ is the moiety

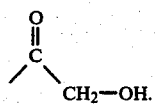

153. An optically active compound according to claim 151, wherein f, and $R_2$ are as previously defined; $C_{13}-C_{14}$ is trans-vinylene; and $R_1$ is the moiety

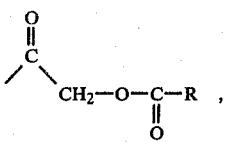

wherein R is as previously defined.

154. The racemic compound according to claim 152, dl-1,9-dioxo-15α-hydroxy-1-hydroxymethyl-17,20-tetranor-16-m-trifluoromethylphenoxy-10,5-cis,-13-trans-prostatriene.

155. The racemic compound according to claim 152, dl-1,9-dioxo-15α-hydroxy-1-hydroxymethyl-17,20-tetranor-16-m-chlorophenoxy-10,5-cis,-13-trans-prostatriene.

156. The racemic compound according to claim 152, dl-1,9-dioxo-15α-hydroxy-1-hydroxymethyl-17,20-tetranor-16-p-fluorophenoxy-10,5-cis,-13-trans-prostatriene.

157. The racemic compound according to claim 152, dl-1,9-dioxo-15α-hydroxy-1-hydroxymethyl-18,20-trinor-17-phenyl-10,5-cis,-13-trans-prostatriene.

158. The racemic compound according to claim 152, nat (and ent)-1,9-dioxo-15-hydroxy-15,16-tetramethylene-17,18,19,20-tetranor-1-hydroxymethyl-10,5cis,-13-trans-prostatriene.

159. The racemic compound according to claim 152, nat (and ent)-1,9-dioxo- 16-hydroxy-16,17-tetramethylene-18,19,20-trinor-1-hydroxymethyl-10,5-cis,-13-trans-prostatriene.

160. The racemic compound according to claim 152, nat-15S,16R (and ent-15R,16S)-1,9-dioxo-15-hydroxy-15,16-trimethylene-1-hydroxymethyl-10,5-cis,-13-trans-prostatriene.

161. The racemic compound according to claim 152, nat -15S,16S (and ent-15R,16R)-1,9-dioxo-15-hydroxy-15,16-trimethylene-1-hydroxymethyl-10,5-cis,-13-trans-prostatriene.

162. The racemic compound according to claim 153, dl-1,9-dioxo-15-hydroxy-1-acetoxymethyl-17,20-tetranor-16-m-trifluoromethylphenoxy-10,5-cis,-13-trans-prostatriene.

163. The racemic compound according to claim 153, dl-1,9-dioxo-15α-hydroxy-1-acetoxymethyl-17,20-tetranor-16-m-chlorophenoxy-10,5-cis,-13-trans-prostatriene.

164. The racemic compound according to claim 153, dl-1,9-dioxo-15α-hydroxy-1-acetoxymethyl-17,20-tetranor-16-p-fluorophenoxy-10,5-cis,-13-trans-prostatriene.

165. The racemic compound according to claim 153, dl-1,9-dioxo-15α-hydroxy-1-acetoxymethyl-18,20-trinor-17-phenyl-10,5-cis,-13-trans-prostatriene.

166. The racemic compound according to claim 153, nat (and ent)-1,9-dioxo-15-hydroxy-15,16-tetramethylene-17,18,19,20-tetranor-1-acetoxymethyl-10,5-cis,-13-trans-prostatriene.

167. The racemic compound according to claim 153, nat(and ent)-1,9-dioxo-16-hydroxy-16,17-tetramethylene-18,19,20-trinor-1-acetoxymethyl-10,5-cis,-13-trans-prostatriene.

168. The racemic compound according to claim 153, nat-15S,16R(and ent-15R,16S)-1,9-dioxo-15-hydroxy-15,16-trimethylene-1-acetoxymethyl-10,5-cis,-13-trans-prostatriene.

169. The racemic compound according to claim 153, nat-15S,16S(and ent-15R,16R)-1,9-dioxo-15-hydroxy-15,16-trimethylene-1-acetoxymethyl-10,5-cis,-13-trans-prostatriene.

170. An optically active compound of the formula:

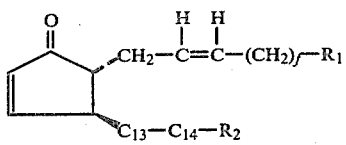

wherein f is an integer from 5 to 7, inclusive; $R_3$ is selected from the group consisting of hydrogen and hydroxyl; $C_{13}$–$C_{14}$ is selected from the group consisting of ethylene and trans-vinylene; $R_1$ is a radical selected from the group consisting of

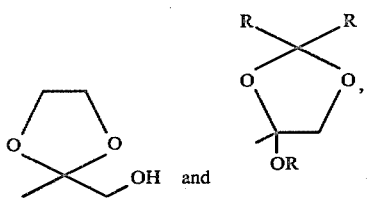

wherein R is selected from the group consisting of $C_1$–$C_4$ alkyl; $R_2$ is a moiety selected from the group consisting of

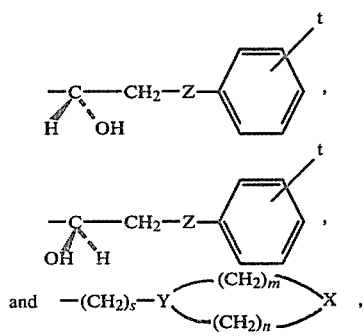

wherein X is a divalent radical selected from the group consisting of

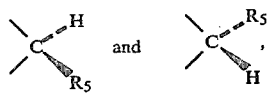

wherein $R_5$ is selected from the group consisting of $C_1$–$C_7$ alkyl, hydrogen and a phenoxy group optionally substituted from the group consisting of halogen, trifluoromethyl and $C_1$–$C_4$ alkyloxy, Y is a trivalent radical selected from the group consisting of

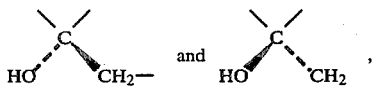

Z is a divalent radical selected from the group consisting of —O— and —CH₂—, m is zero or an integer from 1 to 4, inclusive, n is zero or an integer from 1 to b 4, inclusive, with the proviso that the sum of m and n has the value of 1 to 4, s is zero or the integer 1, t is selected from the group consisting of hydrogen, chloro, fluoro, dichloro, trifluoromethyl, methoxy and t-butyl; the racemic mixture thereof; and the mirror image thereof.

171. An optically active compound according to claim 170, wherein f, and $R_2$ are as previously defined; $C_{13}$–$C_{14}$ is trans-vinylene; and $R_1$ is the moiety

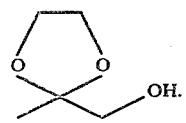

172. An optically active compound according to claim 170, wherein f, and $R_2$ are as previously defined; $C_{13}$–$C_{14}$ is trans-vinylene; and $R_1$ is the moiety

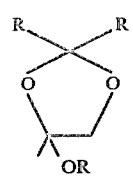

wherein R is as previously defined.

173. The racemic compound according to claim 170, dl-1,9-dioxo- 15α-hydroxy-1-hydroxymethyl-17,20-tetranor-16-m-trifluoromethylphenoxy-10,5-cis,-13-trans-prostatriene-1-ethylene ketal.

174. The racemic compound according to claim 170, dl-1,9-dioxo-15α-hydroxy-1-hydroxymethyl-17,20-tetranor-16-m-chlorophenoxy-10,5-cis,-13-trans-prostatriene-1-ethylene ketal.

175. The racemic compound according to claim 170, dl-1,9-dioxo-15α-hydroxy-1-hydroxymethyl-17,20-tetranor-16-p-fluorophenoxy-10,5-cis,-13-trans-prostatriene-1-ethylene ketal.

176. The racemic compound according to claim 170, dl-1,9-dioxo-15α-hydroxy-1-hydroxymethyl-18,20-trinor-17-phenyl-10,5-cis,-13-trans-prostatriene-1-ethylene ketal.

177. The racemic compound according to claim 171, nat (and ent)-1,9-dioxo-15-hydroxy-15,16-tetramethylene-17,18,19,20-tetranor-1-hydroxymethyl-10,5-cis,-13-trans-prostatriene-1-ethylene ketal.

178. The racemic compound according to claim 171, nat (and ent)-1,9-dioxo- 16-hydroxy-16,17-tetramethylene-18,19,20-trinor-1-hydroxymethyl-10,5-cis,-13-trans-prostatriene-1-ethylene ketal.

179. The racemic compound according to claim 171, nat-15S,16R (and ent-15R,16S)-1,9-dioxo- 15-hydroxy-15,16-trimethylene-1-hydroxymethyl-10,5-cis,-13-trans-prostatriene-1-ethylene ketal.

180. The racemic compound according to claim 171, nat-15S,16S(and ent-15R,16R)-1,9-dioxo- 15-hydroxy-15,16-trimethylene-1-hydroxymethyl-10,5-cis,-13-trans-prostatriene-1-ethylene ketal.

181. The racemic compound according to claim 80, dl-1,9-dioxo-16-hydroxy-1-acetoxymethyl-16-cyclopropyl-20-ethyl-10,5-cis-13-trans-prostatriene.

182. The racemic compound according to claim 80, dl-1,9-dioxo-16-hydroxy-1-acetoxymethyl-16-ethyl-10,5-cis-13-trans-prostatriene.

183. The racemic compound according to claim 80, dl-1,9-dioxo-16-hydroxy-1-acetoxymethyl-16,20-diethyl-10,5-cis-13-trans-prostatriene.

184. The racemic compound according to claim 80, dl-1,9-dioxo-16-hydroxy-1-acetoxymethyl-16-vinyl-10,5-cis-13-trans-prostatriene.

185. The racemic compound according to claim 82, dl-1,9-dioxo-16-hydroxy--acetoxymethyl-17-methyl-10,5-cis-13-trans-prostatriene.

186. The racemic compound according to claim 82, dl-1,9-dioxo-16-hydroxy-1-acetoxymethyl-17,20-dimethyl-10,5-cis-13-trans-prostatriene.

187. The racemic compound according to claim 82, dl-1,9-dioxo-16-hydroxy-1-acetoxymethyl-17-methyl-10-ethyl-10,5-cis-13-trans-prostatriene.

188. The racemic compound according to claim 83, dl-1,9-dioxo-16-hydroxy-1-acetoxymethyl-10,5-cis-13-trans-prostatriene.

189. The racemic compound according to claim 83, dl-1,9-dioxo-16-hydroxy-1-acetoxymethyl-20-ethyl-10,5-cis-13-trans-prostatriene.

* * * * *

UNITED STATES PATENT OFFICE
CERTIFICATE OF CORRECTION

Patent No. 4,212,969  Dated July 15, 1980

Inventor(s) Allan Wissner

It is certified that error appears in the above-identified patent and that said Letters Patent are hereby corrected as shown below:

In the claims:

Claim 34, column 191, line 6, top most structual formula, delete "g", insert -- q --.

Same claim, line 10, second most structual formula, delete "g", insert -- q --.

Claim 52, column 193, lines 45-47, third most structual formula, insert -- t -- as follows:

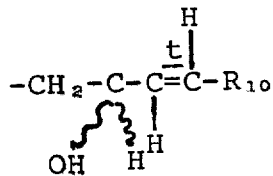

Same claim, lines 49-51, second most structual formula, insert -- t -- as follows:

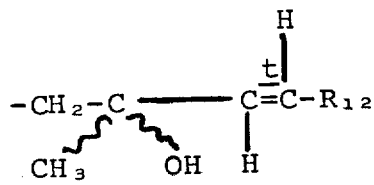

Same claim, lines 54-55, third structural formula, delete $R_7$, insert -- $R_6$ --; before ⤵H, insert -- O -- as follows ⤵OH.

UNITED STATES PATENT OFFICE
CERTIFICATE OF CORRECTION

Patent No. 4,212,969           Dated July 15, 1980

Inventor(s) Allan Wissner

It is certified that error appears in the above-identified patent and that said Letters Patent are hereby corrected as shown below:

Claim 96, column 198, lines 16-19, third most structual formula, insert -- $\underline{t}$ -- as follows

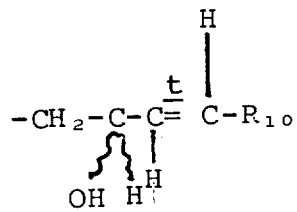

Same claim lines 20-22 in the structure,

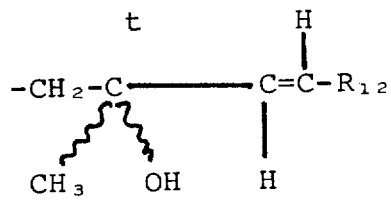

delete "t", insert $\underline{t}$ as follows:

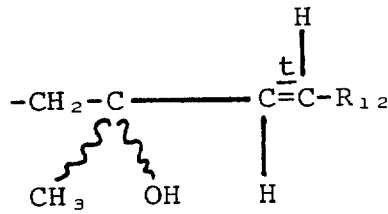

Same claim, lines 24-26, third structual formula, delete $R_7$, insert -- $R_6$ --; before ⁀H, insert -- O -- as follows ⁀OH

UNITED STATES PATENT OFFICE
CERTIFICATE OF CORRECTION

Patent No. 4,212,969            Dated July 15, 1980

Inventor(s) Allan Wissner

It is certified that error appears in the above-identified patent and that said Letters Patent are hereby corrected as shown below:

Claim 98 in structual formula

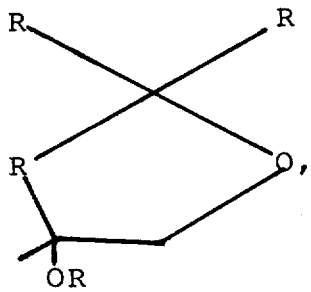

delete "R", insert -- "O" --.

Claim 170, column 207, line 2 from bottom, delete "b".

Signed and Sealed this

Eleventh Day of November 1980

[SEAL]

Attest:

SIDNEY A. DIAMOND

Attesting Officer      Commissioner of Patents and Trademarks